(12) United States Patent
Kawakami et al.

(10) Patent No.: US 9,997,725 B2
(45) Date of Patent: Jun. 12, 2018

(54) HETEROCYCLIC COMPOUND, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Atsugi-shi, Kanagawa-ken (JP)

(72) Inventors: Sachiko Kawakami, Kanagawa (JP); Yoshimi Ishiguro, Kanagawa (JP); Tatsuyoshi Takahashi, Kanagawa (JP); Takao Hamada, Toyama (JP); Hiromi Seo, Kanagawa (JP); Satoshi Seo, Kanagawa (JP)

(73) Assignee: Semiconductor Energy Laboratory Co., Ltd., Atsugi-shi, Kanagawa-ken (JP)

(*) Notice: Subject to any disclaimer, the term of this patent is extended or adjusted under 35 U.S.C. 154(b) by 24 days.

(21) Appl. No.: 15/186,646

(22) Filed: Jun. 20, 2016

(65) Prior Publication Data

US 2016/0380212 A1    Dec. 29, 2016

(30) Foreign Application Priority Data

Jun. 25, 2015  (JP) .................................. 2015-127571

(51) Int. Cl.
*C07D 493/02* (2006.01)
*H01L 51/00* (2006.01)
(Continued)

(52) U.S. Cl.
CPC ........ *H01L 51/0073* (2013.01); *C07D 493/04* (2013.01); *C09K 11/025* (2013.01);
(Continued)

(58) Field of Classification Search
CPC .................................................. C07D 493/04
See application file for complete search history.

(56) References Cited

U.S. PATENT DOCUMENTS

| | | | |
|---|---|---|---|
| 6,723,445 B2 | 4/2004 | Li et al. | |
| 2011/0210316 A1 | 9/2011 | Kadoma et al. | |
| (Continued) | | | |

FOREIGN PATENT DOCUMENTS

| | | |
|---|---|---|
| JP | 2007-189001 A | 7/2007 |
| WO | 03/058667 A1 | 7/2003 |

*Primary Examiner* — Stephen E Rieth
(74) *Attorney, Agent, or Firm* — Fish & Richardson P.C.

(57) ABSTRACT

A novel heterocyclic compound is provided. In particular, a novel heterocyclic compound which can improve the element characteristics of the light-emitting element is provided. The heterocyclic compound is represented by a general formula (G1)

$$\text{DBq}{-}(\text{Ar}^1)_n{-}\text{Ar}^2{-}\text{A} \qquad (\text{G1})$$

in which a substituted or unsubstituted dibenzo[f,h]quinoxalinyl group and a substituted or unsubstituted benzobisbenzofuranyl group are bonded to each other via a substituted or unsubstituted arylene group. In the general formula (G1), DBq represents a substituted or unsubstituted dibenzo[f,h] quinoxalinyl group, $\text{Ar}^1$ represents a substituted or unsubstituted arylene group having 6 to 13 carbon atoms, n represents 0 or 1, $\text{Ar}^2$ represents a substituted or unsubstituted arylene group having 6 to 13 carbon atoms, and A represents a substituted or unsubstituted benzobisbenzofuranyl group. When the arylene group represented by $\text{Ar}^1$ and $\text{Ar}^2$ has substituents, the substituents may be bonded to each other to form a ring.

34 Claims, 29 Drawing Sheets

(51) Int. Cl.
  *C09K 11/02*   (2006.01)
  *C07D 493/04*  (2006.01)
  *H01L 51/50*   (2006.01)

(52) U.S. Cl.
  CPC ...... *H01L 51/0072* (2013.01); *H01L 51/0059* (2013.01); *H01L 51/0074* (2013.01); *H01L 51/0085* (2013.01); *H01L 51/5016* (2013.01); *H01L 2251/5384* (2013.01)

(56) References Cited

U.S. PATENT DOCUMENTS

| | | |
|---|---|---|
| 2012/0157694 A1 | 6/2012 | Osaka et al. |
| 2012/0184755 A1 | 7/2012 | Osaka et al. |
| 2012/0193613 A1 | 8/2012 | Kadoma et al. |
| 2012/0197020 A1 | 8/2012 | Osaka et al. |
| 2013/0082591 A1 | 4/2013 | Sec et al. |
| 2015/0060824 A1 | 3/2015 | Ishiguro et al. |
| 2015/0073147 A1 | 3/2015 | Inoue et al. |
| 2015/0131302 A1 | 5/2015 | Inoue et al. |
| 2015/0166561 A1* | 6/2015 | Kitamura ............ H01L 51/0073 257/40 |
| 2015/0311454 A1 | 10/2015 | Inoue et al. |

* cited by examiner

FIG. 5A1
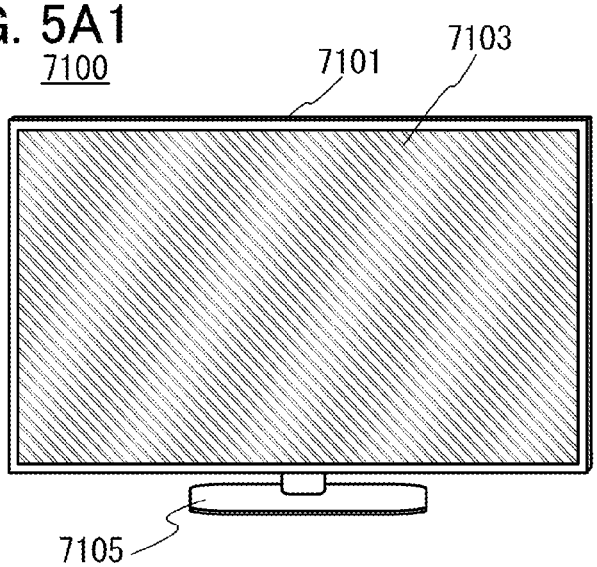
FIG. 5A2
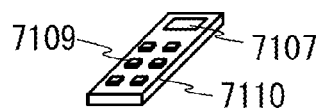
FIG. 5B
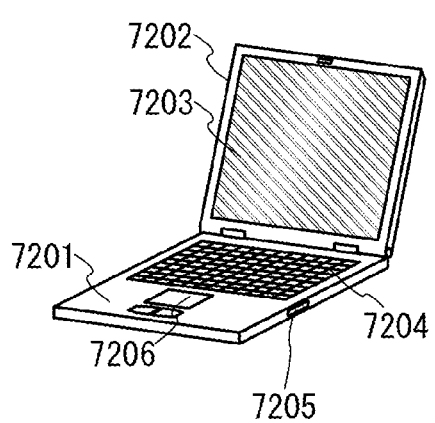
FIG. 5C
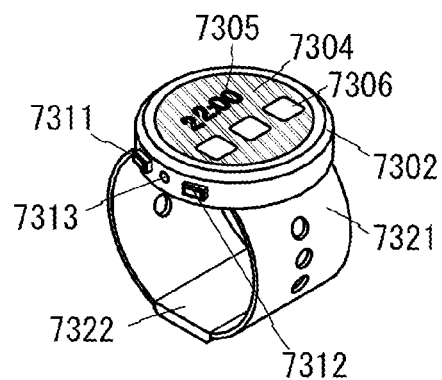
FIG. 5D1
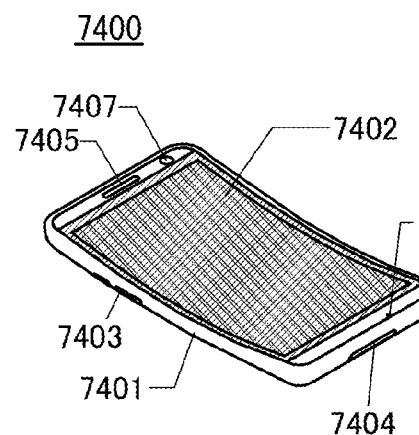
FIG. 5D2
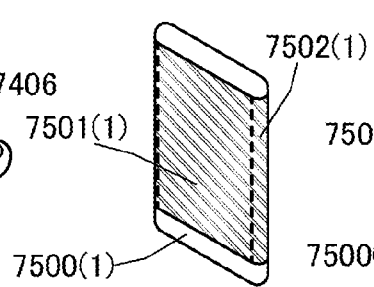
FIG. 5D3
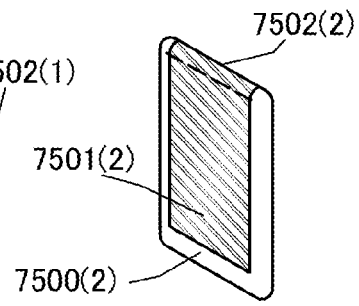

HETEROCYCLIC COMPOUND, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

One embodiment of the present invention relates to an object, a method, and a manufacturing method. In addition, the present invention relates to a process, a machine, manufacture, or a composition of matter. In particular, one embodiment of the present invention relates to a semiconductor device, a light-emitting device, a display device, a lighting device, a light-emitting element, or a manufacturing method thereof. Further, one embodiment of the present invention relates to a heterocyclic compound and a novel method of synthesizing the heterocyclic compound. In addition, one embodiment of the present invention relates to a light-emitting element, a light-emitting device, an electronic device, and a lighting device that include the heterocyclic compound. Note that one embodiment of the present invention is not limited to the above technical field.

2. Description of the Related Art

A light-emitting element using an organic compound as a luminous body, which has features such as thinness, lightness, high-speed response, and DC drive at low voltage, is expected to be applied to a next-generation flat panel display. A display device in which light-emitting elements are arranged in matrix is, in particular, considered to have advantages in a wide viewing angle and excellent visibility over a conventional liquid crystal display device.

It is said that the light emission mechanism of a light-emitting element is as follows: when a voltage is applied between a pair of electrodes with an EL layer including a luminous body provided therebetween, electrons injected from the cathode and holes injected from the anode recombine in the light emission center of the EL layer to form molecular excitons, and energy is released and light is emitted when the molecular excitons relax to the ground state. A singlet excited state and a triplet excited state are known as excited states, and it is thought that light emission can be achieved through either of the excited states.

An organic compound is mainly used in an EL layer in such a light-emitting element and greatly affects an improvement in the characteristics of the light-emitting element. For this reason, a variety of novel organic compounds have been developed (e.g., see Patent Document 1).

REFERENCE

Patent Document

[Patent Document 1] Japanese Published Patent Application No. 2007-189001

SUMMARY OF THE INVENTION

Compounds having a dibenzo[f,h]quinoxaline ring which are reported in Patent Document 1 have planar structures and are thus easily crystallized, which is a problem. A light-emitting element using a compound that is easy to crystallize has a short lifetime. Further, if another skeleton is directly bonded to the dibenzo[f,h]quinoxaline ring so that the compound has a three-dimensionally bulky structure, the conjugated system could possibly extend to cause a decrease in triplet excitation energy. When the triplet excitation energy decreases, emission efficiency is lowered, resulting in degradation of element characteristics of the light-emitting element using such a compound.

In view of the above, one embodiment of the present invention provides a novel heterocyclic compound. In particular, one embodiment of the present invention provides a novel heterocyclic compound which can improve the element characteristics of a light-emitting element. Another embodiment of the present invention provides a novel heterocyclic compound with high emission efficiency and high heat resistance. Another embodiment of the present invention provides a novel heterocyclic compound that can be used in a light-emitting element. Another embodiment of the present invention provides a novel heterocyclic compound that can be used in an EL layer of a light-emitting element. In particular, another embodiment of the present invention provides a light-emitting element with high heat resistance, a light-emitting element with high emission efficiency and low power consumption, or a light-emitting element with a long lifetime. Another embodiment of the present invention provides a novel light-emitting element. Another embodiment of the present invention provides a novel light-emitting device, a novel electronic device, or a novel lighting device. Note that the descriptions of these objects do not disturb the existence of other objects. In one embodiment of the present invention, there is no need to achieve all of these objects. Other objects will be apparent from and can be derived from the description of the specification, the drawings, the claims, and the like.

One embodiment of the present invention is a heterocyclic compound in which a substituted or unsubstituted dibenzo[f,h]quinoxalinyl group is bonded to a substituted or unsubstituted benzobisbenzofuranyl group via a substituted or unsubstituted arylene group.

One embodiment of the present invention is a heterocyclic compound represented by a general formula (G1).

[Chemical Formula 1]

$$\text{DBq}-(\text{Ar}^1)_n-\text{Ar}^2-\text{A} \tag{G1}$$

In the general formula (G1), DBq represents a substituted or unsubstituted dibenzo[f,h]quinoxalinyl group, $Ar^1$ represents a substituted or unsubstituted arylene group having 6 to 13 carbon atoms, n represents 0 or 1, $Ar^2$ represents a substituted or unsubstituted arylene group having 6 to 13 carbon atoms, and A represents a substituted or unsubstituted benzobisbenzofuranyl group. When the arylene group represented by $Ar^1$ and $Ar^2$ has substituents, the substituents may be bonded to each other to form a ring.

According to another embodiment of the present invention, in the general formula (G1), DBq represents a substituted or unsubstituted dibenzo[f,h]quinoxalinyl group, $Ar^1$ represents a substituted or unsubstituted arylene group having 6 to 13 carbon atoms, n represents 0 or 1, $Ar^2$ represents a substituted or unsubstituted arylene group having 6 to 13 carbon atoms, and A represents a substituted or unsubstituted benzobisbenzofuranyl group. Among carbon atoms that do not form a furan ring in the benzobisbenzofuranyl group, any one of carbon atoms adjacent to a carbon atom of the furan ring, which is bonded to oxygen, is bonded to $Ar^2$. When the arylene group represented by $Ar^1$ and $Ar^2$ has substituents, the substituents may be bonded to each other to form a ring.

Another embodiment of the present invention is a heterocyclic compound represented by a general formula (G2).

[Chemical Formula 2]

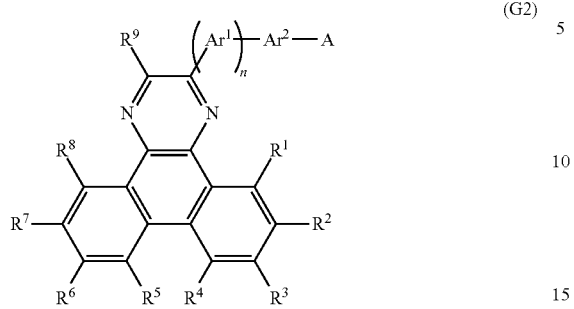

(G2)

In the general formula (G2), A represents a substituted or unsubstituted benzobisbenzofuranyl group, $R^1$ to $R^9$ independently represent any of hydrogen, an alkyl group having carbon atoms of 1 to 4, and a substituted or unsubstituted aryl group having 6 to 13 carbon atoms, $Ar^1$ represents a substituted or unsubstituted arylene group having 6 to 13 carbon atoms, n represents 0 or 1, and $Ar^2$ represents a substituted or unsubstituted arylene group having 6 to 13 carbon atoms. When the arylene group represented by $Ar^1$ and $Ar^2$ has substituents, the substituents may be bonded to each other to form a ring.

In each of the above-described structures, in the general formula (G1) or the general formula (G2), the $Ar^2$ represents a substituted or unsubstituted phenylene group or a substituted or unsubstituted biphenyldiyl group, and the n represents 0.

In each of the above-described structures, in the general formula (G1) or the general formula (G2), the $Ar^2$ represents a substituted or unsubstituted m-phenylene group or a substituted or unsubstituted biphenyl-3,3'-diyl group, and the n represents 0.

In each of the above-described structures, the A in the general formula (G1) or the general formula (G2) is any one of general formulae (A1) to (A3), and among carbon atoms that do not form a furan ring in the general formulae (A1) to (A3), any one of carbon atoms adjacent to a carbon atom of the furan ring, which is bonded to oxygen, is bonded to the $Ar^2$.

[Chemical Formulae 3]

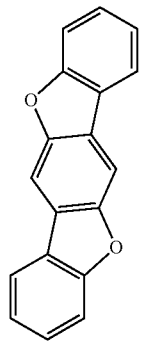

(A1)

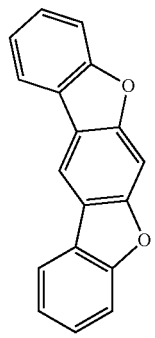

(A2)

(A3)

In the general formulae (A1) to (A3), a benzene ring may have substituents, which are a substituted or unsubstituted alkyl group having carbon atoms of 1 to 6, a substituted or unsubstituted cycloalkyl group having 5 to 7 carbon atoms, or a substituted or unsubstituted aryl group having carbon atoms of 6 to 13.

Another embodiment of the present invention is a heterocyclic compound represented by a structural formula (101), a structural formula (107), a structural formula (149), or a structural formula (150).

[Chemical Formulae 4]

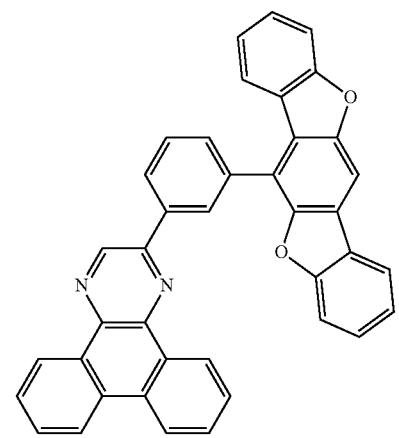

(101)

-continued

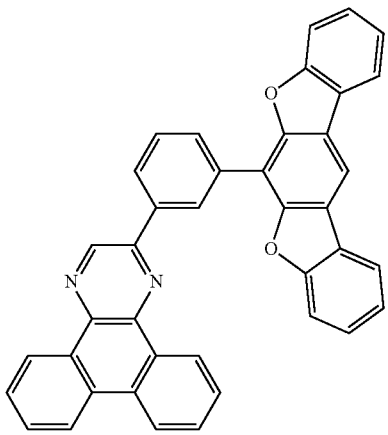

(107)

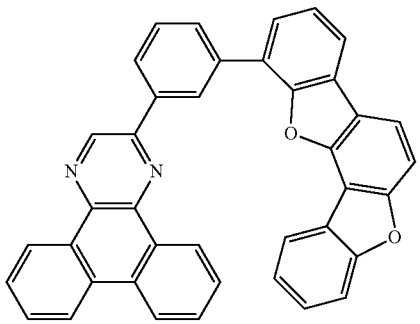

(149)

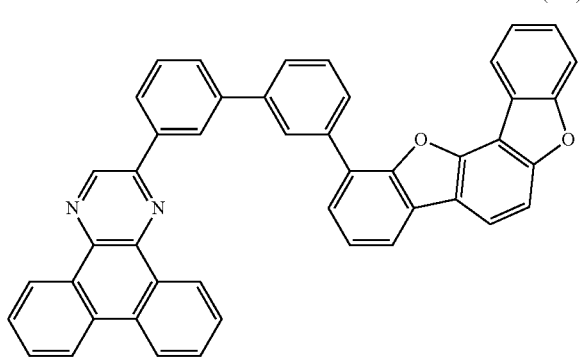

(150)

Because the above-described heterocyclic compounds of embodiments of the present invention are materials having high T1 levels, they can each be used as a host material capable of being used in combination with a light-emitting substance such as a phosphorescent material (dopant).

The heterocyclic compound of one embodiment of the present invention is a material having a high electron transport property, and accordingly can be used in an electron-transport layer or the like as well as a light-emitting layer in an EL layer of a light-emitting element. Furthermore, the heterocyclic compound of one embodiment of the present invention is a light-emitting substance, and accordingly can be used as a light-emitting substance as well as a host material which is used in combination with a light-emitting substance such as a phosphorescent material in a light-emitting layer. Accordingly, one embodiment of the present invention is a light-emitting element that uses the heterocyclic compound of one embodiment of the present invention.

That is, another embodiment of the present invention is a light-emitting element including a heterocyclic compound in which a substituted or unsubstituted dibenzo[f,h]quinoxalinyl group is bonded to a substituted or unsubstituted benzobisbenzofuranyl group via a substituted or unsubstituted arylene group.

Another embodiment of the present invention is a light-emitting element including a heterocyclic compound in which a substituted or unsubstituted dibenzo[f,h]quinoxalinyl group is bonded to a substituted or unsubstituted benzobisbenzofuranyl group via a substituted or unsubstituted arylene group, and among carbon atoms that do not form a furan ring in the benzobisbenzofuranyl group, any one of carbon atoms adjacent to a carbon atom of the furan ring, which is bonded to oxygen, is bonded to the arylene group.

In each of the above-described structures, the light-emitting element includes a light-emitting layer, and the light-emitting layer includes the heterocyclic compound and a light-emitting substance.

The present invention includes, in its scope, not only a light-emitting device including the light-emitting element but also a lighting device including the light-emitting device. The light-emitting device in this specification refers to an image display device and a light source (e.g., a lighting device). In addition, the light-emitting device includes, in its category, all of a module in which a connector such as a flexible printed circuit (FPC) or a tape carrier package (TCP) is connected to a light-emitting device, a module in which a printed wiring board is provided on the tip of a TCP, and a module in which an integrated circuit (IC) is directly mounted on a light-emitting element by a chip on glass (COG) method.

With one embodiment of the present invention, a novel heterocyclic compound can be provided. In particular, a novel heterocyclic compound which can improve the element characteristics of a light-emitting element can be provided. With one embodiment of the present invention, a novel heterocyclic compound with high emission efficiency and high heat resistance can be provided. With one embodiment of the present invention, a novel heterocyclic compound that can be used in a light-emitting element can be provided. With one embodiment of the present invention, a novel heterocyclic compound that can be used in an EL layer of a light-emitting element can be provided. With one embodiment of the present invention, in particular, a light-emitting element with high heat resistance, a light-emitting element with high emission efficiency and low power consumption, or a light-emitting element with a long lifetime can be provided. With one embodiment of the present invention, a novel light-emitting element can be provided. With one embodiment of the present invention, a novel light-emitting device, a novel electronic device, or a novel lighting device can be provided.

BRIEF DESCRIPTION OF THE DRAWINGS

FIGS. 5A1, 5A2, 5B, 5C, 5D1, 5D2, and 5D3 illustrate electronic devices.

DETAILED DESCRIPTION OF THE INVENTION

Figure 1A:
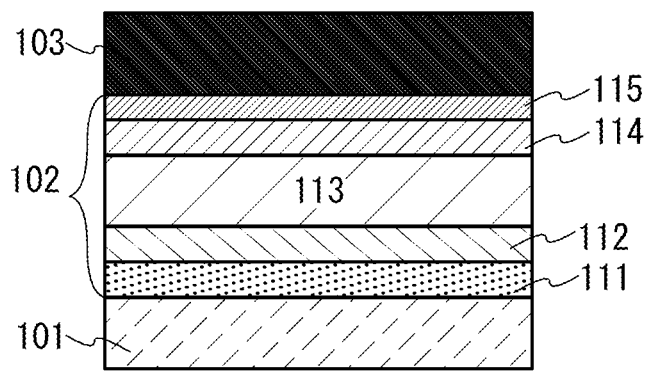
FIGS. 1A and 1B illustrate structures of light-emitting elements.

Hereinafter, embodiments of the present invention will be described with reference to the accompanying drawings. Note that the present invention is not limited to the following description, and modes and details thereof can be variously changed without departing from the spirit and scope of the present invention. Therefore, the present invention should not be construed as being limited to the description in the following embodiments.

Note that the terms "film" and "layer" can be interchanged with each other according to circumstances. For example, in some cases, the term "conductive film" can be used instead of the term "conductive layer," and the term "insulating layer" can be used instead of the term "insulating film".

(Embodiment 1)

In this embodiment, a heterocyclic compound which is one embodiment of the present invention will be described.

In the heterocyclic compound described in this embodiment, a substituted or unsubstituted dibenzo[f,h]quinoxalinyl group is bonded to a substituted or unsubstituted benzobisbenzofuranyl group via a substituted or unsubstituted arylene group.

In general, it is known that when the number of condensed rings that form a molecular structure of an organic compound is increased, the organic compound having more condensed rings is improved in heat resistance with an increase in molecular weight, and long lifetime can be expected when the organic compound is used for a light-emitting element. However, when the number of condensed rings is increased, the molecular structure becomes more planar. Thus, heat resistance and triplet excited level (T1 level) of the organic compound are reduced because a thin film of the organic compound is easily crystallized, for example, and synthesis and purification of the organic compound become difficult by a decrease in solubility of the organic compound. In contrast, the heterocyclic compound of one embodiment of the present invention can provide a compound having a high T1 level by expanding a skeleton of an organic molecule with a condensed ring including a heteroatom. Moreover, the dibenzo[f,h]quinoxalinyl group and the benzobisbenzofuranyl group which are highly planar are bonded to each other via the arylene group, resulting in a bulky compound, which can suppress crystallization and achieve improvement in heat resistance. Thus, the heterocyclic compound described in this embodiment has a structure represented by the following general formula (G1).

[Chemical Formula 5]

DBq$-(Ar^1)_n$-$Ar^2$-A  (G1)

In the general formula (G1), DBq represents a substituted or unsubstituted dibenzo[f,h]quinoxalinyl group, $Ar^1$ represents a substituted or unsubstituted arylene group having 6 to 13 carbon atoms, n represents 0 or 1, $Ar^2$ represents a substituted or unsubstituted arylene group having 6 to 13 carbon atoms, and A represents a substituted or unsubstituted benzobisbenzofuranyl group. When the arylene group represented by $Ar^1$ and $Ar^2$ has substituents, the substituents may be bonded to each other to form a ring.

As another structure, in the heterocyclic compound represented by the general formula (G1), DBq represents a substituted or unsubstituted dibenzo[f,h]quinoxalinyl group, $Ar^1$ represents a substituted or unsubstituted arylene group having 6 to 13 carbon atoms, n represents 0 or 1, $Ar^2$ represents a substituted or unsubstituted arylene group having 6 to 13 carbon atoms, and A represents a substituted or unsubstituted benzobisbenzofuranyl group. Among carbon atoms that do not form a furan ring in the benzobisbenzofuranyl group, any one of carbon atoms adjacent to a carbon atom of the furan ring, which is bonded to oxygen, is bonded to $Ar^2$. When the arylene group represented by $Ar^1$ and $Ar^2$ has substituents, the substituents may be bonded to each other to form a ring.

Examples of the arylene group having 6 to 13 carbon atoms in the general formula (G1), which is represented by $Ar^1$ or $Ar^2$, are a substituted or unsubstituted phenylene group, a substituted or unsubstituted naphthalenediyl group, a substituted or unsubstituted biphenyldiyl group, a substituted or unsubstituted fluorene-diyl group, and the like, more specifically, an arylene group represented by the following structural formulae (α1) to (α15), for example.

[Chemical Formulae 6]
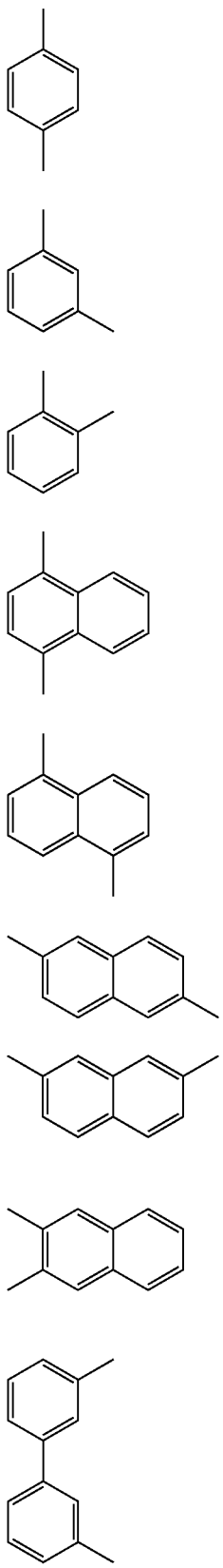
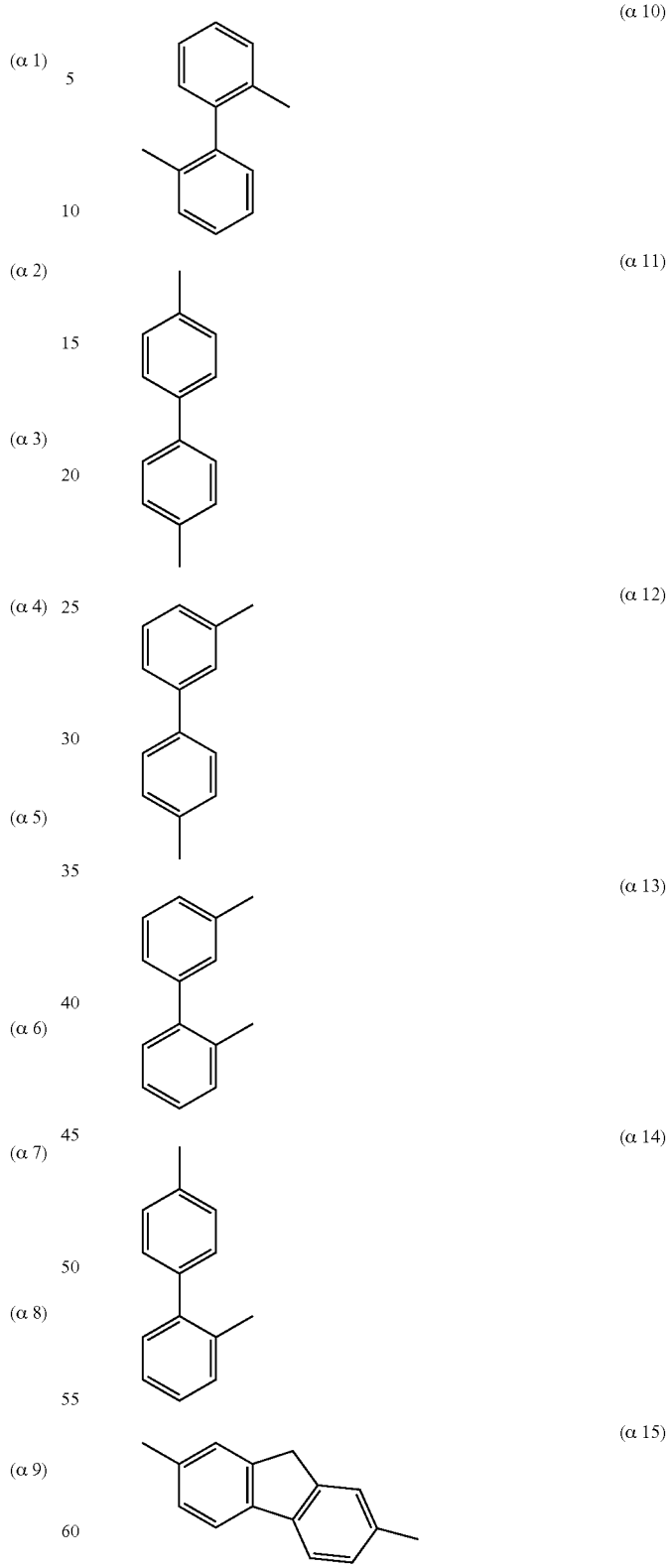
In the general formula (G1), in the substituted or unsubstituted benzobisbenzofuranyl group represented by A, the unsubstituted benzobisbenzofuranyl group is represented by any one of the following general formulae (A1) to (A7).

[Chemical Formulae 7]

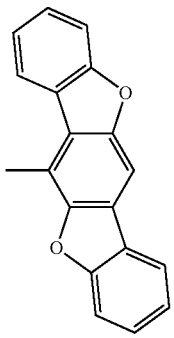
(A1)

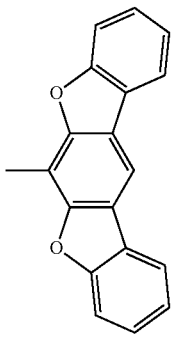
(A2)

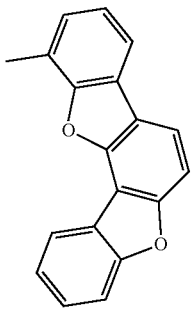
(A3)

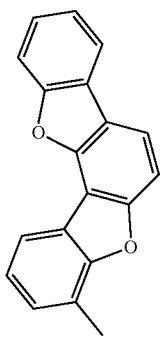
(A4)

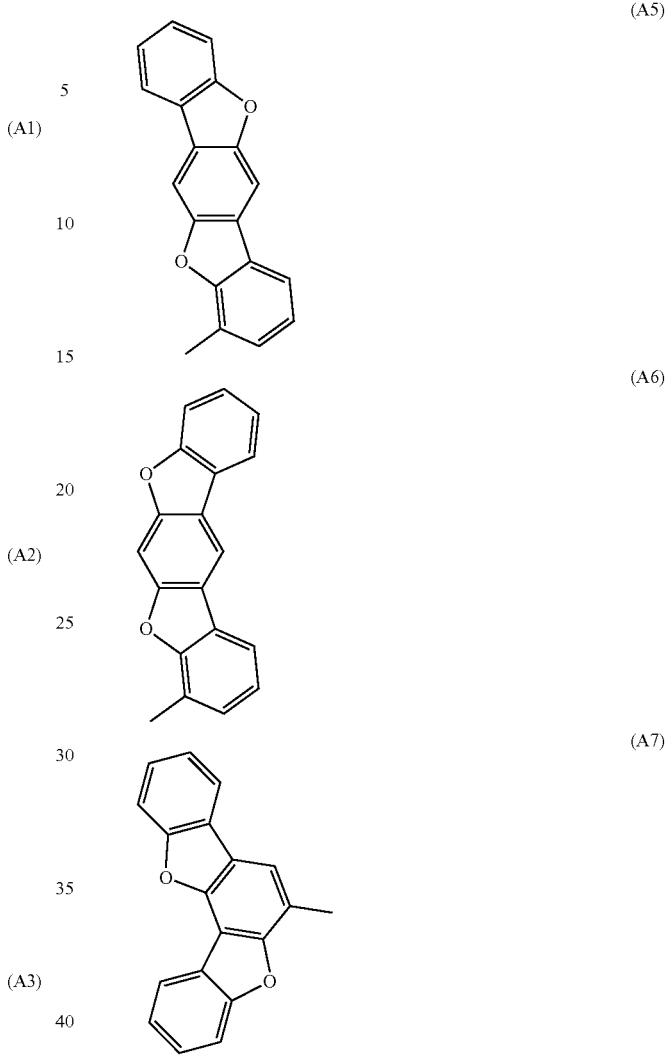

In the case where the benzobisbenzofuranyl group represented by A has a substituent in the general formula (G1), a benzene ring may include a substituent in the general formulae (A1) to (A7). Examples of the substituent are a substituted or unsubstituted alkyl group having 1 to 6 carbon atoms, a substituted or unsubstituted cycloalkyl group having 5 to 7 carbon atoms, and a substituted or unsubstituted aryl group having 6 to 13 carbon atoms.

In the case of having the alkyl group having 1 to 6 carbon atoms as the substituent in the general formulae (A1) to (A7), specific examples are a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a sec-hexyl group, a tert-hexyl group, a neohexyl group, a 3-methylpentyl group, a 2-methylpentyl group, a 2-ethylbutyl group, a 1,2-dimethylbutyl group, and a 2,3-dimethylbutyl group.

In the case of having the cycloalkyl group having 5 to 7 carbon atoms as the substituent in the general formula (A1) to (A7), specific examples are a cyclopentyl group, a cyclohexyl group, and a cycloheptyl group.

Furthermore, in the case of having the aryl group having 6 to 13 carbon atoms as the substituent in the general formulae (A1) to (A7), specific examples are a phenyl group, a biphenyl group, a naphthyl group, a fluorenyl group, and an indenyl group.

In the term "substitute" in the general formula (G1), it is preferable to include a substituent such as the alkyl group having 1 to 6 carbon atoms, for example, a methyl group, an ethyl group, an n-propyl group, an iso-propyl group, a sec-butyl group, a tert-butyl group, an n-pentyl group, or an n-hexyl group, or a substituent such as an aryl group having 6 to 12 carbon atoms, for example, a phenyl group, an o-tolyl group, an m-tolyl group, a p-tolyl group, a 1-napthly group, a 2-naphthyl group, a 2-biphenyl group, a 3-biphenyl group, or a 4-biphenyl group. These substituents may be bonded to each other to form a ring. For example, in the case where the fluorene-diyl group which is an arylene group is a 9,9-dipheyl-9H-fluorene-2,7-diyl group having two phenyl groups at the 9-position as a substituent, the phenyl groups may be bonded to each other to become a spiro-9,9'-bifluorene-2,7-diyl group.

Another structure of the heterocyclic compound of one embodiment of the present invention is represented by the following general formula (G2).

[Chemical Formula 8]

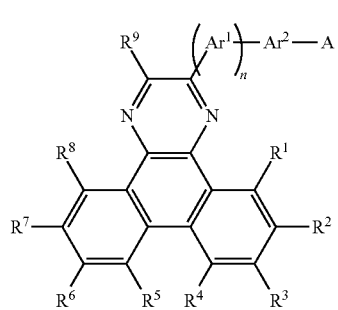

(G2)

In the general formula (G2), A represents a substituted or unsubstituted benzobisbenzofuranyl group, $R^1$ to $R^9$ independently represent any of hydrogen, an alkyl group having carbon atoms of 1 to 6, and a substituted or unsubstituted aryl group having 6 to 13 carbon atoms, $Ar^1$ represents a substituted or unsubstituted arylene group having 6 to 13 carbon atoms, n represents 0 or 1, and $Ar^2$ represents a substituted or unsubstituted arylene group having 6 to 13 carbon atoms. When the arylene group represented by $Ar^1$ and $Ar^2$ has substituents, the substituents may be bonded to each other to form a ring.

A specific example of the arylene group having 6 to 13 carbon atoms in the general formula (G2), which is represented by $A^1$ or $Ar^2$, is the arylene group represented by the following structural formulae (α1) to (α15), for example.

[Chemical Formulae 9]

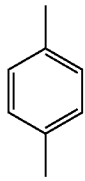

(α1)

-continued

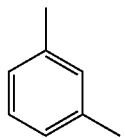

(α2)

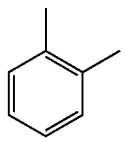

(α3)

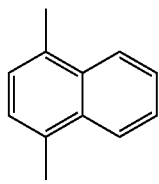

(α4)

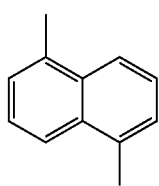

(α5)

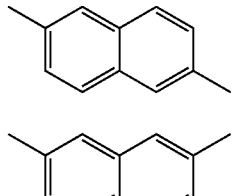

(α6)

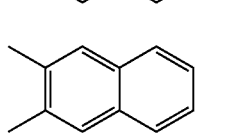

(α7)

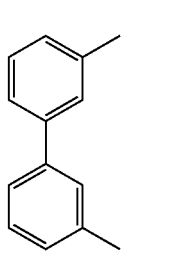

(α8)

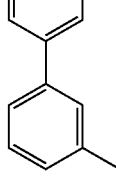

(α9)

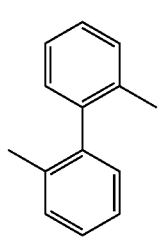

(α10)

(α11)
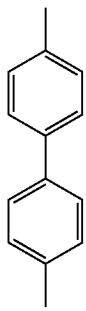
(α12)
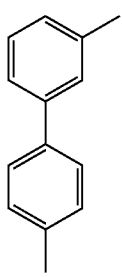
(α13)
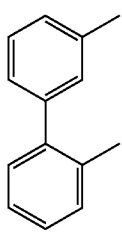
(α14)
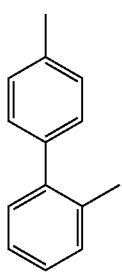
(α15)
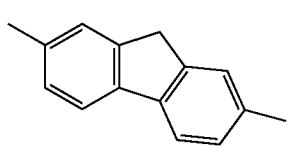
[Chemical Formulae 10]
(A1)
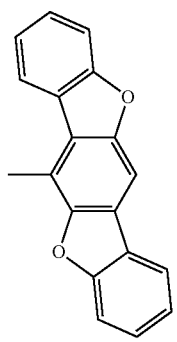
(A2)
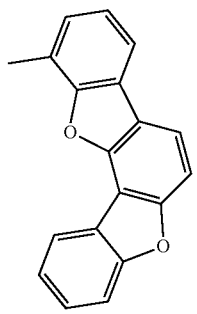
(A3)
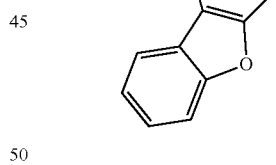
(A4)
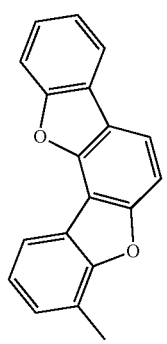
In the general formula (G2), in the substituted or unsubstituted benzobisbenzofuranyl group represented by A, the unsubstituted benzobisbenzofuranyl group is represented by any one of the following general formulae (A1) to (A7).

(A5)

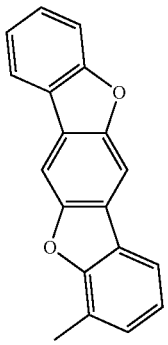

(A6)

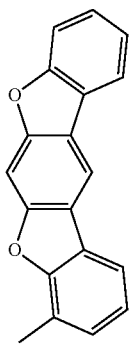

(A7)

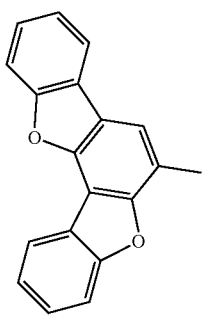

In the case where the benzobisbenzofuranyl group represented by A has a substituent in the general formula (G2), a benzene ring may include a substituent in the general formulae (A1) to (A7). Examples of the substituent are a substituted or unsubstituted alkyl group having 1 to 6 carbon atoms, a substituted or unsubstituted cycloalkyl group having 5 to 7 carbon atoms, and a substituted or unsubstituted aryl group having 6 to 13 carbon atoms.

In the case of having the alkyl group having 1 to 6 carbon atoms as the substituent in the general formulae (A1) to (A7), specific examples are a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a sec-hexyl group, a tert-hexyl group, a neohexyl group, a 3-methylpentyl group, a 2-methylpentyl group, a 2-ethylbutyl group, a 1,2-dimethylbutyl group, and a 2,3-dimethylbutyl group.

In the case of having the cycloalkyl group having 5 to 7 carbon atoms as the substituent in the general formula (A1) to (A7), specific examples are a cyclopentyl group, a cyclohexyl group, and a cycloheptyl group.

Furthermore, in the case of having the aryl group having 6 to 13 carbon atoms as the substituent in the general formulae (A1) to (A7), specific examples are a phenyl group, a biphenyl group, a naphthyl group, a fluorenyl group, and an indenyl group.

Specific examples of the alkyl group having carbon atoms of 1 to 6 in $R^1$ to $R^9$ of the general formula (G2) are a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a sec-hexyl group, a tert-hexyl group, a neohexyl group, a 3-methylpentyl group, a 2-methylpentyl group, a 2-ethylbutyl group, a 1,2-dimethylbutyl group, and a 2,3-dimethylbutyl group.

Specific examples of the aryl group having 6 to 13 carbon atoms in $R^1$ to $R^9$ of the general formula (G2) are a phenyl group, a biphenyl group, a tolyl group, a naphthyl group, a xylyl group, a fluorenyl group, and an indenyl group.

In the term "substitute" in the general formula (G2), it is preferable to include a substituent such as the alkyl group having 1 to 6 carbon atoms, for example, a methyl group, an ethyl group, an n-propyl group, an iso-propyl group, a sec-butyl group, a tert-butyl group, an n-pentyl group, or an n-hexyl group, or a substituent such as an aryl group having 6 to 12 carbon atoms, for example, a phenyl group, an o-tolyl group, an m-tolyl group, a p-tolyl group, a 1-napthly group, a 2-naphthyl group, a 2-biphenyl group, a 3-biphenyl group, or a 4-biphenyl group. These substituents may be bonded to each other to form a ring. For example, in the case where the fluorene-diyl group which is an arylene group is a 9,9-dipheyl-9H-fluorene-2,7-diyl group having two phenyl groups at the 9-position as a substituent, the phenyl groups may be bonded to each other to become a spiro-9,9'-bifluorene-2,7-diyl group.

Next, specific structural formulae of the above-described heterocyclic compounds, each of which is one embodiment of the present invention, are shown below. Note that the present invention is not limited thereto.

[Chemical Formulae 11]

(101)

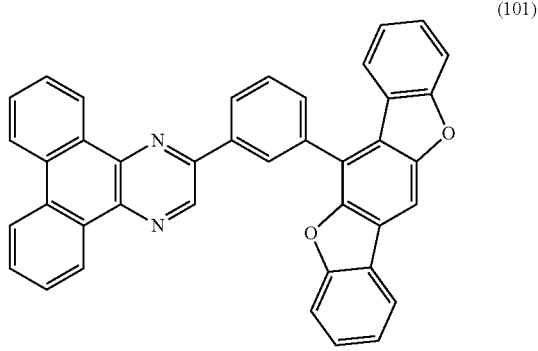

(102)

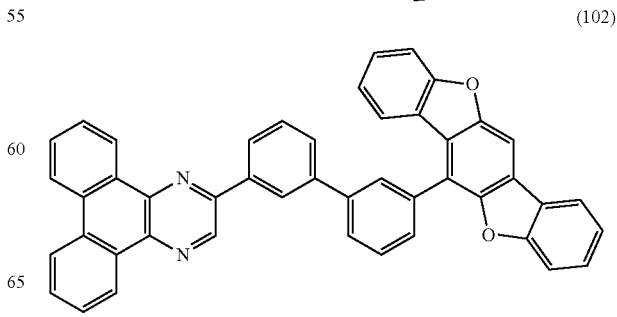

(103)
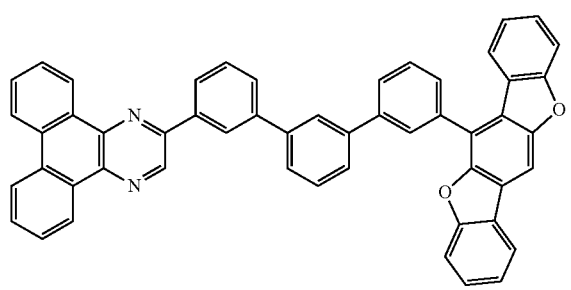
(104)
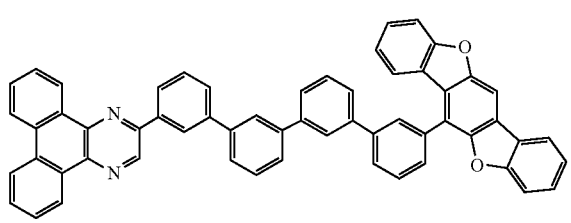
(105)
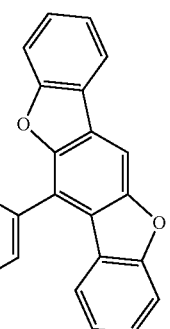
(106)
(107)
(108)
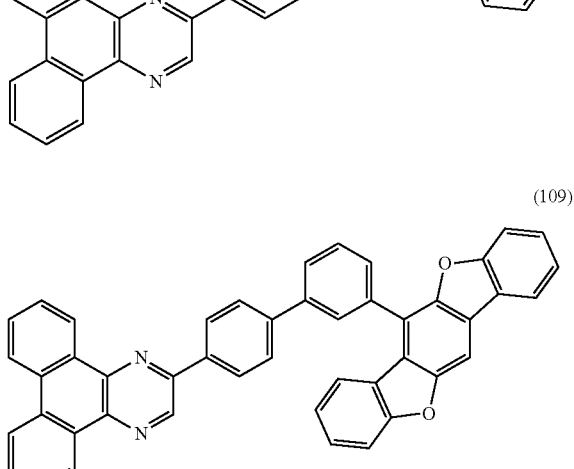
(109)
(110)
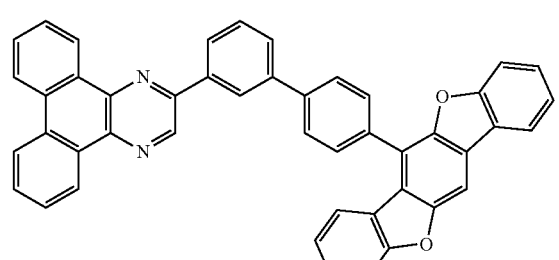
(111)
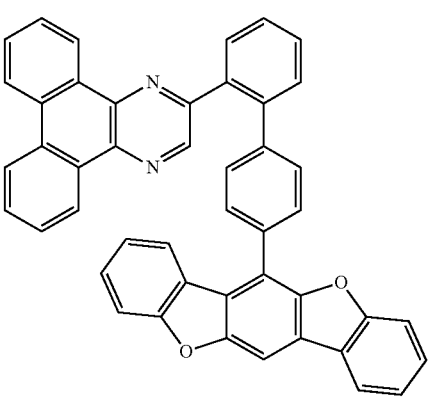

[Chemical Formulae 12]
(112)
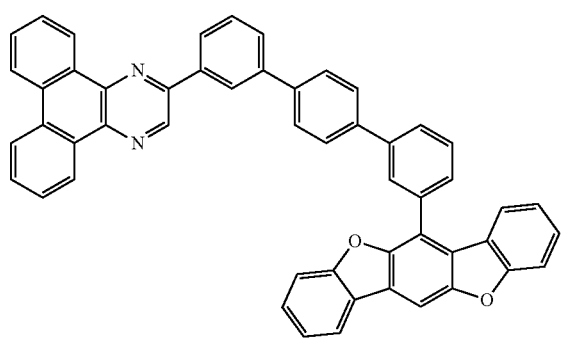
(113)
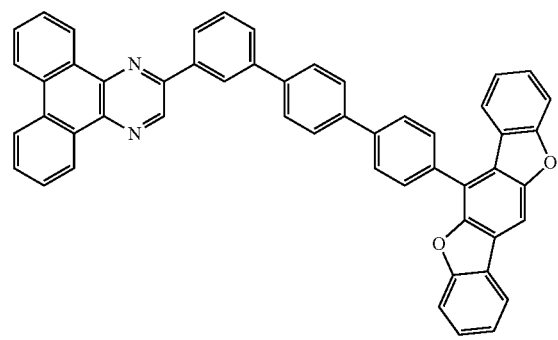
(114)
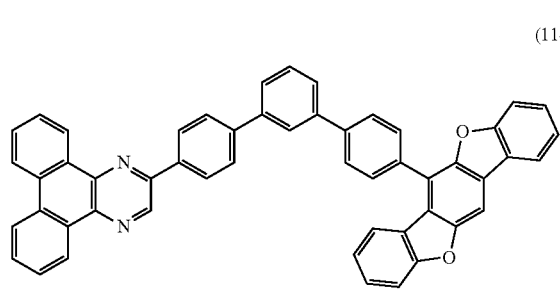
(115)
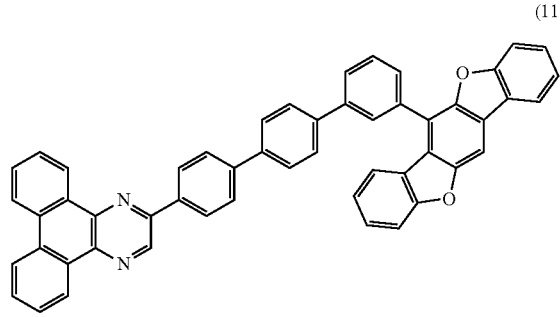
(116)
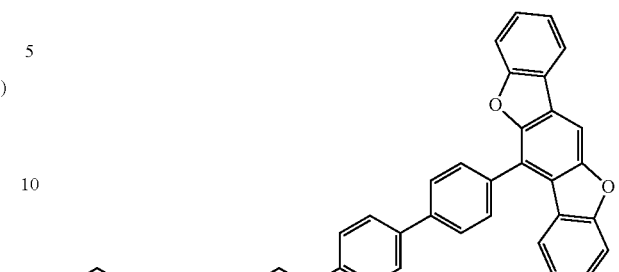
(117)
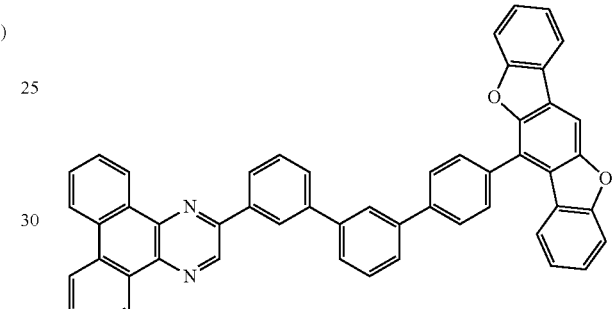
(118)
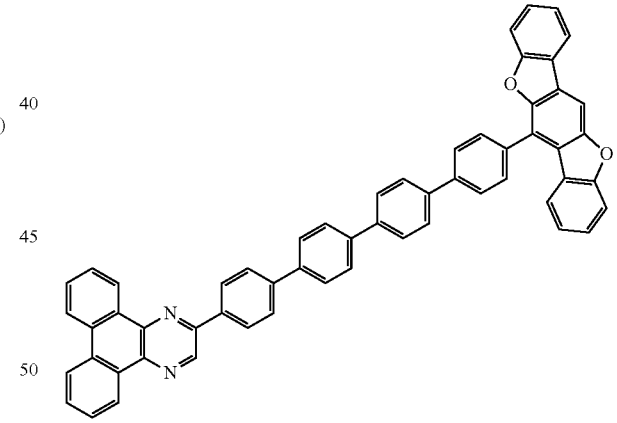
(119)
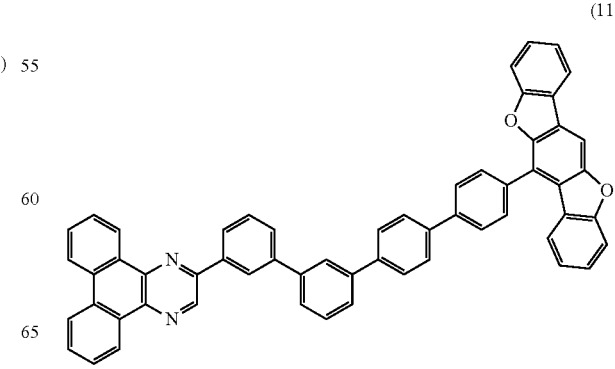

[Chemical Formulae 13]
(120)
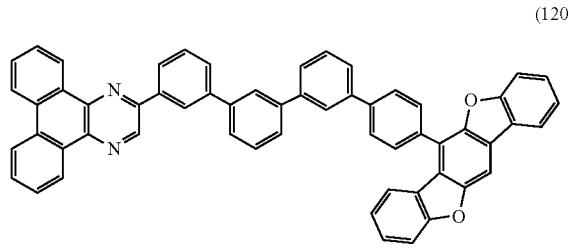
(121)
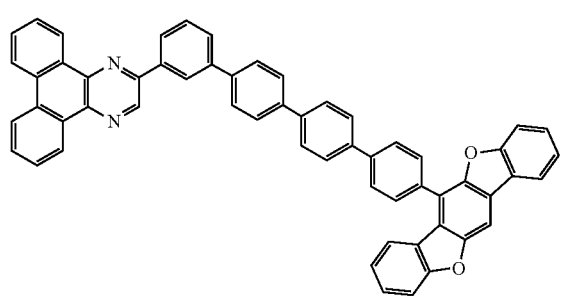
(122)
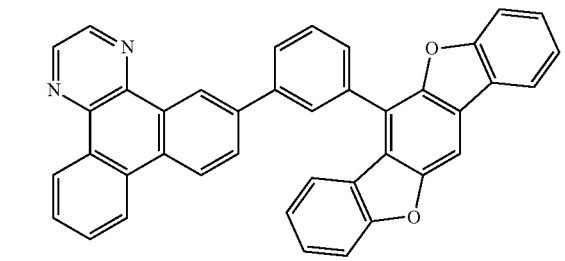
(123)
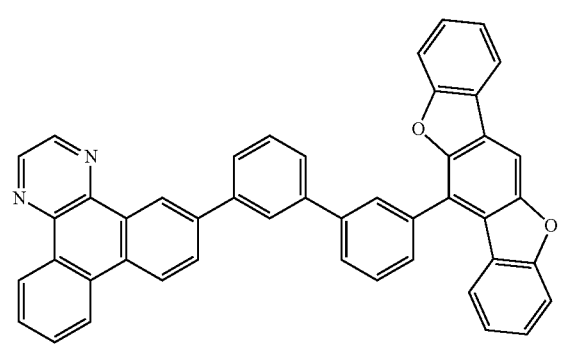
(124)
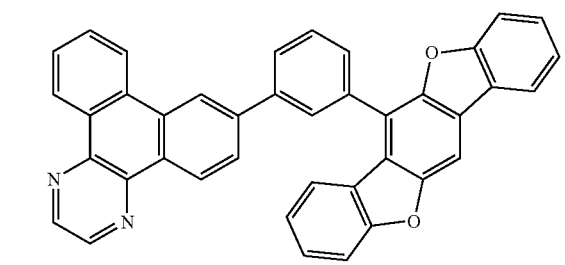
(125)
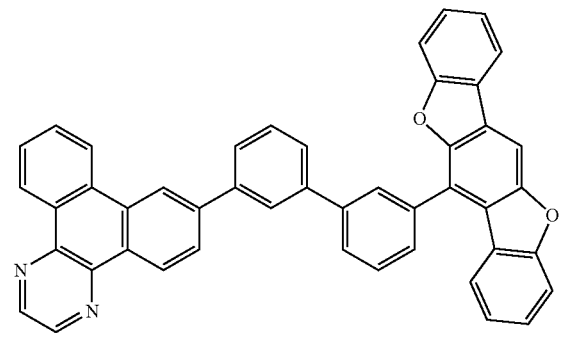
(126)
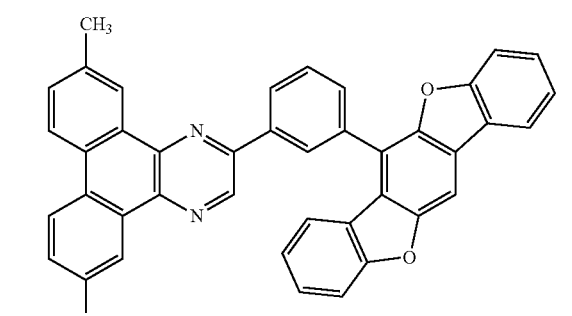
(127)
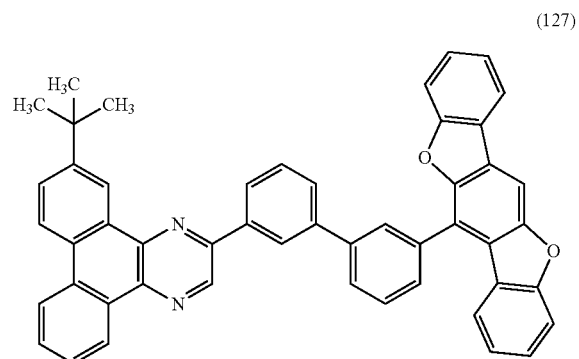
(128)
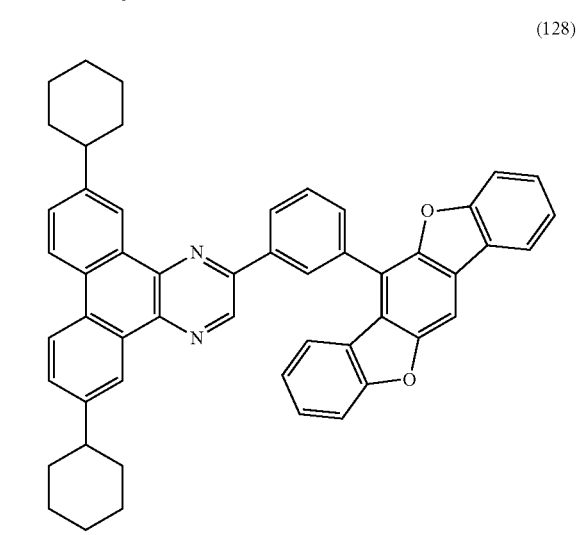

(129)
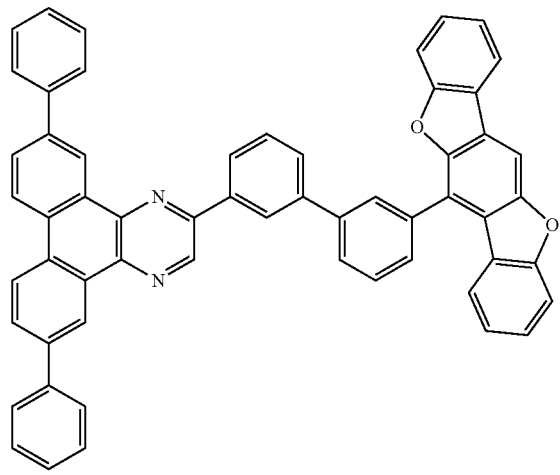
[Chemical Formulae 14]
(130)
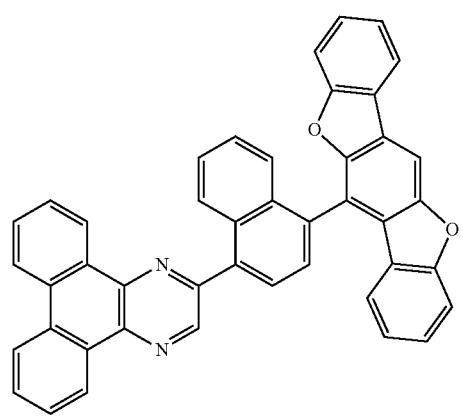
(131)
(132)
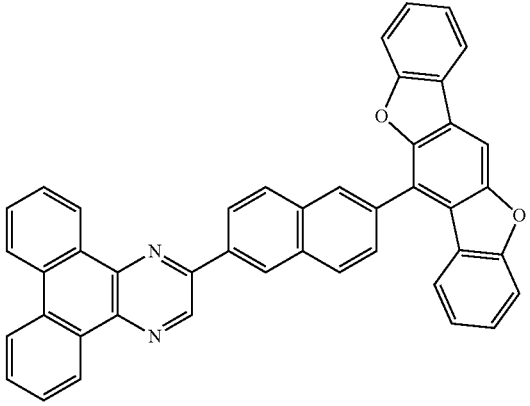
(133)
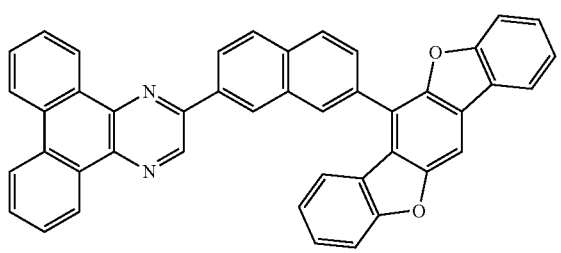
(134)
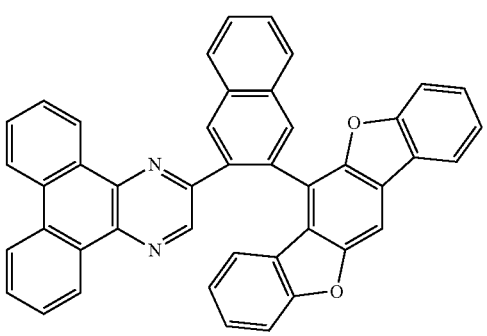
(135)
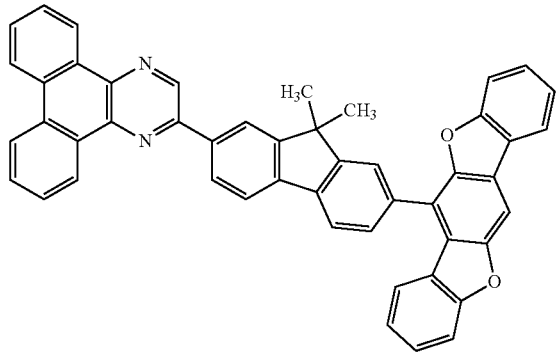

(136)
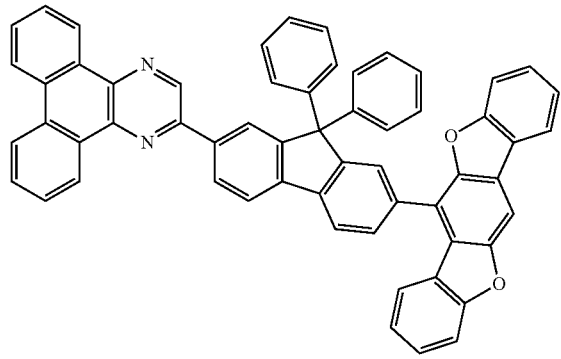
(137)
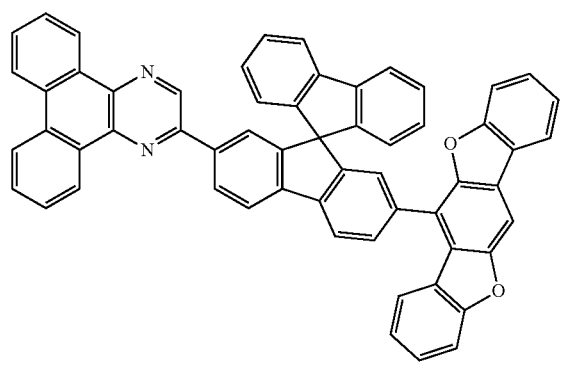
(138)
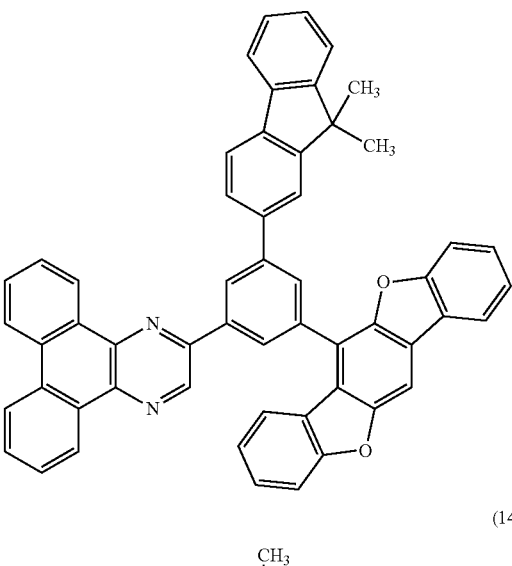
(139)
(140)
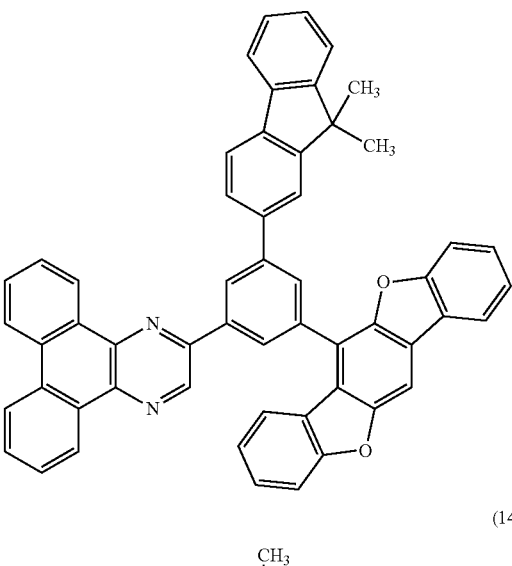
(141)
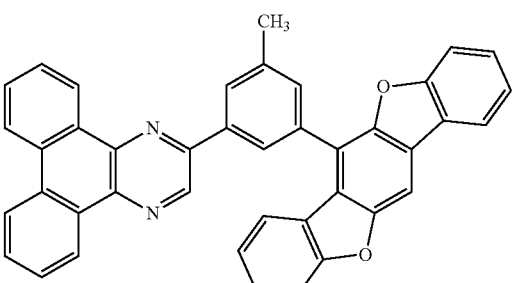
[Chemical Formulae 15]
(142)
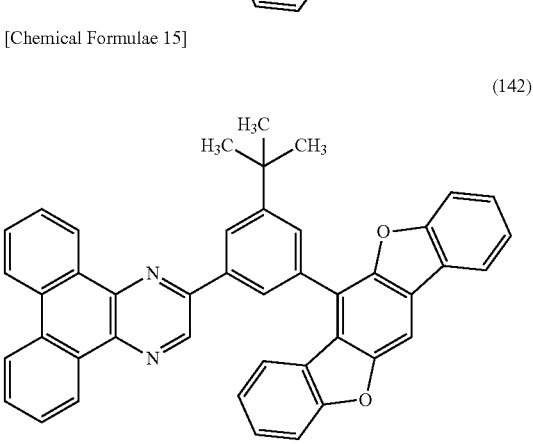
(143)
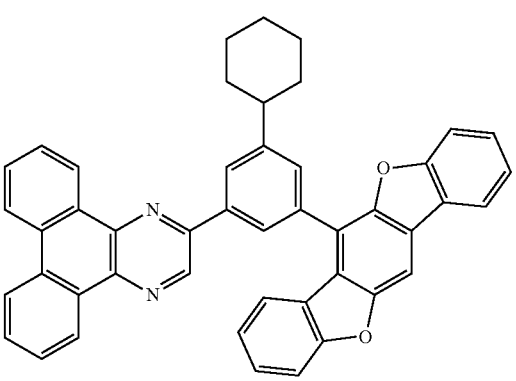

(144)
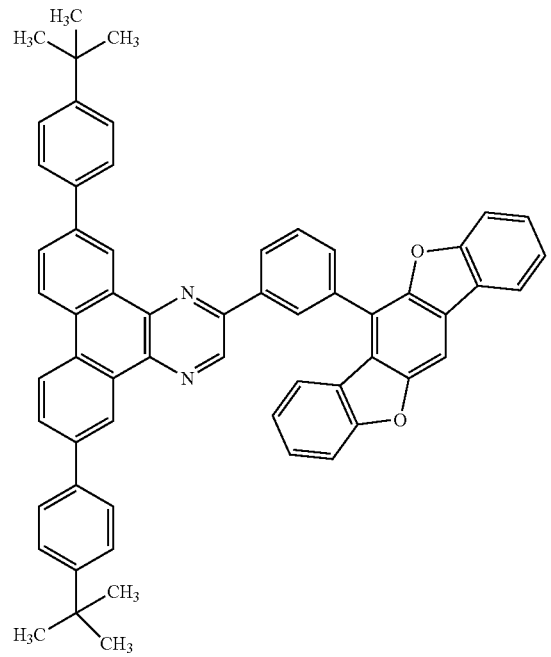
(145)
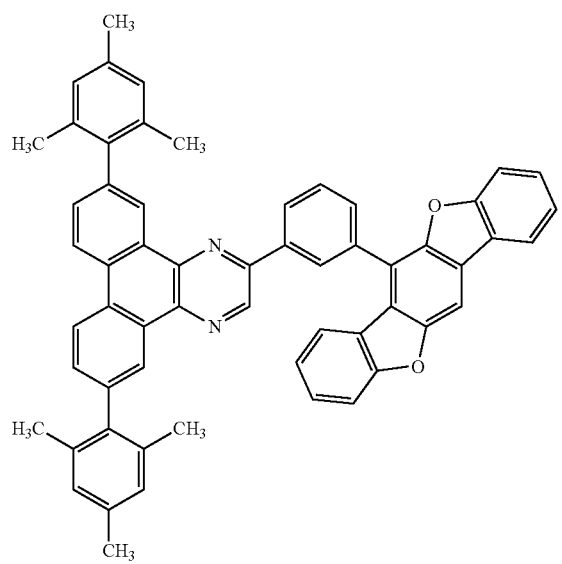
(146)
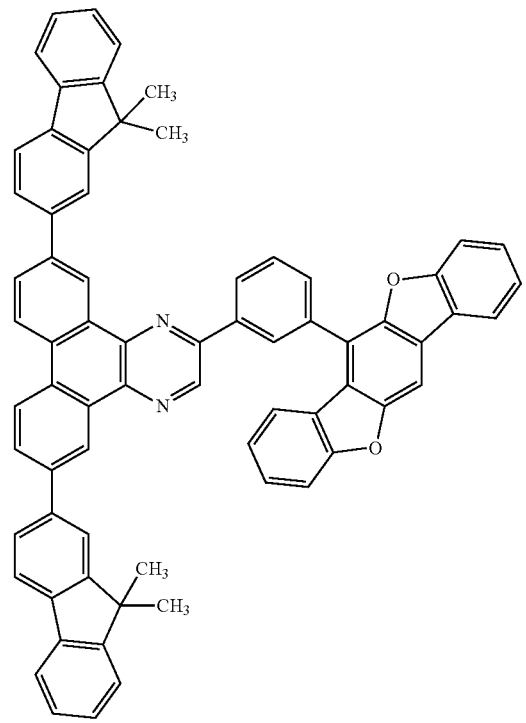
(147)
(148)
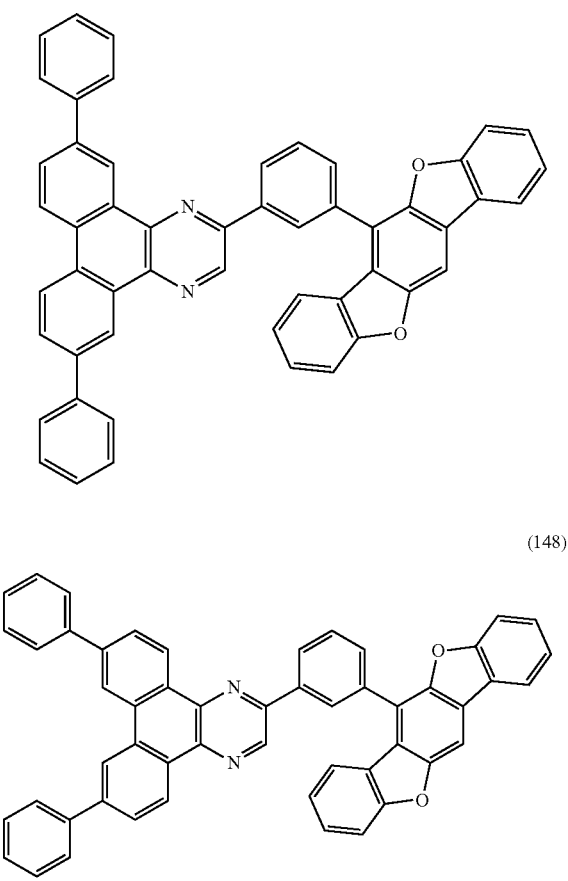

(149)
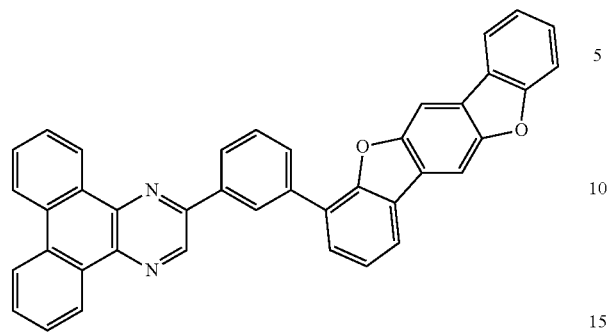
(153)
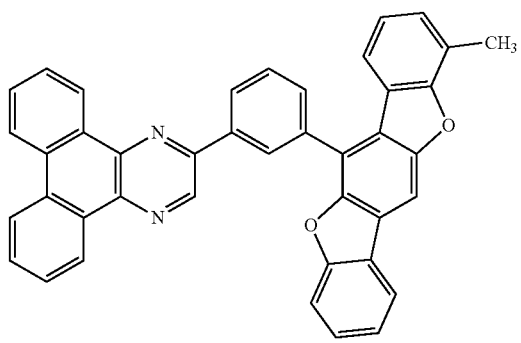
(150)
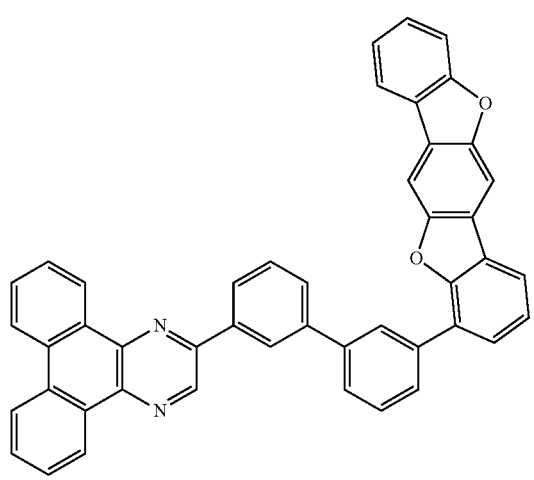
(154)
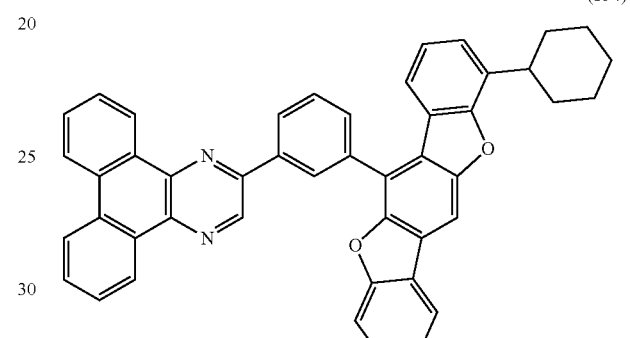
(151)
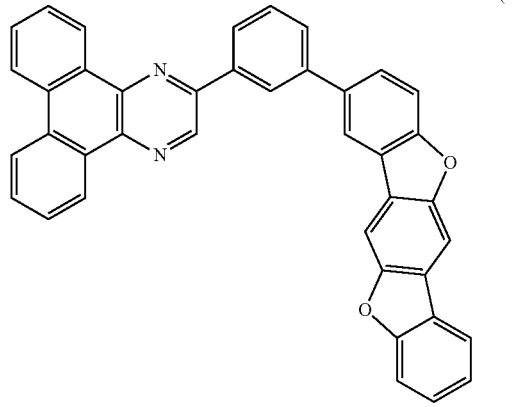
(155)
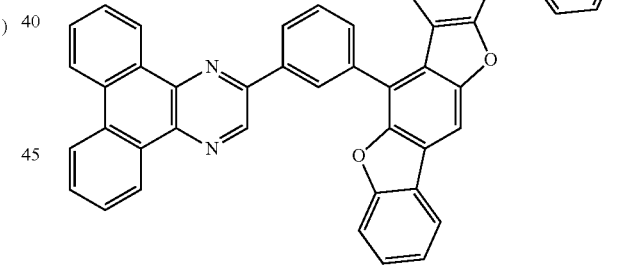
[Chemical Formulae 16]
(152)
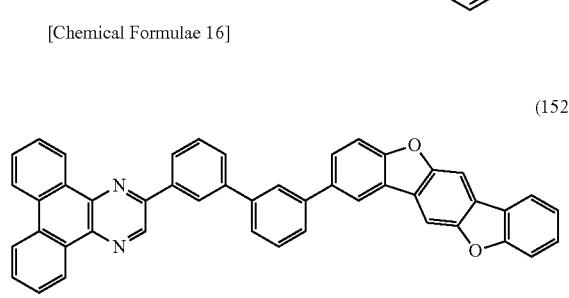
(156)
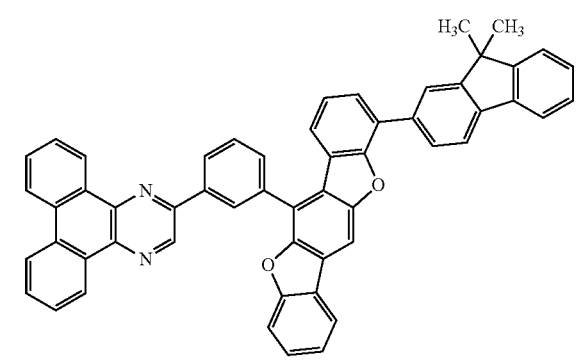

(157)
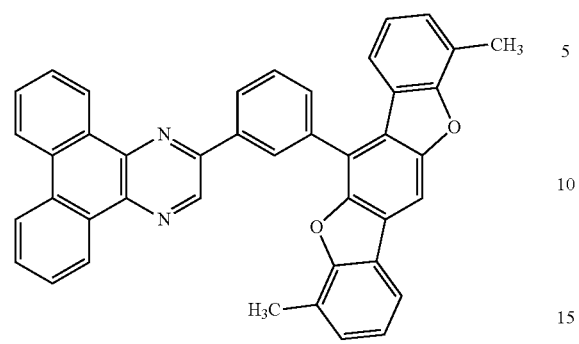
(158)
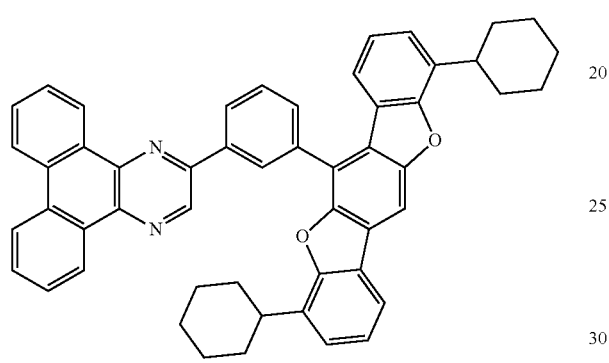
(159)
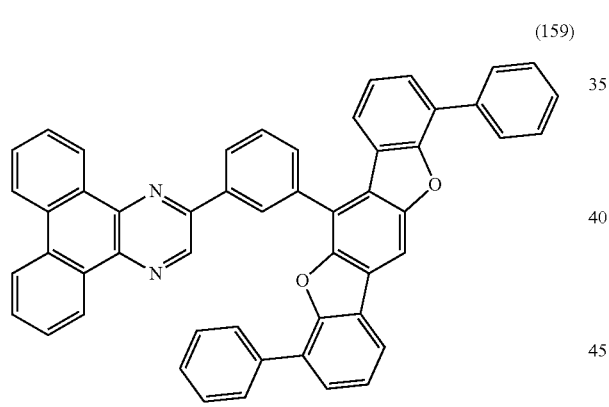
(160)
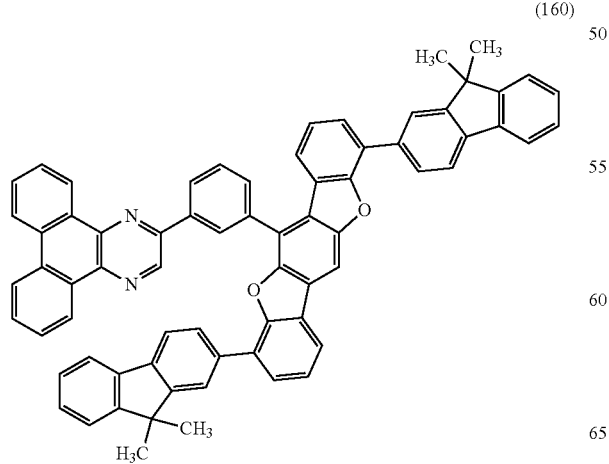
(161)
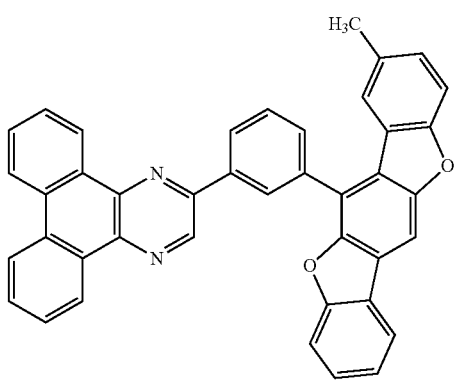
(162)
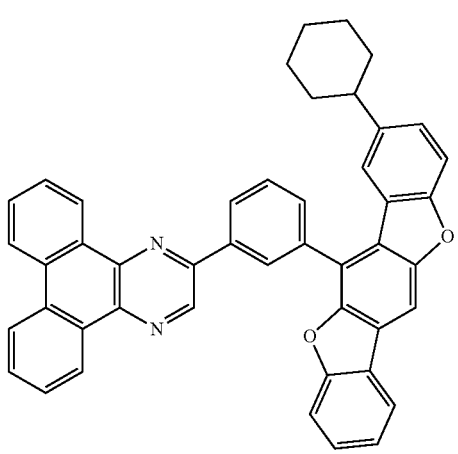
(163)
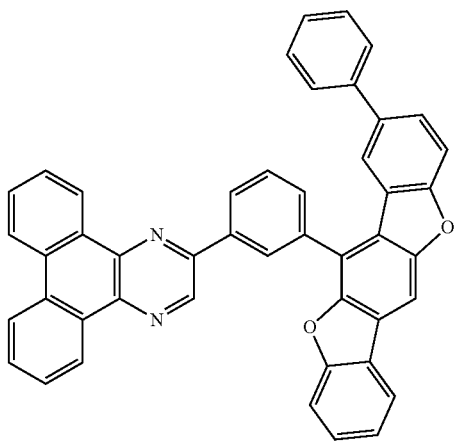

(164)
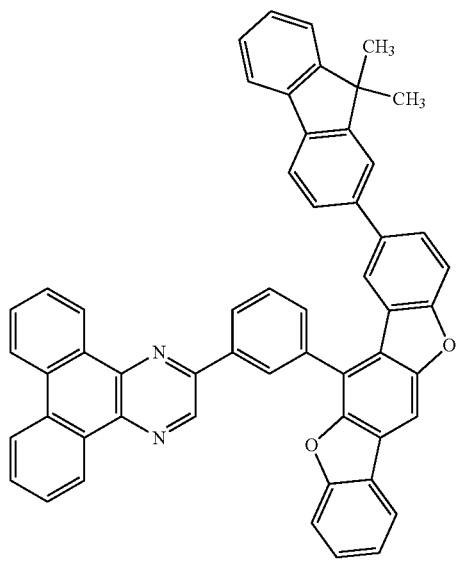
[Chemical Formulae 17]
(165)
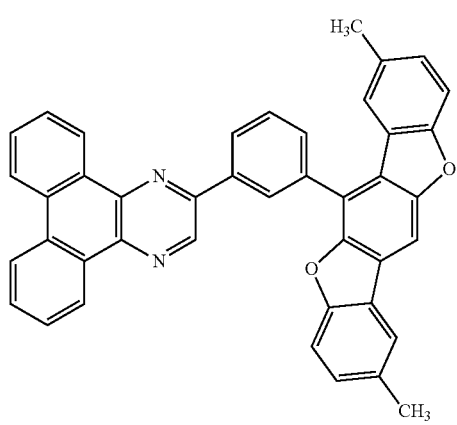
(166)
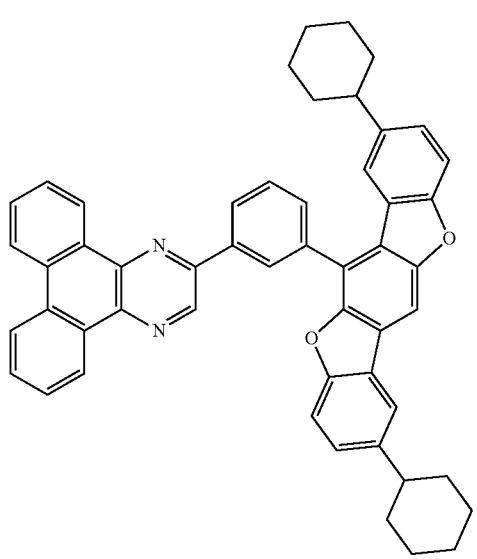
(167)
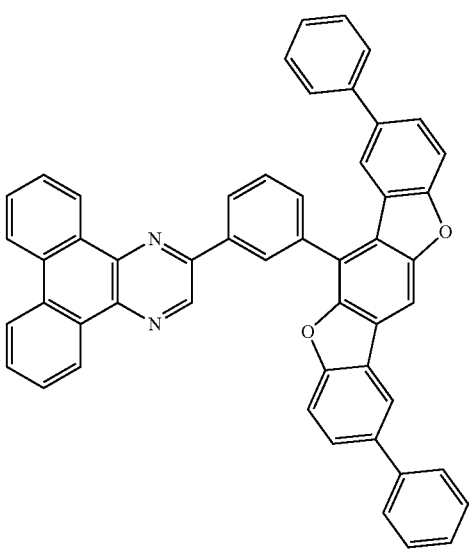
(168)
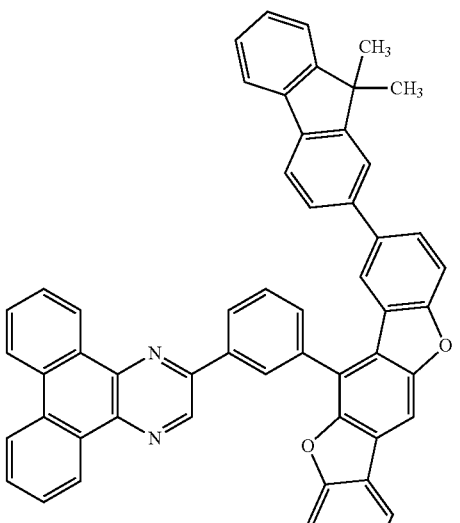
(169)
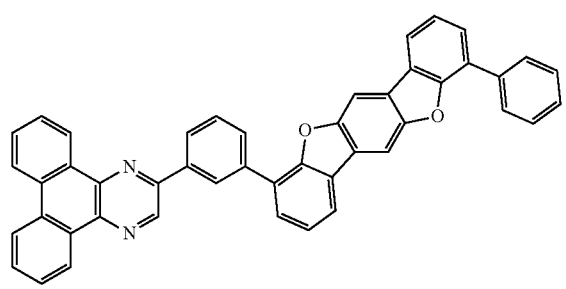

(170)
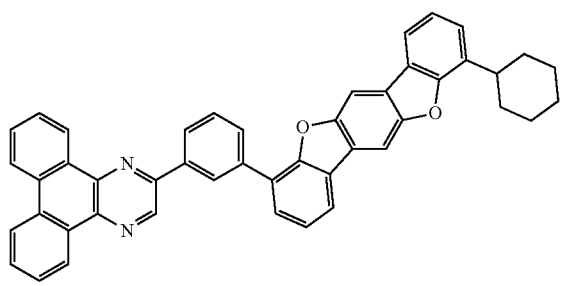
(171)
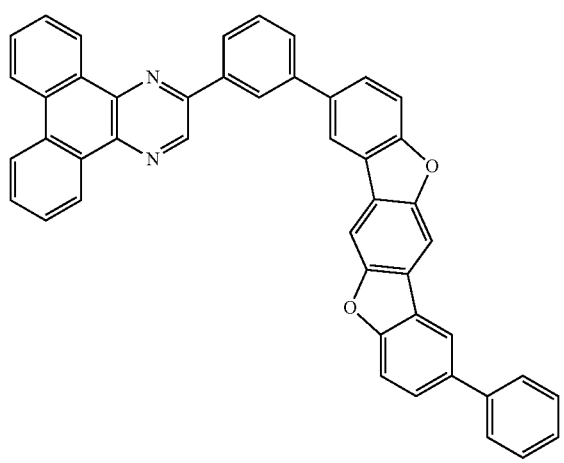
(172)
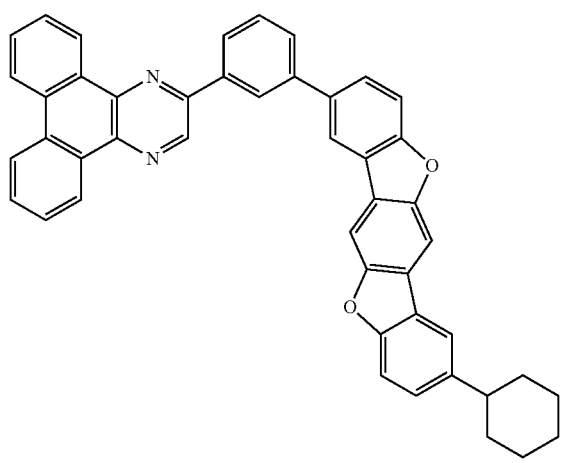
(173)
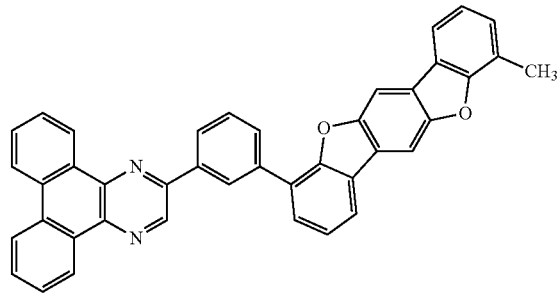
(174)
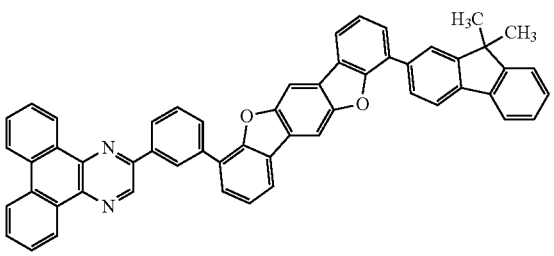
(175)
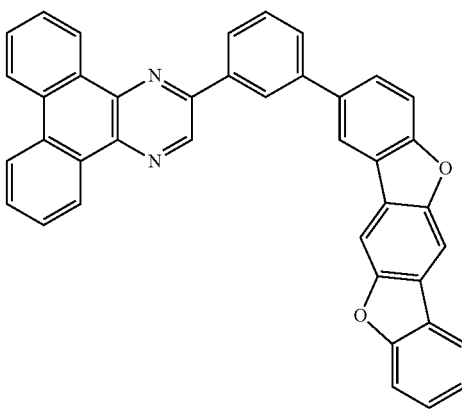
[Chemical Formulae 18]
(176)
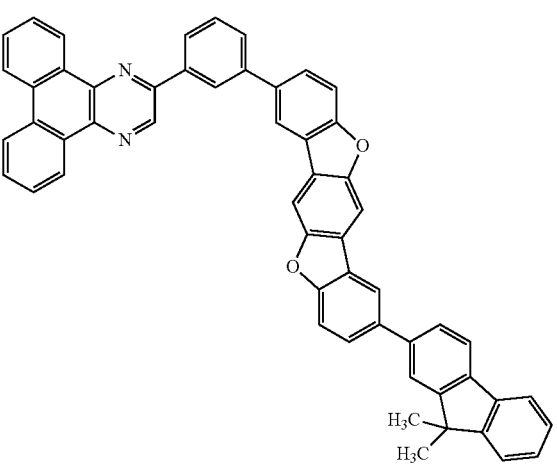
(177)
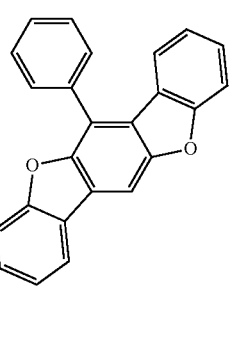

(178)
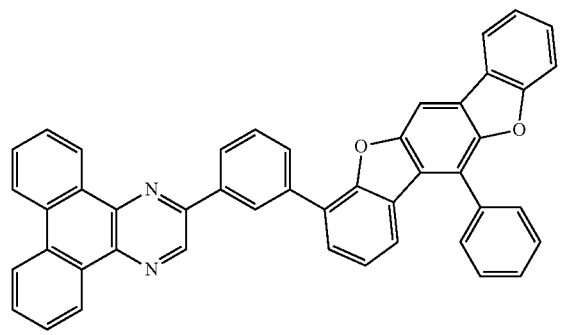
(179)
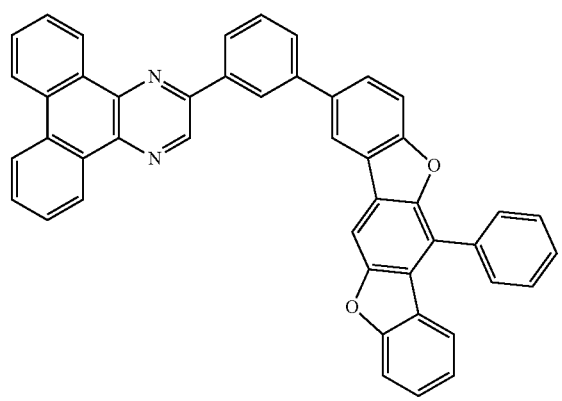
(180)
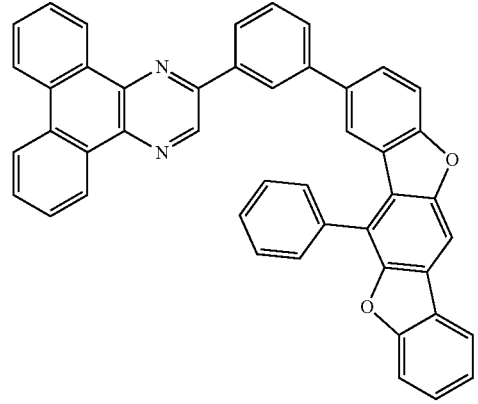
(181)
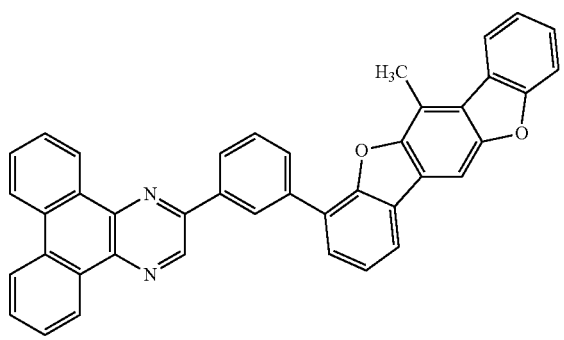
(182)
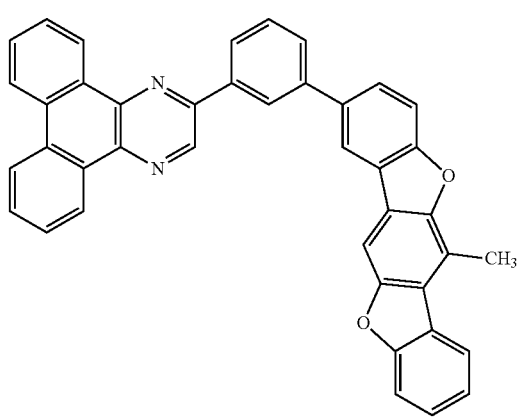
(183)
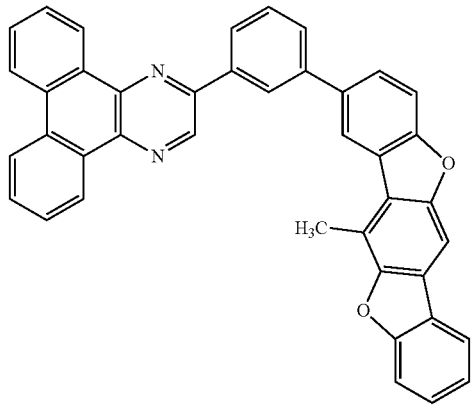
(184)
[Chemical Formulae 19]
(201)
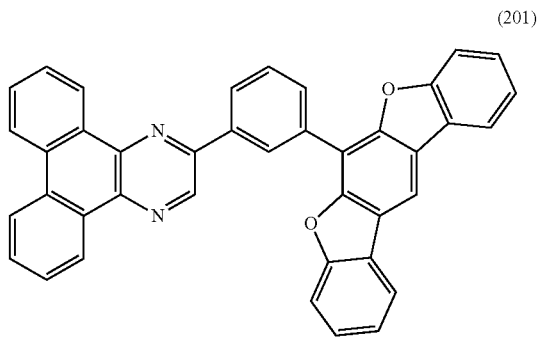

(202)
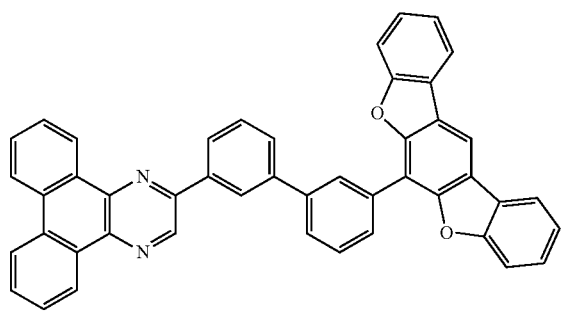
(203)
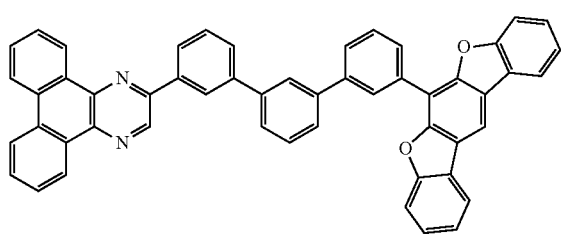
(204)
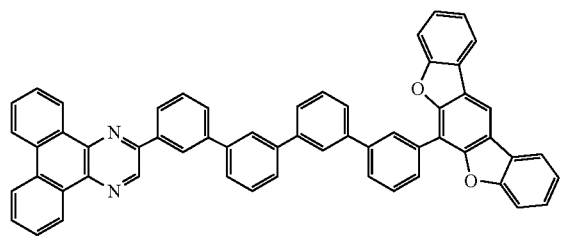
(205)
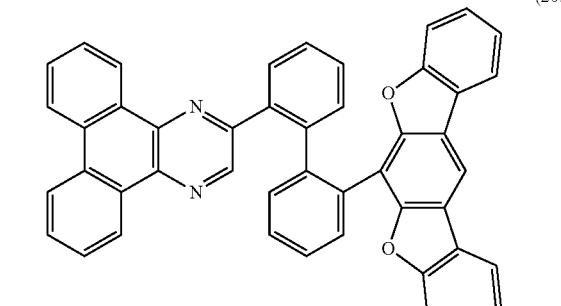
(206)
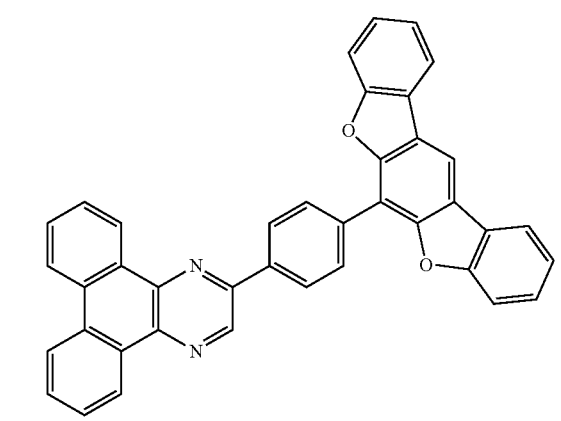
(207)
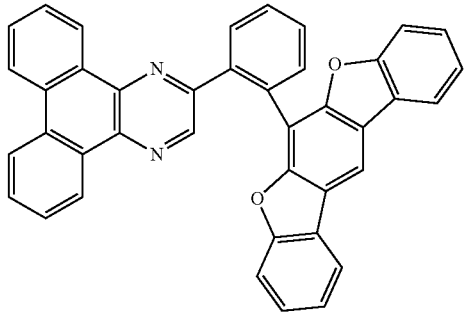
(208)
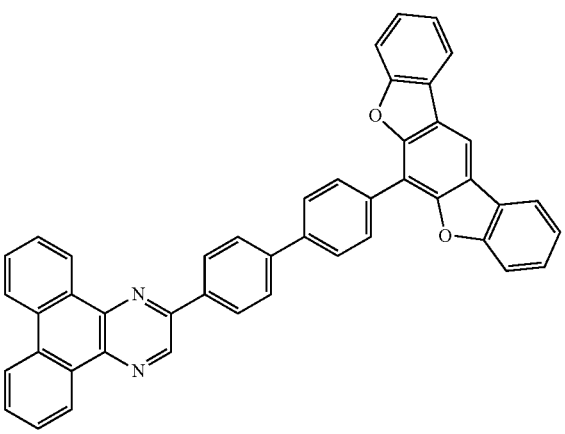
(209)
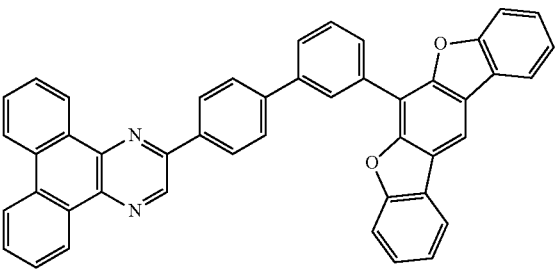
(210)

(211)
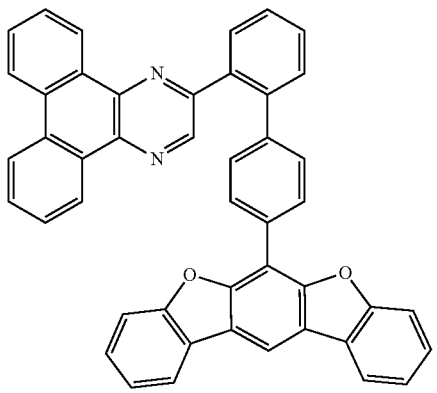
(212)
[Chemical Formulae 20]
(213)
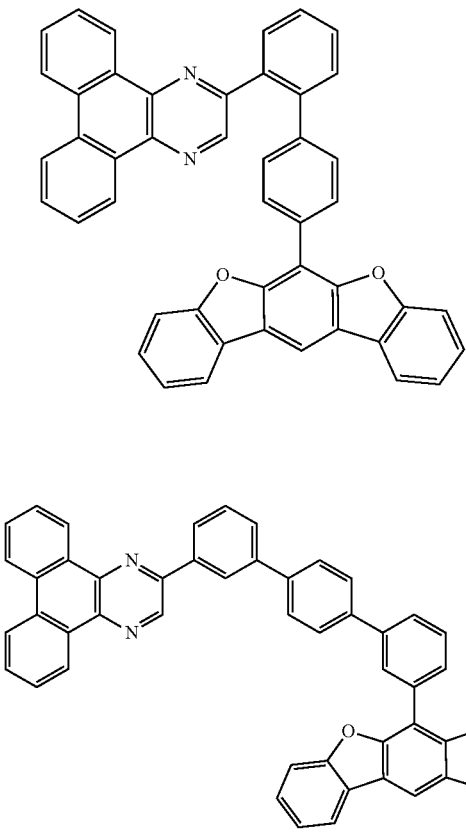
(214)
(215)
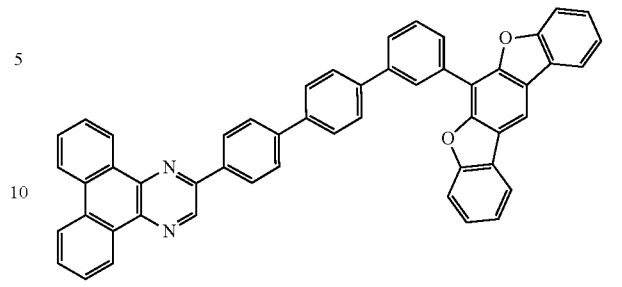
(216)
(217)
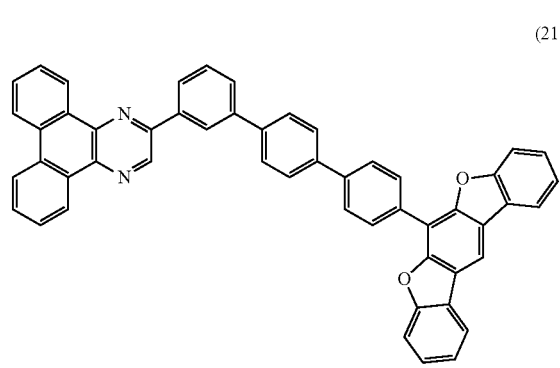
(218)
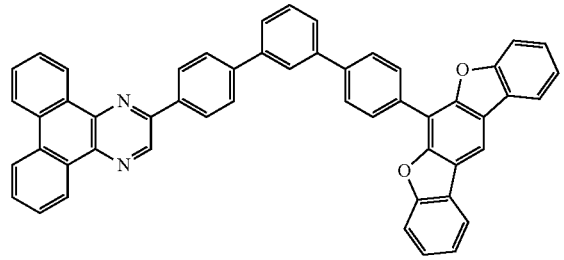

(219)
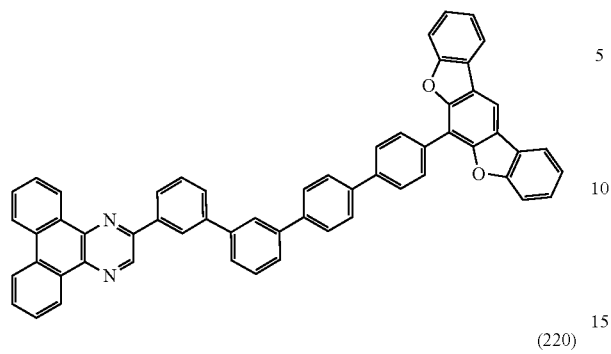
(220)
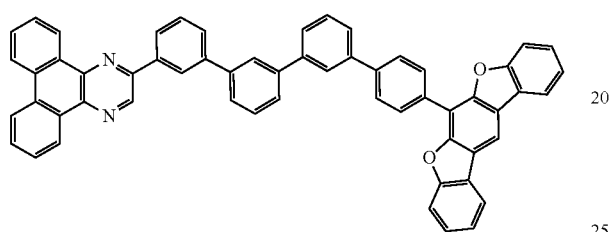
[Chemical Formulae 21]
(221)
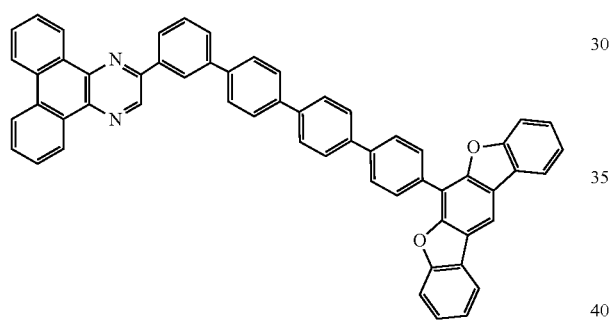
(222)
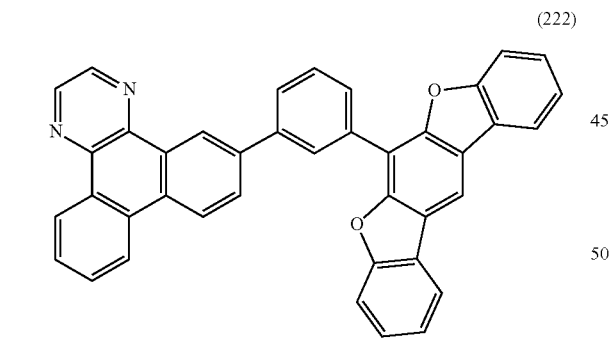
(223)
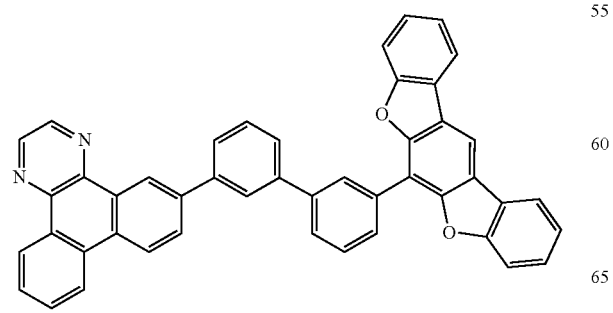
(224)
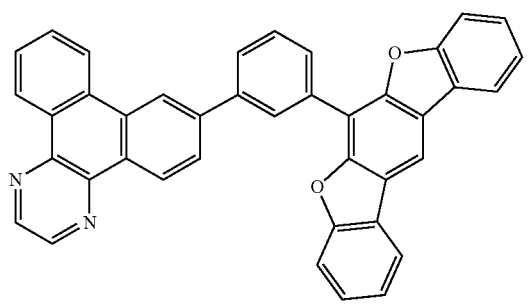
(225)
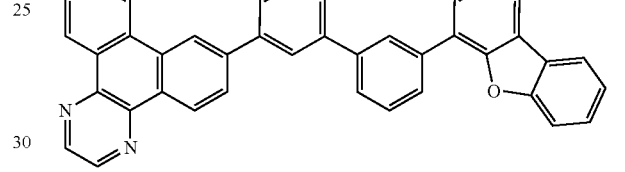
(226)
(227)
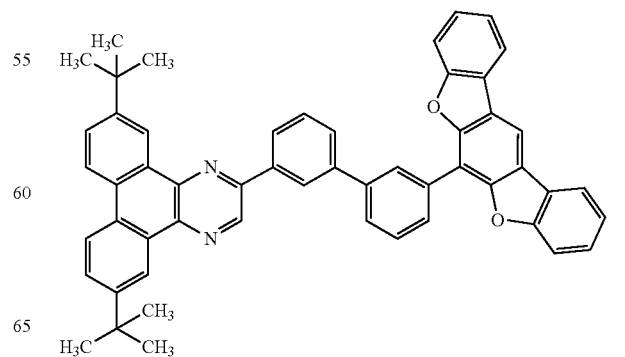

[Chemical Formulae 22]
(228)
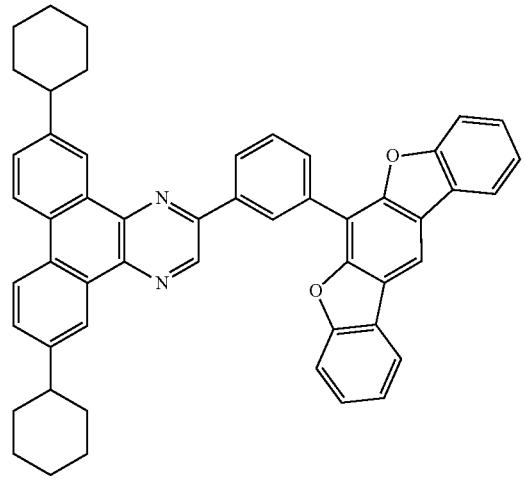
(229)
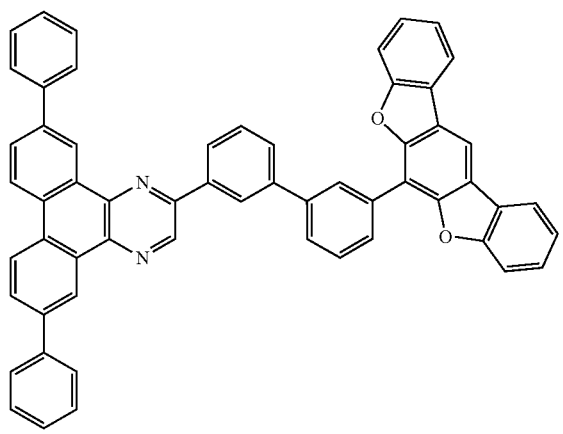
(230)
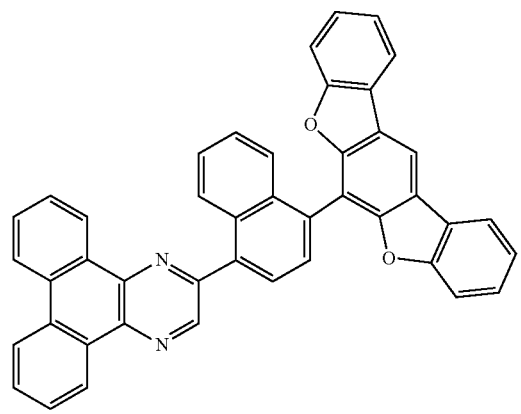
(231)
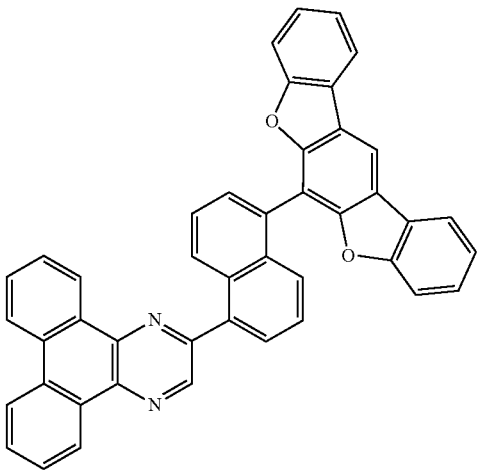
(232)
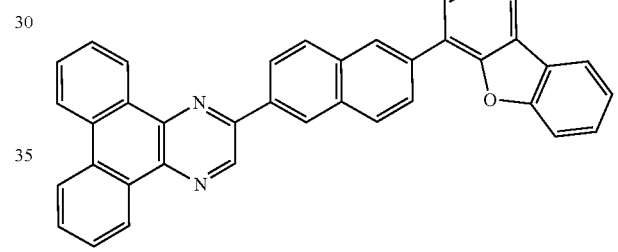
(233)
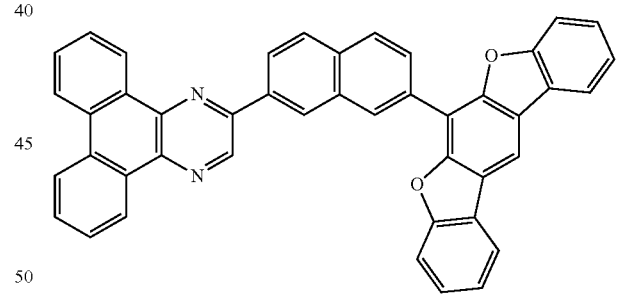
(234)
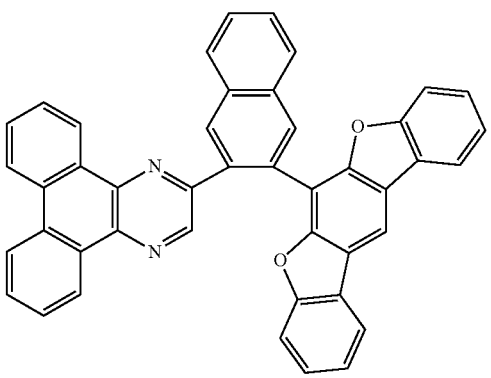

(235)
(236)
(237)
(238)
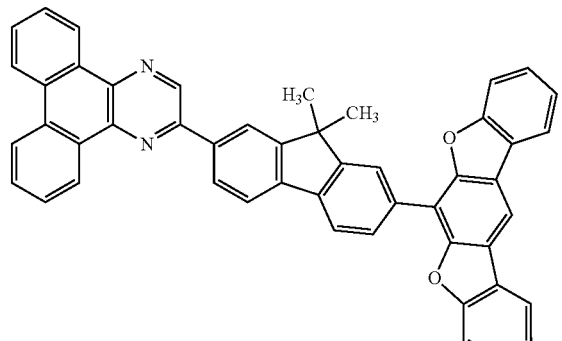
(239)
(240)
(241)
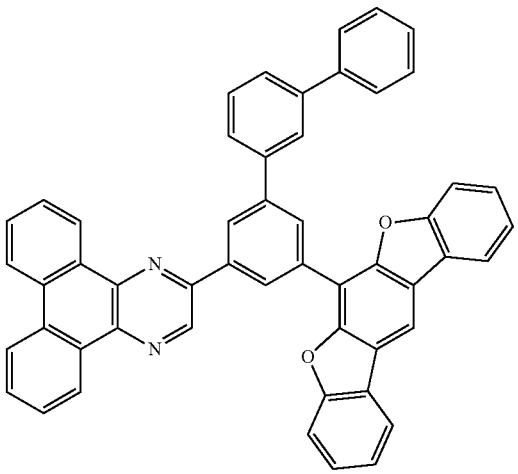
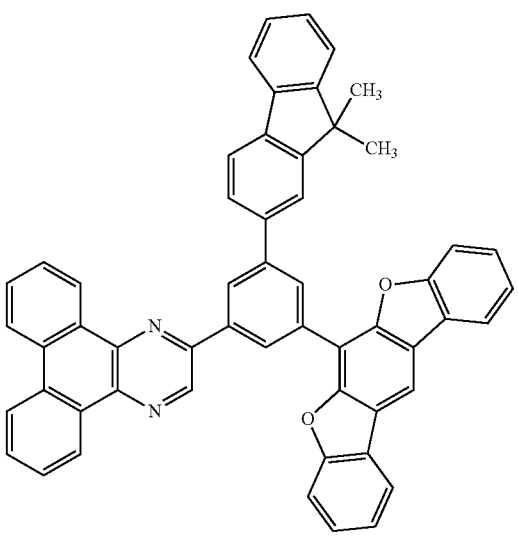
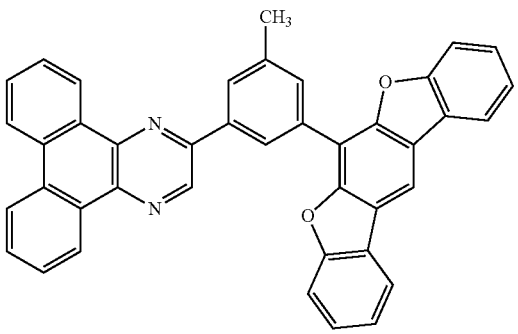

(242)
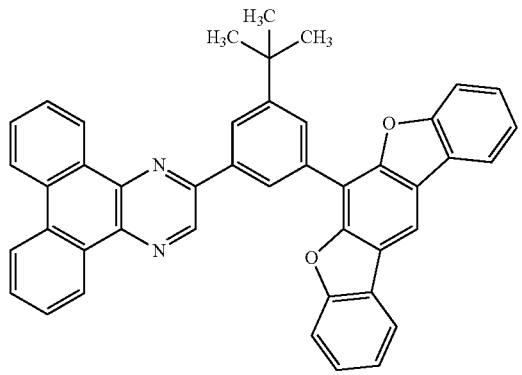
(243)
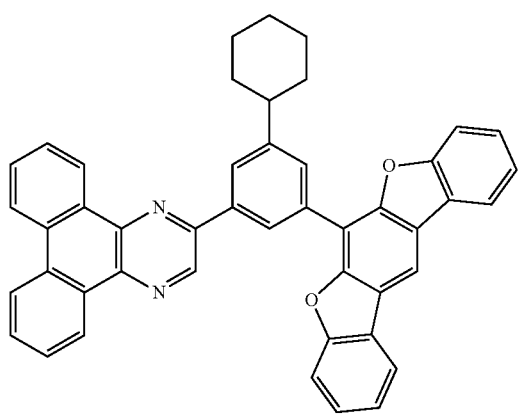
[Chemical Formulae 23]
(244)
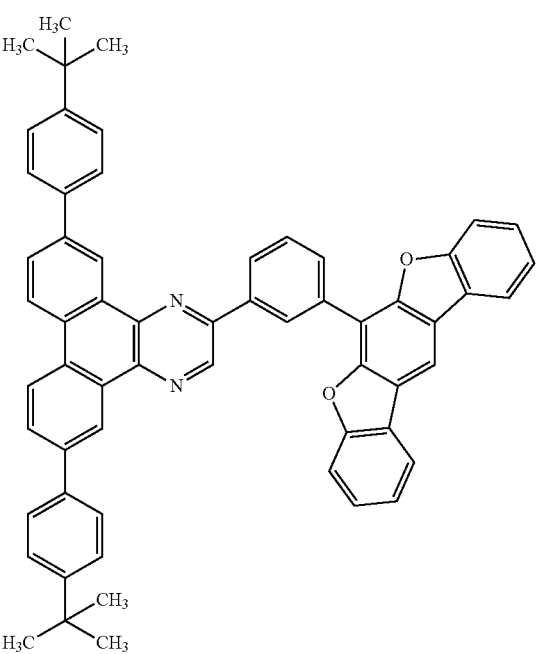
(245)
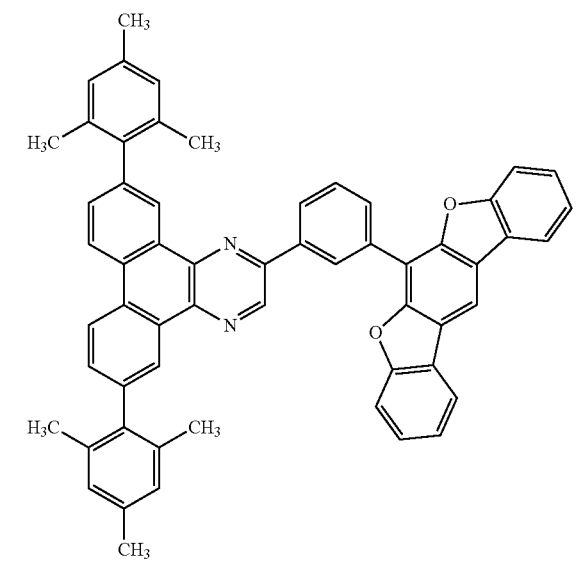
(246)
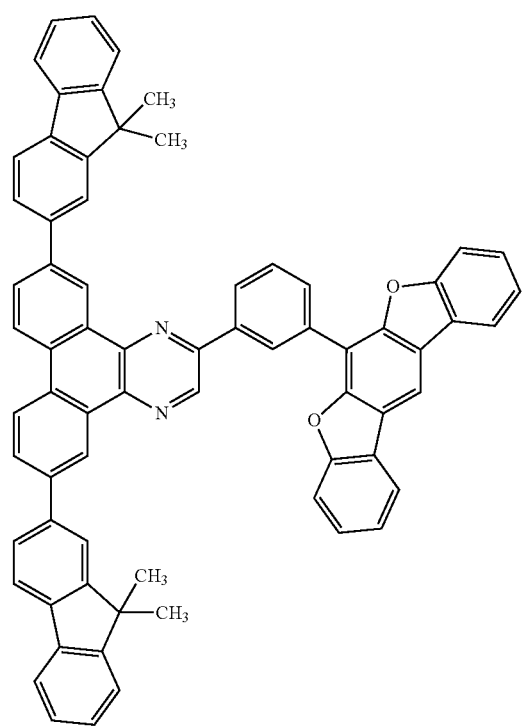

(247)
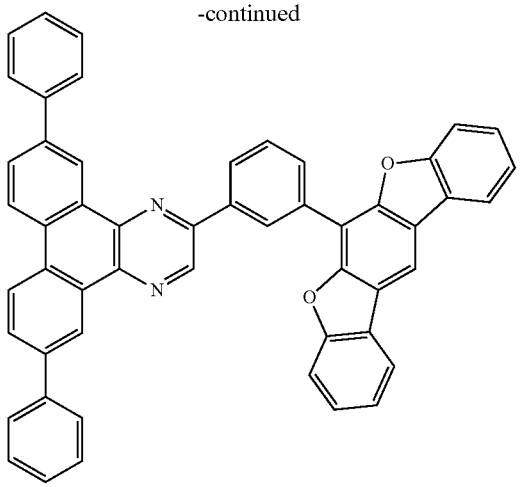
(248)
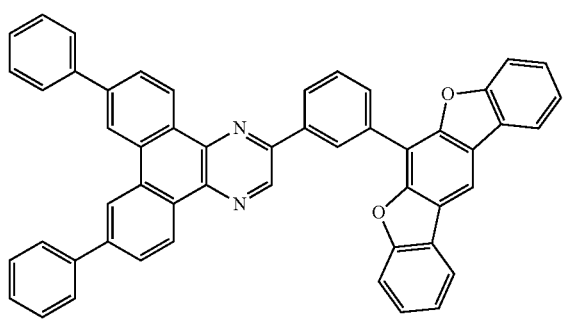
(249)
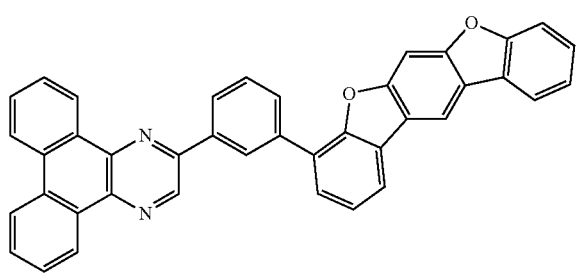
(250)
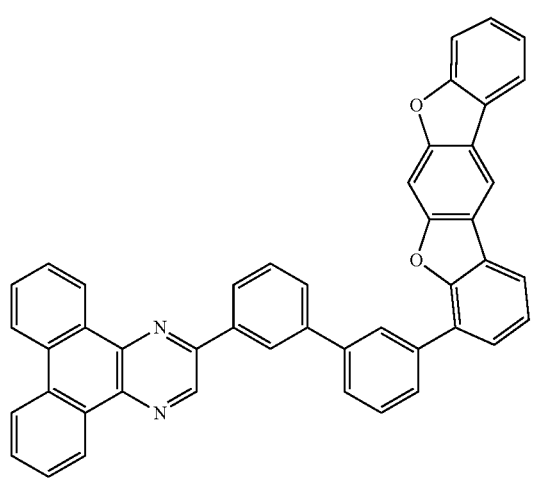
(251)
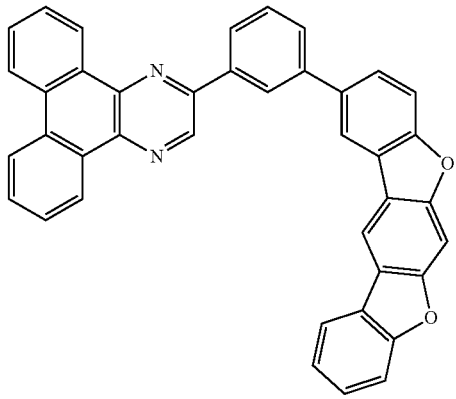
(252)
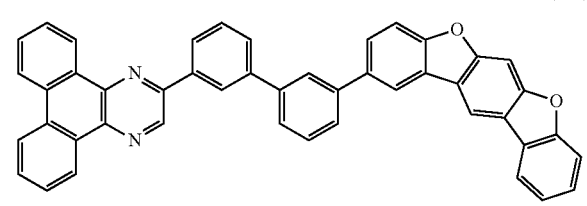
[Chemical Formulae 24]
(253)
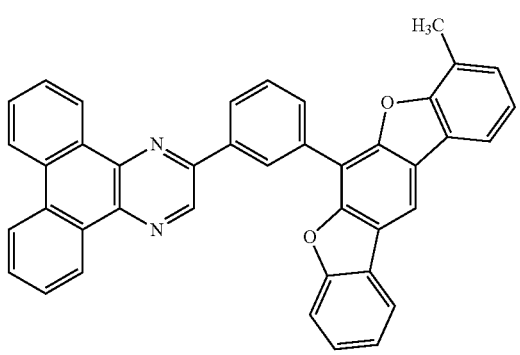
(254)
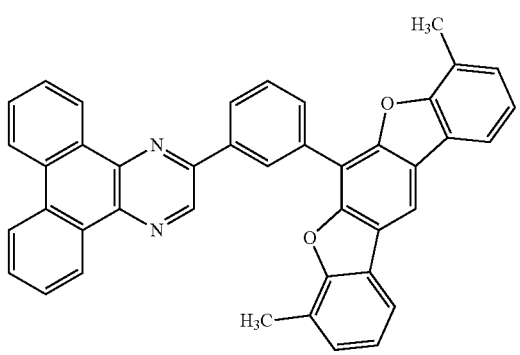

-continued
(255)
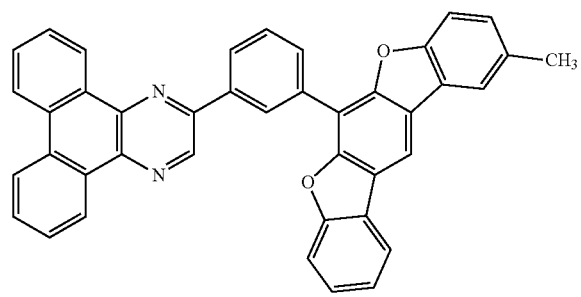
(256)
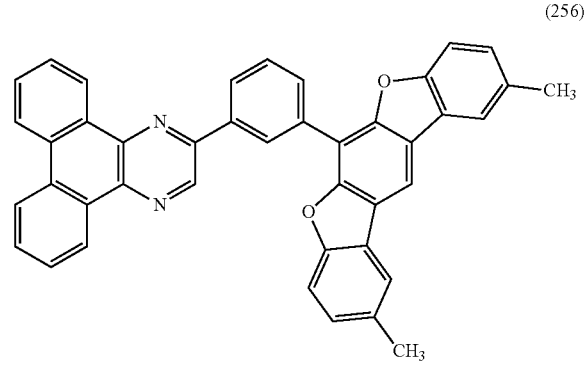
(257)
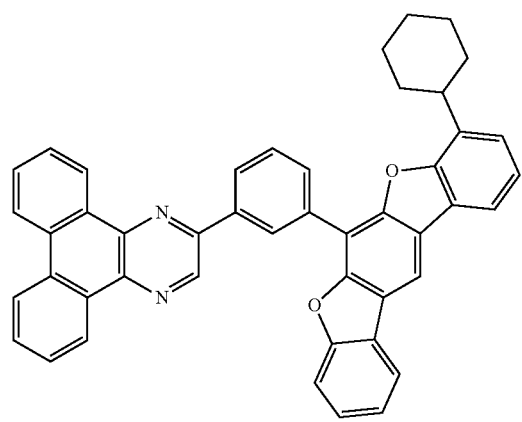
(258)
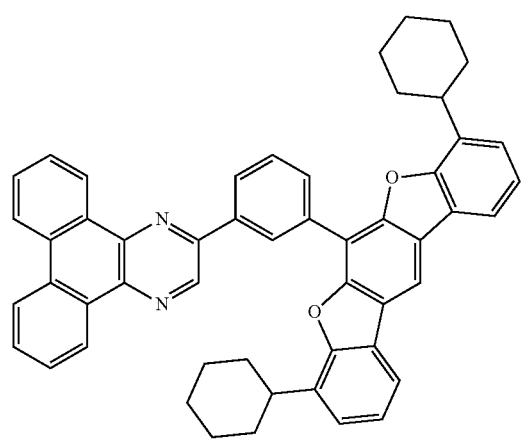
-continued
(259)
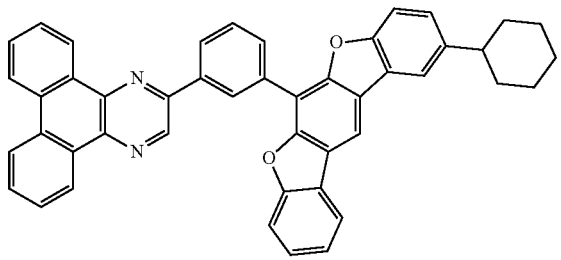
(260)
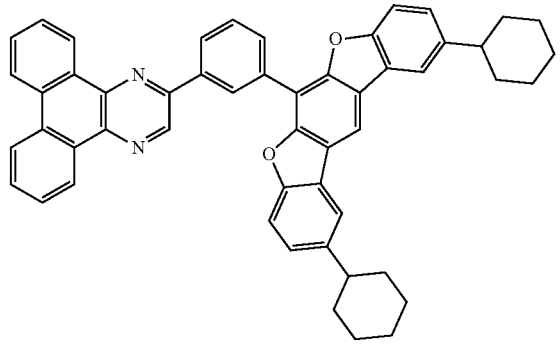
(261)
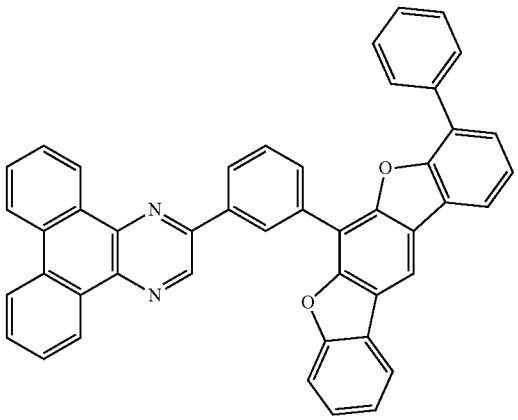
(262)
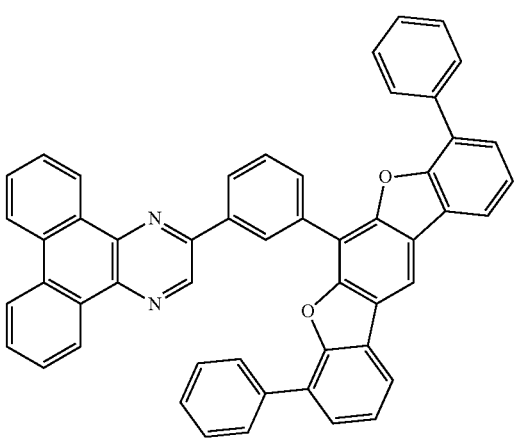

(263)
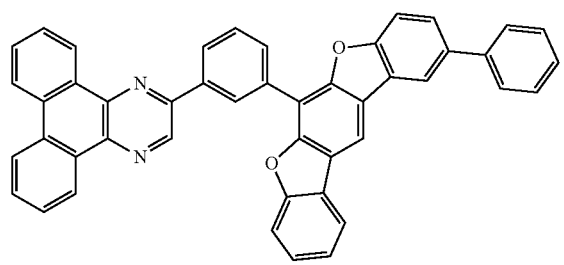
(264)
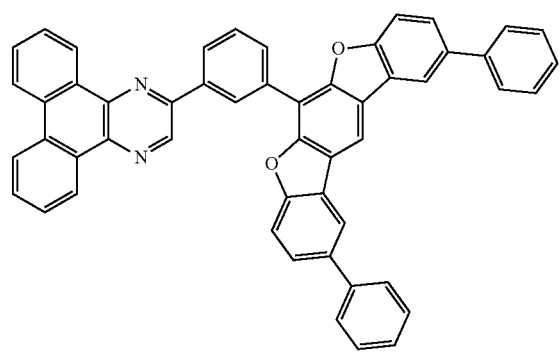
[Chemical Formulae 25]
(265)
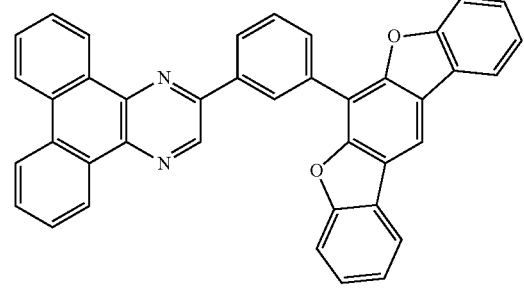
(266)
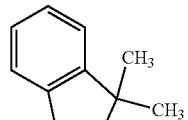
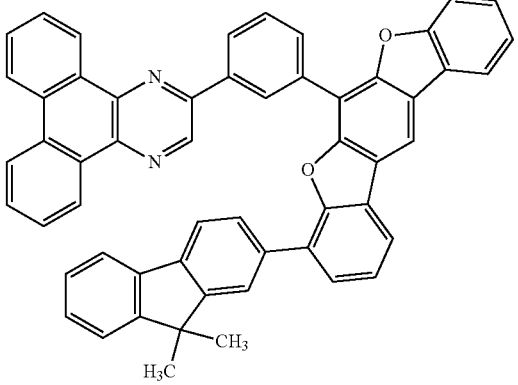
(267)
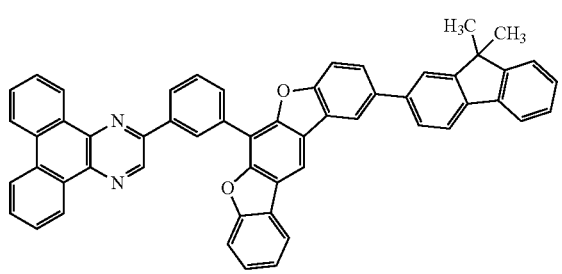
(268)
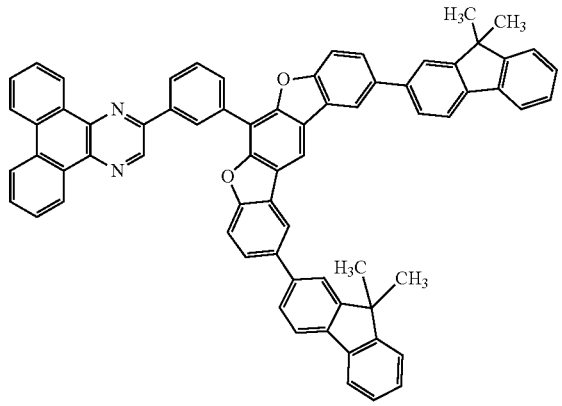
(269)

(270) 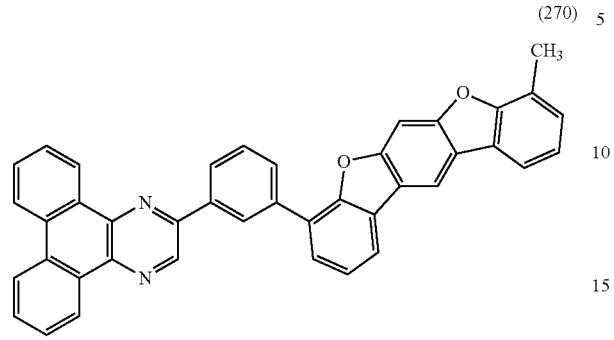
(271) 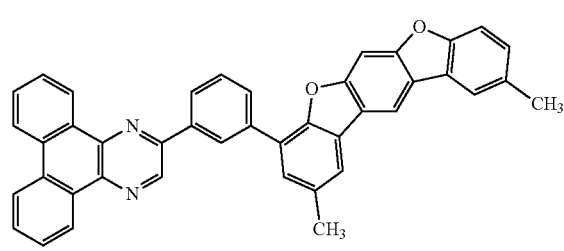
(272) 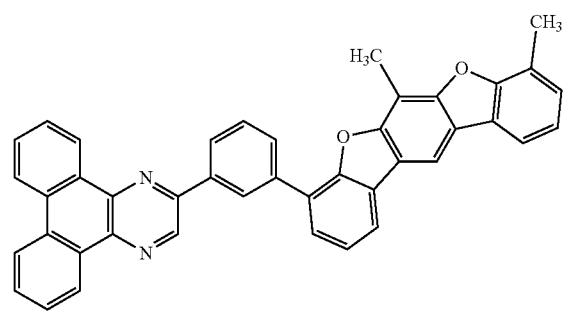
[Chemical Formulae 26]
(273) 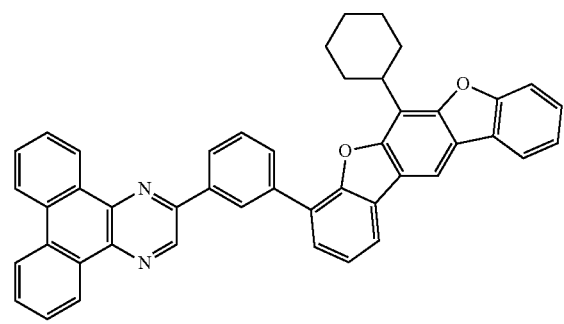
(274) 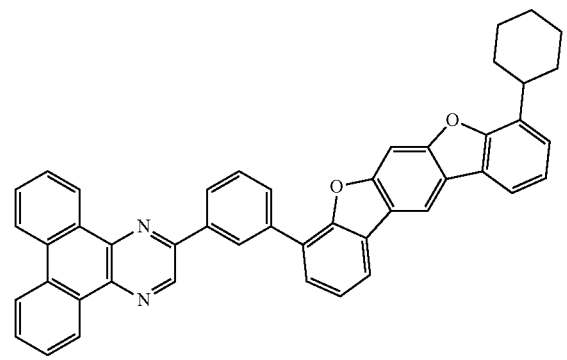
(275) 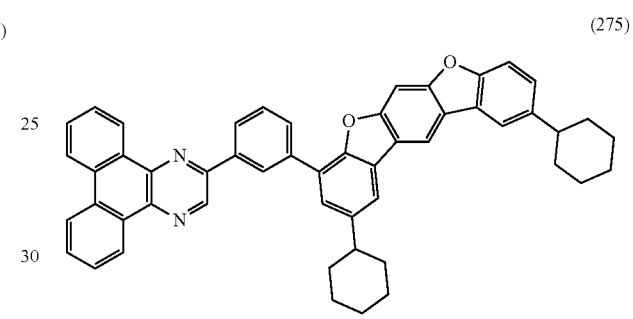
(276) 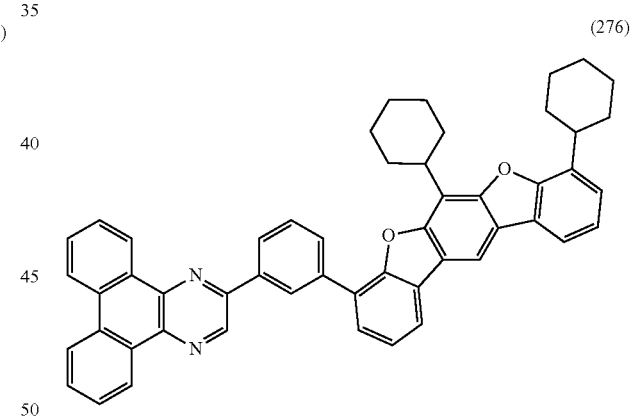
(277) 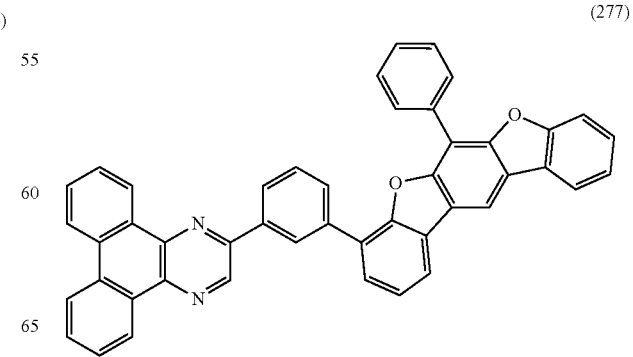

-continued
(278)
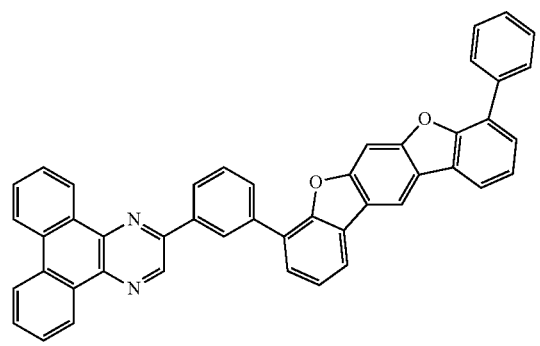
(279)
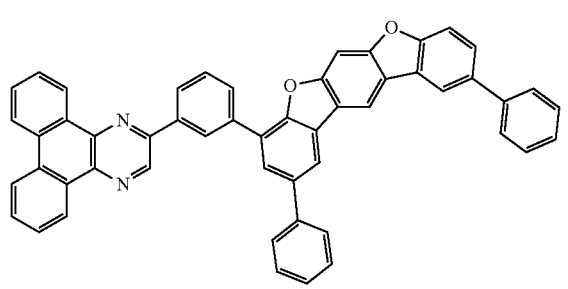
(280)
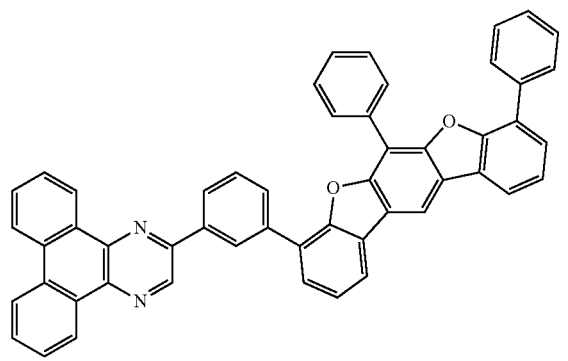
(281)
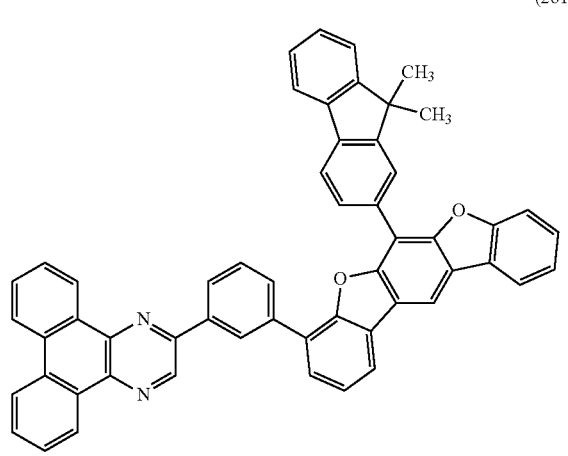
-continued
(282)
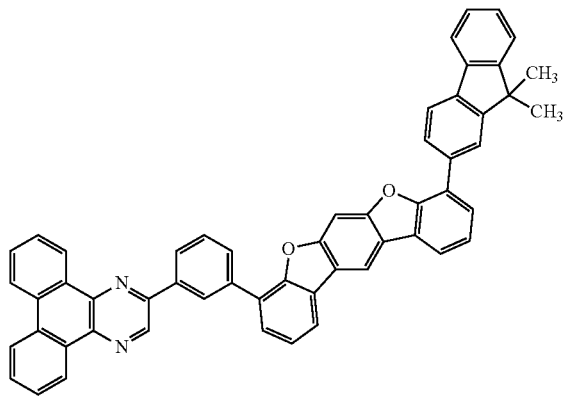
[Chemical Formulae 27]
(283)
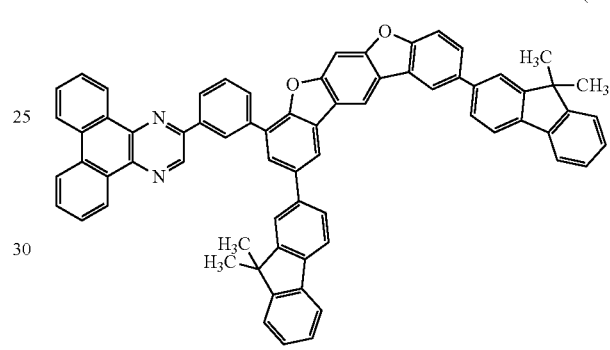
(284)
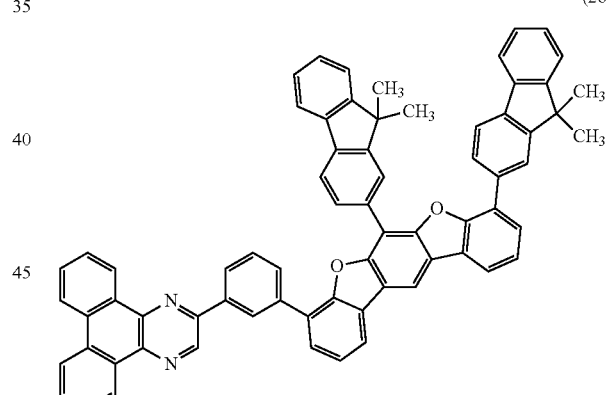
(285)
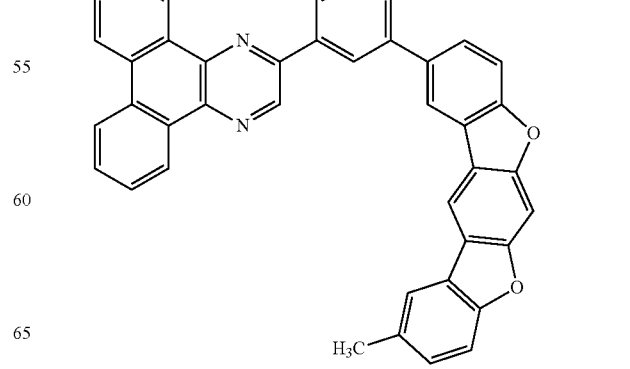

(286)
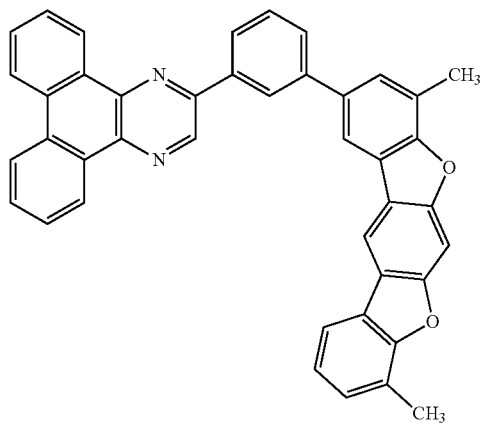
(287)
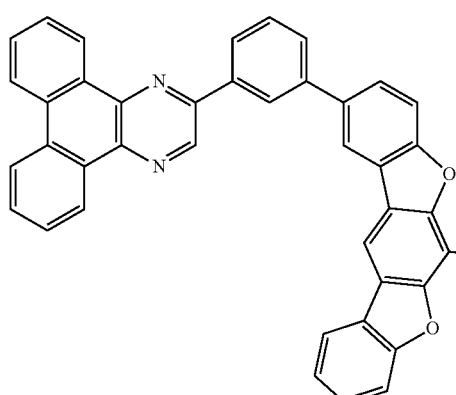
(288)
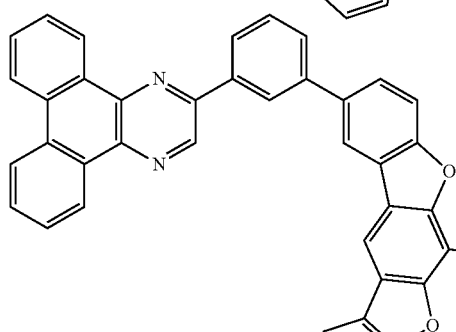
(289)
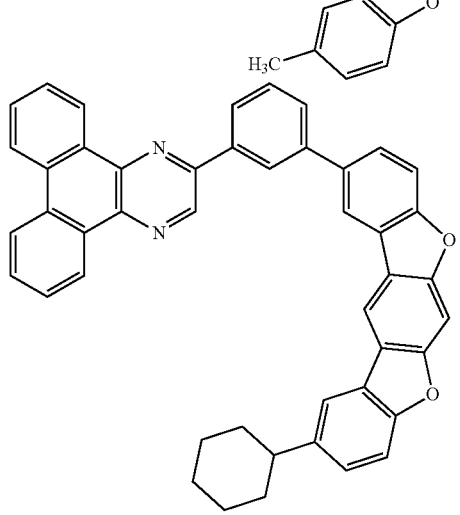
(290)
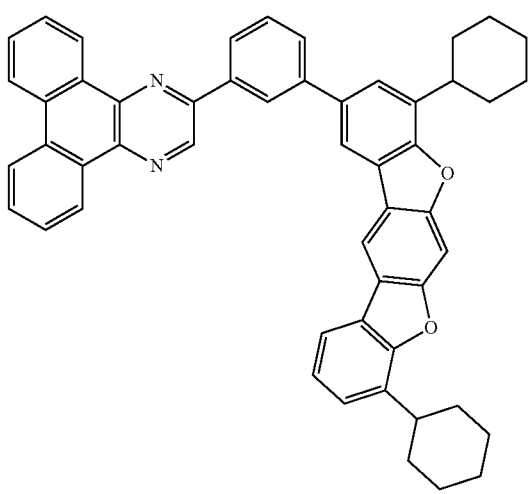
(291)
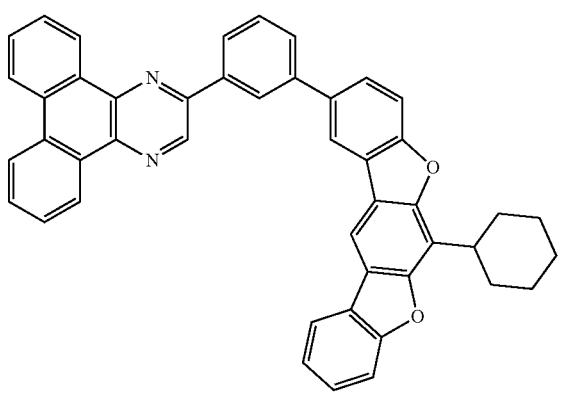
(292)
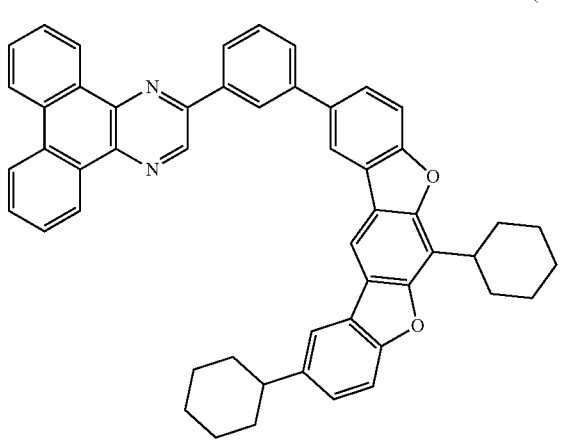

[Chemical Formulae 28]
(293)
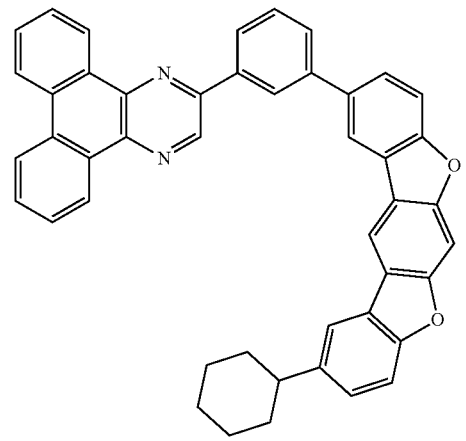
(294)
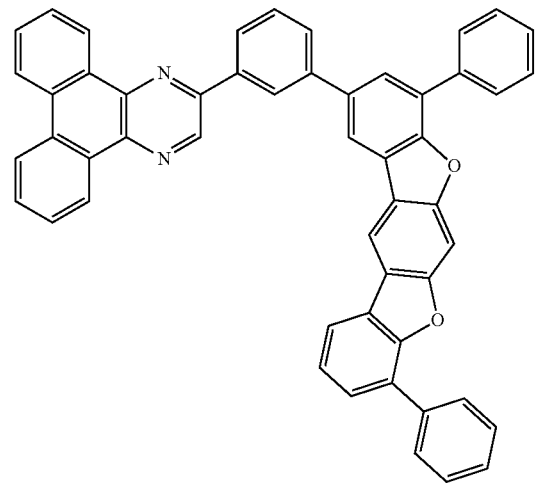
(295)
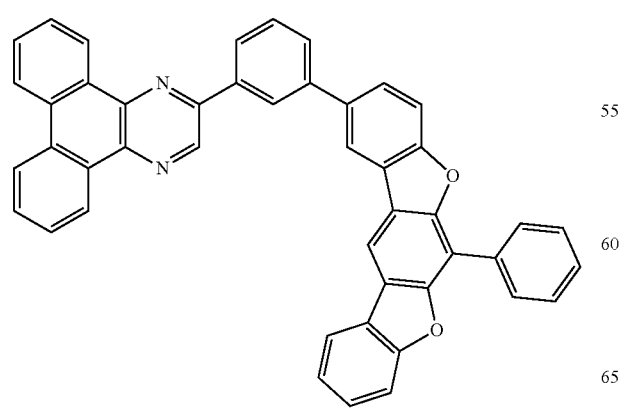
(296)
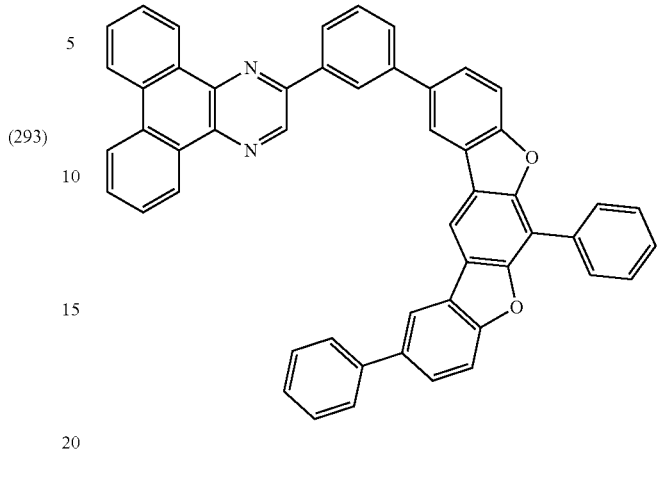
(297)
(298)
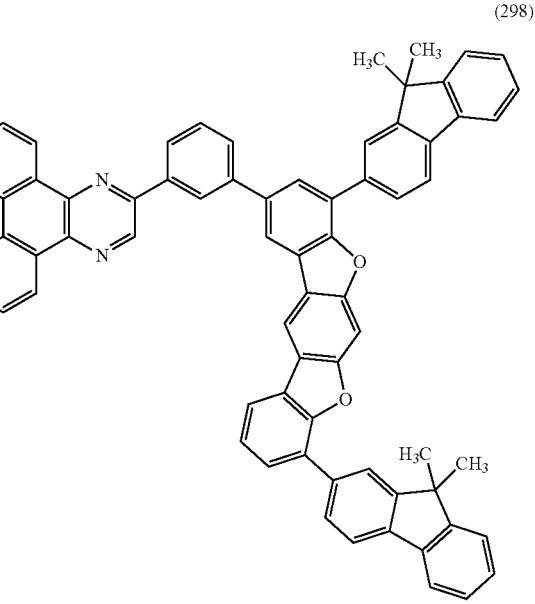

(299)
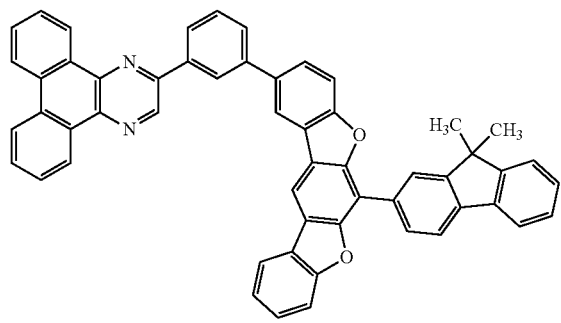
(300)
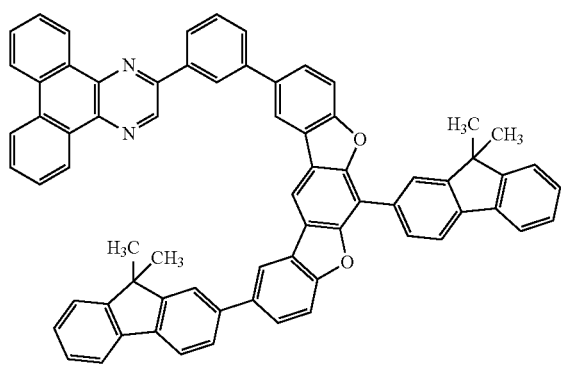
[Chemical Formulae 29]
(301)
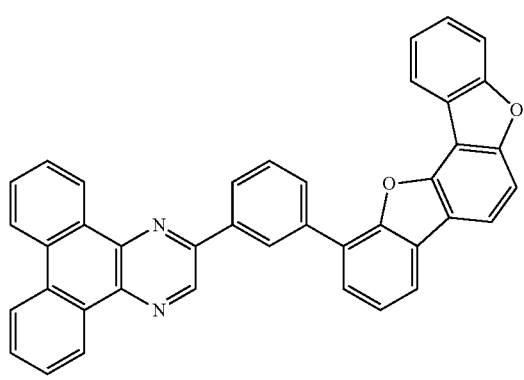
(302)
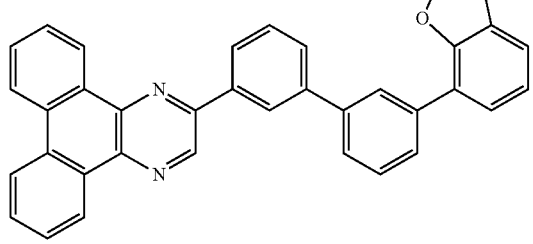
(303)
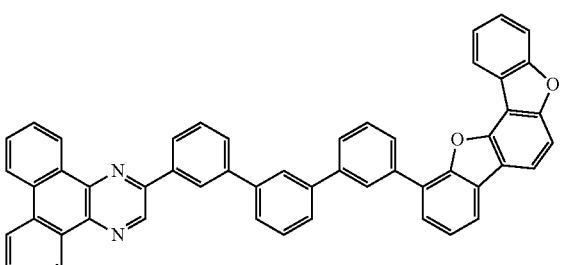
(304)
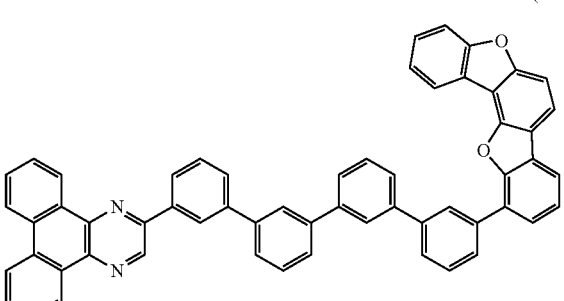
(305)
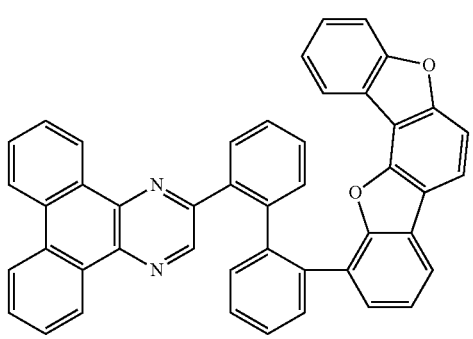
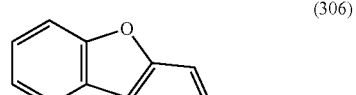
(306)
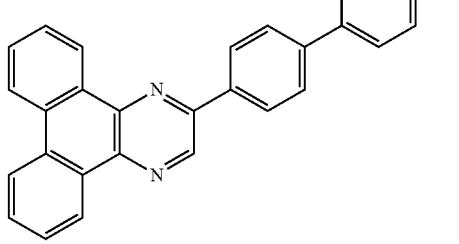

(307)
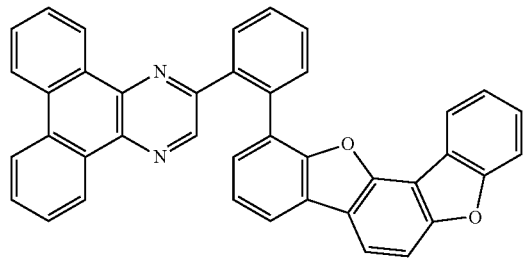
(308)
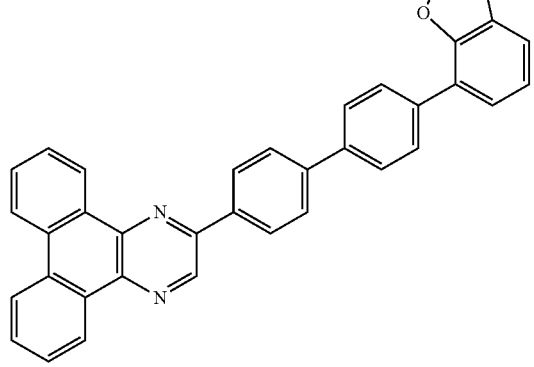
(309)
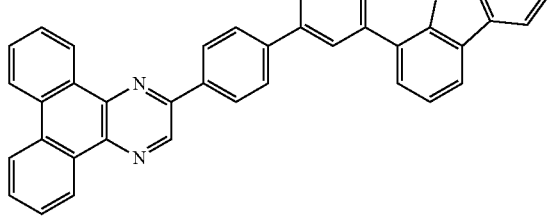
(310)
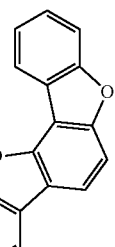
[Chemical Formulae 30]
(311)
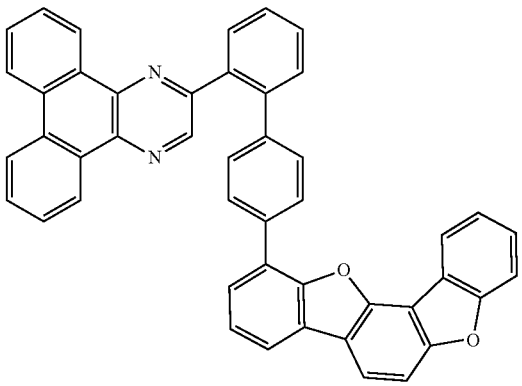
(312)
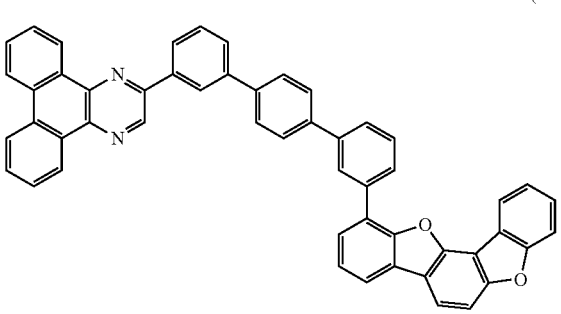
(313)
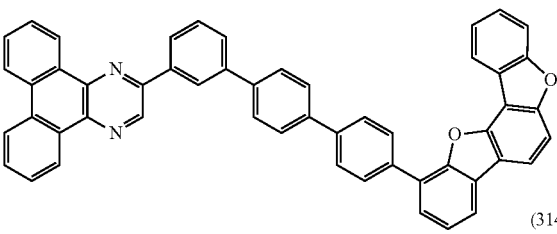
(314)
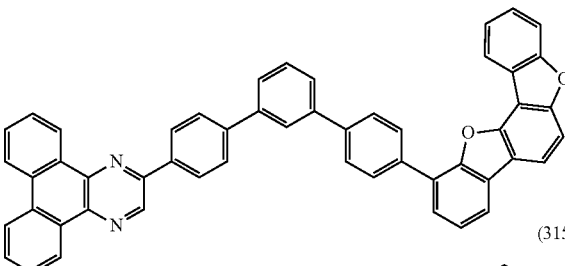
(315)
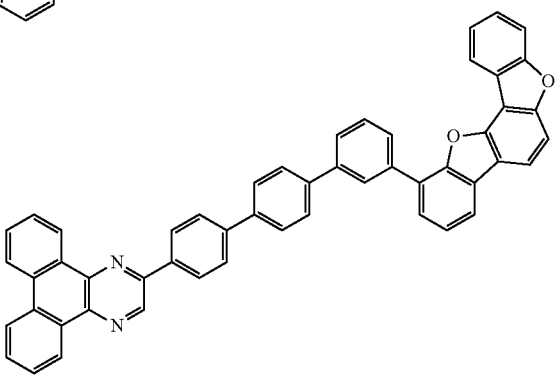

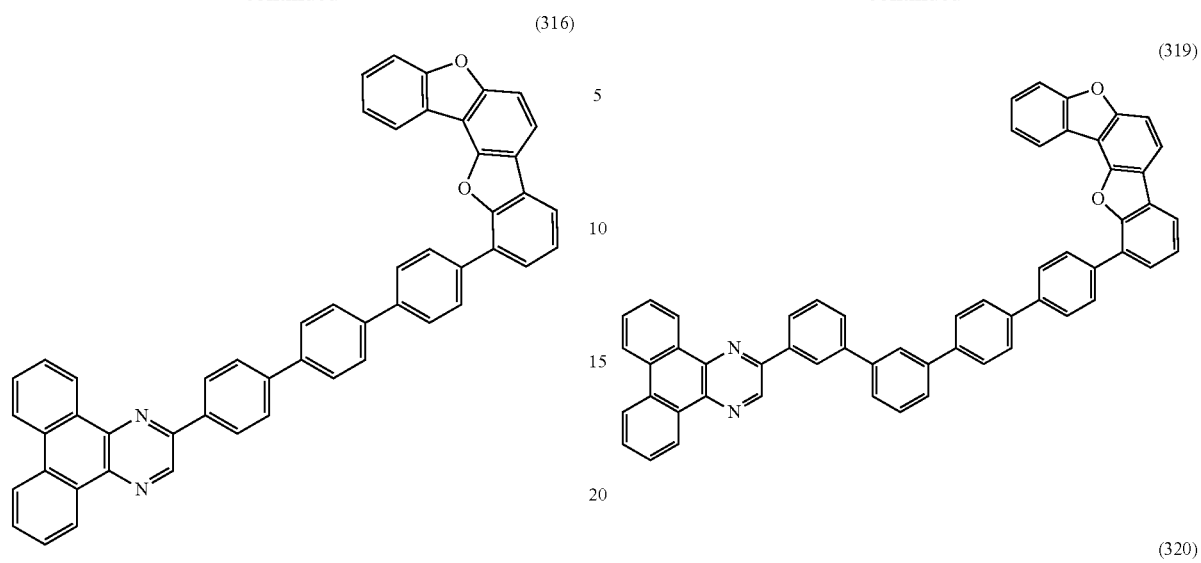
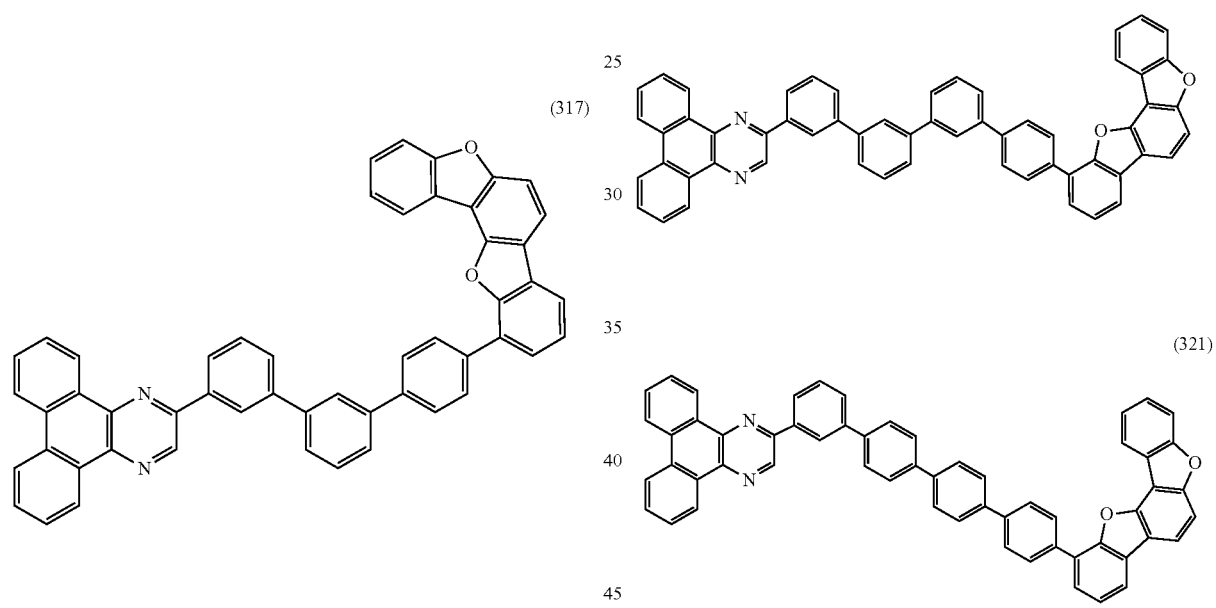
[Chemical Formulae 31]
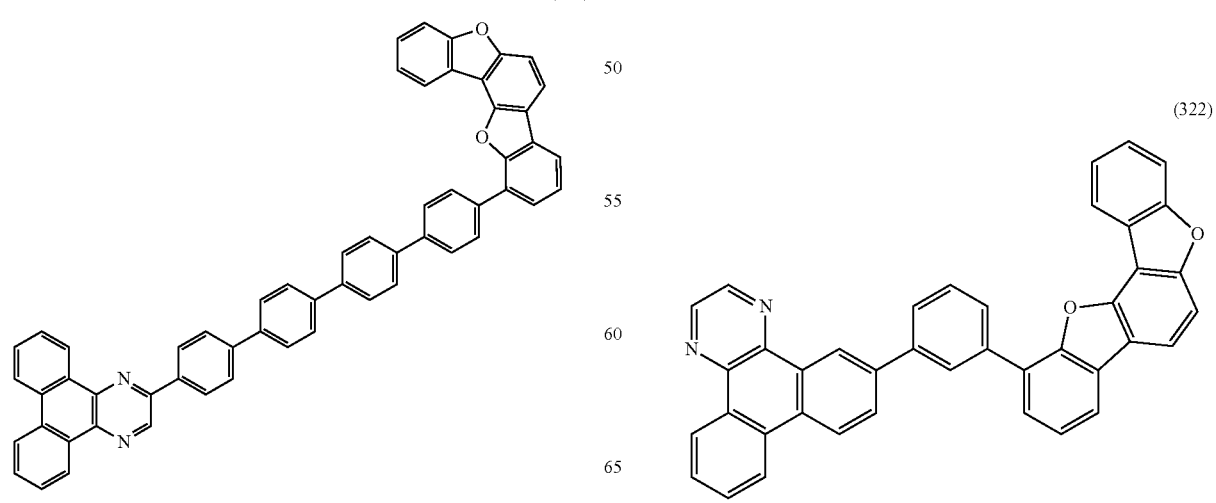

(323)
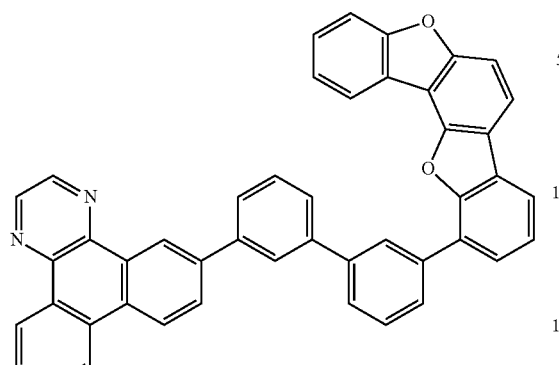
(324)
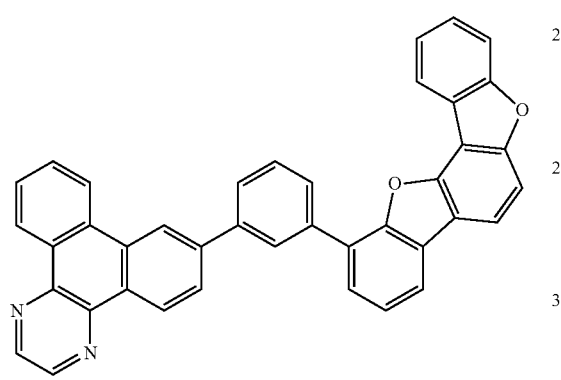
(325)
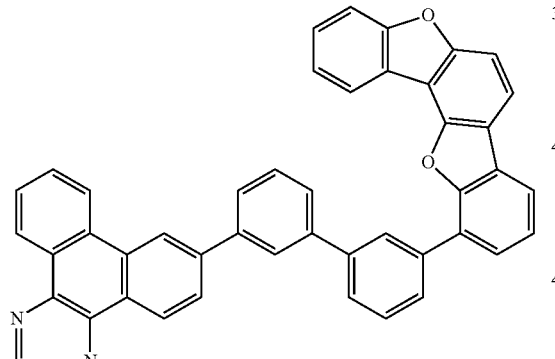
(326)
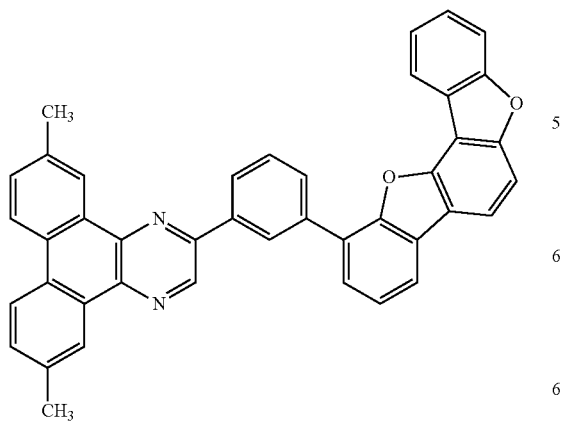
(327)
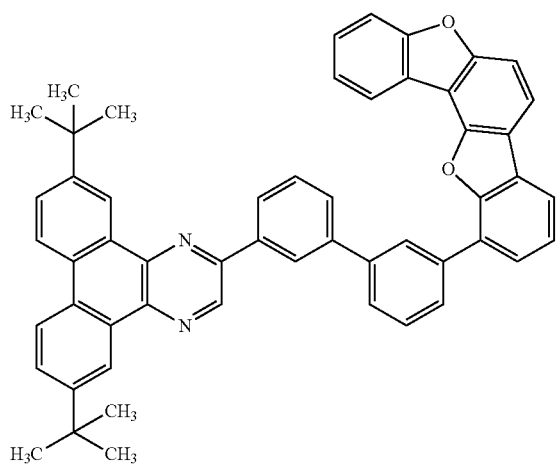
(328)
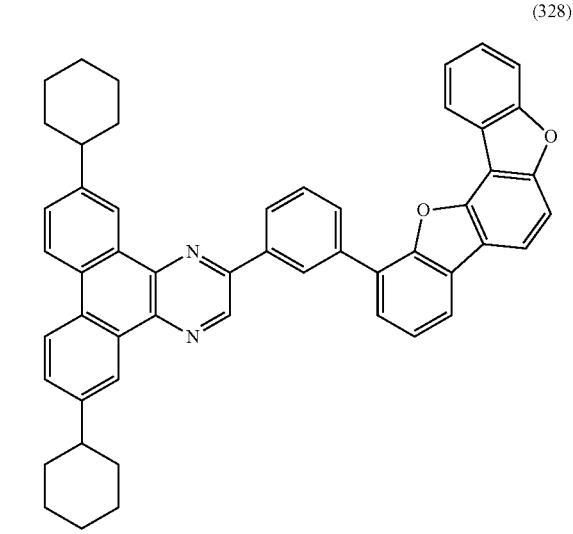
(329)
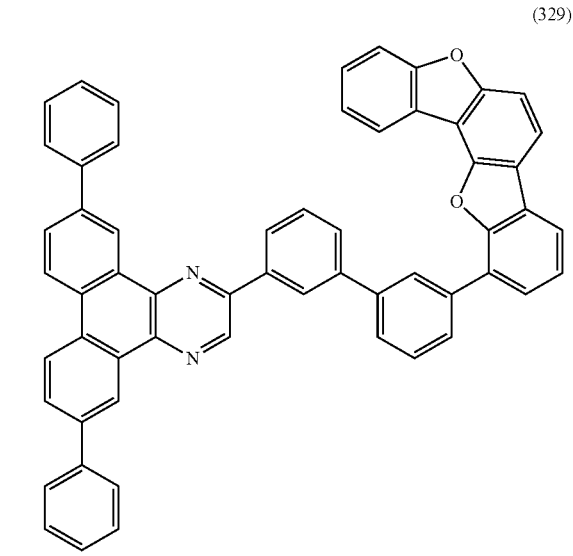

[Chemical Formulae 32]
(330) 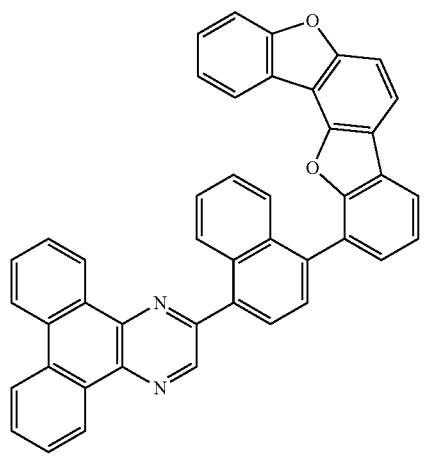
(331) 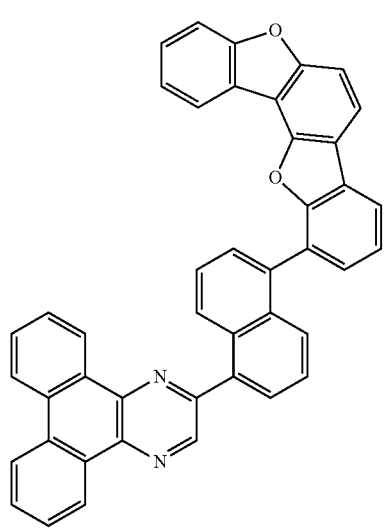
(332) 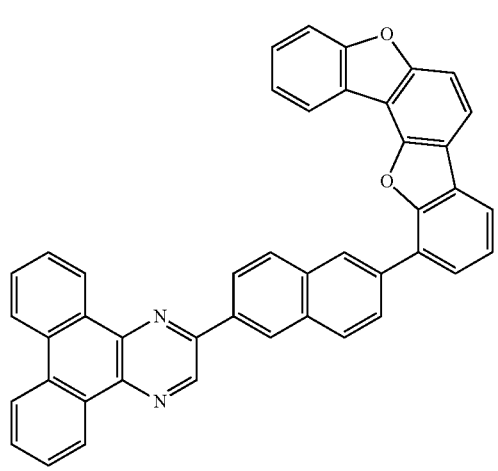
(333) 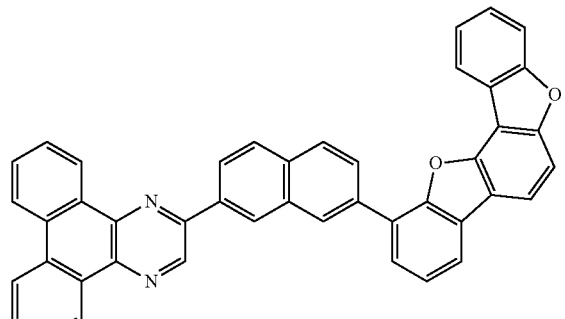
(334) 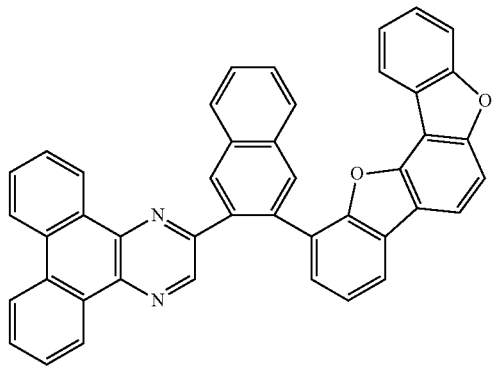
(335) 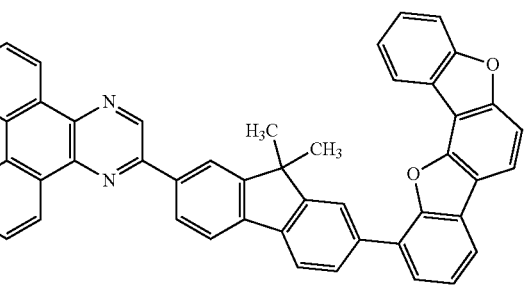
(336) 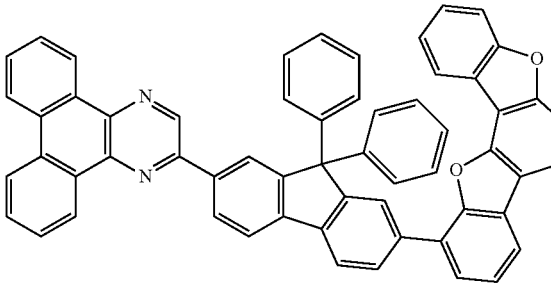

(337)
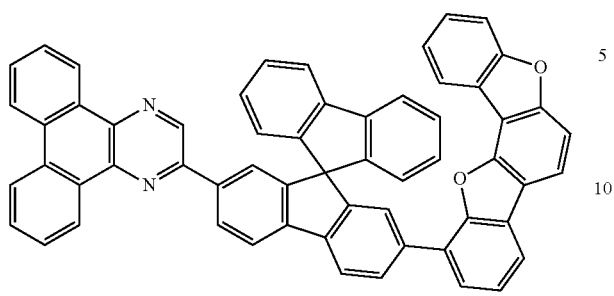
(338)
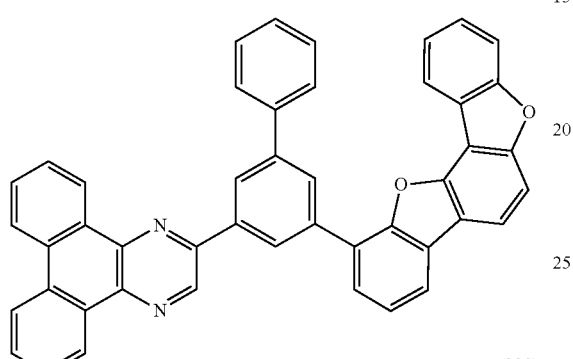
(339)
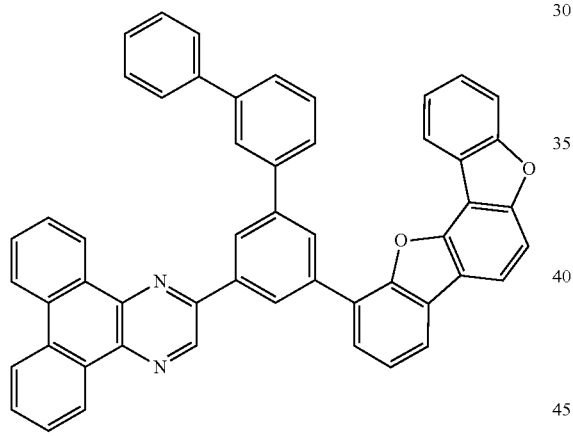
(340)
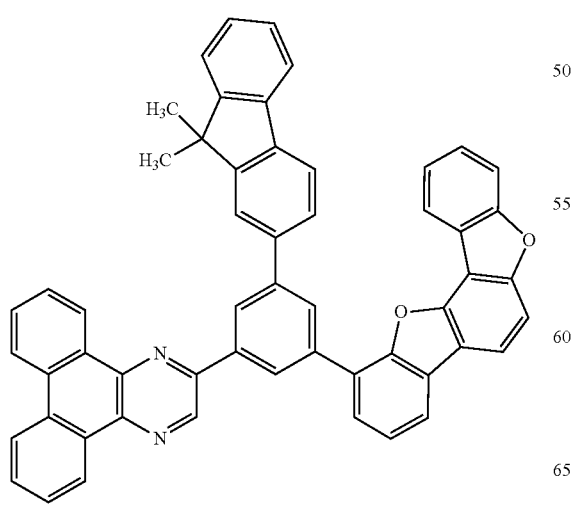
(341)
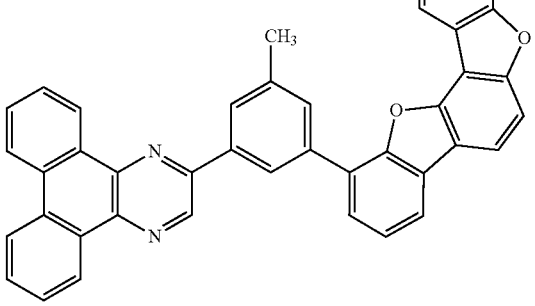
(342)
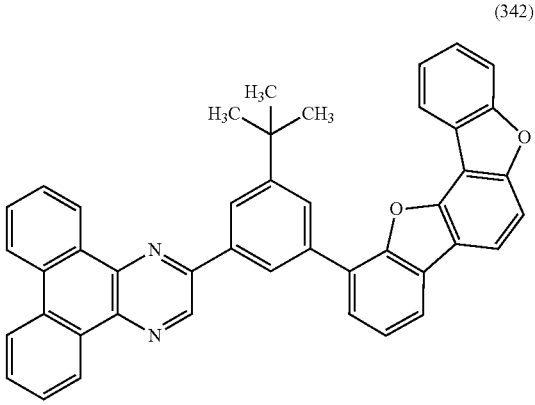
[Chemical Formulae 33]
(343)
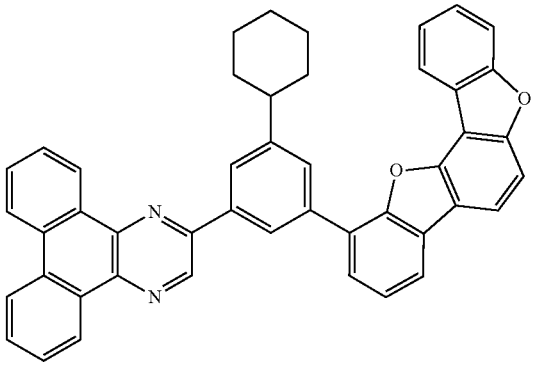

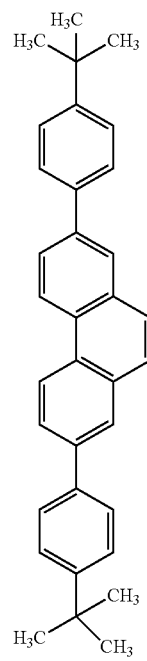
(344)
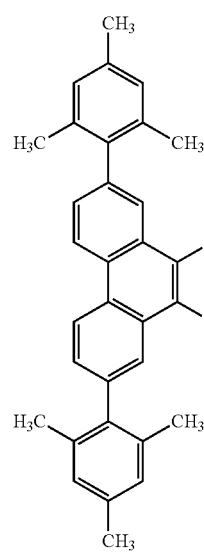
(345)
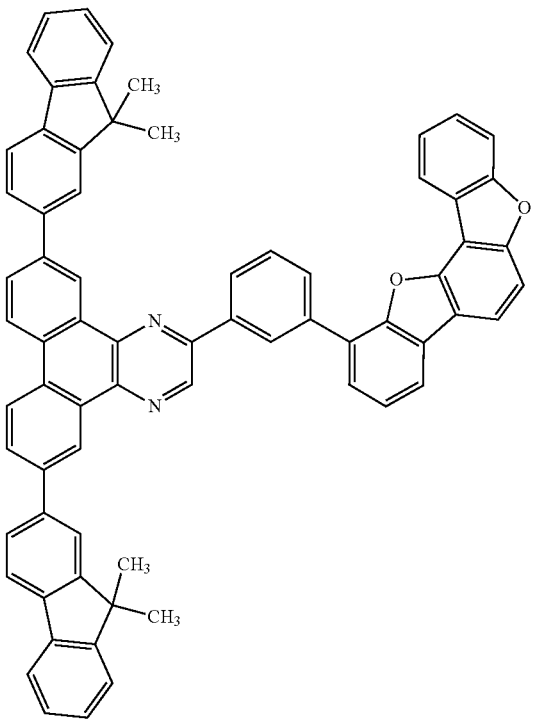
(346)
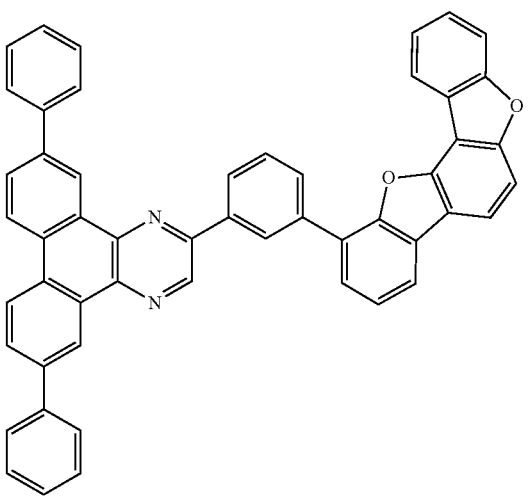
(347)
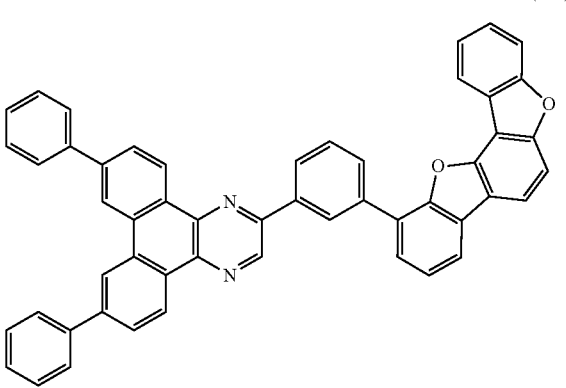
(348)

[Chemical Formulae 34]
(349)
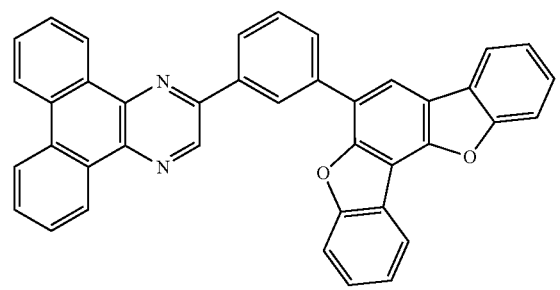
(350)
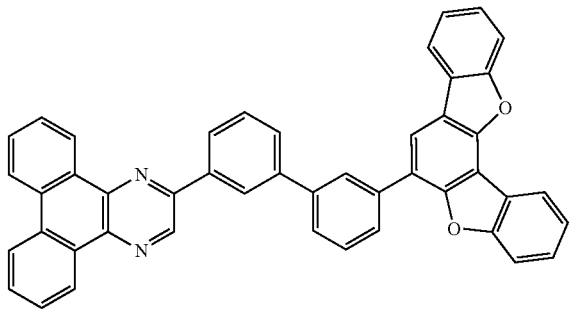
(351)
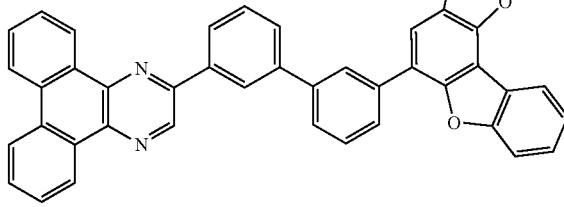
(352)
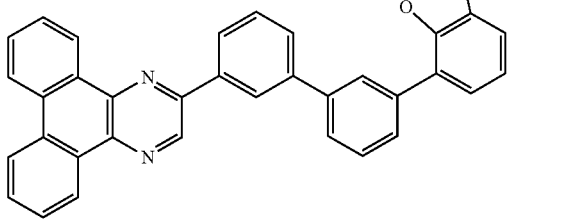
(353)
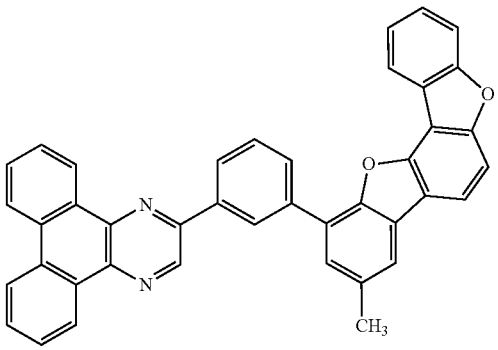
(354)
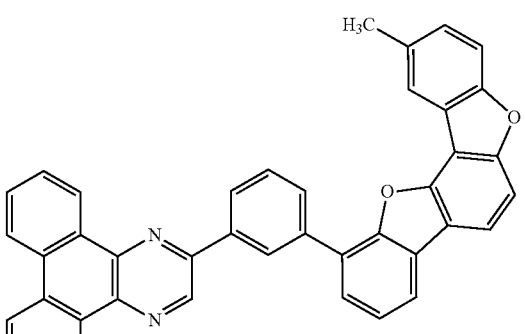
(355)
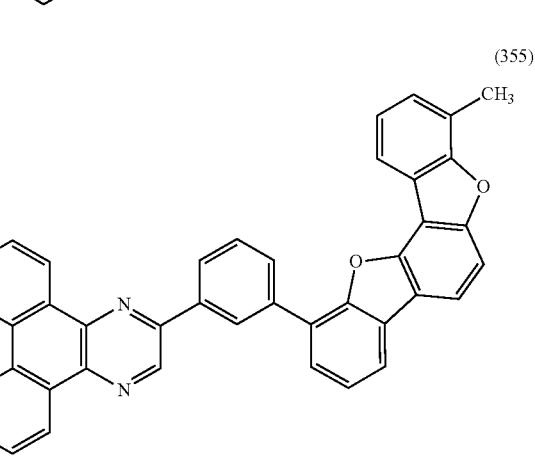
(356)
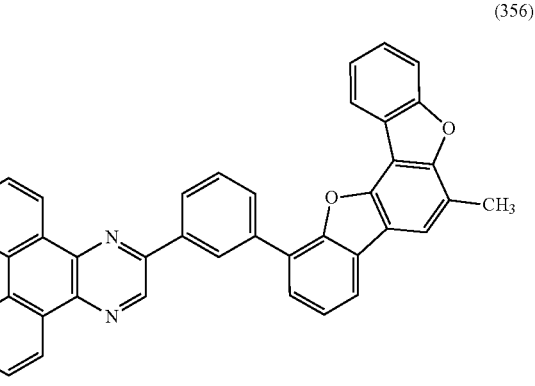

[Chemical Formuale 35]
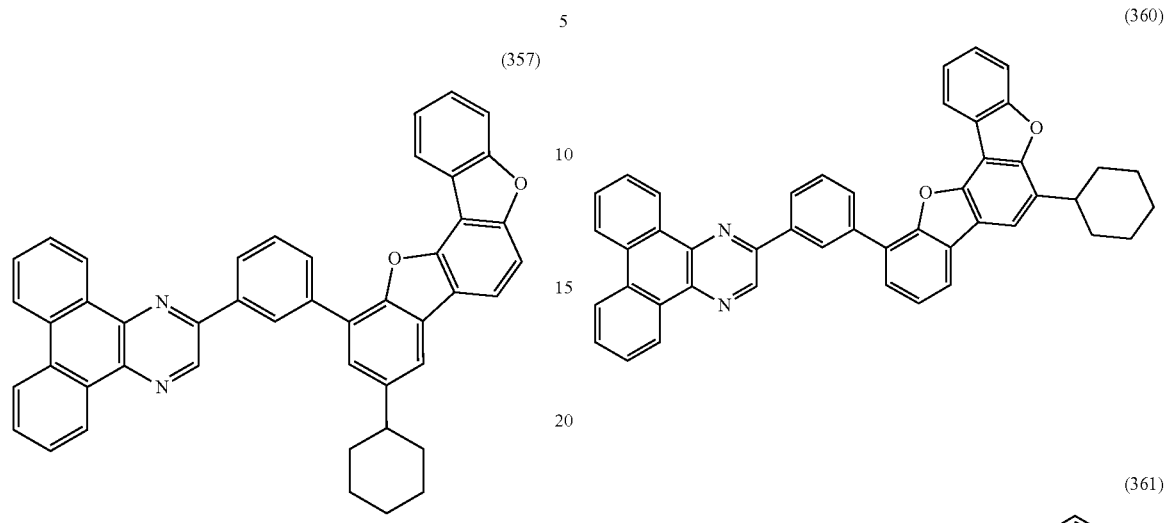
(357)
(358)
(359)
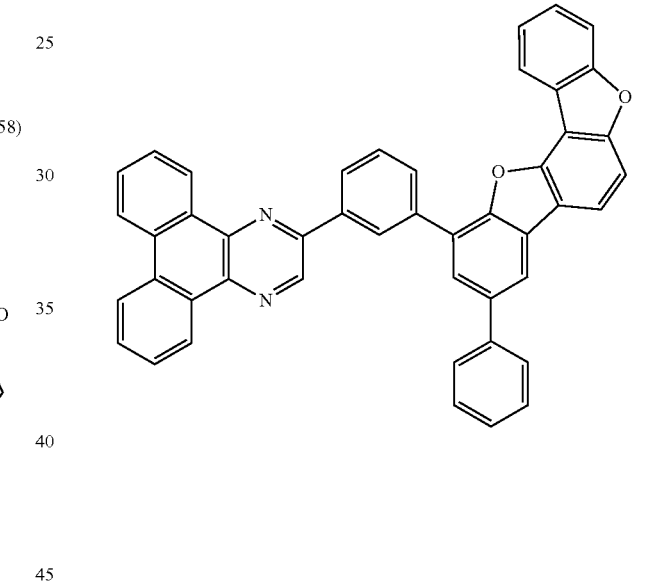
(360)
(361)
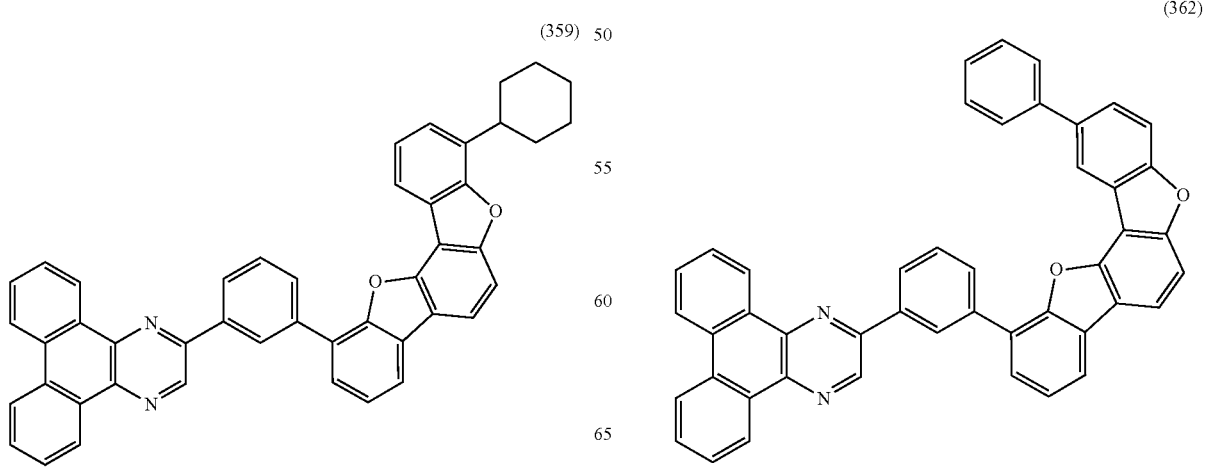
(362)

(363)
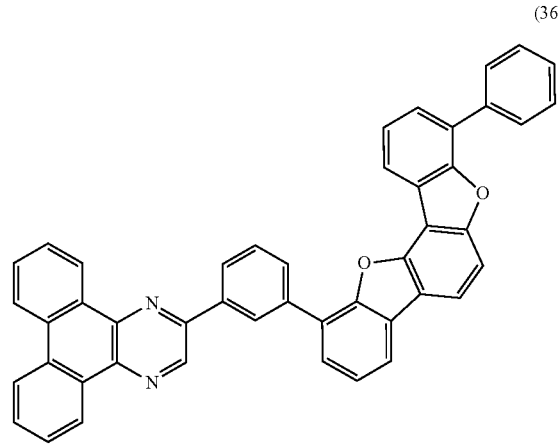
(364)
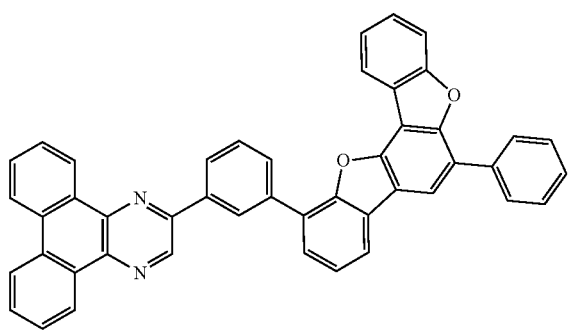
(365)
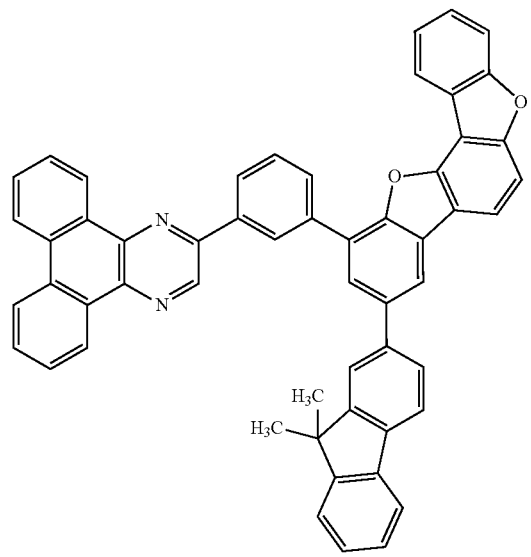
(366)
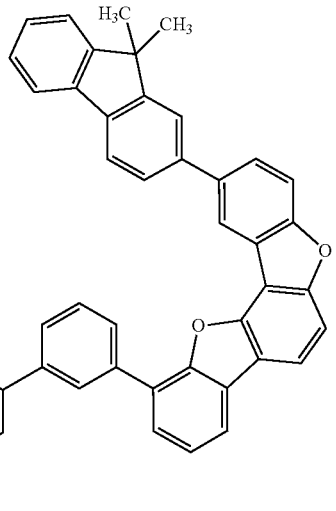
[Chemical Formulae 36]
(367)
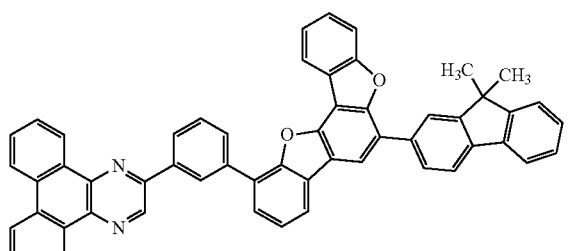
(368)
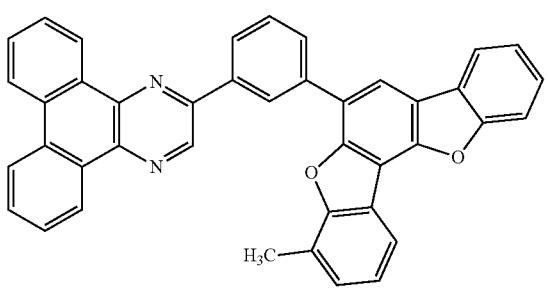
(369)

(370)
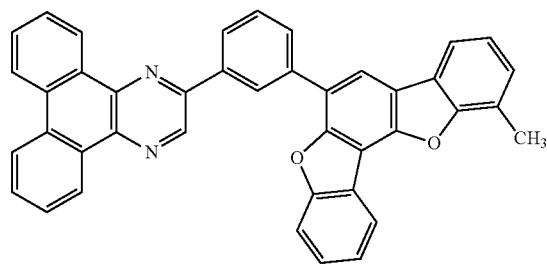
(371)
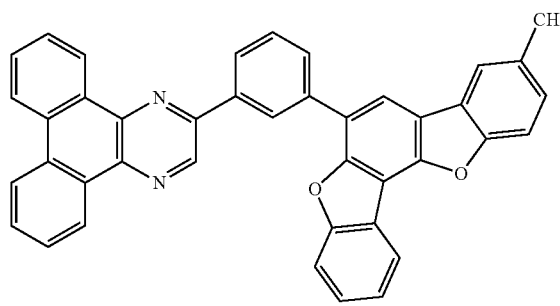
(372)
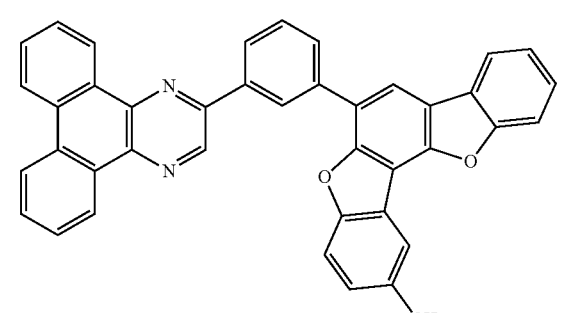
(373)
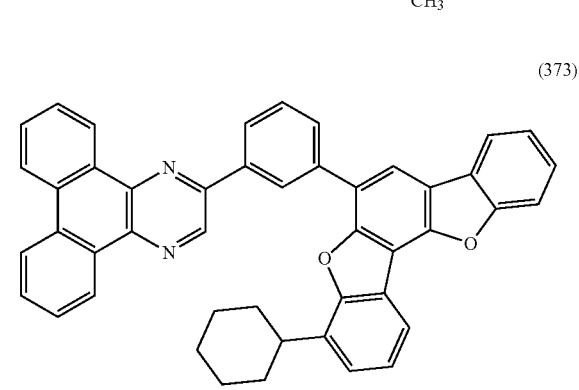
(374)
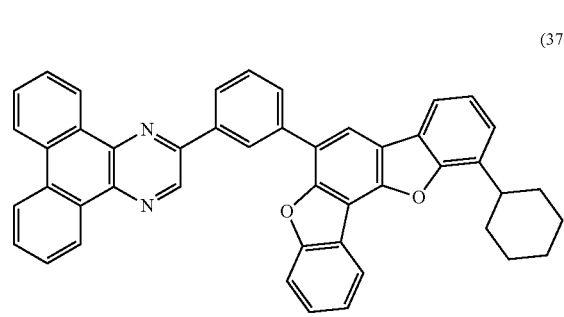
(375)
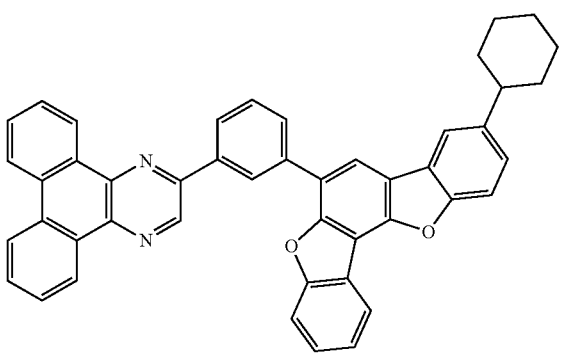
(376)
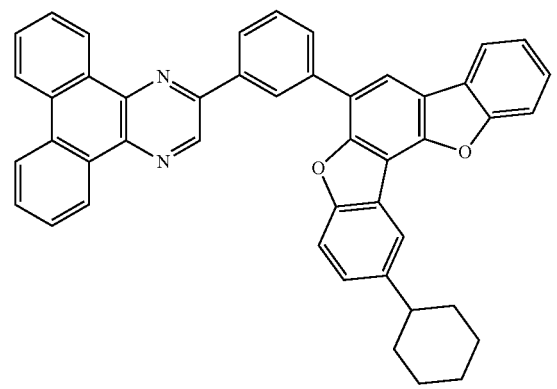
(377)
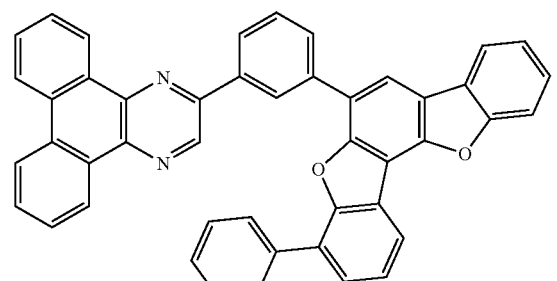
(378)
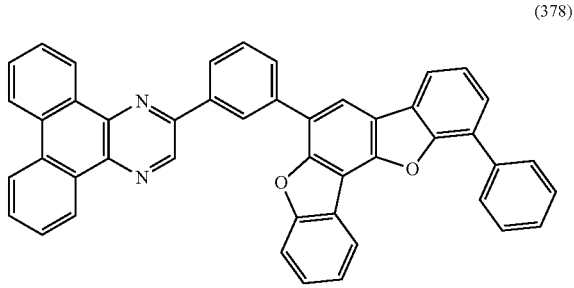

[Chemical Formulae 37]
(379)
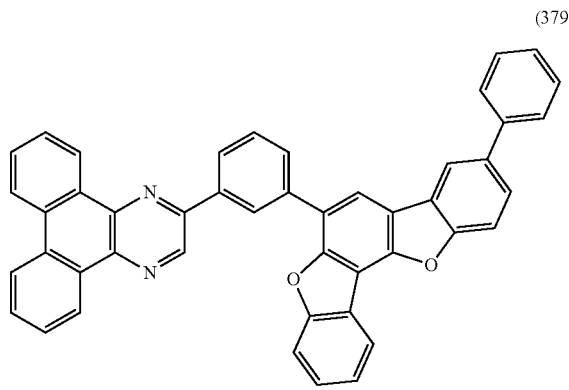
(380)
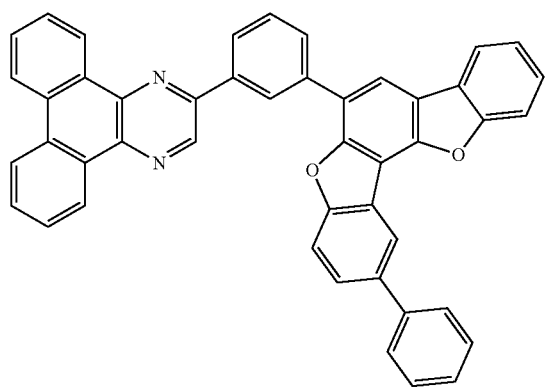
(381)
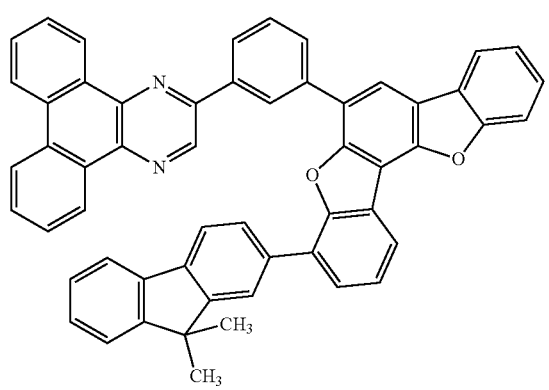
(382)
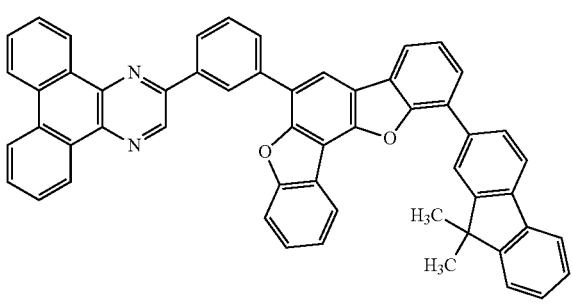
(383)
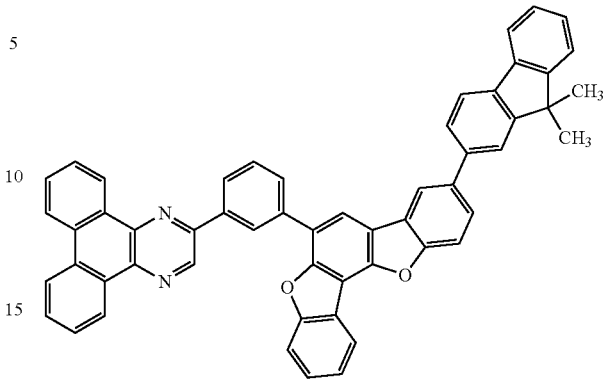
(384)
(385)
(386)
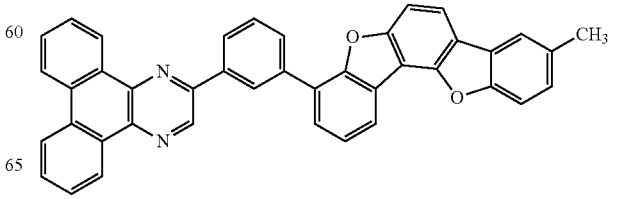

(387)
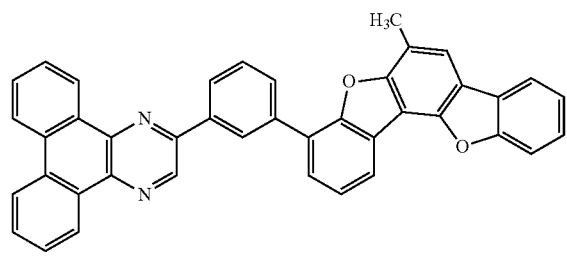
(388)
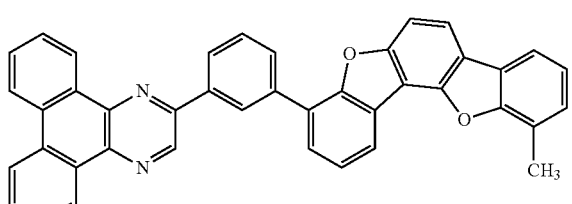
(389)
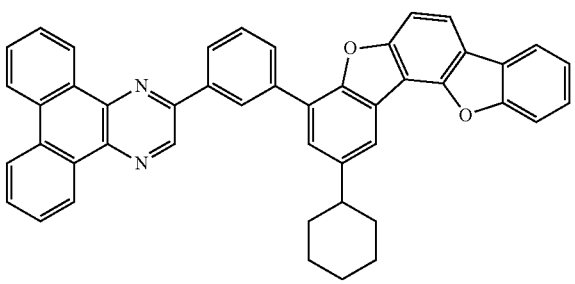
(390)
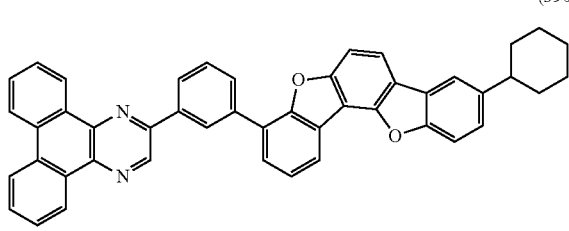
[Chemical Formulae 38]
(391)
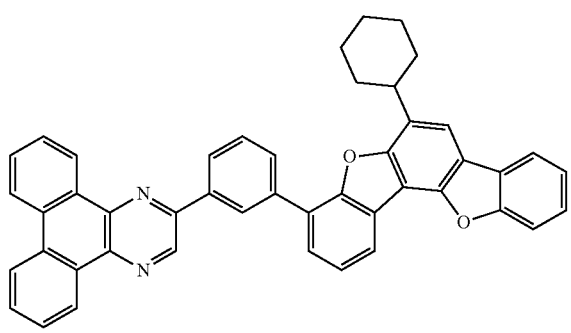
(392)
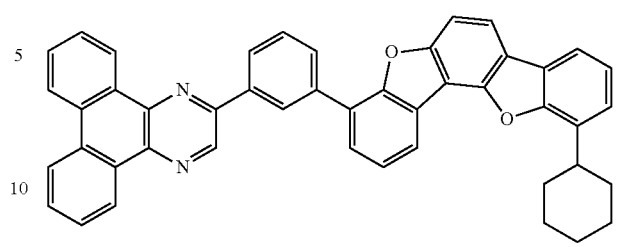
(393)
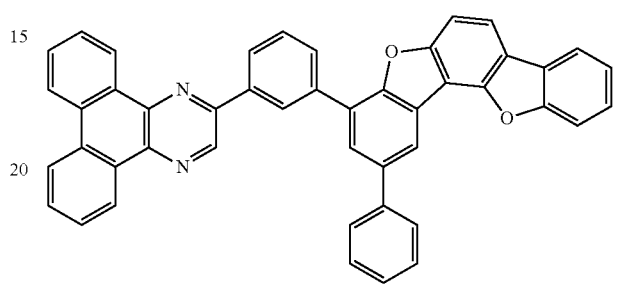
(394)
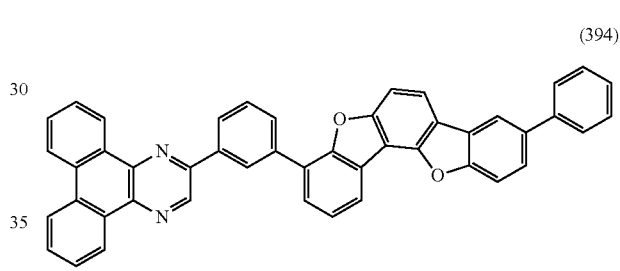
(395)
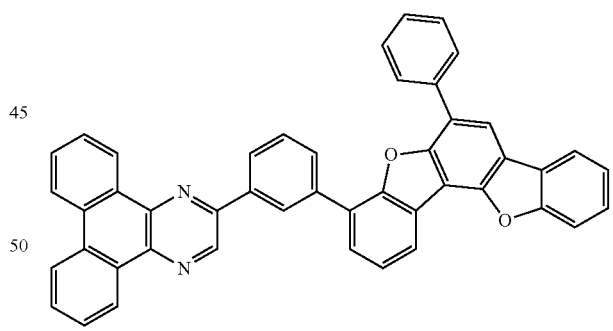
(396)
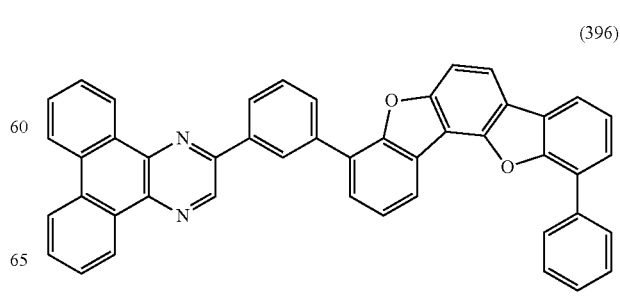

-continued (397)
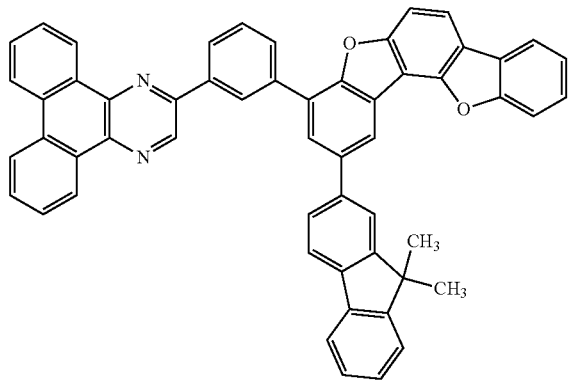

(398)
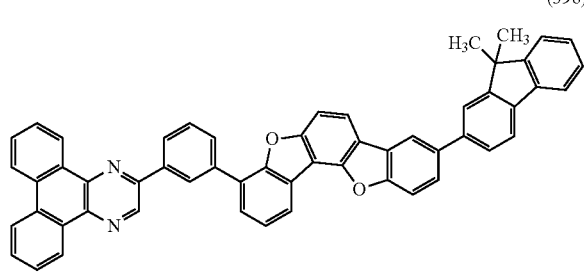

(399)
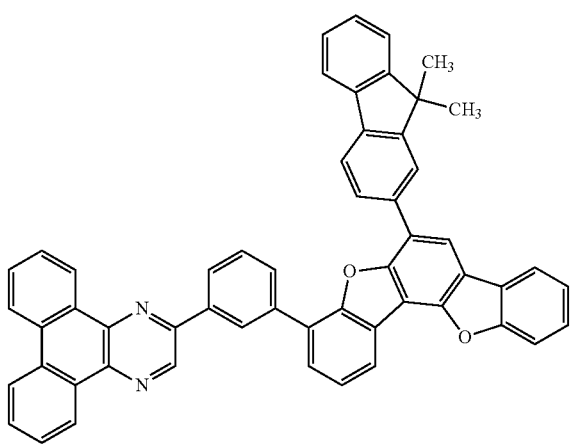

(400)
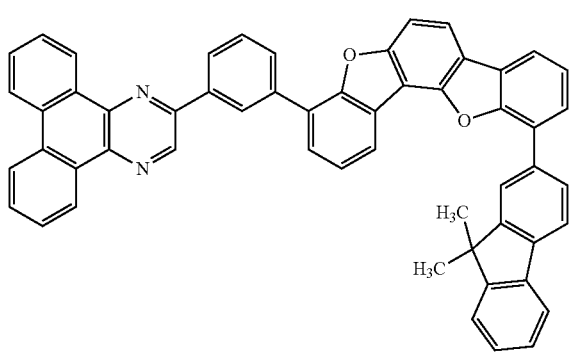

Note that the heterocyclic compounds represented by the structural formulae (101) to (184) and the structural formulae (201) to (400) are examples of the heterocyclic compounds represented by the general formulae (G1) and (G2) and the heterocyclic compound of one embodiment of the present invention is not limited thereto.

Next, an example of a method for synthesizing the heterocyclic compound which is one embodiment of the present invention represented by the following general formula (G1) is described. Note that a variety of reactions can be applied in the method of synthesizing the organic compound represented by the general formula (G1), and the organic compound represented by the general formula (G1) can be synthesized through the following method, for example. However, the method for synthesizing the organic compound of one embodiment of the present invention represented by the general formula (G1) is not limited to the following synthesis method.

[Chemical Formula 39]

In the general formula (G1), DBq represents a substituted or unsubstituted dibenzo[f,h]quinoxalinyl group, $Ar^1$ represents a substituted or unsubstituted arylene group having 6 to 13 carbon atoms, n represents 0 or 1, $Ar^2$ represents a substituted or unsubstituted arylene group having 6 to 13 carbon atoms, and A represents a substituted or unsubstituted benzobisbenzofuranyl group. When the arylene group represented by $Ar^1$ and $Ar^2$ has substituents, the substituents may be bonded to each other to form a ring. Among carbon atoms that do not form a furan ring in the benzobisbenzofuranyl group, any one of carbon atoms adjacent to a carbon atom of the furan ring, which is bonded to oxygen, is bonded to $Ar^2$.

A synthesis scheme (A) of the heterocyclic compound represented by the general formula (G1) is shown below. As shown in the synthesis scheme (A), a dibenzo[f,h]quinoxaline compound (compound 1) and a benzobisbenzofuran compound (compound 2) are coupled, so that the heterocyclic compound represented by the general formula (G1) can be synthesized.

[Chemical Formulae 40]

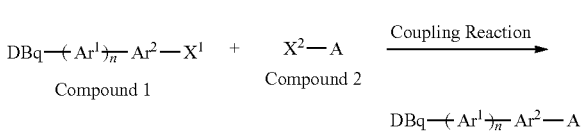

In the synthesis scheme (A), DBq represents a substituted or unsubstituted dibenzo[f,h]quinoxalinyl group, $Ar^1$ represents a substituted or unsubstituted arylene group having 6 to 13 carbon atoms, n represents 0 or 1, $Ar^2$ represents a substituted or unsubstituted arylene group having 6 to 13 carbon atoms, and A represents a substituted or unsubstituted benzobisbenzofuranyl group. When the arylene group represented by $Ar^1$ and $Ar^2$ has substituents, the substituents may be bonded to each other to form a ring.

When a Suzuki—Miyaura coupling reaction using a palladium catalyst is performed in the synthesis scheme (A), $X^1$ and $X^2$ each independently represent a halogen group, a boronic acid group, an organoboron group, or a triflate group, and the halogen group is preferably, iodine, bromine, or chlorine. In the reaction, a palladium compound such as bis(dibenzylideneacetone)palladium(0), palladium(II) acetate, [1,1'-bis(diphenylphosphino)ferrocene]palladium(II) dichloride, or tetrakis(triphenylphosphine)palladium(0)

and a ligand such as tri(tert-butyl)phosphine, tri(n-hexyl) phosphine, tricyclohexylphosphine, di(1-adamantyl)-n-butylphosphine, 2-dicyclohexylphosphino-2',6'-dimethoxybiphenyl, or tri(ortho-tolyl)phosphine can be used.

In addition, in the reaction shown in the synthesis scheme (A), an organic base such as sodium tert-butoxide, an inorganic base such as potassium carbonate, cesium carbonate, or sodium carbonate, or the like can be used. Further, toluene, xylene, benzene, tetrahydrofuran, dioxane, ethanol, methanol, water, or the like can be used as a solvent. Reagents that can be used are not limited thereto.

The reaction in the synthesis scheme (A) is not limited to a Suzuki-Miyaura coupling reaction, and a Migita-Kosugi-Stille coupling reaction using an organotin compound, a Kumada-Tamao-Corriu coupling reaction using a Grignard reagent, a Negishi coupling reaction using an organozinc compound, a reaction using copper or a copper compound, or the like may also be employed.

In the case of using the Migita-Kosugi-Stille coupling reaction in the synthesis scheme (A), one of $X^1$ and $X^2$ represents an organotin group and the other represents a halogen group. That is, one of the compounds 1 and 2 represents an organotin compound.

In the case of using the Kumada-Tamao-Corriu coupling reaction in the synthesis scheme (A), one of $X^1$ and $X^2$ represents a halogenated magnesium group and the other represents a halogen group. That is, one of the compounds 1 and 2 represents a Grignard reagent.

In the case of using the Negishi coupling reaction in the synthesis scheme (A), one of $X^1$ and $X^2$ represents an organozinc group and the other represents a halogen group. That is, one of the compounds 1 and 2 represents an organozinc compound.

Note that in the synthesis of the organic compound (G1) of the present invention, the synthesis method is not limited to the synthesis scheme (A).

The above is the description of the examples of a method for synthesizing the heterocyclic compound of one embodiment of the present invention; however, the present invention is not limited thereto and any other synthesis method may be employed.

Note that the above heterocyclic compounds which are embodiments of the present invention each have an electron-transport property and a hole-transport property, and thus can be used as host materials in light-emitting layers, or can be used in electron-transport layers and hole-transport layers. Furthermore, the above heterocyclic compounds are materials with a high T1 level, and thus are preferably used in combination with a substance that emits phosphorescence (phosphorescent material) as host materials. In addition, the above heterocyclic compounds emit fluorescence and thus can be used as light-emitting substances of light-emitting elements. Accordingly, light-emitting elements containing these heterocyclic compounds are also included as embodiments of the present invention.

With the use of the heterocyclic compound of one embodiment of the present invention, a light-emitting element, a light-emitting device, an electronic device, or a lighting device having high emission efficiency can be obtained. It is also possible to obtain a light-emitting element, a light-emitting device, an electronic device, or a lighting device with low power consumption.

Note that embodiments of the present invention have been described in Embodiment 1. Other embodiments of the present invention are described in Embodiments 2 to 8. However, embodiments of the present invention are not limited to these embodiments. That is, since various embodiments of the present invention are disclosed in Embodiments 1 to 8, one embodiment of the present invention is not limited to a specific embodiment. Although an example in which one embodiment of the present invention is used in a light-emitting element is described, one embodiment of the present invention is not limited thereto. Depending on circumstances or conditions, one embodiment of the present invention may be used in objects other than a light-emitting element. Furthermore, depending on circumstances or conditions, one embodiment of the present invention need not be used in a light-emitting element.

The structure described in this embodiment can be used in appropriate combination with any of the structures described in the other embodiments.

(Embodiment 2)

In this embodiment, a light-emitting element which is one embodiment of the present invention will be described with reference to FIGS. 1A and 1B.

In the light-emitting element described in this embodiment, an EL layer 102 including a light-emitting layer 113 is interposed between a pair of electrodes (a first electrode (anode) 101 and a second electrode (cathode) 103), and the EL layer 102 includes a hole-injection layer 111, a hole-transport layer 112, an electron-transport layer 114, an electron-injection layer 115, and the like in addition to the light-emitting layer 113.

When a voltage is applied to the light-emitting element, holes injected from the first electrode 101 side and electrons injected from the second electrode 103 side recombine in the light-emitting layer 113; with energy generated by the recombination, a light-emitting substance such as an organometallic complex that is contained in the light-emitting layer 113 emits light.

The hole-injection layer 111 in the EL layer 102 can inject holes into the hole-transport layer 112 or the light-emitting layer 113 and can be formed of, for example, a substance having a high hole-transport property and a substance having an acceptor property, in which case electrons are extracted from the substance having a high hole-transport property by the substance having an acceptor property to generate holes. Thus, holes are injected from the hole-injection layer 111 into the light-emitting layer 113 through the hole-transport layer 112. For the hole-injection layer 111, a substance having a high hole-injection property can also be used. For example, molybdenum oxide, vanadium oxide, ruthenium oxide, tungsten oxide, manganese oxide, or the like can be used. Alternatively, the hole-injection layer 111 can be formed using a phthalocyanine-based compound such as phthalocyanine (abbreviation: $H_2Pc$) and copper phthalocyanine (CuPc), an aromatic amine compound such as 4,4'-bis[N-(4-diphenylaminophenyl)-N-phenylamino]biphenyl (abbreviation: DPAB) and N,N'-bis{4-[bis(3-methylphenyl)amino]phenyl}-N,N'-diphenyl-(1,1'-biphenyl)-4,4'-diamine (abbreviation: DNTPD), or a high molecular compound such as poly(3,4-ethylenedioxythiophene)/poly(styrenesulfonic acid) (abbreviation: PEDOT/PSS).

A specific example in which the light-emitting element described in this embodiment is fabricated is described below.

For the first electrode (anode) 101 and the second electrode (cathode) 103, a metal, an alloy, an electrically conductive compound, a mixture thereof, and the like can be used. Specific examples are indium oxide-tin oxide (indium tin oxide), indium oxide-tin oxide containing silicon or silicon oxide, indium oxide-zinc oxide (indium zinc oxide), indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), and titanium (Ti). In addition, an element belonging to Group 1 or Group 2 of the periodic table, for example, an alkali metal such as lithium (Li) or cesium (Cs), an alkaline earth metal such as calcium (Ca) or strontium (Sr), magnesium (Mg), and an alloy containing such an element (MgAg or AlLi); a rare earth metal such as europium (Eu) or ytterbium (Yb) and an alloy containing such an element; a graphene compound such as graphene or graphene oxide; and the like can be used. The first electrode (anode) 101 and the second electrode (cathode) 103 can be formed by, for example, a sputtering method or an evaporation method (including a vacuum evaporation method).

As the substance having a high hole-transport property which is used for the hole-injection layer 111 and the hole-transport layer 112, any of a variety of organic compounds such as aromatic amine compounds, carbazole derivatives, aromatic hydrocarbons, and high molecular compounds (e.g., oligomers, dendrimers, or polymers) can be used. Specifically, a substance having a hole mobility of $1\times10^{-6}$ cm$^2$/Vs or more is preferably used. The layer formed using the substance having a high hole-transport property is not limited to a single layer and may be formed by stacking two or more layers. Organic compounds that can be used as the substance having a hole-transport property are specifically given below.

Examples of the aromatic amine compounds are N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), DNTPD, 1,3,5-tris[N-(4-diphenylaminophenyl)-N-phenylamino]benzene (abbreviation: DPA3B), 4,4'-bis[N-(1-naphthyl)-N-phenylamino]biphenyl (abbreviation: NPB or α-NPD), N,N'-bis(3-methylphenyl)-N,N'- diphenyl-[1,1'-biphenyl]-4,4'-diamine (abbreviation: TPD), 4,4',4"-tris(carbazol-9-yl)triphenylamine (abbreviation: TCTA), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB), and the like.

Specific examples of carbazole derivatives are 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like. Other examples are 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthracenyl)phenyl]-9H-carbazole (abbreviation: CzPA), 1,4-bis[4-(N-carbazolyl)phenyl]-2,3,5,6-tetraphenylbenzene, and the like.

Examples of aromatic hydrocarbons are 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, and the like. Besides, pentacene, coronene, or the like can also be used. The aromatic hydrocarbon which has a hole mobility of $1\times10^{-6}$ cm$^2$/Vs or more and which has 14 to 42 carbon atoms is particularly preferable. The aromatic hydrocarbons may have a vinyl skeleton. Examples of the aromatic hydrocarbon having a vinyl group are 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

A high molecular compound such as poly(N-vinylcarbazole) (abbreviation: PVK), poly(4-vinyltriphenylamine) (abbreviation: PVTPA), poly[N-(4- {N-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine](abbreviation: Poly-TPD) can also be used.

Examples of the substance having an acceptor property which is used for the hole-injection layer 111 and the hole-transport layer 112 are compounds having an electron-withdrawing group (a halogen group or a cyano group) such as 7,7,8,8-tetracyano-2,3,5,6-tetrafluoroquinodimethane (abbreviation: F4-TCNQ), chloranil, and 2,3,6,7,10,11-hexacyano-1,4,5,8,9,12-hexaazatriphenylene (HAT-CN). In particular, a compound in which electron-withdrawing groups are bonded to a condensed aromatic ring having a plurality of heteroatoms, like HAT-CN, is thermally stable and preferable. Oxides of metals belonging to Groups 4 to 8 of the periodic table can be given. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable because it is stable in the air, has a low hygroscopic property, and is easy to handle.

The light-emitting layer 113 contains a light-emitting substance, which may be a fluorescent substance or a phosphorescent substance. As the phosphorescent substance, an organometallic complex is used specifically. In the case where an organometallic complex (guest material) is used in the light-emitting layer 113, it is preferable that a substance having higher triplet excitation energy than this organometallic complex be contained as a host material. Alternatively, the light-emitting layer 113 may contain, in addition to the light-emitting substance, two kinds of organic compounds that can form an excited complex (also called an exciplex) at the time of recombination of carriers (electrons and holes) in the light-emitting layer 113 (the two kinds of organic compounds may be any of host materials as described above). In order to form an exciplex efficiently, it is particularly preferable to combine a compound which easily accepts electrons (a material having an electron-transport property) and a compound which easily accepts holes (a material having a hole-transport property). In the case where the combination of a material having an electron-transport property and a material having a hole-transport property which form an exciplex is used as a host material as described above, the carrier balance between holes and electrons in the light-emitting layer can be easily optimized by adjustment of the mixture ratio of the material having an electron-transport property and the material having a hole-transport property. The optimization of the carrier balance between holes and electrons in the light-emitting layer can prevent a region in which electrons and holes are recombined from existing on one side in the light-emitting layer. By preventing the region in which electrons and holes are recombined from existing on one side, the reliability of the light-emitting element can be improved.

As the compound that is preferably used to form the above exciplex and easily accepts electrons (material having an electron-transport property), a π-electron deficient heteroaromatic compound such as a nitrogen-containing heteroaromatic compound, a metal complex, or the like can be used. Specific examples include metal complexes such as bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds having polyazole skeletons, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2''-(1,3,5-benzenetriyl)tris(1-phenyl-1H-benzimidazole) (abbreviation: TPBI), and 2-[3-(dibenzothiophen-4-yl)phenyl]-1-phenyl-1H-benzimidazole (abbreviation: mDBT-BIm-II); heterocyclic compounds having diazine skeletons, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3 '-(9H-carbazol-9-yl)biphenyl-3-yl]dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[f,h]quinoxaline (abbreviation: 6mDBTPDBq-II), 4,6-bis[3-(phenanthren-9-yl)phenyl]pyrimidine (abbreviation: 4,6mPnP2Pm), 4,6-bis[3-(4-dibenzothienyl)pheny]pyrimidine (abbreviation: 4,6mDBTP2Pm-II), and 4,6-bis[3-(9H-carbazol-9-yl)-phenyl]pyrimidine (abbreviation: 4,6mCzP2Pm); a heterocyclic compound having a triazine skeleton such as 2-{4-[3-(N-phenyl-9H-carbazol-3-yl)-9H-carbazol-9-yl]phenyl}-4,6-diphenyl-1,3,5-triazine (abbreviation: PCCzPTzn); and heterocyclic compounds having pyridine skeletons, such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB). Among the above materials, the heterocyclic compounds having diazine skeletons, those having triazine skeletons, and those having pyridine skeletons are highly reliable and preferred. In particular, the heterocyclic compounds having diazine (pyrimidine or pyrazine) skeletons and those having triazine skeletons have a high electron-transport property and contribute to a decrease in drive voltage.

As the compound that is preferably used to form the above exciplex and easily accepts holes (the material having a hole-transport property), a π-electron rich heteroaromatic compound (e.g., a carbazole derivative or an indole derivative), an aromatic amine compound, or the like can be favorably used. Specific examples are compounds having aromatic amine skeletons, such as 2-[N-(9-phenylcarbazol-3-yl)-N-phenylamino]spiro-9,9'-bifluorene (abbreviation: PCASF), 4,4',4''-tris[N-(1-naphthyl)-N-phenylamino]triphenylamine (abbreviation: 1'-TNATA), 2,7-bis[N-(4-diphenylaminophenyl)-N-phenylamino]-spiro-9,9'-bifluorene (abbreviation: DPA2SF), N,N'-bis(9-phenylcarbazol-3-yl)-N,N'-diphenylbenzene-1,3-diamine (abbreviation: PCA2B), N-(9,9-dimethyl-2-diphenylamino-9H-fluoren-7-yl)diphenylamine (abbreviation: DPNF), N,N',N''-triphenyl-N,N',N''-tris(9-phenylcarbazol-3-yl)benzene-1,3,5-triamine (abbreviation: PCA3B), 2-[N-(4-diphenylaminophenyl)-N-phenylamino]spiro-9,9'-bifluorene (abbreviation: DPASF), N,N'-bis-[4-(carbazol-9-yl)phenyl]-N,N'-diphenyl-9,9-dimethylfluorene-2,7-diamine (abbreviation: YGA2F), NPB, N,N'-bis(3-methylphenyl)-N,N'-diphenyl-[1,1'-biphenyl]-4,4'-diamine (abbreviation: TPD), 4,4'-bis[N-(4-diphenylaminophenyl)-N-phenylamino]biphenyl (abbreviation: DPAB), BSPB, 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), PCzPCA1, 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), DNTPD, 3,6-bis[N-(4-diphenylaminophenyl)-N-(1-naphthyl)amino]-9-phenylcarbazole (abbreviation: PCzTPN2), PCzPCA2, 4-phenyl-4'-(9-phenyl-9H-carbazol-3-yl)triphenylamine (abbreviation: PCBA1BP), 4,4'-diphenyl-4''-(9-phenyl-9H-carbazol-3-yl)triphenylamine (abbreviation: PCBBiIBP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), 3-[N-(1-naphthyl)-N-(9-phenylcarbazol-3-yl)amino]-9-phenylcarbazole (abbreviation: PCzPCN1), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), N-(4-biphenyl)-N-(9,9-dimethyl-9H-fluoren-2-yl)-9-phenyl-9H-carbazol-3-amine (abbreviation: PCBiF), and N-(1,1'-biphenyl-4-yl)-N-[4-(9-phenyl-9H-carbazol-3-yl)phenyl]-9,9-dimethyl-9H-fluoren-2-amine (abbreviation: PCBBiF); compounds having carbazole skeletons, such as 1,3-bis(N-carbazolyl)benzene (abbreviation: mCP), CBP, 3,6-bis(3,5-diphenylphenyl)-9-phenylcarbazole (abbreviation: CzTP), and 9-phenyl-9H-3-(9-phenyl-9H-carbazol-3-yl)carbazole (abbreviation: PCCP); compounds having thiophene skeletons, such as 4,4',4''-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having furan skeletons, such as 4,4',4''-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II). Among the above materials, the compounds having aromatic amine skeletons and the compounds having carbazole skeletons are preferred because these compounds are highly reliable and have a high hole-transport property and contribute to a reduction in drive voltage.

Note that in the case where the light-emitting layer 113 contains the above-described organometallic complex (guest material) and the host material, phosphorescence with high emission efficiency can be obtained from the light-emitting layer 113.

Figure 1B:

In the light-emitting element, the light-emitting layer 113 does not necessarily have the single-layer structure illustrated in FIG. 1A and may have a stacked-layer structure including two or more layers as illustrated in FIG. 1B. In that case, each layer in the stacked-layer structure emits light. For example, fluorescence is obtained from a first light-emitting layer 113(a1), and phosphorescence is obtained from a second light-emitting layer 113(a2) stacked over the first light-emitting layer. Note that the stacking order may be reversed. It is preferable that light emission due to energy transfer from an exciplex to a dopant be obtained from the layer that emits phosphorescence. The emission color of one layer and that of the other layer may be the same or different. In the case where the emission colors are different, a structure in which, for example, blue light from one layer and orange, yellow light, or the like from the other layer can be obtained can be formed. Each layer may contain various kinds of dopants.

Note that in the case where the light-emitting layer 113 has a stacked-layer structure, a light-emitting substance converting singlet excitation energy into light emission or a light-emitting substance converting triplet excitation energy into light emission can be used alone or in combination, for example. In that case, the following substances can be used.

As an example of the light-emitting substance converting singlet excitation energy into light emission, a substance which emits fluorescence (a fluorescent compound) can be given.

Examples of the substance emitting fluorescence are N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N''-(2-tert-butylanthracene-9,10-diyldi-4,1-phenylene)bis[N,N',N'-triphenyl-1,4-phenylenediamine](abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), and the like.

Examples of the light-emitting substance converting triplet excitation energy into light emission are a substance which emits phosphorescence (a phosphorescent compound) and a thermally activated delayed fluorescent (TADF) material which emits thermally activated delayed fluorescence. Note that "delayed fluorescence" exhibited by the TADF material refers to light emission having the same spectrum as normal fluorescence and an extremely long lifetime. The lifetime is $1\times10^{-6}$ seconds or longer, preferably $1\times10^{-3}$ seconds or longer.

Examples of the substance emitting phosphorescence are bis {2-[3',5'-bis(trifluoromethyl)phenyl]pyridinato-N,$C^{2'}$}iridium(III) picolinate (abbreviation: [Ir(CF$_3$ppy)$_2$(pic)], bis[2-(4',6'-difluorophenyl)pyridinato-N,$C^{2'}$]iridium (III) acetylacetonate (abbreviation: FIracac), tris(2-phenylpyridinato)iridium(III) (abbreviation: [Ir(ppy)$_3$]), bis (2-phenylpyridinato)iridium(III) acetylacetonate (abbreviation: [Ir(ppy)$_2$(acac)]), tris(acetylacetonato)(monophenanthroline)terbium(III) (abbreviation: [Tb(acac)$_3$(Phen)]), bis(benzo[h]quinolinato)iridium(III) acetylacetonate (abbreviation: [Ir(bzq)$_2$(acac)]), bis(2,4-diphenyl-1,3-oxazolato-N,$C^{2'}$)iridium(III) acetylacetonate (abbreviation: [Ir(dpo)$_2$(acac)]), bis {2-[4'-(perfluorophenyl)phenyl]pyridinato-N,$C^{2'}$}iridium(III) acetylacetonate (abbreviation: [Ir(p-PF-ph)$_2$(acac)]), bis(2-phenylbenzothiazolato-N,$C^{2'}$)iridium(III) acetylacetonate (abbreviation: [Ir(bt)$_2$(acac)]), bis[2-(2'-benzo[4,5-α]thienyl)pyridinato-N,$C^{3'}$]iridium(III) acetylacetonate (abbreviation: [Ir(btp)$_2$(acac)]), bis(1-phenysoquinolinato-N,$C^{2'}$)iridium(III) acetylacetonate (abbreviation: [Ir(piq)$_2$(acac)]), (acetylacetonato)bis[2,3-bis(4-fluorophenyl)quinoxalinato]iridium(III) (abbreviation: [Ir(Fdpq)$_2$(acac)]), (acetylacetonato)bis(3,5-dimethyl-2-phenylpyrazinato)iridium(III) (abbreviation: [Ir(mppr-Me)$_2$(acac)]), (acetylacetonato)bis(5isopropyl-3-methyl-2-phenylpyrazinato)iridium(III) (abbreviation: [Ir(mppr-iPr)$_2$(acac)]), (acetylacetonato)bis(2,3,5-triphenylpyrazinato) iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)], (acetylacetonato)bis(6-tert-butyl-4-phenylpyrimidinato)iridium(III) (abbreviation: [Ir(tBuppm)$_2$(acac)]), (acetylacetonato)bis(4,6-diphenylpyrimidinato)iridium(III) (abbreviation: [Ir(dppm)$_2$(acac)]), 2,3,7,8,12,13,17,18-octaethyl-21H,23H-porphyrin platinum (II) (abbreviation: PtOEP), tris(1,3-diphenyl-1,3-propanedionato)(monophenanthroline)europium(III) (abbreviation: [Eu(DBM)$_3$(Phen)]), tris[1-(2-thenoyl)-3,3,3-trifluoroacetonato](monophenanthroline)europium(III) (abbreviation: [Eu (TTA)$_3$(Phen)]), and the like.

Examples of the TADF material are fullerene, a derivative thereof, an acridine derivative such as proflavine, eosin, and the like. Other examples are a metal-containing porphyrin, such as a porphyrin containing magnesium (Mg), zinc (Zn), cadmium (Cd), tin (Sn), platinum (Pt), indium (In), or palladium (Pd). Examples of the metal-containing porphyrin are a protoporphyrin-tin fluoride complex (abbreviation: SnF$_2$(Proto IX)), a mesoporphyrin-tin fluoride complex (abbreviation: SnF$_2$(Meso IX)), a hematoporphyrin-tin fluoride complex (abbreviation: SnF$_2$(Hemato IX)), a coproporphyrin tetramethyl ester-tin fluoride complex (abbreviation: SnF$_2$(Copro III-4Me)), an octaethylporphyrin-tin fluoride complex (abbreviation: SnF$_2$(OEP)), an etioporphyrin-tin fluoride complex (abbreviation: SnF$_2$(Etio I)), an octaethylporphyrin-platinum chloride complex (abbreviation: PtCl$_2$OEP), and the like. Alternatively, a heterocyclic compound including a π-electron rich heteroaromatic ring and a π-electron deficient heteroaromatic ring can be used, such as 2-(biphenyl-4-yl)-4,6-bis(12-phenylindolo[2,3-a]carbazol-11-yl)-1,3,5-triazine (abbreviation: PIC-TRZ). Note that a material in which the π-electron rich heteroaromatic ring is directly bonded to the π-electron deficient heteroaromatic ring is particularly preferably used because the donor property of the π-electron rich heteroaromatic ring and the acceptor property of the π-electron deficient heteroaromatic ring are both increased and the energy difference between the S1 level and the T1 level becomes small.

The electron-transport layer 114 is a layer containing a substance having a high electron-transport property (also referred to as an electron-transport compound). For the electron-transport layer 114, a metal complex such as tris (8-quinolinolato)aluminum (abbreviation: Alq$_3$), tris(4-methyl-8-quinolinolato)aluminum (abbreviation: Almq$_3$), BeBq$_2$, BAlq, bis[2-(2-hydroxyphenyl)benzoxazolato]zinc (abbreviation: Zn(BOX)$_2$), or bis[2-(2-hydroxyphenyl)benzothiazolato]zinc (abbreviation: Zn(BTZ)$_2$) can be used. Alternatively, a heteroaromatic compound such as PBD, OXD-7, TAZ, 3-(4-tert-butylphenyl)-4-(4-ethylphenyl)-5-(4-biphenylyl)-1,2,4-triazole (abbreviation: p-EtTAZ), bathophenanthroline (abbreviation: Bphen), bathocuproine (abbreviation: BCP), or 4,4'-bis(5-methylbenzoxazol-2-yl) stilbene (abbreviation: BzOs) can also be used. A high molecular compound such as poly(2,5-pyridinediyl) (abbreviation: PPy), poly[(9,9-dihexylfluorene-2,7-diyl)-co-(pyridine-3,5-diyl)](abbreviation: PF-Py), or poly[(9,9-dioctylfluorene-2,7-diyl)-co-(2,2'-bipyridine-6,6'-diyl)] (abbreviation: PF-BPy) can also be used. The substances listed here are mainly ones that have an electron mobility of 1×10$^{-6}$ cm$^2$/Vs or more. Note that any substance other than the substances listed here may be used for the electron-transport layer 114 as long as the electron-transport property is higher than the hole-transport property.

The electron-transport layer 114 is not limited to a single layer, but may be a stack of two or more layers each containing any of the substances listed above.

The electron-injection layer 115 is a layer containing a substance having a high electron-injection property. For the electron-injection layer 115, an alkali metal, an alkaline earth metal, or a compound thereof such as lithium fluoride (LiF), cesium fluoride (CsF), calcium fluoride (CaF$_2$), or lithium oxide (LiO$_x$) can be used. A rare earth metal compound like erbium fluoride (ErF$_3$) can also be used. An electride may also be used for the electron-injection layer 115. Examples of the electride include a substance in which electrons are added at high concentration to calcium oxide-aluminum oxide. Any of the substances for forming the electron-transport layer 114, which are given above, can be used.

A composite material in which an organic compound and an electron donor (donor) are mixed may also be used for the electron-injection layer 115. Such a composite material is excellent in an electron-injection property and an electron-transport property because electrons are generated in the organic compound by the electron donor. In this case, the organic compound is preferably a material that is excellent in transporting the generated electrons. Specifically, for example, the substances for forming the electron-transport layer 114 (e.g., a metal complex or a heteroaromatic compound), which are given above, can be used. As the electron donor, a substance showing an electron-donating property with respect to the organic compound may be used. Specifically, an alkali metal, an alkaline earth metal, and a rare earth metal are preferable, and lithium, cesium, magnesium, calcium, erbium, ytterbium, and the like are given. In addition, an alkali metal oxide or an alkaline earth metal oxide is preferable, and lithium oxide, calcium oxide, barium oxide, and the like are given. A Lewis base such as magnesium oxide can also be used. An organic compound such as tetrathiafulvalene (abbreviation: TTF) can also be used.

Note that each of the hole-injection layer 111, the hole-transport layer 112, the light-emitting layer 113, the electron-transport layer 114, and the electron-injection layer 115 can be formed by any one or any combination of the following methods: an evaporation method (including a vacuum evaporation method), a printing method (such as relief printing, intaglio printing, gravure printing, planography printing, and stencil printing), an ink-jet method, a coating method, and the like. Besides the above-mentioned materials, an inorganic compound such as a quantum dot or a high molecular compound (e.g., an oligomer, a dendrimer, or a polymer) may be used for the hole-injection layer 111, the hole-transport layer 112, the light-emitting layer 113, the electron-transport layer 114, and the electron-injection layer 115, which are described above.

In the above-described manner, a light-emitting element in which an EL layer is sandwiched between a pair of electrodes can be manufactured.

The structure described in this embodiment can be used in appropriate combination with any of the structures described in the other embodiments.

(Embodiment 3)

In this embodiment, a light-emitting element (hereinafter referred to as a tandem light-emitting element) which is one embodiment of the present invention and includes a plurality of EL layers will be described.

Figure 2A:
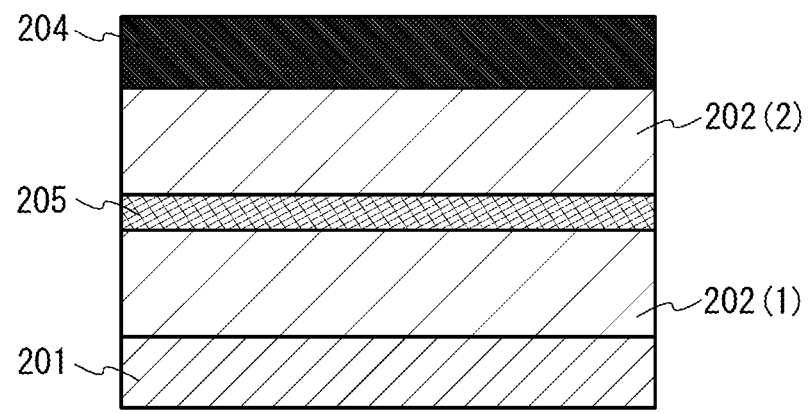
FIGS. 2A and 2B illustrate structures of light-emitting elements.

A light-emitting element described in this embodiment is a tandem light-emitting element including, between a pair of electrodes (a first electrode 201 and a second electrode 204), a plurality of EL layers (a first EL layer 202(1) and a second EL layer 202(2)) and a charge-generation layer 205 provided therebetween, as illustrated in FIG. 2A.

In this embodiment, the first electrode 201 functions as an anode, and the second electrode 204 functions as a cathode. Note that the first electrode 201 and the second electrode 204 can have structures similar to those described in Embodiment 2. In addition, either or both of the EL layers (the first EL layer 202(1) and the second EL layer 202(2)) may have structures similar to those described in Embodiment 2. In other words, the structures of the first EL layer 202(1) and the second EL layer 202(2) may be the same as or different from each other. When the structures are the same, Embodiment 2 can be referred to.

The charge-generation layer 205 provided between the plurality of EL layers (the first EL layer 202(1) and the second EL layer 202(2)) has a function of injecting electrons into one of the EL layers and injecting holes into the other of the EL layers when a voltage is applied between the first electrode 201 and the second electrode 204. In this embodiment, when a voltage is applied such that the potential of the first electrode 201 is higher than that of the second electrode 204, the charge-generation layer 205 injects electrons into the first EL layer 202(1) and injects holes into the second EL layer 202(2).

Note that in terms of light extraction efficiency, the charge-generation layer 205 preferably has a property of transmitting visible light (specifically, the charge-generation layer 205 has a visible light transmittance of 40% or more). The charge-generation layer 205 functions even when it has lower conductivity than the first electrode 201 or the second electrode 204.

The charge-generation layer 205 may have either a structure in which an electron acceptor (acceptor) is added to an organic compound having a high hole-transport property or a structure in which an electron donor (donor) is added to an organic compound having a high electron-transport property. Alternatively, both of these structures may be stacked.

In the case of the structure in which an electron acceptor is added to an organic compound having a high hole-transport property, as the organic compound having a high hole-transport property, the substances having a high hole-transport property which are given in Embodiment 2 as the substances used for the hole-injection layer 111 and the hole-transport layer 112 can be used. For example, an aromatic amine compound such as NPB, TPD, TDATA, MTDATA, or BSPB, or the like can be used. The substances listed here are mainly ones that have a hole mobility of $1 \times 10^{-6}$ cm$^2$/Vs or more. Note that any organic compound other than the compounds listed here may be used as long as the hole-transport property is higher than the electron-transport property.

As the electron acceptor, 7,7,8,8-tetracyano-2,3,5,6-tetra-fluoroquinodimethane (abbreviation: F4-TCNQ), chloranil, and the like can be given. Oxides of metals belonging to Groups 4 to 8 of the periodic table can also be given. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable because it is stable in the air, has a low hygroscopic property, and is easy to handle.

In the case of the structure in which an electron donor is added to an organic compound having a high electron-transport property, as the organic compound having a high electron-transport property, the substances having a high electron-transport property which are given in Embodiment 2 as the substances used for the electron-transport layer 114 can be used. For example, a metal complex having a quinoline skeleton or a benzoquinoline skeleton, such as Alq, Almq$_3$, BeBq$_2$, or BAlq, or the like can be used. Alternatively, a metal complex having an oxazole-based ligand or a thiazole-based ligand, such as Zn(BOX)$_2$ or Zn(BTZ)$_2$, can be used. Alternatively, in addition to such a metal complex, PBD, OXD-7, TAZ, Bphen, BCP, or the like can be used. The substances listed here are mainly ones that have an electron mobility of $1 \times 10^{-6}$ cm$^2$/Vs or more. Note that any organic compound other than the compounds listed here may be used as long as the electron-transport property is higher than the hole-transport property.

As the electron donor, it is possible to use an alkali metal, an alkaline earth metal, a rare earth metal, metals belonging to Groups 2 and 13 of the periodic table, or an oxide or carbonate thereof. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the electron donor.

Note that forming the charge-generation layer 205 by using any of the above materials can suppress a drive voltage increase caused by the stack of the EL layers.

The charge-generation layer 205 can be formed by any one or any combination of the following methods: an evaporation method (including a vacuum evaporation method), a printing method (such as relief printing, intaglio printing, gravure printing, planography printing, and stencil printing), an ink-jet method, a coating method, and the like.

Figure 2B:
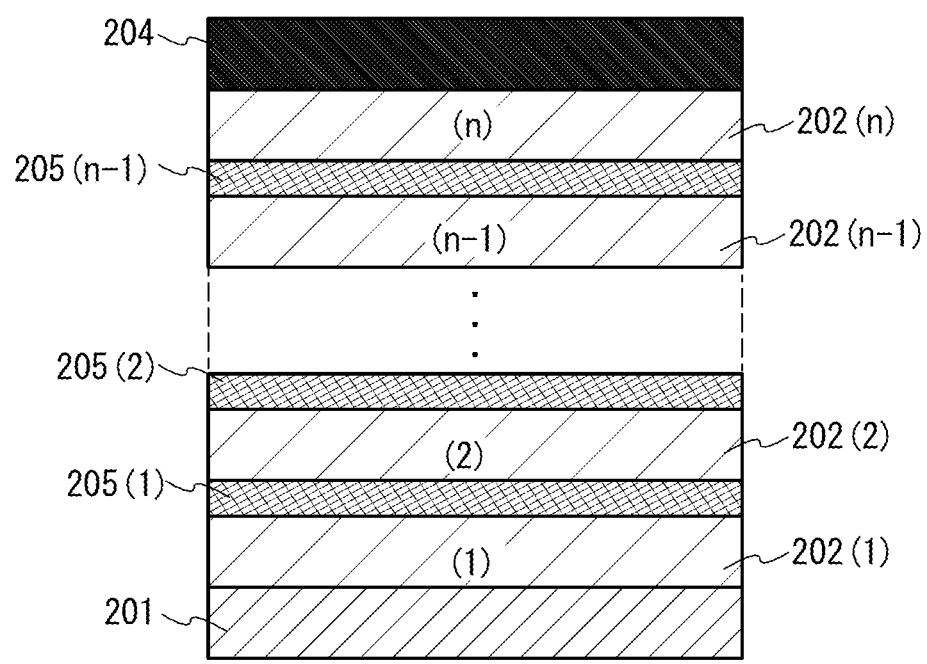

Although the light-emitting element including two EL layers is described in this embodiment, the present invention can be similarly applied to a light-emitting element in which n EL layers (202(1) to 202(n)) (n is three or more) are stacked as illustrated in FIG. 2B. In the case where a plurality of EL layers are included between a pair of electrodes as in the light-emitting element according to this embodiment, by providing charge-generation layers (205(1) to 205(n-1)) between the EL layers, light emission in a high luminance region can be obtained with current density kept low. Since the current density can be kept low, the element can have a long lifetime.

When the EL layers have different emission colors, a desired emission color can be obtained from the whole light-emitting element. For example, in a light-emitting element having two EL layers, when an emission color of the first EL layer and an emission color of the second EL layer are complementary colors, the light-emitting element can emit white light as a whole. Note that "complementary colors" refer to colors that can produce an achromatic color when mixed. In other words, mixing light of complementary colors allows white light emission to be obtained. Specifically, a combination in which blue light emission is obtained from the first EL layer and yellow or orange light emission is obtained from the second EL layer is given as an example. In that case, it is not necessary that both of blue light emission and yellow (or orange) light emission are fluorescence, and the both are not necessarily phosphorescence. For example, a combination in which blue light emission is fluorescence and yellow (or orange) light emission is phosphorescence or a combination in which blue light emission is phosphorescence and yellow (or orange) light emission is fluorescence may be employed.

The same can be applied to a light-emitting element having three EL layers. For example, the light-emitting element as a whole can provide white light emission when the emission color of the first EL layer is red, the emission color of the second EL layer is green, and the emission color of the third EL layer is blue.

The structure described in this embodiment can be used in appropriate combination with any of the structures described in the other embodiments.

(Embodiment 4)

In this embodiment, a light-emitting device which is one embodiment of the present invention will be described.

The light-emitting device may be either a passive matrix light-emitting device or an active matrix light-emitting device. Any of the light-emitting elements described in other embodiments can be used in the light-emitting device described in this embodiment.

In this embodiment, first, an active matrix light-emitting device is described with reference to FIGS. 3A to 3C.

Figure 3A:
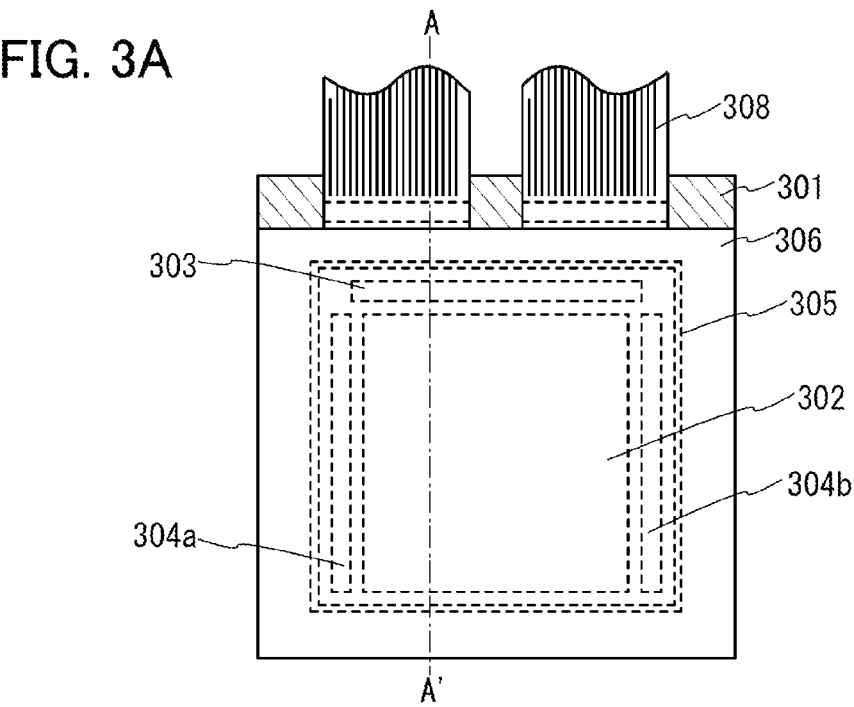
FIGS. 3A to 3C illustrate light-emitting devices.
Figure 3B:
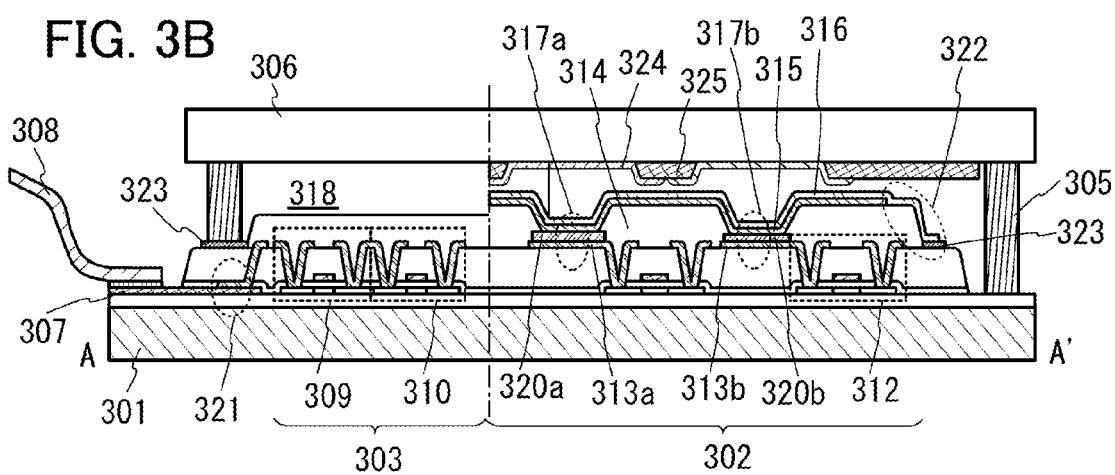

Note that FIG. 3A is a top view illustrating a light-emitting device, and FIG. 3B is a cross-sectional view taken along the chain line A-A' in FIG. 3A. The active matrix light-emitting device includes a pixel portion 302 provided over an element substrate 301, a driver circuit portion (a source line driver circuit) 303, and driver circuit portions (gate line driver circuits) 304a and 304b. The pixel portion 302, the driver circuit portion 303, and the driver circuit portions 304a and 304b are sealed between the element substrate 301 and a sealing substrate 306 with a sealant 305.

In addition, over the element substrate 301, a lead wiring 307 for connecting an external input terminal, through which a signal (e.g., a video signal, a clock signal, a start signal, or a reset signal) or an potential from the outside is transmitted to the driver circuit portion 303 and the driver circuit portions 304a and 304b, is provided. Here, an example is described in which a flexible printed circuit (FPC) 308 is provided as the external input terminal. Although only the FPC is illustrated here, the FPC may be provided with a printed wiring board (PWB). The light-emitting device in this specification includes, in its category, not only the light-emitting device itself but also the light-emitting device provided with the FPC or the PWB.

Next, a cross-sectional structure is described with reference to FIG. 3B. The driver circuit portions and the pixel portion are formed over the element substrate 301; the driver circuit portion 303 that is the source line driver circuit and the pixel portion 302 are illustrated here.

The driver circuit portion 303 is an example in which FETs 309 and 310 are combined. Note that the driver circuit portion 303 may be formed with a circuit including transistors having the same conductivity type (either n-channel transistors or p-channel transistors) or a CMOS circuit including an n-channel transistor and a p-channel transistor. Although this embodiment shows a driver integrated type in which the driver circuit is formed over the substrate, the driver circuit is not necessarily formed over the substrate, and may be formed outside the substrate.

The pixel portion 302 includes a switching FET (not illustrated) and a current control FET 312, and a wiring of the current control FET 312 (a source electrode or a drain electrode) is electrically connected to a first electrode (anode) (313a or 313b) of a light-emitting element 317a or 317b. Although the pixel portion 302 includes two kinds of FETs (the switching FET and the current control FETs 312) in this embodiment, one embodiment of the present invention is not limited thereto. The pixel portion 302 may include, for example, three or more kinds of FETs and a capacitor in combination.

As the FETs 309, 310, and 312, for example, a staggered transistor or an inverted staggered transistor can be used. Examples of a semiconductor material that can be used for the FETs 309, 310, and 312 are a Group 13 semiconductor, a Group 14 semiconductor (e.g., silicon), a compound semiconductor, an oxide semiconductor, and an organic semiconductor. In addition, there is no particular limitation on the crystallinity of the semiconductor material, and an amorphous semiconductor film or a crystalline semiconductor film can be used. In particular, an oxide semiconductor is preferably used for the FETs 309, 310, and 312. Examples of the oxide semiconductor are In-Ga oxides, In-M-Zn oxides (M is Al, Ga, Y, Zr, La, Ce, Hf, or Nd), and the like. For example, an oxide semiconductor material that has an energy gap of 2 eV or more, preferably 2.5 eV or more and further preferably 3 eV or more, is used, so that the off-state current of the transistors can be reduced.

In addition, conductive films (320a and 320b) for optical adjustment are stacked over the first electrodes 313a and 313b. For example, as illustrated in FIG. 3B, in the case where the wavelengths of light extracted from the light-emitting elements 317a and 317b are different from each other, the thicknesses of the conductive films 320a and 320b are different from each other. In addition, an insulator 314 is formed to cover end portions of the first electrodes (313a and 313b). In this embodiment, the insulator 314 is formed using a positive photosensitive acrylic resin. The first electrodes (313a and 313b) are used as the anodes in this embodiment.

The insulator 314 preferably has a curved surface with curvature at an upper end portion or a lower end portion thereof. This enables favorable coverage by a film to be formed over the insulator 314. The insulator 314 can be formed using, for example, either a negative photosensitive resin or a positive photosensitive resin. The material for the insulator 314 is not limited to an organic compound and an inorganic compound such as silicon oxide, silicon oxynitride, or silicon nitride can also be used.

An EL layer 315 and a second electrode 316 are stacked over the first electrodes (313a and 313b). In the EL layer 315, at least a light-emitting layer is provided. In the light-emitting elements (317a and 317b) including the first electrodes (313a and 313b), the EL layer 315, and the second electrode 316, an end portion of the EL layer 315 is covered with the second electrode 316. The structure of the EL layer 315 may be the same as or different from the single-layer structure and the stacked layer structure described in Embodiments 2 and 3. Furthermore, the structure may differ between the light-emitting elements.

For the first electrode 313, the EL layer 315, and the second electrode 316, any of the materials given in Embodiment 2 can be used. The first electrodes (313a and 313b) of the light-emitting elements (317a and 317b) are electrically connected to the lead wiring 307 in a region 321, so that an external signal is input through the FPC 308. The second electrode 316 of the light-emitting elements (317a and 317b) is electrically connected to a lead wiring 323 in a region 322, so that an external signal is input through the FPC 308 although it is not illustrated.

Although the cross-sectional view in FIG. 3B illustrates only the two light-emitting elements 317, a plurality of light-emitting elements are arranged in a matrix in the pixel portion 302. Specifically, in the pixel portion 302, light-emitting elements that emit light of two kinds of colors (e.g., B and Y), light-emitting elements that emit light of three kinds of colors (e.g., R, G, and B), light-emitting elements that emit light of four kinds of colors (e.g. R, G, B, and Y) or (R, G, B, and W)), or the like are formed so that a light-emitting device capable of full color display can be obtained. In such cases, full color display may be achieved as follows: materials different according to the emission colors or the like of the light-emitting elements are used to form light-emitting layers (so-called separate coloring formation); alternatively, the plurality of light-emitting elements share one light-emitting layer formed using the same material and further include color filters. Thus, the light-emitting elements that emit light of a plurality of kinds of colors are used in combination, so that effects such as an improvement in color purity and a reduction in power consumption can be achieved. Furthermore, the light-emitting device may have improved emission efficiency and reduced power consumption by combination with quantum dots.

The sealing substrate 306 is attached to the element substrate 301 with the sealant 305, whereby the light-emitting elements 317a and 317b are provided in a space 318 surrounded by the element substrate 301, the sealing substrate 306, and the sealant 305.

The sealing substrate 306 is provided with coloring layers (color filters) 324, and a black layer (black matrix) 325 is provided between adjacent coloring layers. Note that one or both of the adjacent coloring layers (color filters) 324 may be provided so as to partly overlap with the black layer (black matrix) 325. Light emission obtained from the light-emitting elements 317a and 317b is extracted through the coloring layers (color filters) 324.

Note that the space 318 may be filled with an inert gas (such as nitrogen or argon) or the sealant 305. In the case where the sealant is applied for attachment of the substrates, one or more of UV treatment, heat treatment, and the like are preferably performed.

An epoxy-based resin or glass frit is preferably used for the sealant 305. The material preferably allows as little moisture and oxygen as possible to penetrate. As the sealing substrate 306, a glass substrate, a quartz substrate, or a plastic substrate formed of fiber-reinforced plastic (FRP), poly(vinyl fluoride) (PVF), polyester, acrylic, or the like can be used. In the case where glass frit is used as the sealant, the element substrate 301 and the sealing substrate 306 are preferably glass substrates for high adhesion.

Figure 3C:
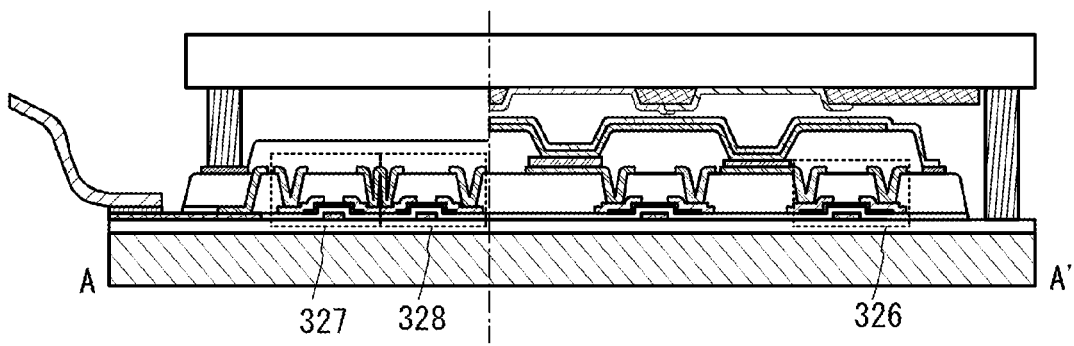

Structures of the FETs electrically connected to the light-emitting elements may be different from those in FIG. 3B in the position of a gate electrode; that is, the structures of FETs 326, 327, and 328 as illustrated in FIG. 3C may be employed. The coloring layer (color filter) 324 with which the sealing substrate 306 is provided may be provided as illustrated in FIG. 3C such that, at a position where the coloring layer (color filter) 324 overlaps with the black layer (black matrix) 325, the coloring layer (color filter) 324 further overlaps with an adjacent coloring layer (color filter) 324.

As described above, the active matrix light-emitting device can be obtained.

The light-emitting device of one embodiment of the present invention may be of the passive matrix type, as well as the active matrix type described above.

Figure 4A:
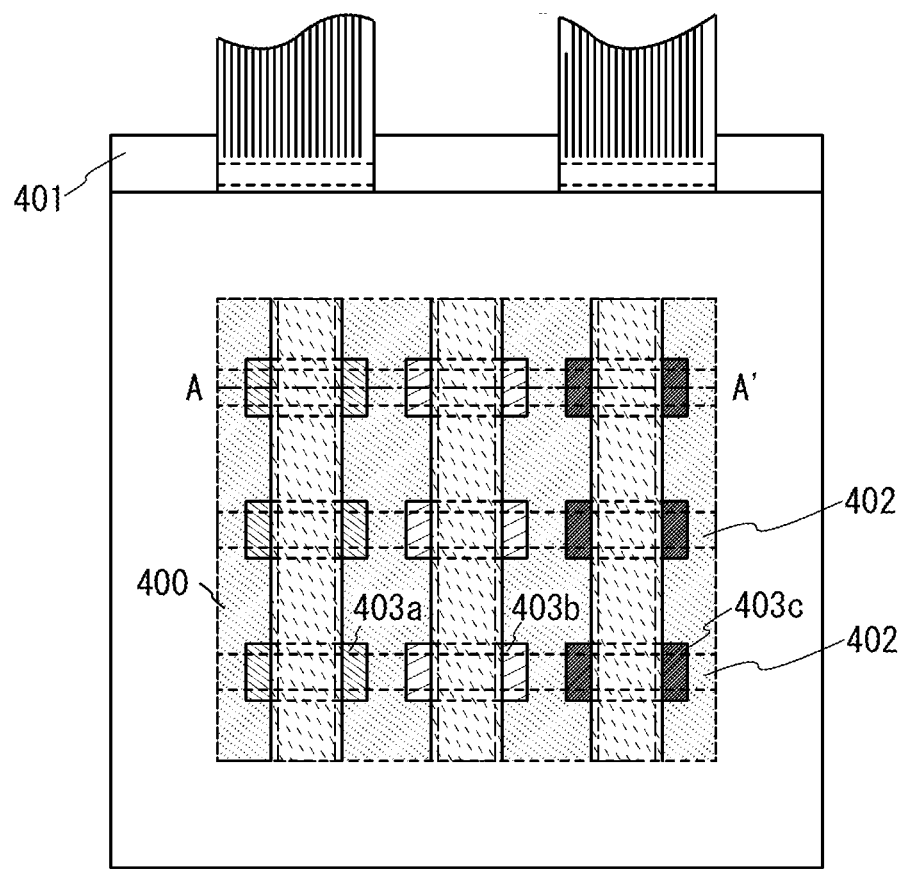
FIGS. 4A and 4B illustrate a light-emitting device.
Figure 4B:
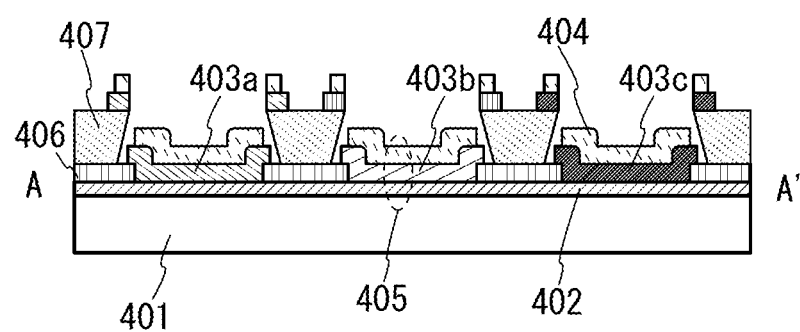

FIGS. 4A and 4B illustrate a passive-matrix light-emitting device. FIG. 4A is a top view of the passive-matrix light-emitting device, and FIG. 4B is a cross-sectional view thereof As illustrated in FIGS. 4A and 4B, light-emitting elements 405 including a first electrode 402, EL layers (403a, 403b, and 403c), and second electrodes 404 are formed over a substrate 401. Note that the first electrode 402 has an island-like shape, and a plurality of the first electrodes 402 are formed in one direction (the lateral direction in FIG. 4A) to form a striped pattern. An insulating film 406 is formed over part of the first electrode 402. A partition 407 formed using an insulating material is provided over the insulating film 406. The sidewalls of the partition 407 slope so that the distance between one sidewall and the other sidewall gradually decreases toward the surface of the substrate as illustrated in FIG. 4B.

Since the insulating film 406 has openings in part of the first electrode 402, the EL layers (403a, 403b, and 403c) and second electrodes 404 which are divided as desired can be formed over the first electrode 402. In the example in FIGS. 4A and 4B, a mask such as a metal mask and the partition 407 over the insulating film 406 are employed to form the EL layers (403a, 403b, and 403c) and the second electrodes 404. In this example, the EL layers 403a, 403b, and 403c emit light of different colors (e.g., red, green, blue, yellow, orange, and white).

After the formation of the EL layers (403a, 403b, and 403c), the second electrodes 404 are formed. Thus, the second electrode 404 is formed over the EL layers (403a, 403b, and 403c) without contact with the first electrode 402.

Note that sealing can be performed by a method similar to that used for the active matrix light-emitting device, and description thereof is not made.

As described above, the passive matrix light-emitting device can be obtained.

Note that in this specification and the like, a transistor or a light-emitting element can be formed using any of a variety of substrates, for example. The type of a substrate is not limited to a certain type. As the substrate, a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, a base material film, or the like can be used, for example. As an example of a glass substrate, a barium borosilicate glass substrate, an aluminoborosilicate glass substrate, a soda lime glass substrate, or the like can be given. Examples of the flexible substrate, the attachment film, the base film, and the like are substrates of plastics typified by polyethylene terephthalate (PET), polyethylene naphthalate (PEN), polyether sulfone (PES), and polytetrafluoroethylene (PTFE). Another example is a synthetic resin such as acrylic. Alternatively, polypropylene, polyester, polyvinyl fluoride, polyvinyl chloride, or the like can be used. Alternatively, polyamide, polyimide, aramid, epoxy, an inorganic vapor deposition film, paper, or the like can be used. Specifically, the use of semiconductor substrates, single crystal substrates, SOI substrates, or the like enables the manufacture of small-sized transistors with a small variation in characteristics, size, shape, or the like and with high current supply capability. A circuit using such transistors achieves low power consumption of the circuit or high integration of the circuit.

Alternatively, a flexible substrate may be used as the substrate, and a transistor or a light-emitting element may be provided directly on the flexible substrate. Still alternatively, a separation layer may be provided between the substrate and the transistor or the light-emitting element. The separation layer can be used when part or the whole of a semiconductor device formed over the separation layer is separated from the substrate and transferred onto another substrate. In such a case, the transistor or the light-emitting element can be transferred to a substrate having low heat resistance or a flexible substrate. For the separation layer, a stack including inorganic films, which are a tungsten film and a silicon oxide film, or an organic resin film of polyimide or the like formed over a substrate can be used, for example.

In other words, a transistor or a light-emitting element may be formed using one substrate, and then transferred to another substrate. Examples of a substrate to which a transistor or a light-emitting element is transferred are, in addition to the above-described substrates over which a transistor or a light-emitting element can be formed, a paper substrate, a cellophane substrate, an aramid film substrate, a polyimide film substrate, a stone substrate, a wood substrate, a cloth substrate (including a natural fiber (e.g., silk, cotton, or hemp), a synthetic fiber (e.g., nylon, polyurethane, or polyester), a regenerated fiber (e.g., acetate, cupra, rayon, or regenerated polyester), or the like), a leather substrate, a rubber substrate, and the like. When such a substrate is used, a transistor with excellent characteristics or a transistor with low power consumption can be formed, a device with high durability or high heat resistance can be provided, or a reduction in weight or thickness can be achieved.

The structure described in this embodiment can be used in appropriate combination with any of the structures described in the other embodiments.

(Embodiment 5)

In this embodiment, examples of a variety of electronic devices and an automobile manufactured using a light-emitting device which is one embodiment of the present invention will be described.

Examples of the electronic device including the light-emitting device are television devices (also referred to as TV or television receivers), monitors for computers and the like, digital cameras, digital video cameras, digital photo frames, cellular phones (also referred to as portable telephone devices), portable game consoles, portable information terminals, audio playback devices, large game machines such as pachinko machines, and the like. Specific examples of the electronic devices are illustrated in FIGS. 5A1, 5A2, 5B, 5C, 5D1, 5D2, and 5D3.

FIG. 5A1 illustrates an example of a television device. In the television device 7100, a display portion 7103 is incorporated in a housing 7101. The display portion 7103 can display images and may be a touch panel (an input/output device) including a touch sensor (an input device). Note that the light-emitting device which is one embodiment of the present invention can be used for the display portion 7103. In addition, here, the housing 7101 is supported by a stand 7105.

The television device 7100 can be operated by an operation switch of the housing 7101 or a separate remote controller 7110 as illustrated in FIG. 5A2. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the use of the receiver, general television broadcasts can be received. Moreover, when the television device is connected to a communication network with or without wires via the modem, one-way (from a sender to a receiver) or two-way (between a sender and a receiver or between receivers) information communication can be performed.

FIG. 5B illustrates a computer, which includes a main body 7201, a housing 7202, a display portion 7203, a keyboard 7204, an external connection port 7205, a pointing device 7206, and the like. Note that this computer can be manufactured using the light-emitting device which is one embodiment of the present invention for the display portion 7203. The display portion 7203 may be a touch panel (an input/output device) including a touch sensor (an input device).

FIG. 5C illustrates a smart watch, which includes a housing 7302, a display portion 7304, operation buttons 7311 and 7312, a connection terminal 7313, a band 7321, a clasp 7322, and the like.

The display portion 7304 mounted in the housing 7302 serving as a bezel includes a non-rectangular display region. The display portion 7304 can display an icon 7305 indicating time, another icon 7306, and the like. The display portion 7304 may be a touch panel (an input/output device) including a touch sensor (an input device).

The smart watch illustrated in FIG. 5C can have a variety of functions, such as a function of displaying a variety of information (e.g., a still image, a moving image, and a text image) on a display portion, a touch panel function, a function of displaying a calendar, date, time, and the like, a function of controlling processing with a variety of software (programs), a wireless communication function, a function of being connected to a variety of computer networks with a wireless communication function, a function of transmitting and receiving a variety of data with a wireless communication function, and a function of reading program or data stored in a recording medium and displaying the program or data on a display portion.

The housing 7302 can include a speaker, a sensor (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone, and the like. Note that the smart watch can be manufactured using the light-emitting device for the display portion 7304.

FIGS. 5D1, 5D2, and 5D3 illustrate an example of a cellular phone (e.g., smartphone). A cellular phone 7400 includes a housing 7401 provided with a display portion 7402, a microphone 7406, a speaker 7405, a camera 7407, an external connection portion 7404, an operation button 7403, and the like. In the case where a light-emitting device is manufactured by forming a light-emitting element of one embodiment of the present invention over a flexible substrate, the light-emitting element can be used for the display portion 7402 having a curved surface as illustrated in FIG. 5D1.

When the display portion 7402 of the cellular phone 7400 illustrated in FIG. 5D1 is touched with a finger or the like, data can be input to the cellular phone 7400. In addition, operations such as making a call and composing e-mail can be performed by touch on the display portion 7402 with a finger or the like.

There are mainly three screen modes of the display portion 7402. The first mode is a display mode mainly for displaying an image. The second mode is an input mode mainly for inputting data such as characters. The third mode is a display-and-input mode in which two modes of the display mode and the input mode are combined.

For example, in the case of making a call or creating e-mail, a character input mode mainly for inputting characters is selected for the display portion 7402 so that characters displayed on the screen can be input. In this case, it is preferable to display a keyboard or number buttons on almost the entire screen of the display portion 7402.

When a detection device such as a gyroscope or an acceleration sensor is provided inside the cellular phone 7400, display on the screen of the display portion 7402 can be automatically changed by determining the orientation of the cellular phone 7400 (whether the cellular phone is placed horizontally or vertically for a landscape mode or a portrait mode).

The screen modes are changed by touch on the display portion 7402 or operation with the operation button 7403 of the housing 7401. The screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, if a signal detected by an optical sensor in the display portion 7402 is detected and the input by touch on the display portion 7402 is not performed for a certain period, the screen mode may be controlled so as to be changed from the input mode to the display mode.

The display portion 7402 may function as an image sensor. For example, an image of a palm print, a fingerprint, or the like is taken by touch on the display portion 7402 with the palm or the finger, whereby personal authentication can be performed. In addition, by providing a backlight or a sensing light source that emits near-infrared light in the display portion, an image of a finger vein, a palm vein, or the like can be taken.

The light-emitting device can be used for a cellular phone having a structure illustrated in FIG. 5D2 or FIG. 5D3, which is another structure of the cellular phone (e.g., a smartphone).

Note that in the case of the structure illustrated in FIG. 5D2 or FIG. 5D3, text data, image data, or the like can be displayed on second screens 7502(1) and 7502(2) of housings 7500(1) and 7500(2) as well as first screens 7501(1) and 7501(2). Such a structure enables a user to easily see text data, image data, or the like displayed on the second screens 7502(1) and 7502(2) while the cellular phone is placed in user's breast pocket.

Figure 6A:
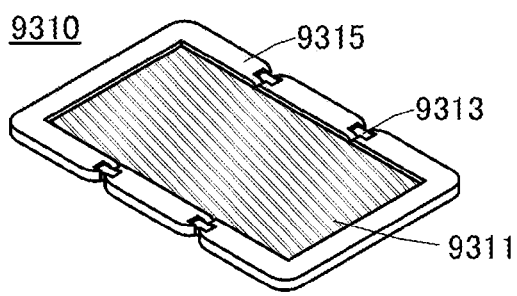
FIGS. 6A to 6C illustrate an electronic device.
Figure 6B:
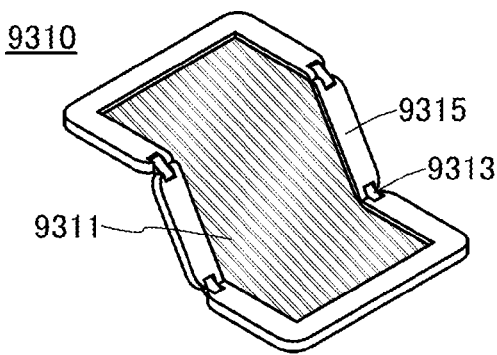
Figure 6C:
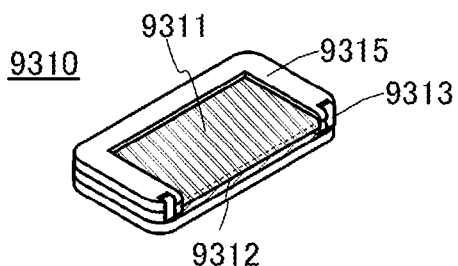

Another electronic device including a light-emitting device is a foldable portable information terminal illustrated in FIGS. 6A to 6C. FIG. 6A illustrates a portable information terminal 9310 which is opened. FIG. 6B illustrates the portable information terminal 9310 which is being opened or being folded. FIG. 6C illustrates the portable information terminal 9310 that is folded. The portable information terminal 9310 is highly portable when folded. The portable information terminal 9310 is highly browsable when opened because of a seamless large display region.

A display portion 9311 is supported by three housings 9315 joined together by hinges 9313. Note that the display portion 9311 may be a touch panel (an input/output device) including a touch sensor (an input device). By bending the display portion 9311 at a connection portion between two housings 9315 with the use of the hinges 9313, the portable information terminal 9310 can be reversibly changed in shape from an opened state to a folded state. A light-emitting device of one embodiment of the present invention can be used for the display portion 9311. A display region 9312 in the display portion 9311 is a display region that is positioned at a side surface of the portable information terminal 9310 that is folded. On the display region 9312, information icons, file shortcuts of frequently used applications or programs, and the like can be displayed, and confirmation of information and start of application can be smoothly performed.

Figure 7A:
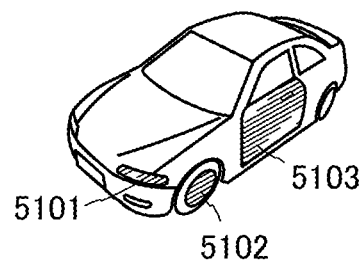
FIGS. 7A and 7B illustrate an automobile.
Figure 7B:
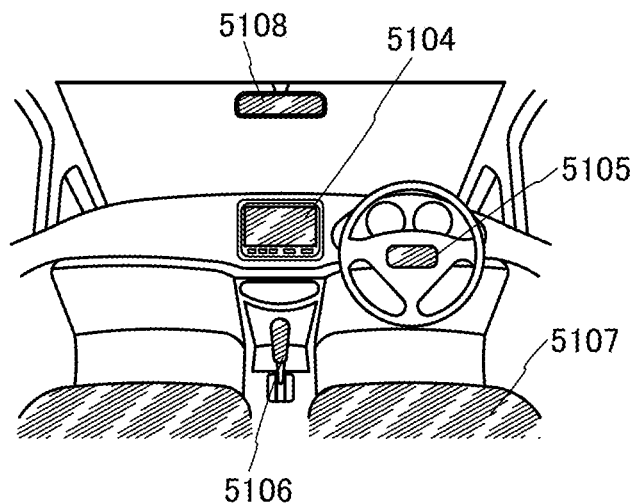

FIGS. 7A and 7B illustrate an automobile including a light-emitting device. The light-emitting device can be incorporated in the automobile, and specifically, can be included in lights 5101 (including lights of the rear part of the car), a wheel 5102 of a tire, part or whole of a door 5103, or the like on the outer side of the automobile which is illustrated in FIG. 7A. The light-emitting device can also be included in a display portion 5104, a steering wheel 5105, a gear lever 5106, a seat 5107, an inner rearview mirror 5108, or the like on the inner side of the automobile which is illustrated in FIG. 7B, or in part of a glass window.

As described above, the electronic devices and automobiles can be obtained using the light-emitting device which is one embodiment of the present invention. Note that the light-emitting device can be used for electronic devices and automobiles in a variety of fields without being limited to the electronic devices described in this embodiment.

The structure described in this embodiment can be used in appropriate combination with any of the structures described in the other embodiments.

(Embodiment 6)

In this embodiment, a structure of a lighting device fabricated using the light-emitting element which is one embodiment of the present invention will be described with reference to FIGS. 8A to 8D.

Figure 8A:
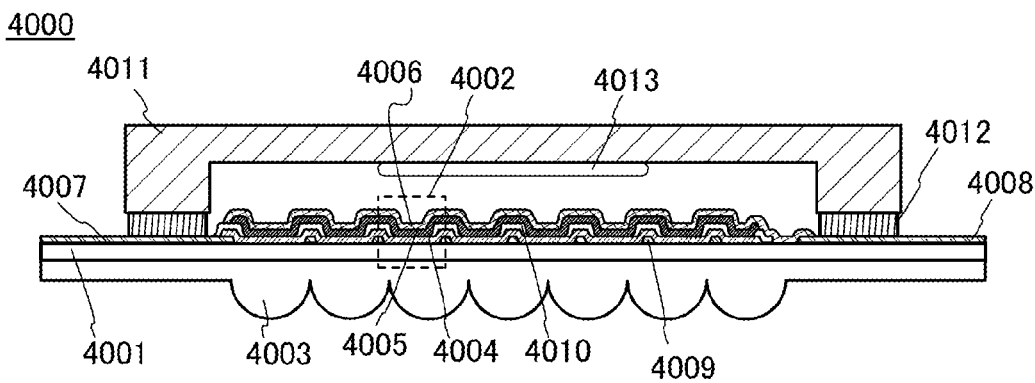
FIGS. 8A to 8D illustrate lighting devices.
Figure 8B:
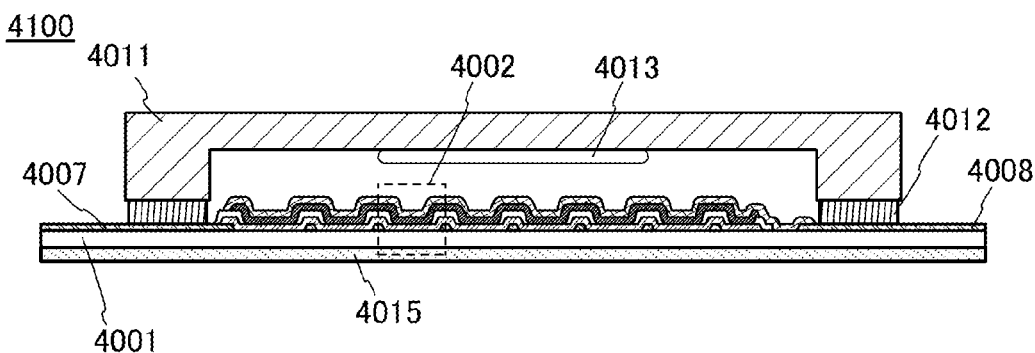
Figure 8C:
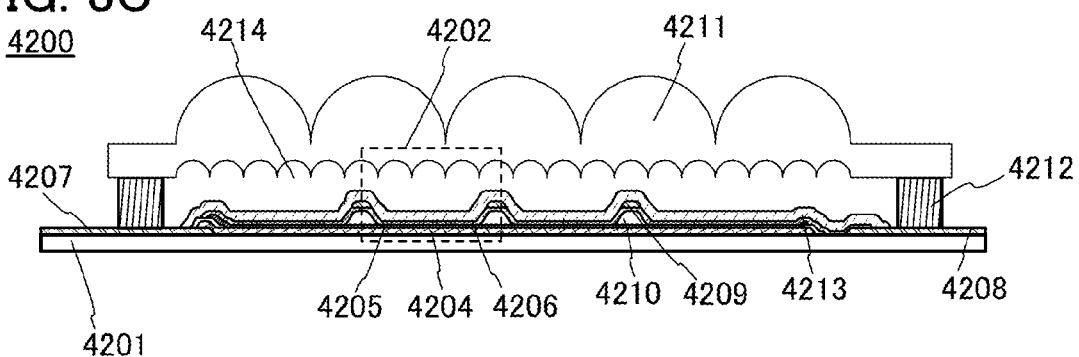
Figure 8D:
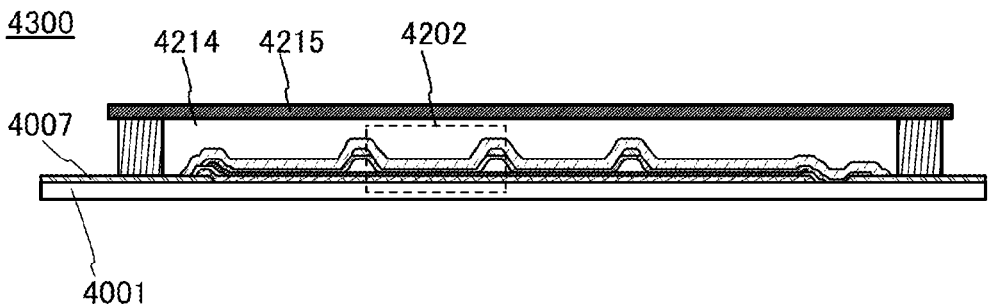

FIGS. 8A to 8D are examples of cross-sectional views of lighting devices. FIGS. 8A and 8B illustrate bottom-emission lighting devices in which light is extracted from the substrate side, and FIGS. 8C and 8D illustrate top-emission lighting devices in which light is extracted from the sealing substrate side.

A lighting device 4000 illustrated in FIG. 8A includes a light-emitting element 4002 over a substrate 4001. In addition, the lighting device 4000 includes a substrate 4003 with unevenness on the outside of the substrate 4001. The light-emitting element 4002 includes a first electrode 4004, an EL layer 4005, and a second electrode 4006.

The first electrode 4004 is electrically connected to an electrode 4007, and the second electrode 4006 is electrically connected to an electrode 4008. In addition, an auxiliary wiring 4009 electrically connected to the first electrode 4004 may be provided. Note that an insulating layer 4010 is formed over the auxiliary wiring 4009.

The substrate 4001 and a sealing substrate 4011 are bonded to each other by a sealant 4012. A desiccant 4013 is preferably provided between the sealing substrate 4011 and the light-emitting element 4002. The substrate 4003 has the unevenness illustrated in FIG. 8A, whereby the extraction efficiency of light emitted from the light-emitting element 4002 can be increased.

Instead of the substrate 4003, a diffusion plate 4015 may be provided on the outside of the substrate 4001 as in a lighting device 4100 illustrated in FIG. 8B.

A lighting device 4200 illustrated in FIG. 8C includes a light-emitting element 4202 over a substrate 4201. The light-emitting element 4202 includes a first electrode 4204, an EL layer 4205, and a second electrode 4206.

The first electrode 4204 is electrically connected to an electrode 4207, and the second electrode 4206 is electrically connected to an electrode 4208. An auxiliary wiring 4209 electrically connected to the second electrode 4206 may be provided. An insulating layer 4210 may be provided under the auxiliary wiring 4209.

The substrate 4201 and a sealing substrate 4211 with unevenness are bonded to each other by a sealant 4212. A barrier film 4213 and a planarization film 4214 may be provided between the sealing substrate 4211 and the light-emitting element 4202.

The sealing substrate 4211 has the unevenness illustrated in FIG. 8C, whereby the extraction efficiency of light emitted from the light-emitting element 4202 can be increased.

Instead of the sealing substrate 4211, a diffusion plate 4215 may be provided over the light-emitting element 4202 as in a lighting device 4300 illustrated in FIG. 8D.

Note that the EL layers 4005 and 4205 in this embodiment can include the organometallic complex which is one embodiment of the present invention. In that case, a lighting device with low power consumption can be provided.

The structure described in this embodiment can be used in appropriate combination with any of the structures described in the other embodiments.

(Embodiment 7)

In this embodiment, examples of a lighting device which is an application of the light-emitting device of one embodiment of the present invention will be described with reference to FIG. 9.

Figure 9:
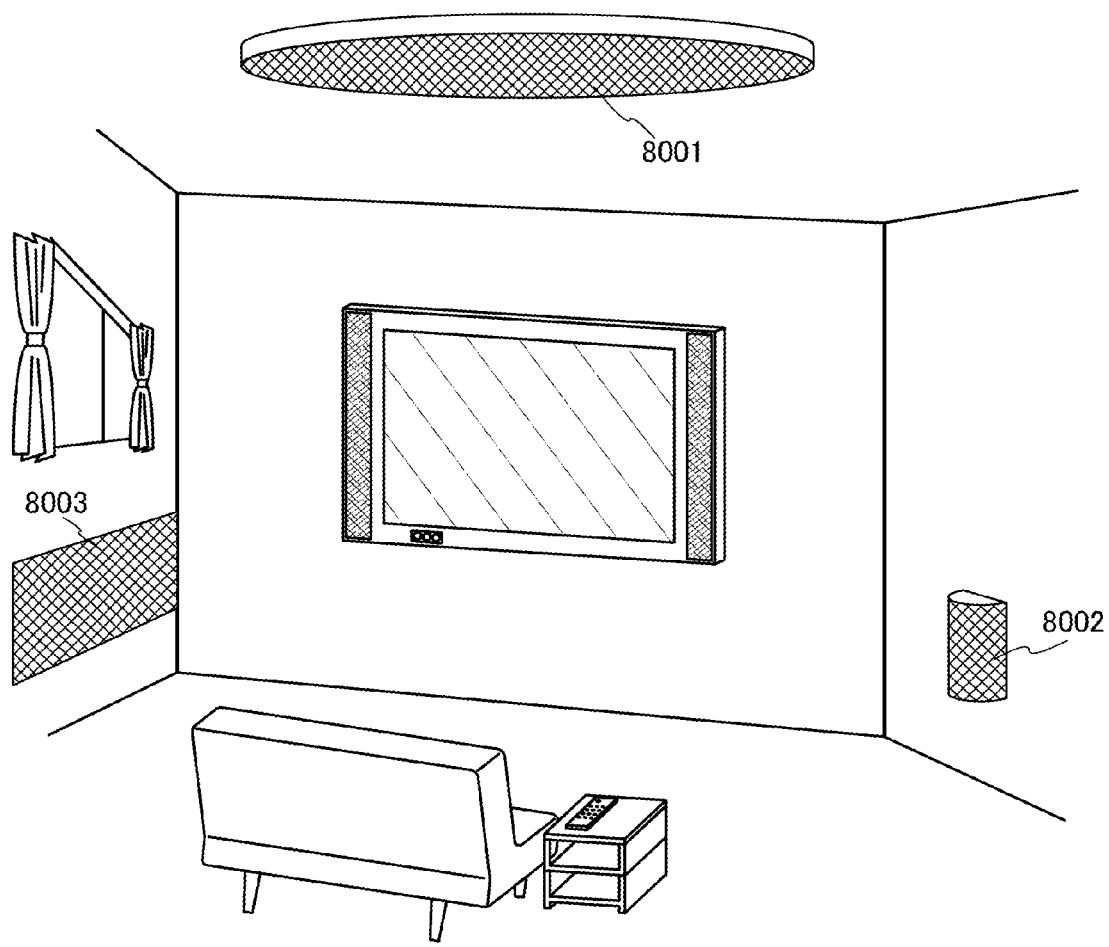
FIG. 9 illustrates lighting devices.

FIG. 9 illustrates an example in which the light-emitting device is used in an indoor lighting device 8001. Since the light-emitting device can have a large area, it can be used for a lighting device having a large area. In addition, with the use of a housing with a curved surface, a lighting device 8002 in which a light-emitting region has a curved surface can also be obtained. A light-emitting element included in the light-emitting device described in this embodiment is in a thin film form, which allows the housing to be designed more freely. Thus, the lighting device can be elaborately designed in a variety of ways. In addition, a wall of the room may be provided with a lighting device 8003.

Besides the above examples, when the light-emitting device is used as part of furniture in a room, a lighting device that functions as the furniture can be obtained.

As described above, a variety of lighting devices that include the light-emitting device can be obtained. Note that these lighting devices are also embodiments of the present invention.

The structure described in this embodiment can be used in appropriate combination with any of the structures described in the other embodiments.

(Embodiment 8)

In this embodiment, touch panels including a light-emitting element of one embodiment of the present invention or a light-emitting device of one embodiment of the present invention will be described with reference to FIGS. 10A and 10B, FIGS. 11A and 11B, FIGS. 12A and 12B, FIGS. 13A and 13B, and FIG. 14.

Figure 10A:
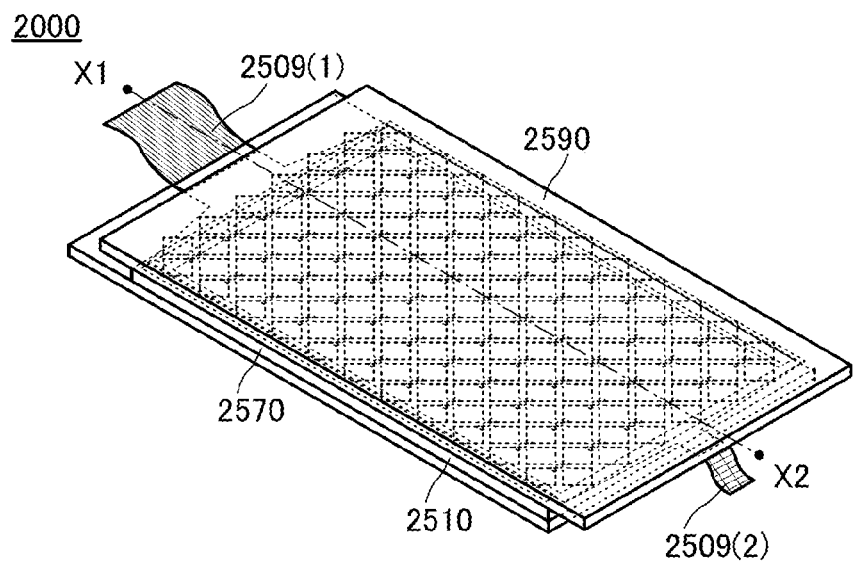
FIGS. 10A and 10B illustrate an example of a touch panel.
Figure 10B:
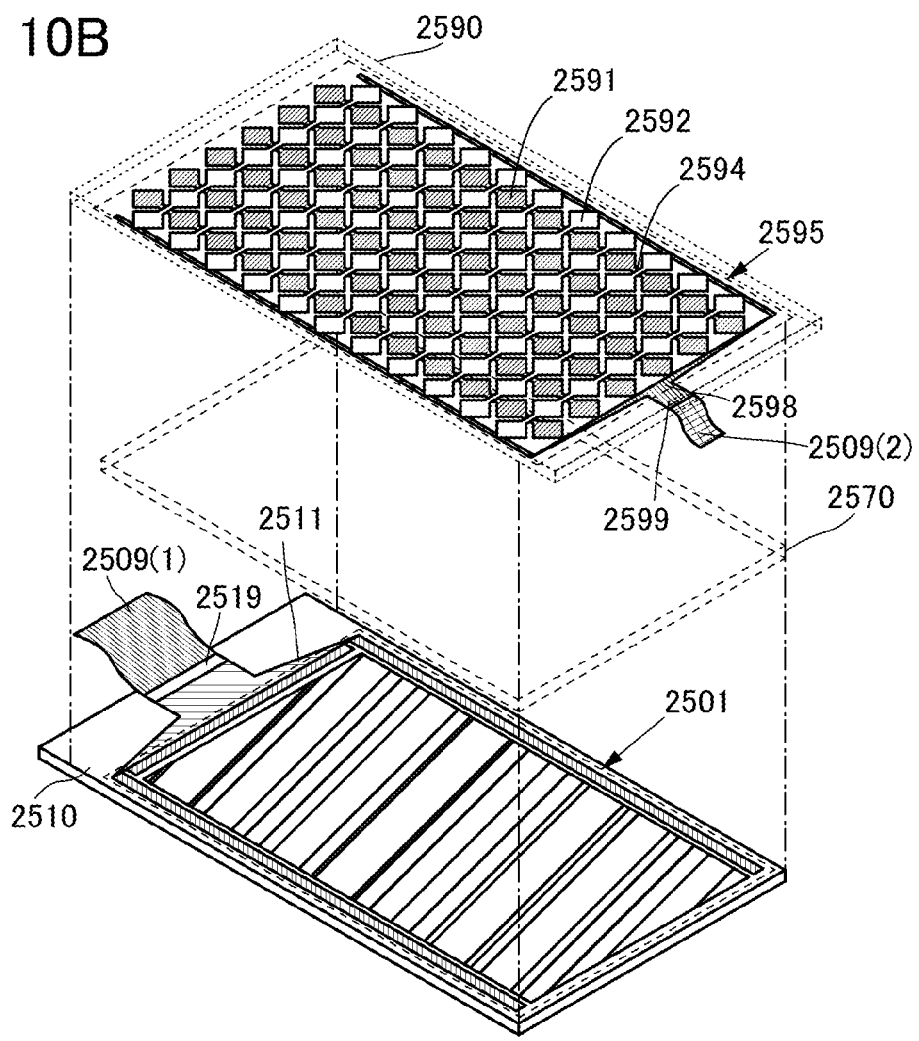

FIGS. 10A and 10B are perspective views of a touch panel 2000. Note that FIGS. 10A and 10B illustrate typical components of the touch panel 2000 for simplicity.

The touch panel 2000 includes a display panel 2501 and a touch sensor 2595 (see FIG. 10B). Furthermore, the touch panel 2000 includes substrates 2510, 2570, and 2590.

The display panel 2501 includes a plurality of pixels over the substrate 2510, and a plurality of wirings 2511 through which signals are supplied to the pixels. The plurality of wirings 2511 are led to a peripheral portion of the substrate 2510, and part of the plurality of wirings 2511 forms a terminal 2519. The terminal 2519 is electrically connected to an FPC 2509(1).

The substrate 2590 includes the touch sensor 2595 and a plurality of wirings 2598 electrically connected to the touch sensor 2595. The plurality of wirings 2598 are led to a peripheral portion of the substrate 2590, and part of the plurality of wirings 2598 forms a terminal 2599. The terminal 2599 is electrically connected to an FPC 2509(2). Note that in FIG. 10B, electrodes, wirings, and the like of the touch sensor 2595 provided on the back side of the substrate 2590 (the side facing the substrate 2510) are indicated by solid lines for clarity.

As the touch sensor 2595, a capacitive touch sensor can be used, for example. Examples of the capacitive touch sensor are a surface capacitive touch sensor, a projected capacitive touch sensor, and the like.

Examples of the projected capacitive touch sensor are a self-capacitive touch sensor, a mutual capacitive touch sensor, and the like, which differ mainly in the driving method. The use of a mutual capacitive touch sensor is preferable because multiple points can be sensed simultaneously.

First, an example of using a projected capacitive touch sensor is described with reference to FIG. 10B. Note that in the case of a projected capacitive touch sensor, a variety of sensors that can sense the closeness or the contact of a sensing target such as a finger can be used.

The projected capacitive touch sensor 2595 includes electrodes 2591 and 2592. The electrodes 2591 are electrically connected to any of the plurality of wirings 2598, and the electrodes 2592 are electrically connected to any of the other wirings 2598. The electrodes 2592 each have a shape of a plurality of quadrangles arranged in one direction with one corner of a quadrangle connected to one corner of another quadrangle with a wiring 2594 in one direction, as illustrated in FIGS. 10A and 10B. In the same manner, the electrodes 2591 each have a shape of a plurality of quadrangles arranged with one corner of a quadrangle connected to one corner of another quadrangle; however, the direction in which the electrodes 2591 are connected is a direction crossing the direction in which the electrodes 2592 are connected. Note that the direction in which the electrodes 2591 are connected and the direction in which the electrodes 2592 are connected are not necessarily perpendicular to each other, and the electrodes 2591 may be arranged to intersect with the electrodes 2592 at an angle greater than 0° and less than 90°.

The intersecting area of the wiring 2594 and one of the electrodes 2592 is preferably as small as possible. Such a structure allows a reduction in the area of a region where the electrodes are not provided, reducing unevenness in transmittance. As a result, unevenness in the luminance of light from the touch sensor 2595 can be reduced.

Note that the shapes of the electrodes 2591 and the 2592 are not limited to the above-described shapes and can be any of a variety of shapes. For example, the plurality of electrodes 2591 may be provided so that a space between the electrodes 2591 are reduced as much as possible, and the plurality of electrodes 2592 may be provided with an insulating layer sandwiched between the electrodes 2591 and 2592.

In that case, it is preferable to provide, between two adjacent electrodes 2592, a dummy electrode which is electrically insulated from these electrodes because the area of a region having a different transmittance can be reduced.

Figure 11A:
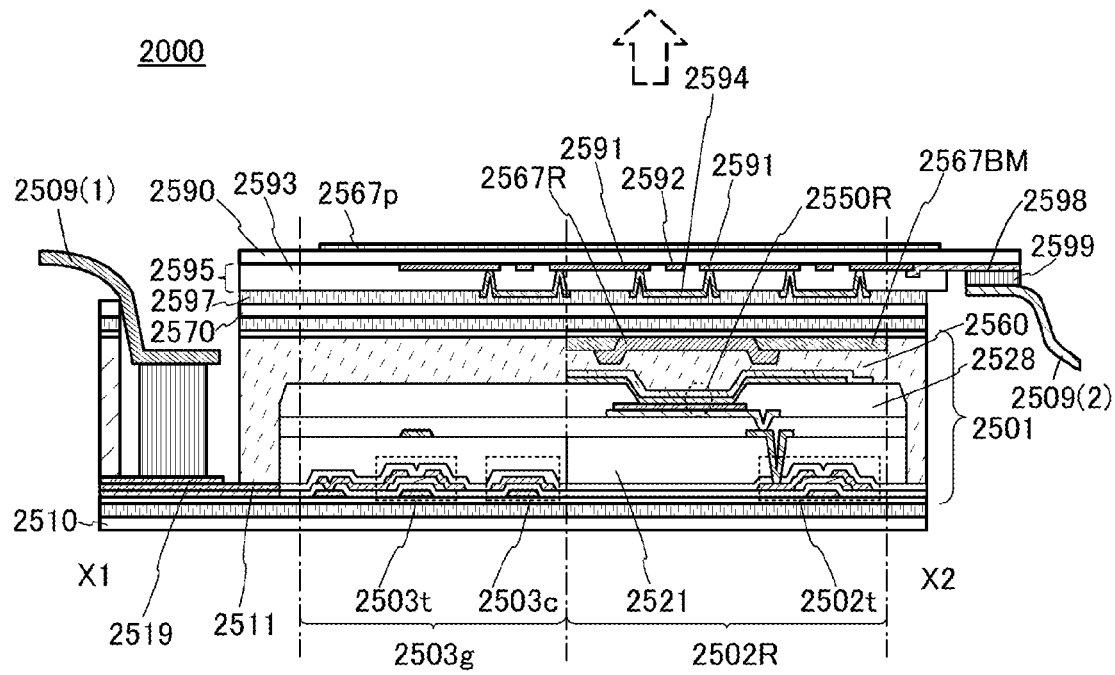
FIGS. 11A and 11B illustrate an example of a touch panel.
Figure 11B:
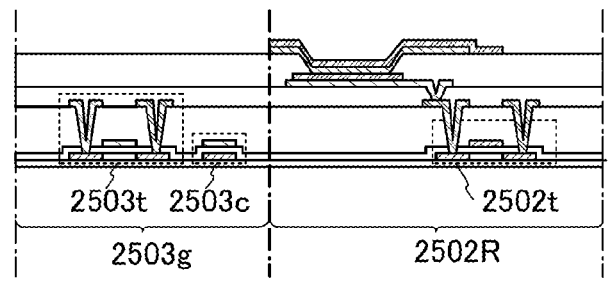

Next, the touch panel 2000 is described in detail with reference to FIGS. 11A and 11B. FIGS. 11A and 11B are cross-sectional views taken along the dashed-dotted line X1-X2 in FIG. 10A.

The touch panel 2000 includes the touch sensor 2595 and the display panel 2501.

The touch sensor 2595 includes the electrodes 2591 and 2592 that are provided in a staggered arrangement and in contact with the substrate 2590, an insulating layer 2593 covering the electrodes 2591 and 2592, and the wiring 2594 that electrically connects the adjacent electrodes 2591 to each other. Between the adjacent electrodes 2591, the electrode 2592 is provided.

The electrodes 2591 and 2592 can be formed using a light-transmitting conductive material. As a light-transmitting conductive material, a conductive oxide such as indium oxide, indium tin oxide, indium zinc oxide, zinc oxide, or zinc oxide to which gallium is added can be used. A graphene compound may be used as well. When a graphene compound is used, it can be formed, for example, by reducing a graphene oxide film. As a reducing method, a method with application of heat, a method with laser irradiation, or the like can be employed.

For example, the electrodes 2591 and 2592 can be formed by depositing a light-transmitting conductive material on the substrate 2590 by a sputtering method and then removing an unneeded portion by any of various patterning techniques such as photolithography.

Examples of a material for the insulating layer 2593 are a resin such as acrylic or epoxy resin, a resin having a siloxane bond, and an inorganic insulating material such as silicon oxide, silicon oxynitride, or aluminum oxide.

The adjacent electrodes 2591 are electrically connected to each other with the wiring 2594 formed in part of the insulating layer 2593. Note that a material for the wiring 2594 preferably has higher conductivity than materials for the electrode 2591 and 2592 to reduce electrical resistance.

One wiring 2598 is electrically connected to any of the electrodes 2591 and 2592. Part of the wiring 2598 serves as a terminal. For the wiring 2598, a metal material such as aluminum, gold, platinum, silver, nickel, titanium, tungsten, chromium, molybdenum, iron, cobalt, copper, or palladium or an alloy material containing any of these metal materials can be used.

Through the terminal 2599, the wiring 2598 and the FPC 2509(2) are electrically connected to each other. The terminal 2599 can be formed using any of various kinds of anisotropic conductive films (ACF), anisotropic conductive pastes (ACP), and the like.

An adhesive layer 2597 is provided in contact with the wiring 2594. That is, the touch sensor 2595 is attached to the display panel 2501 so that they overlap with each other with the adhesive layer 2597 provided therebetween. Note that the substrate 2570 as illustrated in FIG. 11A may be provided over the surface of the display panel 2501 that is in contact with the adhesive layer 2597; however, the substrate 2570 is not always needed.

The adhesive layer 2597 has a light-transmitting property. For example, a thermosetting resin or an ultraviolet curable resin can be used; specifically, a resin such as an acrylic-based resin, a urethane-based resin, an epoxy-based resin, or a siloxane-based resin can be used.

The display panel 2501 in FIG. 11A includes, between the substrate 2510 and the substrate 2570, a plurality of pixels arranged in a matrix and a driver circuit. Each pixel includes a light-emitting element and a pixel circuit driving the light-emitting element.

In FIG. 11A, a pixel 2502R is shown as an example of the pixel of the display panel 2501, and a scan line driver circuit 2503g is shown as an example of the driver circuit.

The pixel 2502R includes a light-emitting element 2550R and a transistor 2502t that can supply electric power to the light-emitting element 2550R.

The transistor 2502t is covered with an insulating layer 2521. The insulating layer 2521 covers unevenness caused by the transistor and the like that have been already formed to provide a flat surface. The insulating layer 2521 may serve also as a layer for preventing diffusion of impurities. That is preferable because a reduction in the reliability of the transistor or the like due to diffusion of impurities can be prevented.

The light-emitting element 2550R is electrically connected to the transistor 2502t through a wiring. It is one electrode of the light-emitting element 2550R that is directly connected to the wiring. An end portion of the one electrode of the light-emitting element 2550R is covered with an insulator 2528.

The light-emitting element 2550R includes an EL layer between a pair of electrodes. A coloring layer 2567R is provided to overlap with the light-emitting element 2550R, and part of light emitted from the light-emitting element 2550R is transmitted through the coloring layer 2567R and extracted in the direction indicated by an arrow in the drawing. A light-blocking layer 2567BM is provided at an end portion of the coloring layer, and a sealing layer 2560 is provided between the light-emitting element 2550R and the coloring layer 2567R.

Note that when the sealing layer 2560 is provided on the side from which light from the light-emitting element 2550R is extracted, the sealing layer 2560 preferably has a light-transmitting property. The sealing layer 2560 preferably has a higher refractive index than the air.

The scan line driver circuit 2503g includes a transistor 2503t and a capacitor 2503c. Note that the driver circuit and the pixel circuits can be formed in the same process over the same substrate. Thus, in a manner similar to that of the transistor 2502t in the pixel circuit, the transistor 2503t in the driver circuit (scan line driver circuit 2503g) is also covered with the insulating layer 2521.

The wirings 2511 through which a signal can be supplied to the transistor 2503t are provided. The terminal 2519 is provided in contact with the wiring 2511. The terminal 2519 is electrically connected to the FPC 2509(1), and the FPC 2509(1) has a function of supplying signals such as an image signal and a synchronization signal. Note that a printed wiring board (PWB) may be attached to the FPC 2509(1).

Although the case where the display panel 2501 illustrated in FIG. 11A includes a bottom-gate transistor is described, the structure of the transistor is not limited thereto, and any of transistors with various structures can be used. In each of the transistors 2502t and 2503t illustrated in FIG. 11A, a semiconductor layer containing an oxide semiconductor can be used for a channel region. Alternatively, a semiconductor layer containing amorphous silicon or a semiconductor layer containing polycrystalline silicon that is obtained by crystallization process such as laser annealing can be used for a channel region.

FIG. 11B illustrates the structure of the display panel 2501 that includes a top-gate transistor instead of the bottom-gate transistor illustrated in FIG. 11A. The kind of the semiconductor layer that can be used for the channel region does not depend on the structure of the transistor.

In the touch panel 2000 illustrated in FIG. 11A, an anti-reflection layer 2567p overlapping with at least the pixel is preferably provided on a surface of the touch panel on the side from which light from the pixel is extracted, as illustrated in FIG. 11A. As the anti-reflection layer 2567p, a circular polarizing plate or the like can be used.

For the substrates 2510, 2570, and 2590 in FIG. 11A, for example, a flexible material having a vapor permeability of $1\times10^{-5}$ g/(m$^2$·day) or lower, preferably $1\times10^{-6}$ g/(m$^2$·day) or lower, can be favorably used. Alternatively, it is preferable to use the materials that make these substrates have substantially the same coefficient of thermal expansion. For example, the coefficients of linear expansion of the materials are $1\times10^{-3}$/K or lower, preferably $5\times10^{-5}$/K or lower and further preferably $1\times10^{-5}$/K or lower.

Next, a touch panel 2000' having a structure different from that of the touch panel 2000 illustrated in FIGS. 11A and 11B is described with reference to FIGS. 12A and 12B. It can be used as a touch panel as well as the touch panel 2000.

Figure 12A:
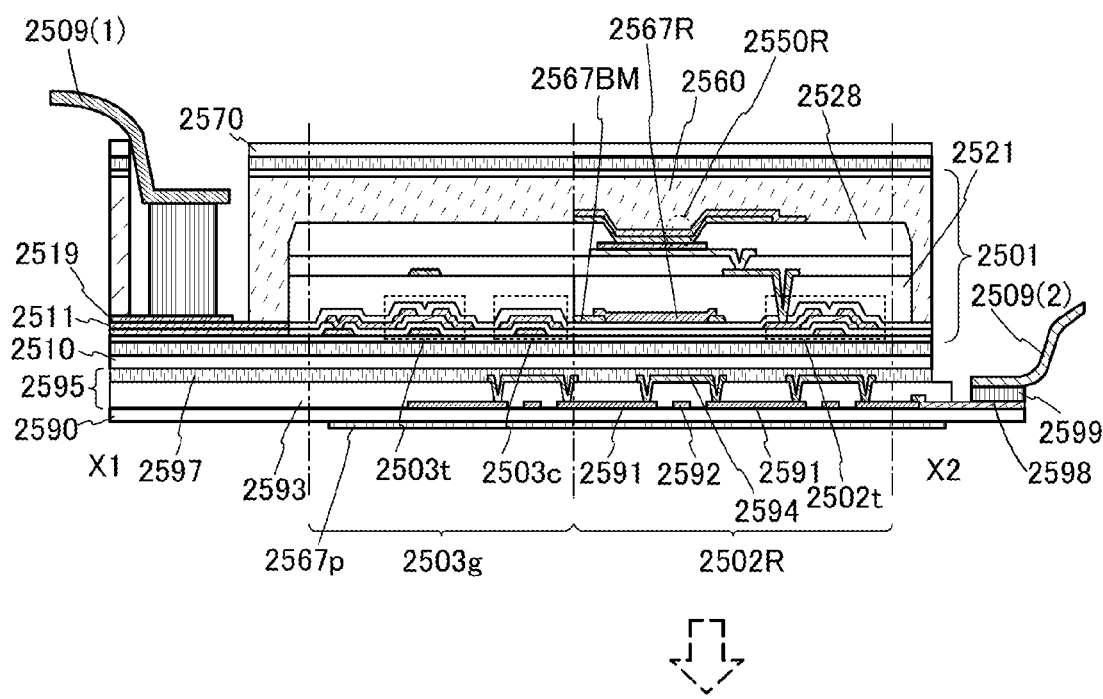
FIGS. 12A and 12B illustrate an example of a touch panel.
Figure 12B:
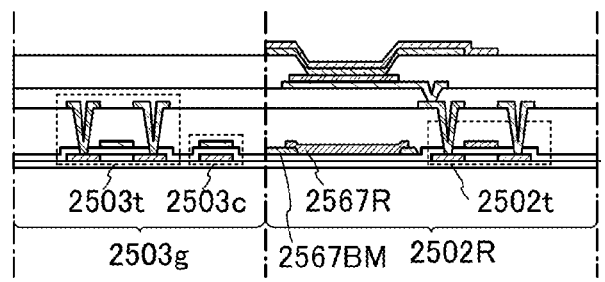

FIGS. 12A and 12B are cross-sectional views of the touch panel 2000'. In the touch panel 2000' illustrated in FIGS. 12A and 12B, the position of the touch sensor 2595 relative to the display panel 2501 is different from that in the touch panel 2000 illustrated in FIGS. 11A and 11B. Only different structures are described below, and the above description of the touch panel 2000 can be referred to for the other similar structures.

The coloring layer 2567R overlaps with the light-emitting element 2550R. Light from the light-emitting element 2550R illustrated in FIG. 12A is emitted to the side where the transistor 2502t is provided. That is, (part of) light emitted from the light-emitting element 2550R passes through the coloring layer 2567R and is extracted in the direction indicated by an arrow in FIG. 12A. Note that the light-blocking layer 2567BM is provided at an end portion of the coloring layer 2567R.

The touch sensor 2595 is provided on the transistor 2502t side (the far side from the light-emitting element 2550R) of the display panel 2501 (see FIG. 12A).

The adhesive layer 2597 is in contact with the substrate 2510 of the display panel 2501 and attaches the display panel 2501 and the touch sensor 2595 to each other in the structure illustrated in FIG. 12A. The substrate 2510 is not necessarily provided between the display panel 2501 and the touch sensor 2595 that are attached to each other by the adhesive layer 2597.

As in the touch panel 2000, transistors with a variety of structures can be used for the display panel 2501 in the touch panel 2000'. Although a bottom-gate transistor is used in FIG. 12A, a top-gate transistor may be used as illustrated in FIG. 12B.

An example of a driving method of the touch panel is described with reference to FIGS. 13A and 13B.

Figure 13A:
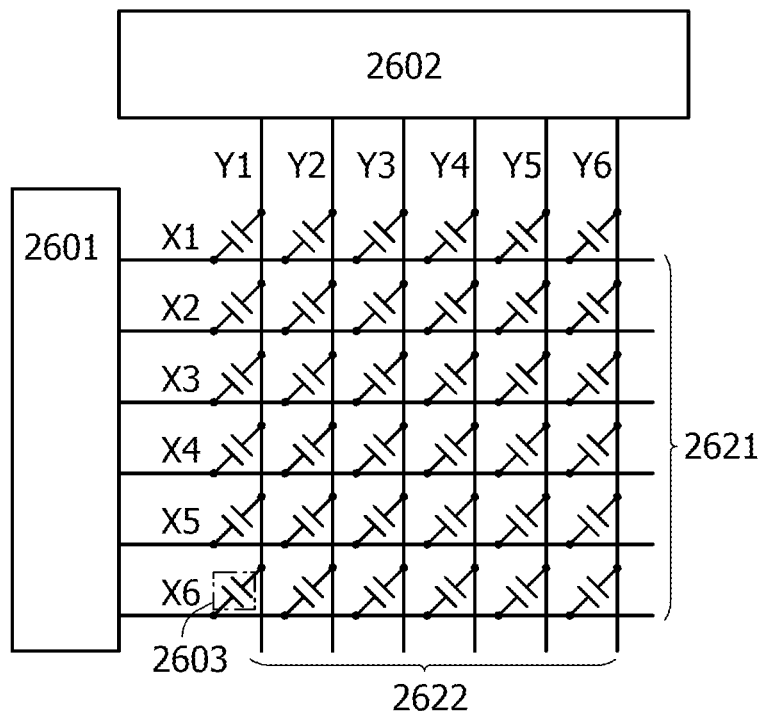
FIGS. 13A and 13B are a block diagram and a timing chart of a touch sensor.

FIG. 13A is a block diagram illustrating the structure of a mutual capacitive touch sensor. FIG. 13A illustrates a pulse voltage output circuit 2601 and a current sensing circuit 2602. Note that in the example of FIG. 13A, six wirings X1-X6 represent electrodes 2621 to which a pulse voltage is supplied, and six wirings Y1-Y6 represent electrodes 2622 that sense a change in current. FIG. 13A also illustrates a capacitor 2603 which is formed in a region where the electrodes 2621 and 2622 overlap with each other. Note that functional replacement between the electrodes 2621 and 2622 is possible.

The pulse voltage output circuit 2601 is a circuit for sequentially applying a pulse voltage to the wirings X1 to X6. By application of a pulse voltage to the wirings X1 to X6, an electric field is generated between the electrodes 2621 and 2622 of the capacitor 2603. When the electric field between the electrodes is shielded, for example, a change occurs in the capacitor 2603 (mutual capacitance). The approach or contact of a sensing target can be sensed by utilizing this change.

The current sensing circuit 2602 is a circuit for sensing changes in current flowing through the wirings Y1 to Y6 that are caused by the change in mutual capacitance in the capacitor 2603. No change in current value is sensed in the wirings Y1 to Y6 when there is no approach or contact of a sensing target, whereas a decrease in current value is sensed when mutual capacitance is decreased owing to the approach or contact of a sensing target. Note that an integrator circuit or the like is used for sensing of current.

Figure 13B:
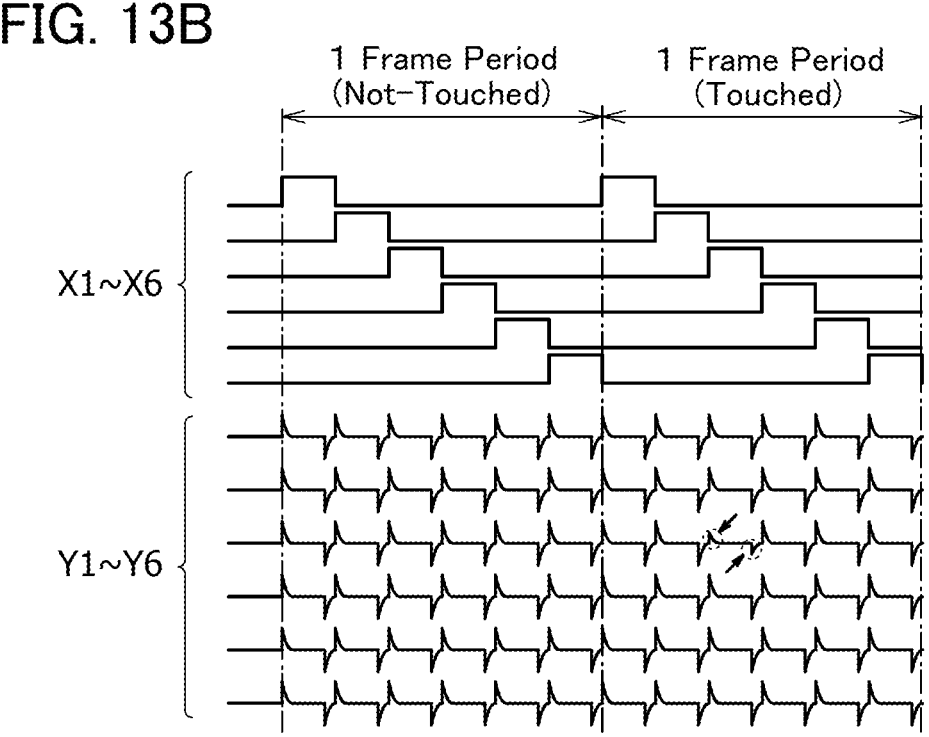

FIG. 13B is a timing chart showing input and output waveforms in the mutual capacitive touch sensor illustrated in FIG. 13A. In FIG. 13B, sensing of a sensing target is performed in all the rows and columns in one frame period. FIG. 13B shows a period when a sensing target is not sensed (not touched) and a period when a sensing target is sensed (touched). Sensed current values of the wirings Y1 to Y6 are shown as the waveforms of voltage values.

A pulse voltage is sequentially applied to the wirings X1 to X6, and the waveforms of the wirings Y1 to Y6 change in accordance with the pulse voltage. When there is no approach or contact of a sensing target, the waveforms of the wirings Y1 to Y6 change uniformly in accordance with changes in the voltages of the wirings X1 to X6. The current value is decreased at the point of approach or contact of a sensing target and accordingly the waveform of the voltage value changes. By sensing a change in mutual capacitance in this manner, the approach or contact of a sensing target can be sensed.

Figure 14:
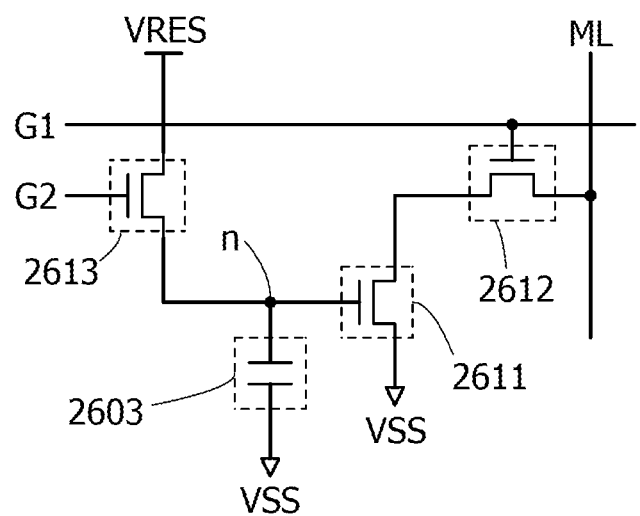
FIG. 14 is a circuit diagram of a touch sensor.

Although FIG. 13A illustrates a passive touch sensor in which only the capacitor 2603 is provided at the intersection of wirings as a touch sensor, an active touch sensor including a transistor and a capacitor may be used. FIG. 14 is a sensor circuit included in an active touch sensor.

The sensor circuit illustrated in FIG. 14 includes the capacitor 2603 and transistors 2611, 2612, and 2613.

A signal G2 is input to a gate of the transistor 2613. A voltage VRES is applied to one of a source and a drain of the transistor 2613, and one electrode of the capacitor 2603 and a gate of the transistor 2611 are electrically connected to the other of the source and the drain of the transistor 2613. One of a source and a drain of the transistor 2611 is electrically connected to one of a source and a drain of the transistor 2612, and a voltage VSS is applied to the other of the source and the drain of the transistor 2611. A signal G1 is input to a gate of the transistor 2612, and a wiring ML is electrically connected to the other of the source and the drain of the transistor 2612. The voltage VSS is applied to the other electrode of the capacitor 2603.

Next, the operation of the sensor circuit illustrated in FIG. 14 is described. First, a potential for turning on the transistor 2613 is supplied as the signal G2, and a potential with respect to the voltage VRES is thus applied to a node n connected to the gate of the transistor 2611. Then, a potential for turning off the transistor 2613 is applied as the signal G2, whereby the potential of the node n is maintained. Then, mutual capacitance of the capacitor 2603 changes owing to the approach or contact of a sensing target such as a finger; accordingly, the potential of the node n is changed from VRES.

In reading operation, a potential for turning on the transistor 2612 is supplied as the signal G1. A current flowing through the transistor 2611, that is, a current flowing through the wiring ML is changed in accordance with the potential of the node n. By sensing this current, the approach or contact of a sensing target can be sensed.

In each of the transistors 2611, 2612, and 2613, an oxide semiconductor layer is preferably used as a semiconductor layer in which a channel region is formed. In particular, such a transistor is preferably used as the transistor 2613, so that the potential of the node n can be held for a long time and the frequency of operation of resupplying VRES to the node n (refresh operation) can be reduced.

At least part of this embodiment can be implemented in combination with any of the other embodiments described in this specification as appropriate.

EXAMPLE 1

SYNTHESIS EXAMPLE 1

In this example, a method of synthesizing 2-[3-(benzo[1,2-b:4,5-b']bisbenzofuran-6-yl)phenyl]dibenzo[f,h]quinoxaline (abbreviation: 2mBbfPDBq) (the structural formula (101)), which is a heterocyclic compound of one embodiment of the present invention, will be described. The structure of 2mBbfPDBq is shown below.

[Chemical Formula 41]

(101)

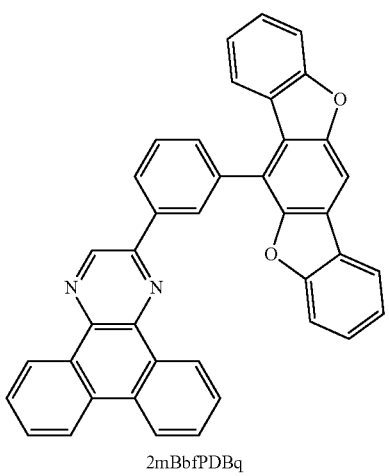

2mBbfPDBq

<Synthesis of 2mBbfPDBq>
<Step 1>

Into a 200-mL three-neck flask were put 8.9 g (30 mmol) of 1,4-dibromo-2,5-dimethoxybenzene, 10 g (72 mmol) of 2-fluorophenylboronic acid, 15 mL of toluene, 15 mL of diethylene glycol dimethyl ether (diglyme), and 60 mL of a sodium carbonate aqueous solution (2.0 mol/L). This mixture was degassed by being stirred while the pressure in the flask was reduced.

After the degassing, the atmosphere in the flask was replaced with nitrogen, and the mixture was heated to 80° C. To this mixture was added 0.69 g (0.60 mmol) of tetrakis(triphenylphosphine)palladium(0), and the mixture was stirred at the same temperature for 2 hours. The mixture was cooled down to room temperature and degassed again under reduced pressure. Then, the atmosphere in the flask was replaced with nitrogen, and the mixture was heated to 80° C. After the heating, 0.69 g (0.60 mmol) of tetrakis(triphenylphosphine)palladium(0) was added to this mixture, and the mixture was heated at the same temperature for 5 hours.

After the heating, 2.0 g (14 mmol) of 2-fluorophenylboronic acid was added to this mixture, and the mixture was further stirred at the same temperature for 3 hours. After the heating, the mixture was cooled down to the room temperature and degassed under reduced pressure. Then, the atmosphere in the flask was replaced with nitrogen. This mixture was heated to 80° C., 0.64 g (0.55 mmol) of tetrakis(triphenylphosphine)palladium(0) and 3.0 g (21 mmol) of 2-fluorophenylboronic acid were added to the mixture, and the mixture was stirred at the same temperature for 2 hours. After the stirring, the mixture was cooled down to the room temperature, and the mixture was separated into an organic layer and an aqueous layer.

The obtained aqueous layer was subjected to extraction with toluene three times, the extracted solution and the organic layer were combined, and this mixture was washed with saturated saline and dried with anhydrous magnesium sulfate. The obtained mixture was gravity-filtered, and then the obtained filtrate was concentrated to give a compound. The obtained compound was recrystallized with toluene to give 2.5 g of a target. The compound obtained by the concentration of the filtrate was purified by column chromatography (a developing solvent: a mixed solvent of hexane and ethyl acetate in a ratio of 30:1) to give 0.3 g of a target. The targets were 2.8 g in total, and the yield was 29%. A synthesis scheme of the above synthesis method is shown in (A-1) below.

[Chemical Formula 42]

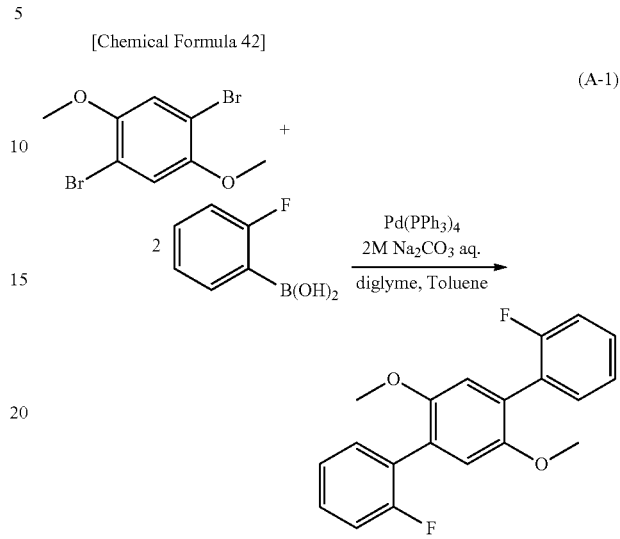

(A-1)

<Step 2>

Into a 300-mL three-neck flask was put 2.8 g (8.7 mmol) of 1,4-bis(2-fluorophenyl)-2,5-dimethoxybenzene. After the atmosphere in the flask was replaced with nitrogen, 20 mL of dehydrated dichloromethane was added to obtain a solution. This solution was put into an ice bath and stirred. Then, a solution in which 21 mL (21 mmol) of a boron tribromide solution (a 1 mol/L dichloromethane solution) was diluted with 22 mL of dehydrated dichloromethane was dropped to this solution, and the solution obtained after the drop was stirred at the room temperature for approximately 15 hours.

After the stirring, the obtained solution was put into an ice bath and cooled, and 10 mL of water and 5 mL of ethanol were dropped. After the drop, a precipitated solid was collected by suction filtration to give a target white solid. The obtained filtrate was separated into an organic layer and an aqueous layer, and the obtained aqueous layer was subjected to extraction with dichloromethane three times. The extracted solution and the organic layer were combined, and this mixture was washed with saturated saline and a sodium hydrogen carbonate solution and dried with anhydrous magnesium sulfate. The obtained mixture was gravity-filtered, and then the obtained filtrate was concentrated to give a target white solid. A synthesis scheme of the above synthesis method is shown in (A-2) below.

[Chemical Formula 43]

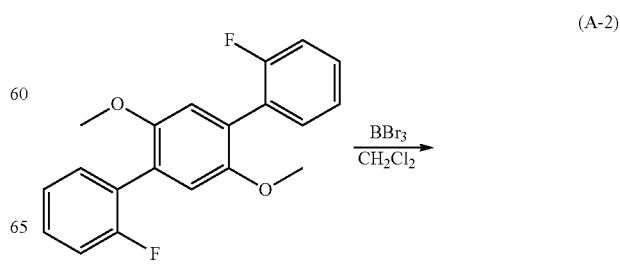

(A-2)

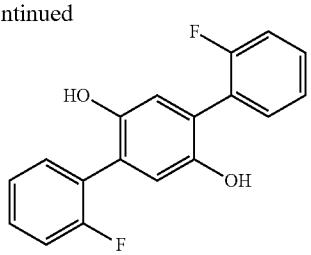

<Step 3>

Into a 100-mL three-neck flask were put 2.3 g (7.8 mmol) of 1,4-bis(2-fluorophenyl)-2,5-dihydroxybenzene obtained in Step 2, 4.2 g (30 mmol) of potassium carbonate, and 44 mL of N-methyl-2-pyrrolidinone. This mixture was degassed by being stirred while the pressure in the flask was reduced. After the degassing, the atmosphere in the flask was replaced with nitrogen, and the mixture was stirred at 200° C. for 4.5 hours. After the stirring, the mixture was cooled down to the room temperature, toluene, water, and hydrochloric acid were added to the mixture, the mixture was stirred, and then the mixture was separated into an organic layer and an aqueous layer.

The obtained aqueous layer was subjected to extraction with toluene three times. The obtained extracted solution and the organic layer were combined, and a solid was precipitated, whereby the precipitated solid was collected by suction filtration. The obtained filtrate was washed with saturated saline and a sodium hydrogen carbonate solution and dried with anhydrous magnesium sulfate. A solid which was obtained by concentration of the obtained filtrate which was gravity-filtered was recrystallized with toluene to give 0.53 g of a target solid. The above precipitated solid was recrystallized with toluene to give 0.94 g of a target white solid. The target solids were 1.5 g (5.7 mmol) in total, and the yield was 73%. A synthesis scheme of the above synthesis method is shown in (A-3) below.

[Chemical Formula 44]

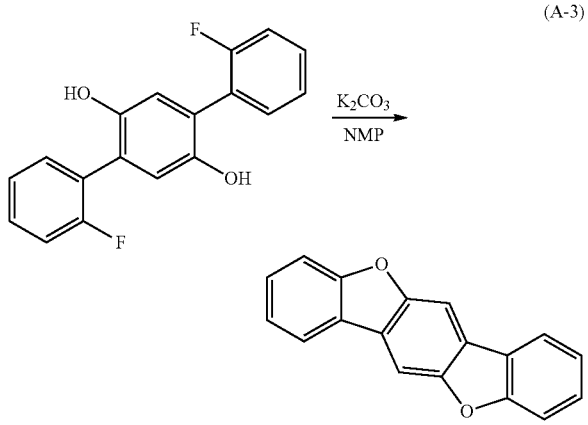

(A-3)

<Step 4>

Into a 100-mL three-neck flask was put 1.4 g (5.5 mmol) of benzo[1,2-b:4,5-b']bisbenzofuran. After the atmosphere in the flask was replaced with nitrogen, 34 mL of dehydrated tetrahydrofuran was added, and the obtained solution was stirred at −78° C. To this solution, 4.0 mL of an n-butyllithium hexane solution (1.6 mol/L, 6.3 mmol) was dropped. After the drop, the solution was stirred for 20 minutes at the same temperature and for 1 hour after the temperature rose to the room temperature. After a predetermined period of time, the obtained solution was cooled to −78° C., and after the cooling, 1.5 mL (13 mmol) of trimethyl borate was dropped at the same temperature.

After the temperature of the obtained solution rose to the room temperature, the obtained solution was stirred at the room temperature for 15 hours. After the stirring, 50 mL of hydrochloric acid (1 mol/L) was added and then this mixture was stirred for 1 hour. After the stirring, the mixture was separated into an organic layer and an aqueous layer, and the obtained aqueous layer was subjected to extraction with ethyl acetate twice. The obtained extracted solution and the organic layer were combined, and this mixture was washed with saturated saline and a sodium hydrogen carbonate solution and dried with anhydrous magnesium sulfate. The obtained mixture was gravity-filtered, and then the obtained filtrate was concentrated to give a solid.

The obtained solid was washed with chloroform and subjected to suction filtration to give 0.53 g of a target solid. A compound obtained by concentration of the filtrate was recrystallized with toluene/hexane to give 0.60 g of a target solid. The target solids were 1.1 g (3.7 mmol) in total, and the yield was 67%. A synthesis scheme of the above synthesis method is shown in (A-4) below.

[Chemical Formula 45]

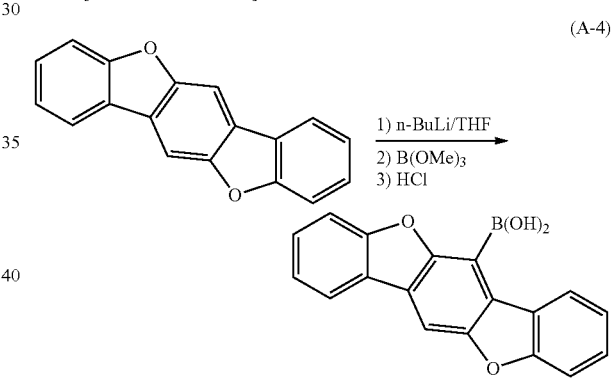

(A-4)

<Step 5>

Into a 100-mL three-neck flask were put 1.2 g (3.1 mmol) of 2-(3-bromophenyl)dibenzo[f,h]quinoxaline, 1.1 g (3.6 mmol) of benzo[1,2-b:4,5-b']bisbenzofuran-6-boronic acid, 50 mg (0.16 mmol) of tris(2-methylphenyl)phosphine, 15 mL of toluene, 2 mL of ethanol, and 5 mL of an aqueous potassium carbonate solution (2.0 mol/L). This mixture was degassed by being stirred while the pressure in the flask was reduced.

After the degassing, the atmosphere in the flask was replaced with nitrogen, and the mixture was heated to 80° C. Then, 10 mg (45 μmol) of palladium(II) acetate was added to this mixture, and stirring was performed for 7 hours. After the stirring, the mixture was cooled down to the room temperature, and a precipitated solid was collected by suction filtration. The obtained solid was washed with water and ethanol to give a target solid. The obtained solid was dissolved by heat in toluene, and the obtained solution was filtered through Celite and alumina. The obtained filtrate was concentrated to give a solid and the solid was recrystallized with toluene to give 1.0 g (1.8 mmol) of a target solid at a yield of 58%.

Then, 1.0 g of the obtained solid was purified by train sublimation. In the purification by sublimation, the solid was heated at 335° C. under a pressure of 2.6 Pa with a flow rate of argon of 5 mL/min for 16.5 hours. After the purification by sublimation, 0.61 g of a target pale yellow solid was obtained at a collection rate of 59%. A synthesis scheme of the above synthesis method is shown in (A-5) below.

[Chemical Formula 46]

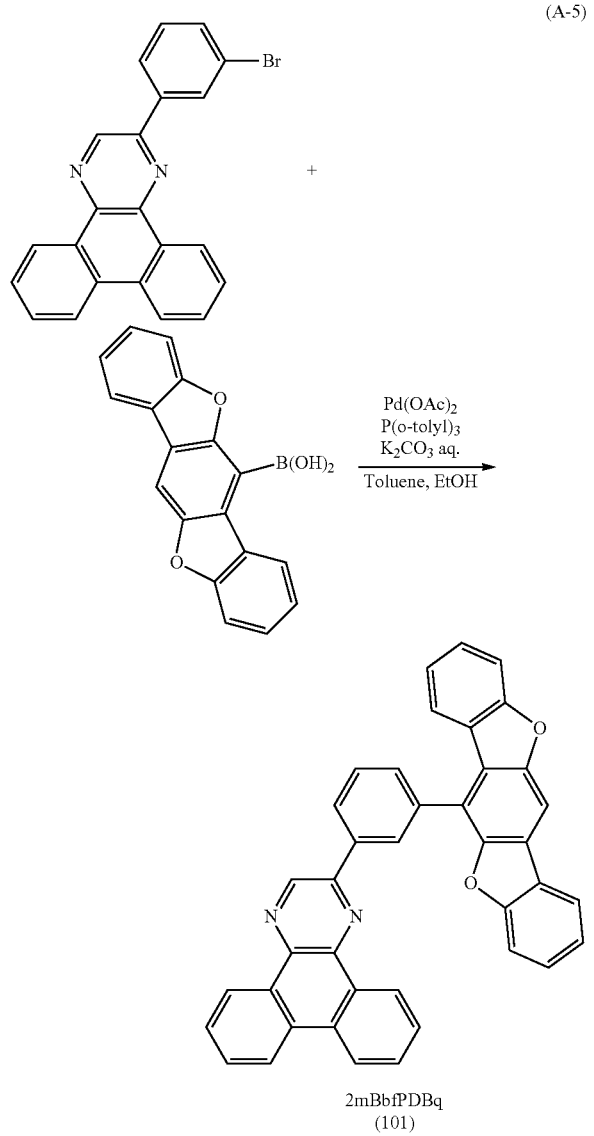

Figure 15A:
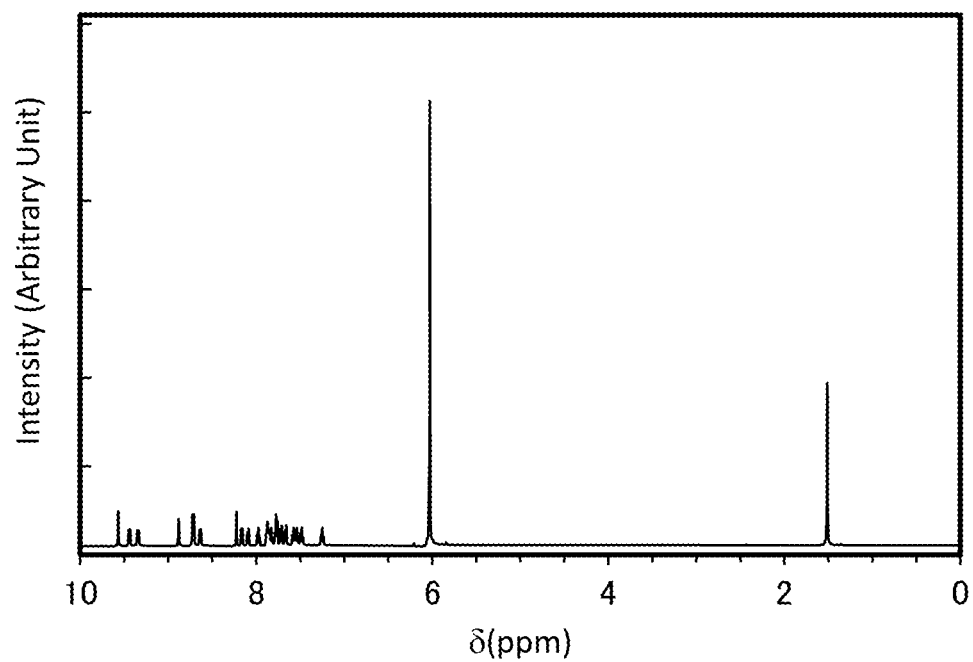
FIGS. 15A and 15B show a $^1$H-NMR chart of a heterocyclic compound represented by the structural formula (101).
Figure 15B:
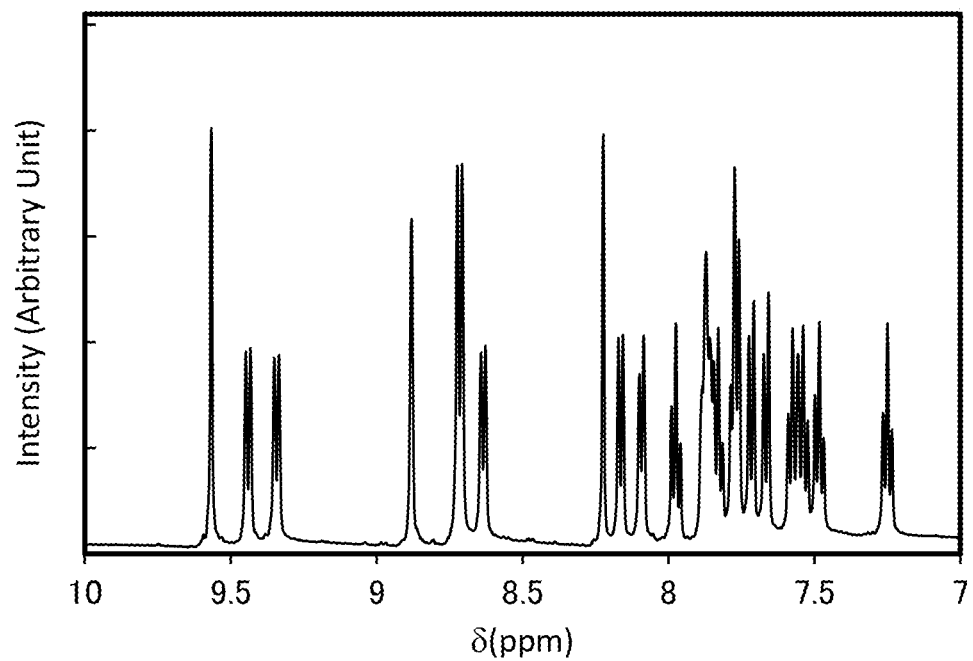

Analysis results by nuclear magnetic resonance ($^1$H-NMR) spectroscopy of the pale yellow solid obtained by the above-described synthesis method are described below. FIGS. 15A and 15B show the $^1$H-NMR chart. The results revealed that 2mBbfPDBq, which is a heterocyclic compound of one embodiment of the present invention represented by the structural formula (101), was obtained in Synthesis example 1.

$^1$H-NMR (tetrachloroethane-d$_2$, 500 MHz): δ=7.25 (t, J=7.5 Hz, 1H), 7.48 (t, J=7.5 Hz, 1H), 7.52-7.59 (m, 2H), 7.67 (d, J=8.0 Hz, 1H), 7.72 (d, J=8.0 Hz, 1H), 7.77 (t, J=7.0 Hz, 2H), 7.82-7.89 (m, 3H), 7.98 (t, J=7.5 Hz, 1H), 8.09 (d, J=7.5 Hz, 1H), 8.16 (d, J=7.5 Hz, 1H), 8.22 (d, J=1.0 Hz, 1H), 8.63 (d, J=7.5 Hz, 1H), 8.71 (d, J=7.5 Hz, 2H), 8.88 (s, 1H), 9.34 (d, J=8.0 Hz, 1H), 9.43 (d, J=8.0 Hz, 1H), 9.57 (s, 1H).

Figure 16A:
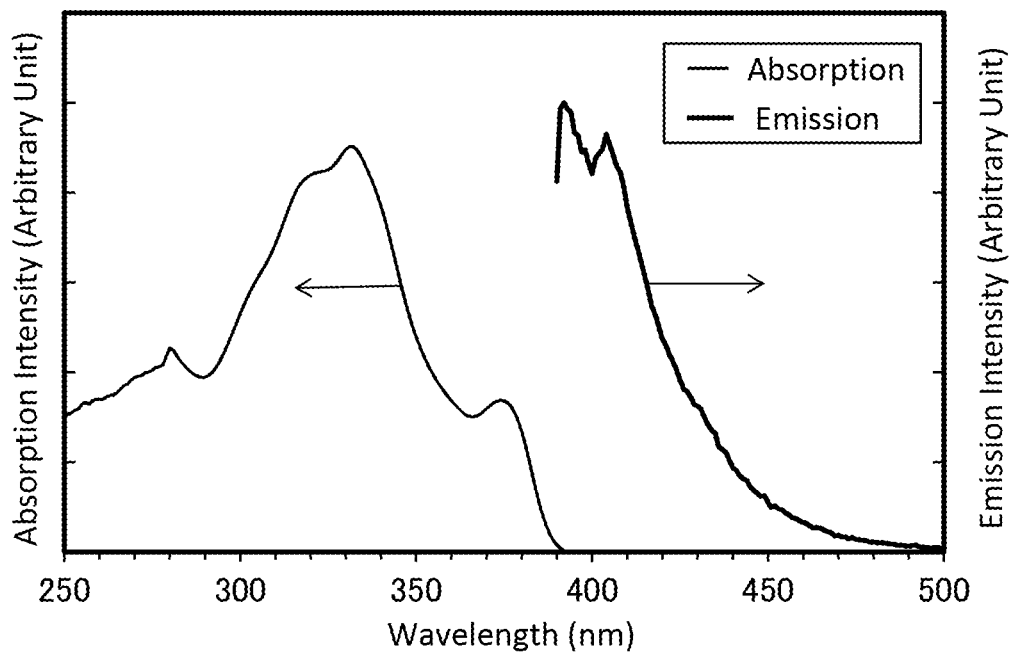
FIGS. 16A and 16B show ultraviolet-visible absorption spectra and emission spectra of the heterocyclic compound represented by the structural formula (101).
Figure 16B:
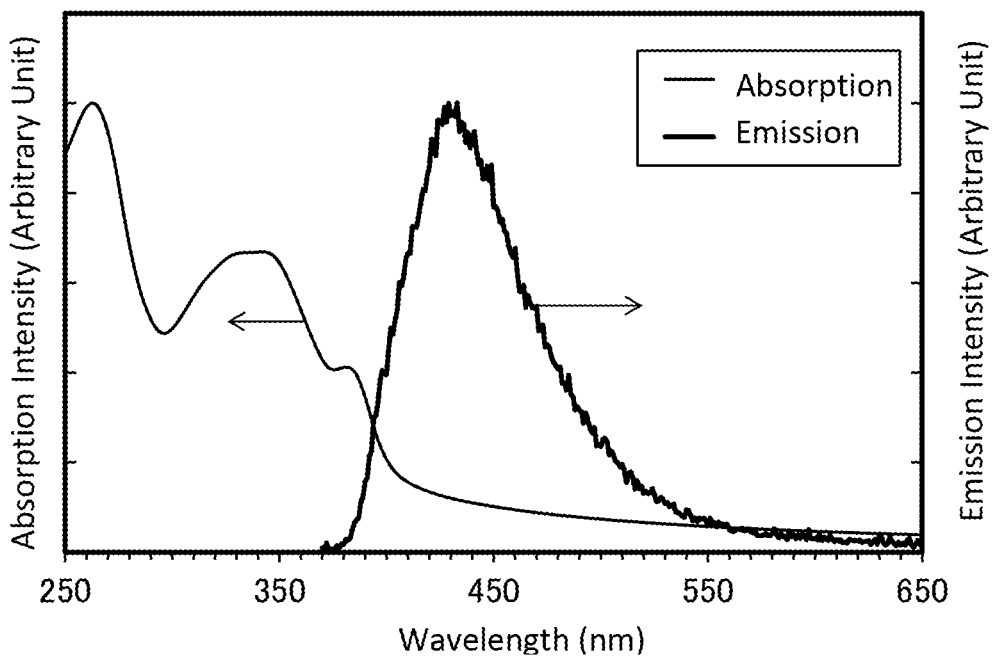

Next, ultraviolet-visible absorption spectra (hereinafter simply referred to as "absorption spectra") and emission spectra of 2mBbfPDBq in a toluene solution of 2mBbfPDBq and a solid thin film of 2mBbfPDBq were measured. The solid thin film was formed over a quartz substrate by a vacuum evaporation method. The absorption spectra were measured using an ultraviolet-visible light spectrophotometer (V550 type manufactured by JASCO Corporation). The emission spectra were measured using a fluorescence spectrophotometer (FS920 manufactured by Hamamatsu Photonics K.K.). FIG. 16A shows the obtained absorption and emission spectra of 2mBbfPDBq in the toluene solution. The horizontal axis represents wavelength, and the vertical axis represents absorption intensity. FIG. 16B shows the obtained absorption and emission spectra of the solid thin film. The horizontal axis represents wavelength, and the vertical axis represents absorption intensity.

FIG. 16A shows that 2mBbfPDBq in the toluene solution has absorption peaks at around 282 nm and 333 nm, and emission wavelength peaks at around 392 nm and 404 nm. FIG. 16B shows that 2mBbfPDBq in the solid thin film has absorption peaks at around 263 nm and 337 nm, and an emission wavelength peak at around 429 nm.

EXAMPLE 2

SYNTHESIS EXAMPLE 2

In this example, a method of synthesizing 2-[3-(benzo[1,2-b:5,4-b']bisbenzofuran-6-yl)phenyl]dibenzo[f,h]quinoxaline (abbreviation: 2mBbf(II)PDBq) (the structural formula (107)), which is a heterocyclic compound of one embodiment of the present invention, will be described. The structure of 2mBbf(II)PDBq is shown below.

[Chemical Formula 47]

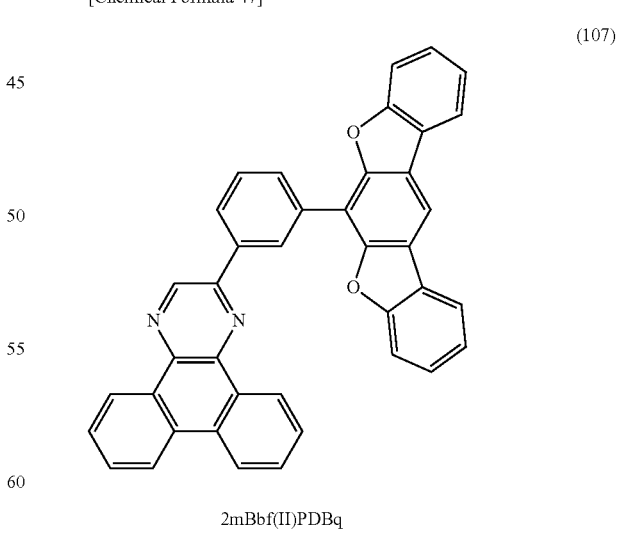

<Synthesis of 2mBbf(II)PDBq>
<Step 1>
Into a 200-mL three-neck flask was put 5.0 g (36 mmol) of 1,3-dimethoxybenzene. The pressure in the flask was reduced while stirring, and degassing was performed. After the degassing, the atmosphere in the flask was replaced with nitrogen, 80 mL of dehydrated dichloromethane was added, and the mixture was stirred. A solution in which 12 g (75 mmol) of bromine was dissolved in 14 mL of dehydrated dichloromethane was dropped to the flask while the obtained solution was cooled in an ice bath.

After the dropping, the obtained solution was stirred at room temperature for 15 hours. After the stirring, a sodium hydrogen carbonate solution and a saturated sodium thiosulfate aqueous solution were added to the obtained solution until the solution reaches pH8 while the solution was cooled in an ice bath. The obtained mixture was separated into an organic layer and an aqueous layer, and the aqueous layer was subjected to extraction with dichloromethane three times. The obtained extracted solution and the organic layer were combined and this mixture was washed with saturated saline. The obtained organic layer was dried with anhydrous magnesium sulfate, and this mixture was gravity-filtered to give filtrate.

Hexane was added to a solid obtained by concentration of the obtained filtrate and the mixture was irradiated with ultrasonic waves. After that, this mixture was subjected to suction filtration to give a solid. The obtained solid was recrystallized with hexane/ethyl acetate to give 7.2 g (24 mmol) of a target solid at a yield of 67%. A synthesis scheme of the above synthesis method is shown in (B-1) below.

[Chemical Formula 48]

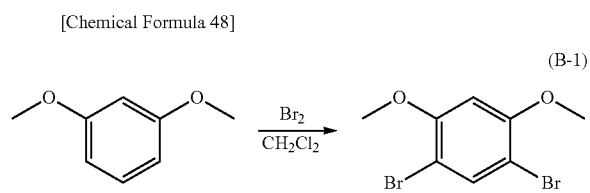

(B-1)

<Step 2>

Into a 200-mL three-neck flask were put 7.1 g (24 mmol) of 1,5-dibromo-2,4-dimethoxybenzene, 2.8 g (20 mmol) of 2-fluorophenylboronic acid, 12 mL of toluene, 12 mL of diethylene glycol dimethyl ether, and 50 mL of a sodium carbonate aqueous solution (2 mol/L). This mixture was degassed by being stirred while the pressure in the flask was reduced. After the degassing, the atmosphere in the flask was replaced with nitrogen, and the mixture was heated to 80° C.

To this mixture was added 0.55 g (0.48 mmol) of tetrakis(triphenylphosphine)palladium(0), and the mixture was stirred at the same temperature for 3 hours. After the mixture was cooled down to the room temperature, 4.5 g (32 mmol) of 2-fluorophenylboronic acid and 0.12 g (0.29 mmol) of 2-dicyclohexylphosphino-2',6'-dimethoxybiphenyl were added to the mixture and then the mixture was degassed under reduced pressure. After the degassing, the atmosphere in the flask was replaced with nitrogen, and the mixture was heated to 80° C. again. After that, 30 mg (0.13 mmol) of palladium(II) acetate was added to the mixture, and stirring was performed at the same temperature for 4 hours.

After the stirring, the mixture was cooled down to the room temperature, and the mixture was separated into an organic layer and an aqueous layer. The obtained aqueous layer was subjected to extraction with toluene three times, the extracted solution and the organic layer were combined, and this mixture was washed with saturated saline and dried with anhydrous magnesium sulfate. The obtained mixture was gravity-filtered, and then the obtained filtrate was concentrated to give a brown oily substance. This oily substance was purified by silica gel column chromatography (a developing solvent was subjected to a gradient to change from hexane to chloroform gradually) to give 7.2 g (22 mmol) of a target pale yellow oily substance at a yield of 92%. A synthesis scheme of the above synthesis method is shown in (B-2) below.

[Chemical Formula 49]

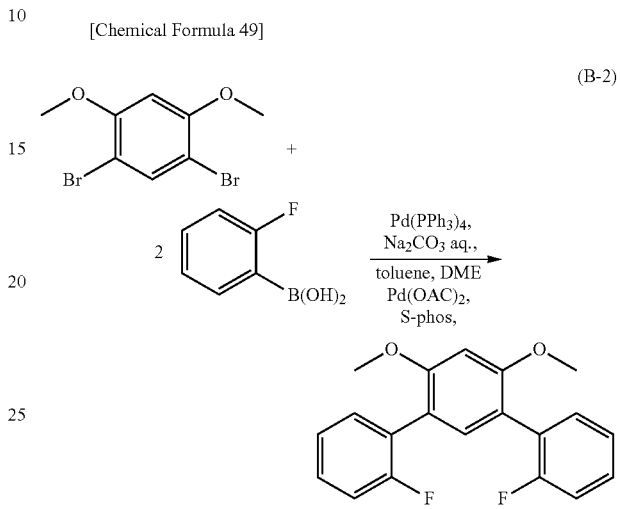

(B-2)

<Step 3>

Into a 500-mL three-neck flask was put 7.2 g (22 mmol) of 1,5-bis(2-fluorophenyl)-2,4-dimethoxybenzene. After the atmosphere in the flask was replaced with nitrogen, 60 mL of dehydrated dichloromethane was added to give a solution. The obtained solution was put into an ice bath and stirred. Then, a solution in which 53 mL (53 mmol) of a boron tribromide solution (a 1 mol/L dichloromethane solution) was diluted with 50 mL of dehydrated dichloromethane was dropped to this solution, and the solution obtained after the drop was stirred at the room temperature for 15 hours. After the stirring, the solution was put into the ice bath again, 40 mL of methanol and 40 mL of water were dropped, and the obtained mixture was separated into an organic layer and an aqueous layer. The obtained aqueous layer was subjected to extraction with dichloromethane three times, the obtained extracted solution and the organic layer were combined, and this mixture was washed with a sodium hydrogen carbonate solution and saturated saline and then dried with anhydrous magnesium sulfate. The obtained mixture was gravity-filtered, and then the obtained filtrate was concentrated to give approximately 7 g of a target pale yellow oily substance. A synthesis scheme of the above synthesis method is shown in (B-3) below.

[Chemical Formula 50]

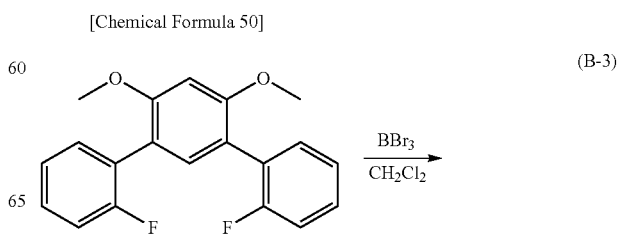

(B-3)

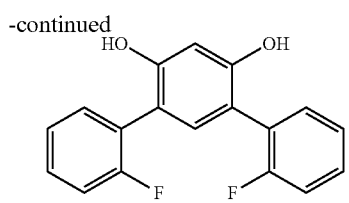

\<Step 4\>

Into a 300-mL three-neck flask were put approximately 7 g (approximately 22 mmol) of 1,5-bis(2-fluorophenyl)-2,4-dihydroxybenzene obtained in Step 3, 13 g (96 mmol) of potassium carbonate, and 140 mL of N-methyl-2-pyrrolidinone. This mixture was degassed by being stirred while the pressure in the flask was reduced. After the degassing, the atmosphere in the flask was replaced with nitrogen, and the mixture was stirred at 200° C. for 7 hours.

After the stirring, the mixture was cooled down to the room temperature, toluene, water, and hydrochloric acid were added to the mixture, the mixture was stirred, the obtained mixture was separated into an organic layer and an aqueous layer, and then the aqueous layer was subjected to extraction with toluene three times. The obtained extracted solution and the organic layer were combined, and this mixture was washed with a sodium hydrogen carbonate solution and saturated saline and dried with anhydrous magnesium sulfate. This mixture was gravity-filtered, and then the obtained filtrate was concentrated to give a yellow oily substance. The obtained oily substance was recrystallized with toluene/hexane to give a target white powdered solid.

The obtained solid was recrystallized with toluene/hexane to give a target solid. An oily substance obtained by concentration of the recrystallized filtrate was purified by silica gel column chromatography (a developing solvent: hexane) and recrystallized with hexane to give a target white powdered solid. The obtained white powdered solids were 2.2 g (8.5 mmol) in total, and the yield was 39% in Step 3 and Step 4. A synthesis scheme of the above synthesis method is shown in (B-4) below.

[Chemical Formula 51]

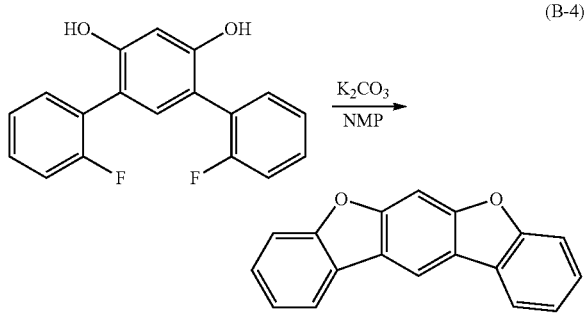

(B-4)

\<Step 5\>

Into a 200-mL three-neck flask was put 2.2 g (8.5 mmol) of benzo[1,2-b:5,4-b']bisbenzofuran. This compound was degassed by being stirred while the pressure in the flask was reduced. After the degassing, the atmosphere in the flask was replaced with nitrogen, 40 mL of dehydrated tetrahydrofuran was added to the mixture, and then the obtained solution was stirred at −78° C.

After the stirring, 5.6 mL of an n-butyllithium hexane solution (1.60 mol/L, 9.0 mmol) was dropped at the same temperature. After the drop, the solution was stirred for 30 minutes after the temperature rose to the room temperature. After the stirring, the obtained solution was cooled to −78° C., and a solution in which 2.20 g (8.7 mmol) of iodine was dissolved in 10 mL of dehydrated tetrahydrofuran was dropped at the same temperature. After the drop, the temperature of the obtained solution rose to the room temperature, and then the obtained solution was stirred at the same temperature for approximately 15 hours.

After the stirring, water was added to the obtained solution, the mixture was stirred, and then the obtained mixture was separated into an organic layer and an aqueous layer. The obtained aqueous layer was subjected to extraction with toluene three times, the obtained extracted solution and the organic layer were combined, and this mixture was washed with a sodium hydrogen carbonate solution, a sodium thiosulfate aqueous solution, and saturated saline and then dried with anhydrous magnesium sulfate. The obtained mixture was gravity-filtered, and then the obtained filtrate was concentrated to give a solid. The solid was recrystallized with toluene/hexane to give 2.5 g (6.5 mmol) of a target pale brown solid at a yield of 76%. A synthesis scheme of the above synthesis method is shown in (B-5) below.

[Chemical Formula 52]

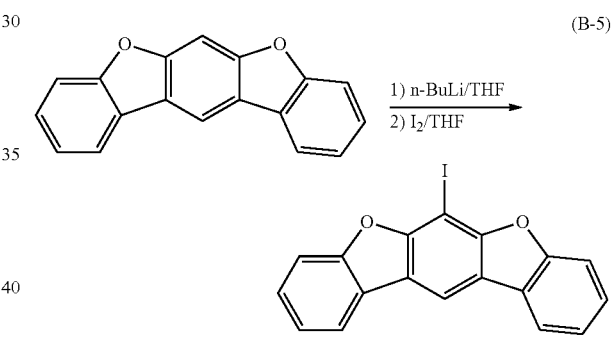

(B-5)

\<Step 6\>

Into a 200-mL three-neck flask were put 1.5 g (3.8 mmol) of 6-iodo-benzo[1,2-b:5,4-b']bisbenzofuran, 1.8 g (4.2 mmol) of 2-[3-(2-dibenzo[f,h]quinoxalinyl)phenyl]-4,4,5,5-tetramethyl-1,3,2-dioxaborolan, 70 mg (0.23 mmol) of tris(2-methylphenyl)phosphine, 20 mL of toluene, 2 mL of ethanol, and 6 mL of an aqueous potassium carbonate solution (2.0 mol/L). This mixture was degassed by being stirred while the pressure in the flask was reduced.

After the degassing, the atmosphere in the flask was replaced with nitrogen, and the mixture was heated to 80° C. After the heating, 10 mg (45 μmol) of palladium(II) acetate was added, and this mixture was stirred at the same temperature for 2.5 hours. After the stirring, the mixture was cooled down to the room temperature, 10 mg (45 μmol) of palladium(II) acetate was added again, and the mixture was stirred for 8 hours. After the mixture was cooled down to the room temperature, this mixture was concentrated, and 20 mL of ethylene glycol dimethyl ether and 6 mL of a sodium carbonate aqueous solution (2.0 mol/L) were added to the mixture. The mixture was degassed by being stirred while the pressure in the flask was reduced.

After the degassing, the atmosphere in the flask was replaced with nitrogen, and the mixture was heated to 80° C.

After the heating, 0.10 g (87 μmol) of tetrakis(triphenylphosphine)palladium(0) was added to the mixture and the mixture was stirred for 1.5 hours. After the stirring, the obtained mixture was cooled down to the room temperature, and a precipitated solid was collected by suction filtration. The obtained solid was washed with water and ethanol. The obtained solid was dissolved in toluene, and the obtained solution was filtered through Celite and alumina. The obtained filtrate was concentrated to give a solid, and the solid was recrystallized with toluene to give 1.2 g (2.1 mmol) of a target pale yellow solid at a yield of 55%.

The obtained solid was purified by train sublimation. In the purification by sublimation, the solid was heated at 310° C. under a pressure of 2.5 Pa with a flow rate of argon of 5 mL/min for 15.5 hours to give 0.90 g of a target pale yellow solid at a correction rate of 75%. A synthesis scheme of the above synthesis method is shown in (B-6) below.

[Chemical Formula 53]

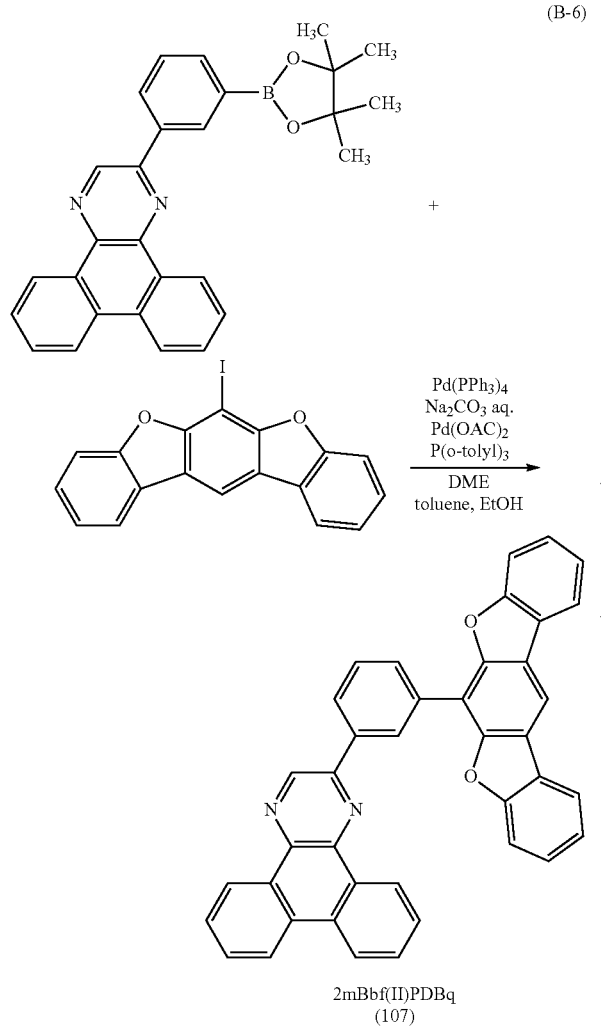

Figure 17A:
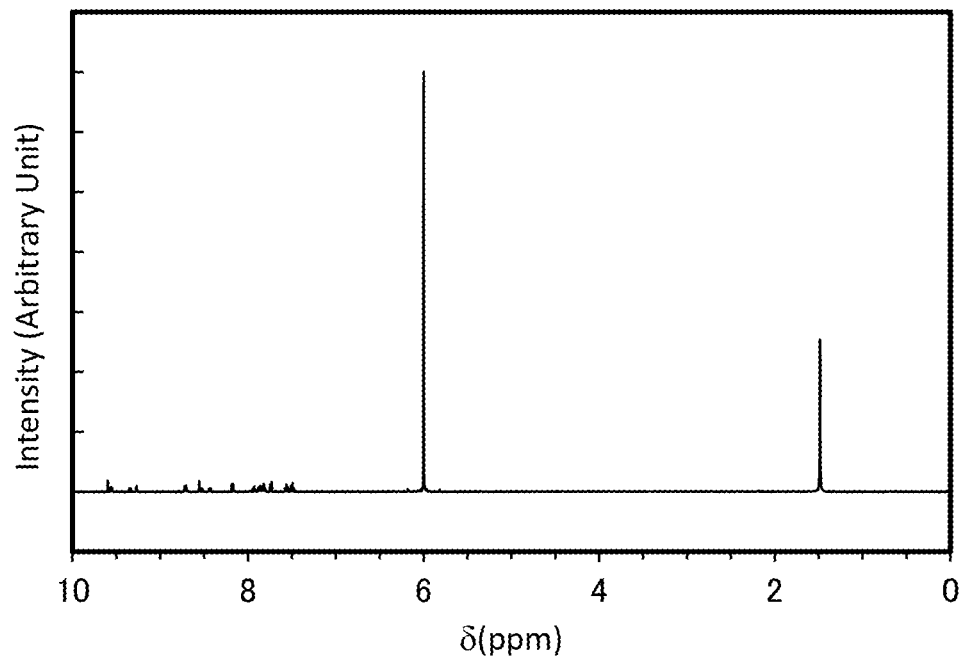
FIGS. 17A and 17B show a $^1$H-NMR chart of a heterocyclic compound represented by the structural formula (107).
Figure 17B:
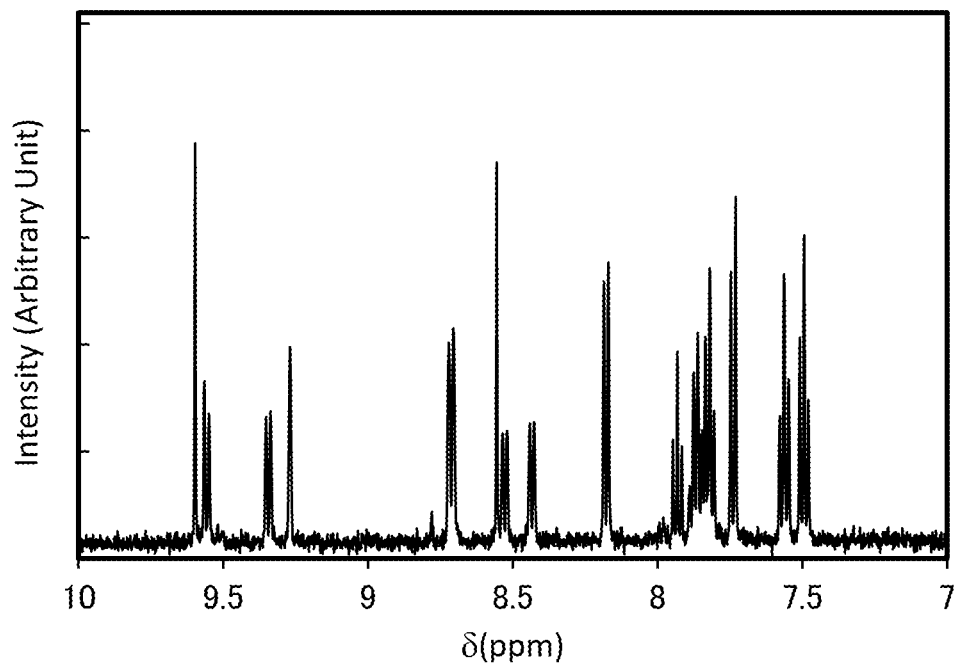

Analysis results by nuclear magnetic resonance ($^1$H-NMR) spectroscopy of the pale yellow solid obtained by the above-described synthesis method are described below. FIGS. 17A and 17B show the $^1$H-NMR chart. The results revealed that 2mBbf(II)PDBq, which is a heterocyclic compound of one embodiment of the present invention represented by the structural formula (107), was obtained in Synthesis example 2.

$^1$H-NMR (tetrachloroethane-d$_2$, 500 MHz): δ=7.49 (t, J=8.0 Hz, 2H), 7.56 (t, J=8.0 Hz, 2H), 7.74 (d, J=8.0 Hz, 2H), 7.81-7.89 (m, 4H), 7.93 (t, J=8.0 Hz, 1H), 8.18 (d, J=7.5 Hz, 2H), 8.43 (d, J=6.5 Hz, 1H), 8.53 (d, J=8.0 Hz, 1H), 8.56 (s, 1H), 8.71 (d, J=8.0 Hz, 2H), 9.27 (s, 1H), 9.34 (d, J=7.5 Hz, 1H), 9.56 (d, J=8.0 Hz, 1H), 9.60 (s, 1H).

Figure 18A:
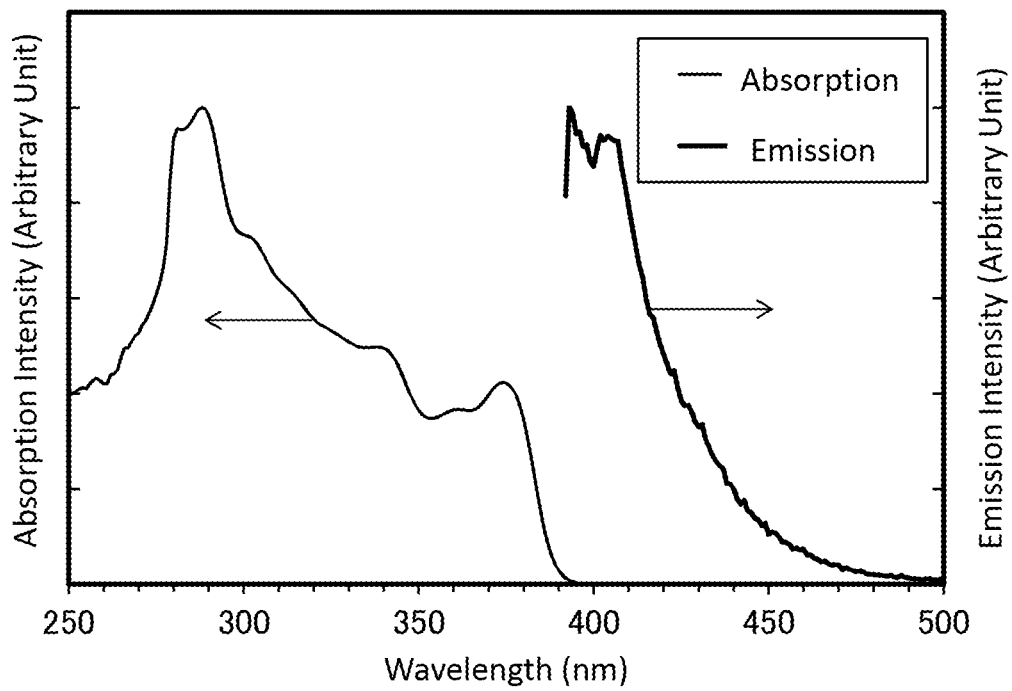
FIGS. 18A and 18B show ultraviolet-visible absorption spectra and emission spectra of the heterocyclic compound represented by the structural formula (107).
Figure 18B:
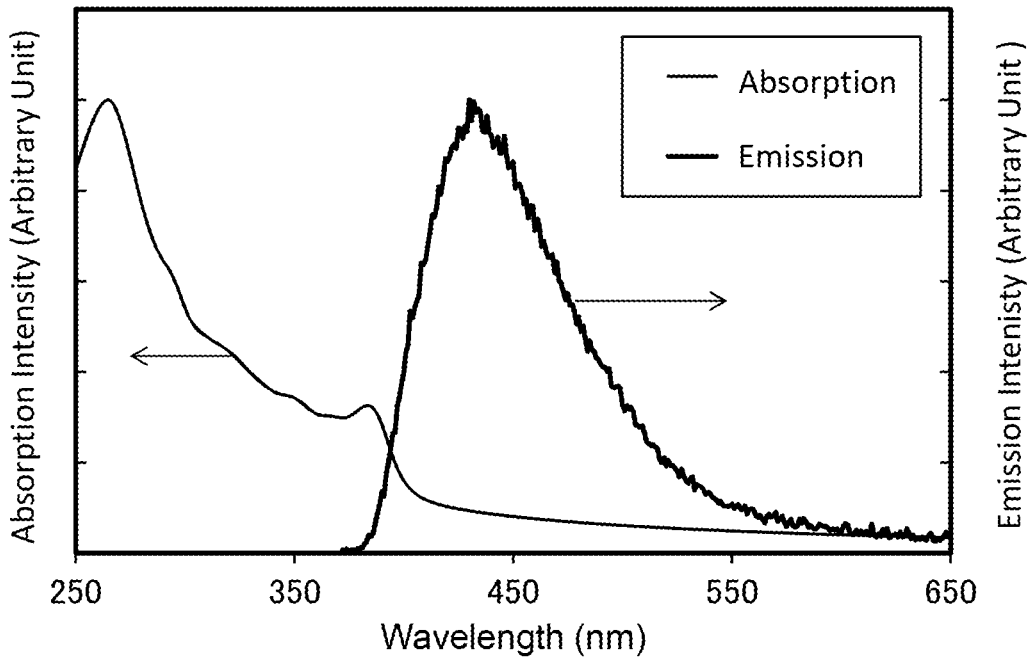

Next, ultraviolet-visible absorption spectra (hereinafter simply referred to as "absorption spectra") and emission spectra of 2mBbf(II)PDBq in a toluene solution of 2mBbf(II)PDBq and a solid thin film of 2mBbf(II)PDBq were measured. The solid thin film was formed over a quartz substrate by a vacuum evaporation method. The absorption spectra were measured using an ultraviolet-visible light spectrophotometer (V550 type manufactured by JASCO Corporation). The emission spectra were measured using a fluorescence spectrophotometer (FS920 manufactured by Hamamatsu Photonics K.K.). FIG. 18A shows the obtained absorption and emission spectra of 2mBbf(II)PDBq in the toluene solution. The horizontal axis represents wavelength, and the vertical axis represents absorption intensity. FIG. 18B shows the obtained absorption and emission spectra of the solid thin film. The horizontal axis represents wavelength, and the vertical axis represents absorption intensity.

FIG. 18A shows that 2mBbf(II)PDBq in the toluene solution has absorption peaks at around 281 nm and 288 nm, and emission wavelength peaks at around 393 nm and 404 nm. FIG. 18B shows that 2mBbf(II)PDBq in the solid thin film has absorption peaks at around 265 nm and 384 nm, and an emission wavelength peak at around 430 nm.

EXAMPLE 3

SYNTHESIS EXAMPLE 3

In this example, a method of synthesizing 2-[3-(benzo[1,2-b:5,6-b']bisbenzofuran-4-yl)phenyl]dibenzo[f,h]quinoxaline (abbreviation: 2mBbf(III)PDBq) (the structural formula (149)), which is a heterocyclic compound of one embodiment of the present invention, will be described. The structure of 2mBbf(III)PDBq is shown below.

[Chemical Formula 54]

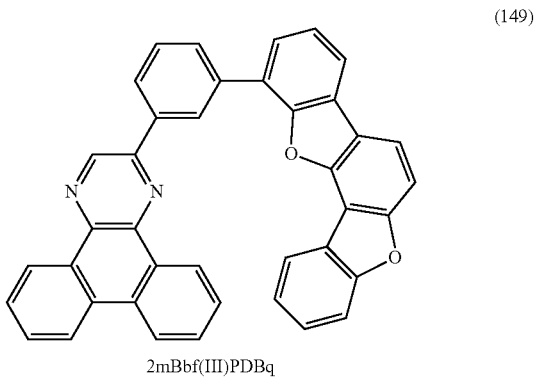

<Synthesis of 2mBbf(III)PDBq>
<Step 1>
Into a 500-mL three-neck flask were put 10 g (46 mmol) of 2-bromo-1,3-dimethoxybenzene, 7.2 g (51 mmol) of 2-fluorophenylboronic acid, 66 mL of toluene, 66 mL of diethylene glycol dimethyl ether (diglyme), and 76 mL of a sodium carbonate aqueous solution (2.0 mol/L). This mixture was degassed by being stirred while the pressure in the flask was reduced. After the degassing, the atmosphere in the flask was replaced with nitrogen, and the mixture was heated to 80° C. To this mixture was added 1.1 g (0.95 mmol) of tetrakis(trismethylphenylphosphine)palladium(0), and the mixture was stirred for 5 hours.

After the stirring, the obtained mixture was cooled down to room temperature. Then, 3.2 g (23 mmol) of 2-fluorophenylboronic acid and 1.0 g (0.87 mmol) of tetrakis(trismethylphenylphosphine)palladium(0) were added to the mixture. The mixture was degassed by being stirred while the pressure in the flask was reduced. The atmosphere in the flask was replaced with nitrogen, and the mixture was stirred at 80° C. for 8 hours. After the stirring, the mixture was cooled down to the room temperature. Then, 5.2 g (37 mmol) of 2-fluorophenylboronic acid, 0.19 g (0.46 mmol) of 2-dicyclohexylphosphino-2',6'-dimethoxybiphenyl, and 50 mg (0.22 mmol) of palladium(II) acetate were added to the mixture. The mixture was degassed by being stirred while the pressure in the flask was reduced. The atmosphere in the flask was replaced with nitrogen, and the mixture was stirred at 80° C. for 4 hours.

After the stirring, this mixture was cooled down to the room temperature, and the mixture was separated into an organic layer and an aqueous layer. The obtained aqueous layer was subjected to extraction with toluene three times, the extracted solution and the organic layer were combined, and this mixture was washed with saturated saline and dried with anhydrous magnesium sulfate. The obtained mixture was gravity-filtered, and then the obtained filtrate was concentrated to give a brown oily substance. The obtained oily substance was purified by silica gel column chromatography (a developing solvent was subjected to a gradient to change from hexane to chloroform gradually) and was then recrystallized with toluene/hexane to give 8.4 g (36 mmol) of a target solid at a yield of 78%. A synthesis scheme of the above synthesis method is shown in (C-1) below.

[Chemical Formula 55]

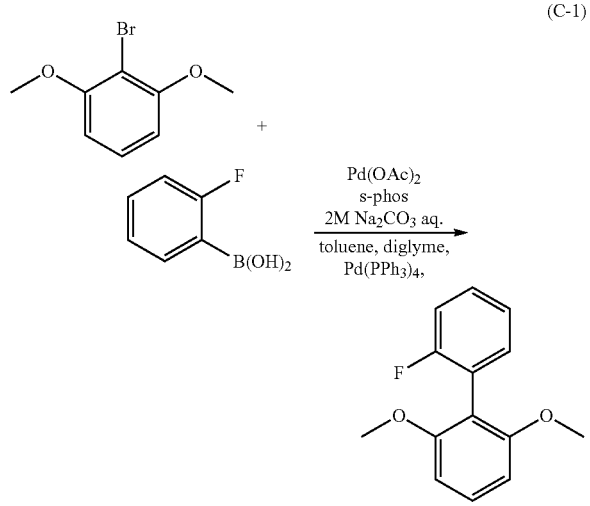

(C-1)

<Step 2>

Into a 300-mL Erlenmeyer flask were put 8.4 g (36 mmol) of 2'-fluoro-1,3-dimethoxy-2,1'-biphenyl and 130 mL of acetonitrile. Then, 6.4 g (36 mmol) of N-bromosuccinimide was added to the obtained solution, and the obtained solution was stirred at the room temperature for 23.5 hours. After the stirring, water and dichloromethane were added to this obtained solution, and this mixture was separated into an organic layer and an aqueous layer.

The aqueous layer was subjected to extraction with dichloromethane three times, the obtained extracted solution and the organic layer were combined, and this mixture was washed with a saturated sodium thiosulfate aqueous solution and saturated saline and then dried with anhydrous magnesium sulfate. The obtained mixture was gravity-filtered, and then the obtained filtrate was concentrated to give 11 g (35 mmol) of target yellow oily substance at a yield of 97%. A synthesis scheme of the above synthesis method is shown in (C-2).

[Chemical Formula 56]

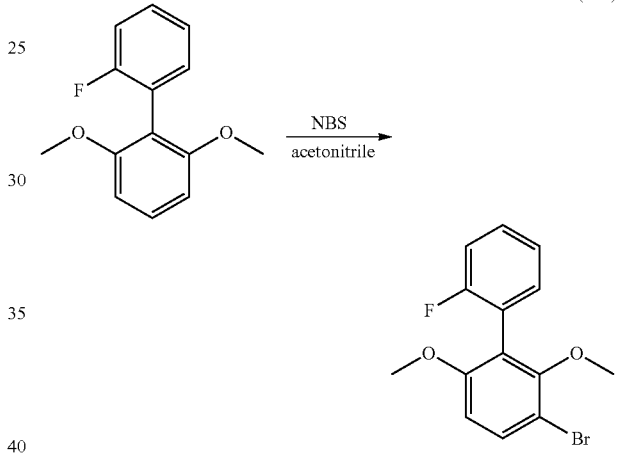

(C-2)

<Step 3>

Into a 300-mL three-neck flask was put 11 g (35 mmol) of 4-bromo-2'-fluoro-1,3-dimethoxy-2,1'-biphenyl. Then, the atmosphere in the flask was replaced with nitrogen, and 6.51 g (37 mmol) of 3-chloro-2-fluoro-benzeneboronic acid, 55 mL of a sodium carbonate aqueous solution (2.0 mol/L), 50 mL of toluene, 50 mL of ethylene glycol dimethyl ether, and 0.16 g (0.39 mmol) of 2-dicyclohexylphosphino-2',6'-dimethoxybiphenyl were added. This mixture was degassed by being stirred while the pressure in the flask was reduced. After the degassing, the atmosphere in the flask was replaced with nitrogen, and the mixture was heated to 80° C. After that, 40 mg (0.18 mmol) of palladium(II) acetate was added to the mixture, and stirring was performed at the same temperature for 2 hours.

After the stirring, the obtained mixture was cooled down to the room temperature. Then, 3.4 g (19 mmol) of 3-chloro-2-fluoro-benzeneboronic acid was added and the mixture was heated to 80° C. After that, 40 mg (0.18 mmol) of palladium(II) acetate was added to this mixture, and stirring was performed at the same temperature for 3 hours. After the stirring, 0.90 g (5.2 mmol) of 3-chloro-2-fluoro-benzeneboronic acid and 40 mg (0.18 mmol) of palladium(II) acetate were added and the mixture was heated to 80° C. Then, this mixture was stirred for 7 hours. After the stirring, the mixture was cooled down to the room temperature, and the mixture was separated into an organic layer and an aqueous layer. The aqueous layer was subjected to extraction with toluene three times, the obtained extracted solution and the organic layer were combined, and this mixture was washed with saturated saline and dried with anhydrous magnesium sulfate. This mixture was gravity-filtered, and then the obtained filtrate was concentrated to give an oily substance.

The obtained oily substance was purified by silica gel column chromatography (a developing solvent: a mixed solvent of hexane and ethyl acetate in a ratio of 10:1) and was then recrystallized with toluene/hexane to give a target solid. Mother liquor obtained by the recrystallization was concentrated to give a solid, and the solid was purified by high performance liquid chromatography (a developing solvent: chloroform) and recrystallized with toluene/hexane to give a target solid. The target solids were 9.9 g (28 mmol) in total, and the yield was 80%. A synthesis scheme of the above synthesis method is shown in (C-3) below.

aqueous layer. The obtained aqueous layer was subjected to extraction with dichloromethane three times, the extracted solution and the organic layer were combined, and this mixture was washed with a sodium hydrogen carbonate solution and saturated saline and dried with anhydrous magnesium sulfate. The obtained mixture was gravity-filtered, and then the obtained filtrate was concentrated to give a brown oily substance. The obtained oily substance was purified by silica gel column chromatography (a developing solvent: a mixed solvent of hexane and ethyl acetate in a ratio of 8:1) and was then recrystallized with hexane/chloroform to give 8.7 g (26 mmol) of a target white solid at a yield of 96%. A synthesis scheme of the above synthesis method is shown in (C-4) below.

[Chemical Formula 58]

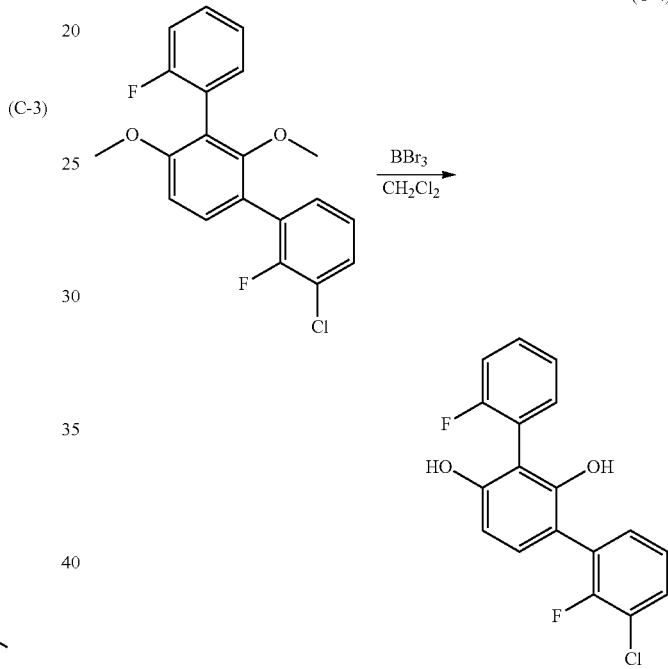

[Chemical Formula 57]

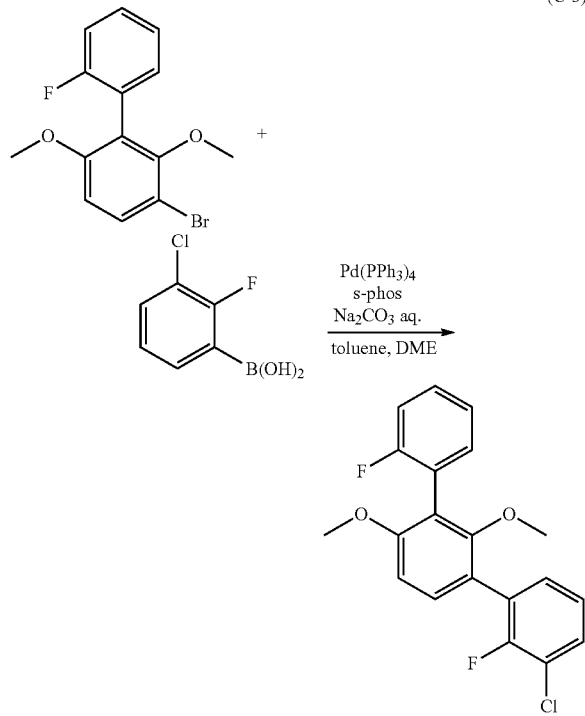

<Step 4>

Into a 500-mL three-neck flask was put 9.8 g (27 mmol) of 4-(3-chloro-2-fluorophenyl)-2-(2-fluorophenyl)-1,3-dimethoxybenzene. After the atmosphere in the flask was replaced with nitrogen, 150 mL of dehydrated dichloromethane was added. The obtained solution was put into an ice bath and stirred. Then, a solution in which 70 mL (70 mmol) of a boron tribromide solution (a 1 mol/L dichloromethane solution) was diluted with 90 mL of dehydrated dichloromethane was dropped to this solution. After the drop, the temperature of the obtained solution rose to the room temperature, and then the obtained solution was stirred for 15 hours. After the stirring, the obtained solution was put into an ice bath and cooled, and 20 mL of methanol was dropped and further 40 mL of water was dropped. The obtained mixture was separated into an organic layer and an <Step 5>

Into a 500-mL recovery flask were put 8.7 g (26 mmol) of 4-(3-chloro-2-fluorophenyl)-2-(2-fluorophenyl)-1,3-dihydroxybenzene, 14 g (0.10 mmol) of potassium carbonate, and 150 mL of N-methyl-2-pyrrolidinone. This mixture was degassed by being stirred while the pressure in the flask was reduced. After the degassing, the atmosphere in the flask was replaced with nitrogen, and the mixture was stirred at 200° C. for 9 hours. After the stirring, the mixture was cooled down to the room temperature, toluene, water, and hydrochloric acid were added to the mixture, the mixture was stirred, and then the obtained mixture was separated into an organic layer and an aqueous layer.

The obtained aqueous layer was subjected to extraction with toluene three times, the obtained extracted solution and the organic layer were combined, and this mixture was washed with a sodium hydrogen carbonate solution and saturated saline and then dried with anhydrous magnesium sulfate. This mixture was gravity-filtered, and then the obtained filtrate was concentrated to give a brown solid. The obtained solid was recrystallized with toluene/hexane to give 3.4 g (12 mmol) of a first crystal product and 1.6 g (5.4 mmol) of a second crystal product at a yield of 67% in both of the first crystal product and the second crystal product. A synthesis scheme of the above synthesis method is shown in (C-5) below.

[Chemical Formula 59]

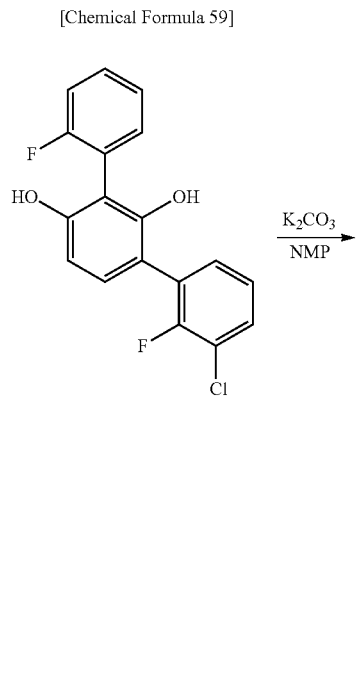

(C-5)

<Step 6>
Into a 100-mL three-neck flask were put 1.5 g (5.2 mmol) of 4-chlorobenzo[1,2-b;5,6-b']bisbenzofuran, 2.5 g (5.7 mmol) of 2-[3-(2-dibenzo[f,h]quinoxalinyl)phenyl]-4,4,5,5-tetramethyl-1,3,2-dioxaborolan, 80 mg (0.22 mmol) of di(1-adamantyl)(n-butyl)phosphine, 1.5 mL (16 mmol) of t-butanol, 3.6 g (17 mmol) of potassium phosphate (III) , and 26 mL of diethylene glycol dimethyl ether (diglyme). This mixture was degassed by being stirred while the pressure in the flask was reduced. After the degassing, the atmosphere in the flask was replaced with nitrogen, and the mixture was heated to 80° C.

After that, 10 mg (45 μmol) of palladium acetate (II) was added, and this mixture was stirred at the same temperature for 4 hours. After the stirring, the mixture was cooled down to the room temperature, 10 mg (45 μmol) of palladium acetate (II) was added, and the mixture was stirred at 100° C. for 7 hours. Then, the mixture was cooled down to the room temperature, 20 mg (89 μmol) of palladium acetate (II) was added, and the mixture was stirred at 120° C. for 4.5 hours. After the stirring, the mixture was cooled down to the room temperature and then a precipitate was collected by suction filtration.

The obtained solid was washed with water and ethanol. The obtained solid was dissolved by heat in toluene, and the obtained solution was filtered through Celite and alumina. The obtained filtrate was concentrated to give a solid, and the solid was recrystallized with toluene to give 1.4 g (2.4 mmol) of a target solid at a yield of 46%.

Then, the obtained solid was purified by train sublimation. In the purification by sublimation, the solid was heated at 305° C. under a pressure of 2.8 Pa with a flow rate of argon of 10 mL/min for 20 hours. After the purification by sublimation, 1.1 g of a target pale yellow solid was obtained at a collection rate of 77%. A synthesis scheme of the above synthesis method is shown in (C-6) below.

[Chemical Formula 60]

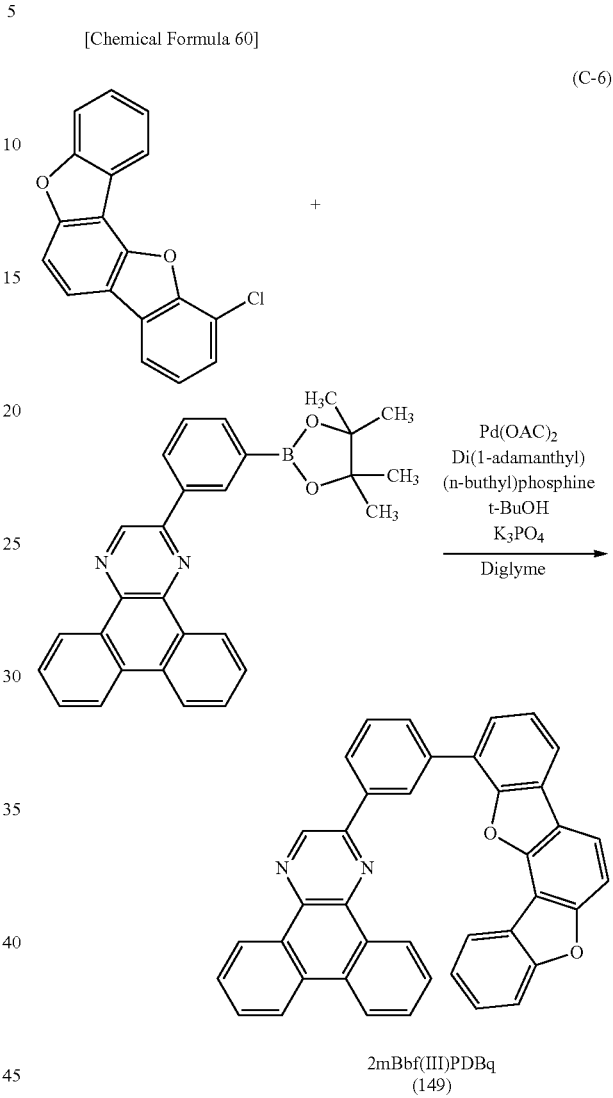

2mBbf(III)PDBq
(149)

Figure 19A:
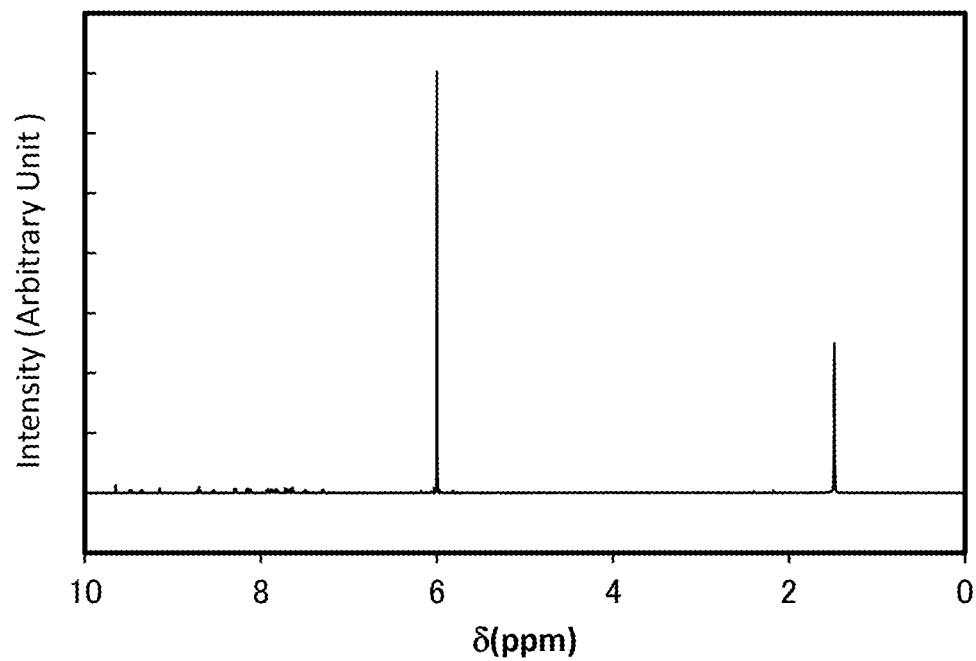
FIGS. 19A and 19B show a $^1$H-NMR chart of a heterocyclic compound represented by the structural formula (149).
Figure 19B:
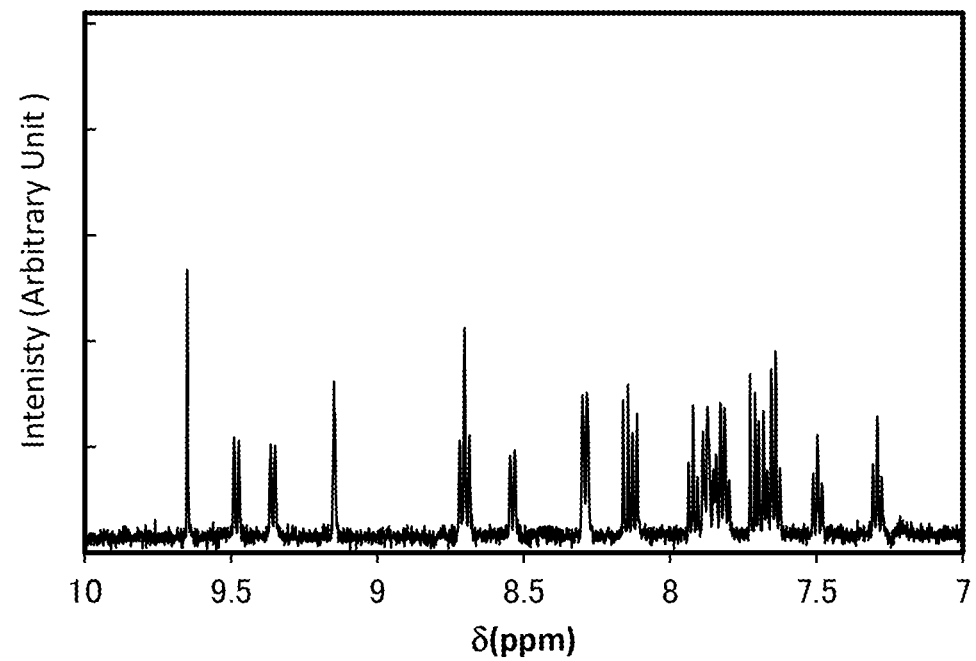

Analysis results by nuclear magnetic resonance ($^{1}$H-NMR) spectroscopy of the pale yellow solid obtained by the above-described synthesis method are described below. FIGS. 19A and 19B show the $^{1}$H-NMR chart. The results revealed that 2mBbf(III)PDBq, which is a heterocyclic compound of one embodiment of the present invention represented by the structural formula (149), was obtained in Synthesis example 3.

$^{1}$H-NMR (tetrachloroethane-d$_{2}$, 500 MHz): δ=7.29 (t, J=7.5 Hz, 1H), 7.50 (t, J=7.5 Hz, 1H), 7.62-7.73 (m, 4H), 7.80-7.89 (m, 4H), 7.92 (t, J=7.5 Hz, 1H), 8.12 (d, J=7.5 Hz, 1H), 8.15 (d, J=8.5 Hz, 1H), 8.29 (d, J=7.5 Hz, 2H), 8.54 (d, J=8.0 Hz, 1H), 8.70 (t, J=8.0 Hz, 2H), 9.15 (s, 1H), 9.36 (d, J=7.5 Hz, 1H), 9.48 (d, J=7.5 Hz, 1H), 9.65 (s, 1H).

Figure 20A:
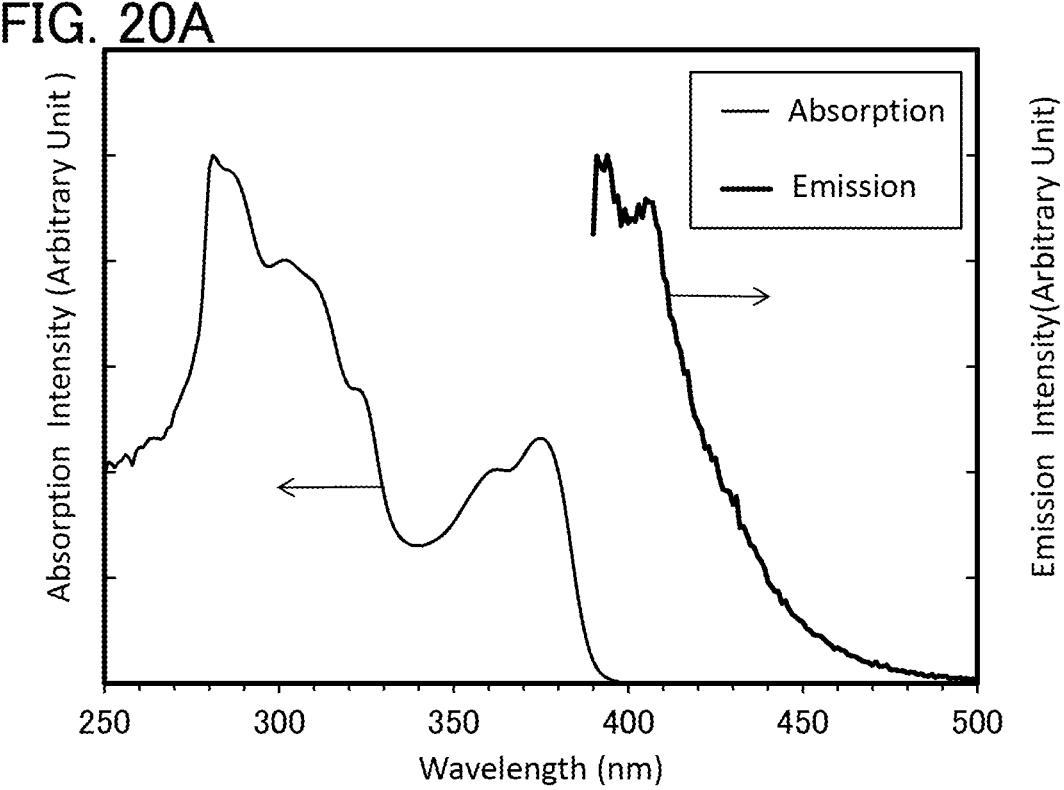
FIGS. 20A and 20B show ultraviolet-visible absorption spectra and emission spectra of the heterocyclic compound represented by the structural formula (149).
Figure 20B:
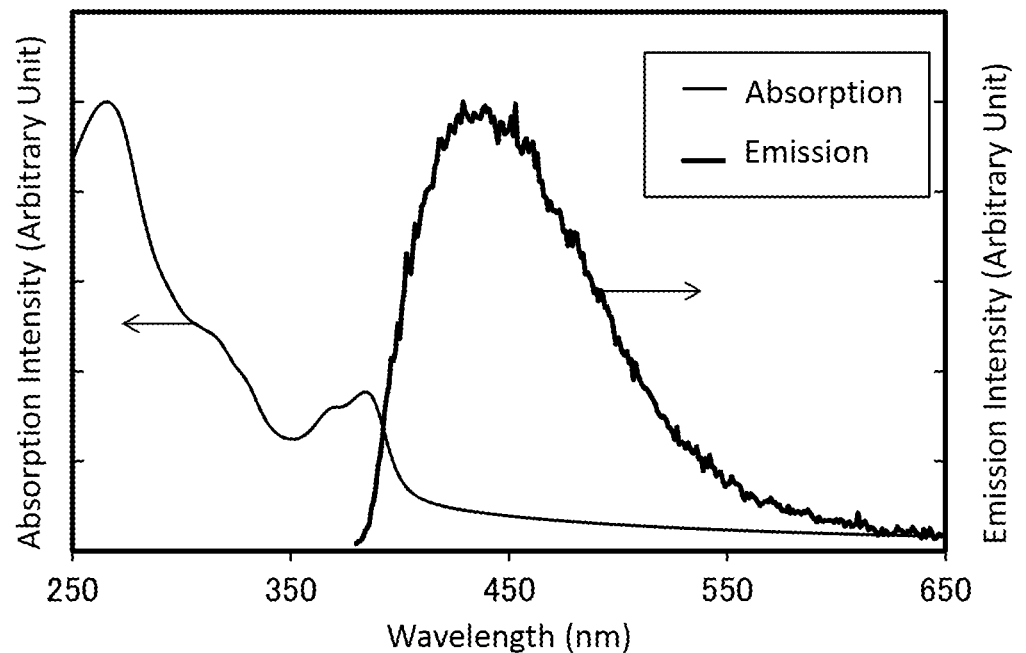

Next, ultraviolet-visible absorption spectra (hereinafter simply referred to as "absorption spectra") and emission spectra of 2mBbf(III)PDBq in a toluene solution of 2mBbf(III)PDBq and a solid thin film of 2mBbf(III)PDBq were measured. The solid thin film was formed over a quartz substrate by a vacuum evaporation method. The absorption spectra were measured using an ultraviolet-visible light spectrophotometer (V550 type manufactured by JASCO Corporation). The emission spectra were measured using a fluorescence spectrophotometer (FS920 manufactured by Hamamatsu Photonics K.K.). FIG. 20A shows the obtained absorption and emission spectra of 2mBbf(III)PDBq in the toluene solution. The horizontal axis represents wavelength, and the vertical axis represents absorption intensity. FIG. 20B shows the obtained absorption and emission spectra of the solid thin film. The horizontal axis represents wavelength, and the vertical axis represents absorption intensity.

FIG. 20A shows that 2mBbf(III)PDBq in the toluene solution has absorption peaks at around 281 nm and 376 nm, and emission wavelength peaks at around 394 nm and 407 nm. FIG. 20B shows that 2mBbf(III)PDBq in the solid thin film has absorption peaks at around 266 nm and 384 nm, and an emission wavelength peak at around 429 nm.

EXAMPLE 4

SYNTHESIS EXAMPLE 4

In this example, a method of synthesizing 2-[3'-(benzo[1,2-b:5,6-b']bisbenzofuran-4-yl)-1,1'-biphenyl-3-yl]dibenzo[f,h]quinoxaline (abbreviation: 2mBbf(III)BPDBq) (the structural formula (150)), which is a heterocyclic compound of one embodiment of the present invention, will be described. The structure of 2mBbf(III)BPDBq is shown below.

[Chemical Formula 61]

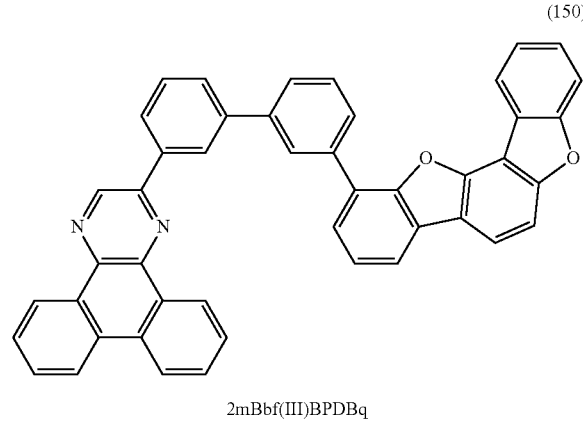

2mBbf(III)BPDBq

<Synthesis of 2mBbf(III)BPDBq>
<Step 1>

Into a 200-mL three-neck flask were put 1.5 g (2.8 mmol) of 4-chlorobenzo[1,2-b;5,6-b']bisbenzofuran, 1.4 g (3.2 mmol) of 2-[3'-(2-dibenzo[f,h]quinoxalinyl)-1,1'-biphenyl-3-yl]-4,4,5,5-tetramethyl-1,3,2-dioxaborolan, 60 mg (0.17 mmol) of di(1-adamantyl)(n-butyl)phosphine, 1 mL of t-butanol, 1.7 g (8.2 mmol) of potassium phosphate (III), and 15 mL of diethylene glycol dimethyl ether (diglyme). This mixture was degassed by being stirred while the pressure in the flask was reduced.

After the degassing, the atmosphere in the flask was replaced with nitrogen, and the mixture was heated to 80° C. After the heating, 10 mg (45 µmol) of palladium acetate (II) was added, and this mixture was stirred at the same temperature for 6 hours. After the stirring, the obtained mixture was cooled down to room temperature, 10 mg (45 µmol) of palladium acetate (II) was added, and the mixture was stirred at 120° C. for 4.5 hours and then at 140° C. for 3 hours. After the stirring, the mixture was cooled down to the room temperature and then a precipitated solid was collected by suction filtration. The obtained solid was washed with water and ethanol to give 1.6 g (2.4 mmol) of a target pale brown solid at a yield of 86%.

Then, 1.49 g of the obtained solid was purified by train sublimation. In the purification by sublimation, the solid was heated at 350° C. under a pressure of 5.1 Pa with a flow rate of argon of 15 mL/min for 15 hours. After the purification by sublimation, 1.1 g of a target pale yellow solid was obtained at a collection rate of 76%. A synthesis scheme of the above synthesis method is shown in (D-1) below.

[Chemical Formula 62]

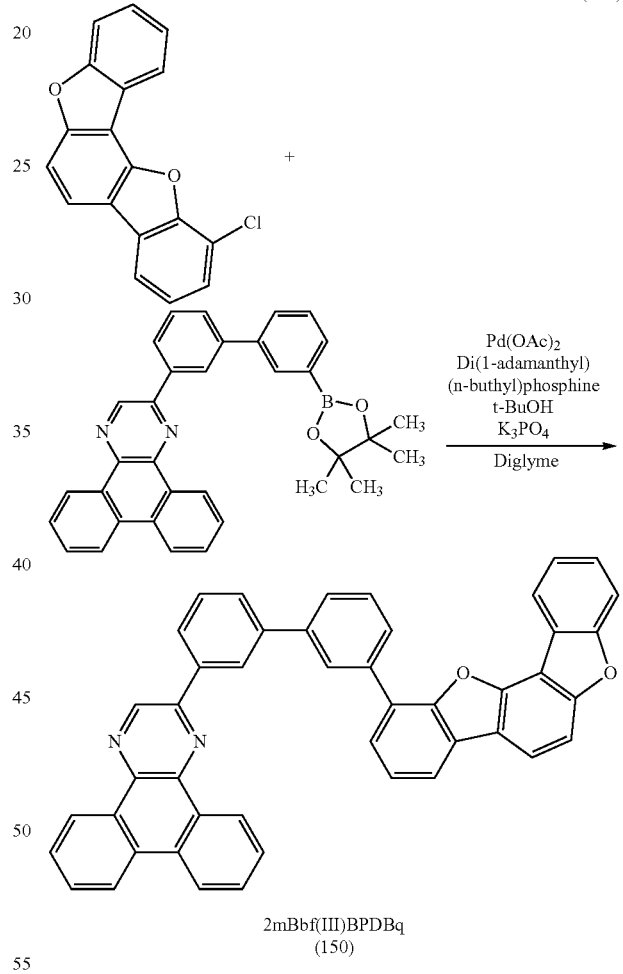

2mBbf(III)BPDBq
(150)

Figure 21A:
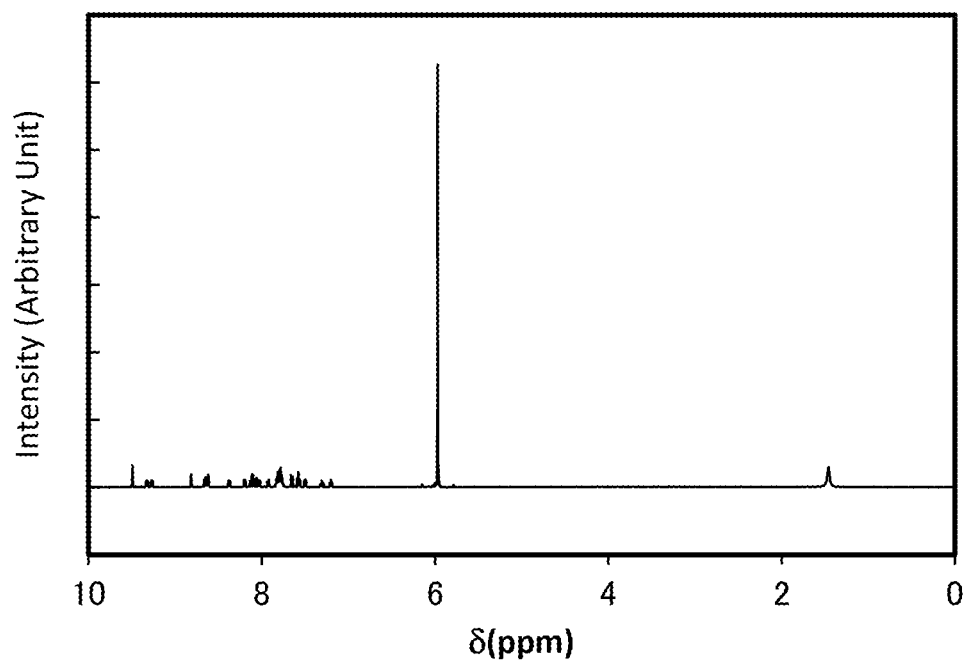
FIGS. 21A and 21B show a $^1$H-NMR chart of a heterocyclic compound represented by the structural formula (150).
Figure 21B:
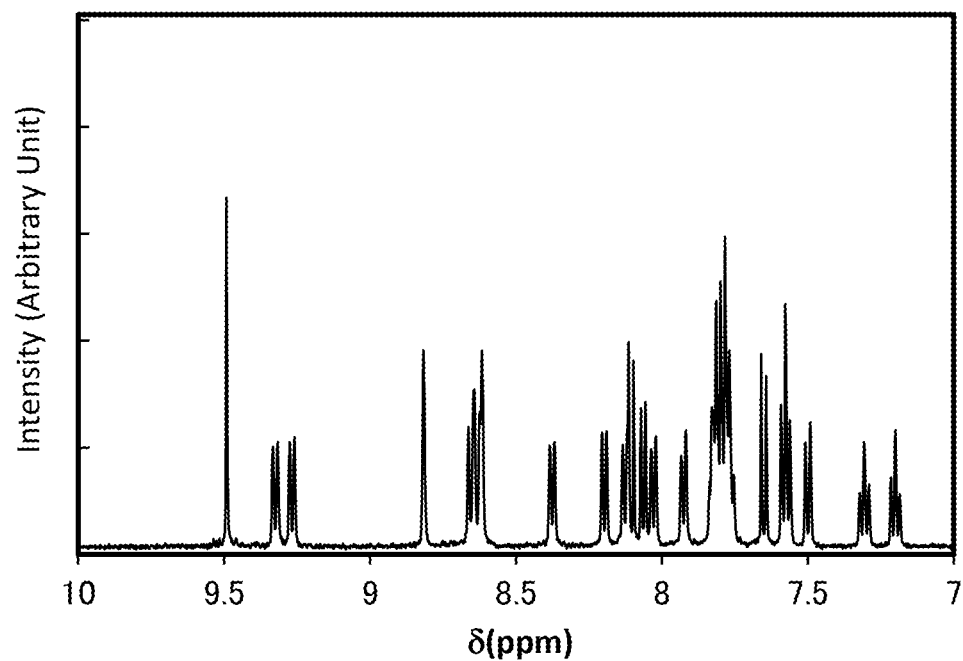

Analysis results by nuclear magnetic resonance ($^1$H-NMR) spectroscopy of the pale yellow solid obtained by the above-described synthesis method are described below. FIGS. 21A and 21B show the $^1$H-NMR chart. The results revealed that 2mBbf(III)BPDBq, which is a heterocyclic compound of one embodiment of the present invention represented by the structural formula (150), was obtained in Synthesis example 4.

$^1$H-NMR (tetrachloroethane-d$_2$, 500 MHz): δ=7.20 (t, J=7.5 Hz, 1H), 7.31 (t, J=7.5 Hz, 1H), 7.50 (d, J=7.5 Hz, 1H), 7.58 (t, J=7.5 Hz, 2H), 7.65 (d, J=7.5 Hz, 1H), 7.75-7.84 (m, 6H), 7.93 (d, J=7.5 Hz, 1H), 8.03 (d, J=7.5 Hz, 1H), 8.07 (d, J=7.5 Hz, 1H), 8.12 (t, J=7.5 Hz, 2H), 8.20 (d, J=7.5 Hz, 1H), 8.38 (d, J=7.5 Hz, 1H), 8.62-8.66 (m, 3H), 8.82 (s, 1H), 9.27 (d, J=7.5 Hz, 1H), 9.32 (d, J=7.5 Hz, 1H), 9.49 (s, 1H).

Next, ultraviolet-visible absorption spectra (hereinafter simply referred to as "absorption spectra") and emission spectra of 2mBbf(III)BPDBq in a toluene solution of 2mBbf(III)BPDBq and a solid thin film of 2mBbf(III)BPDBq were measured. The solid thin film was formed over a quartz substrate by a vacuum evaporation method.

Figure 22A:
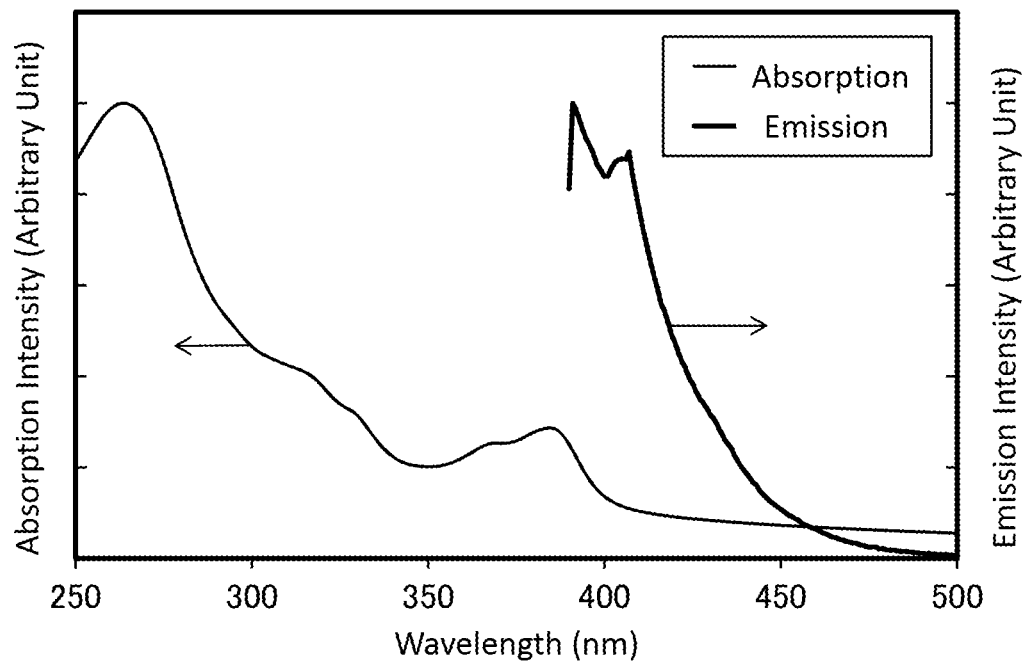
FIGS. 22A and 22B show ultraviolet-visible absorption spectra and emission spectra of the heterocyclic compound represented by the structural formula (150).
Figure 22B:
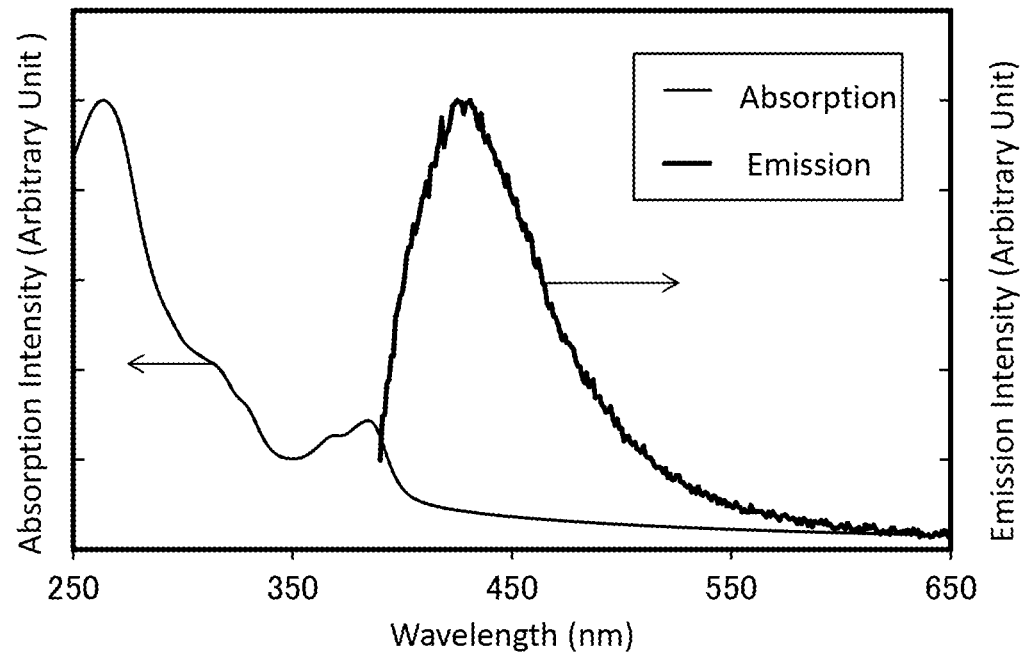

The absorption spectra were measured using an ultraviolet-visible light spectrophotometer (V550 type manufactured by JASCO Corporation). The emission spectra were measured using a fluorescence spectrophotometer (FS920 manufactured by Hamamatsu Photonics K.K.). FIG. 22A shows the obtained absorption and emission spectra of 2mBbf(III)BPDBq in the toluene solution. The horizontal axis represents wavelength, and the vertical axis represents absorption intensity. FIG. 22B shows the obtained absorption and emission spectra of the solid thin film. The horizontal axis represents wavelength, and the vertical axis represents absorption intensity.

FIG. 22A shows that 2mBbf(III)BPDBq in the toluene solution has absorption peaks at around 264 nm and 385 nm, and emission wavelength peaks at around 391 nm and 407 nm. FIG. 22B shows that 2mBbf(III)BPDBq in the solid thin film has absorption peaks at around 264 nm and 385 nm, and an emission wavelength peak at around 425 nm.

EXAMPLE 5

Figure 23:
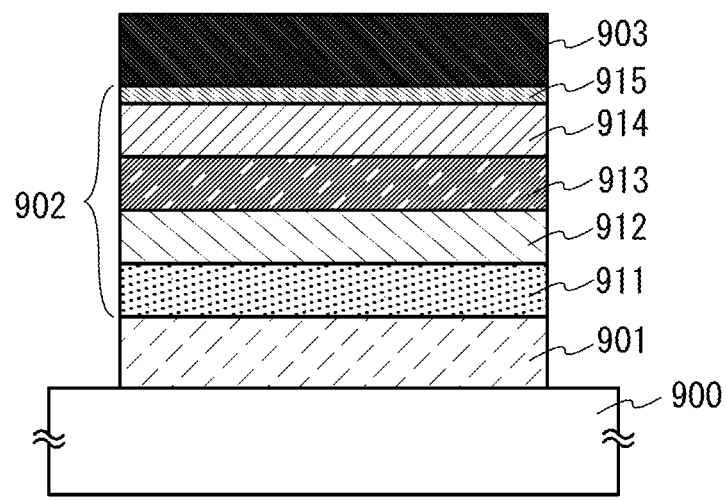
FIG. 23 illustrates a light-emitting element.
Figure 24:
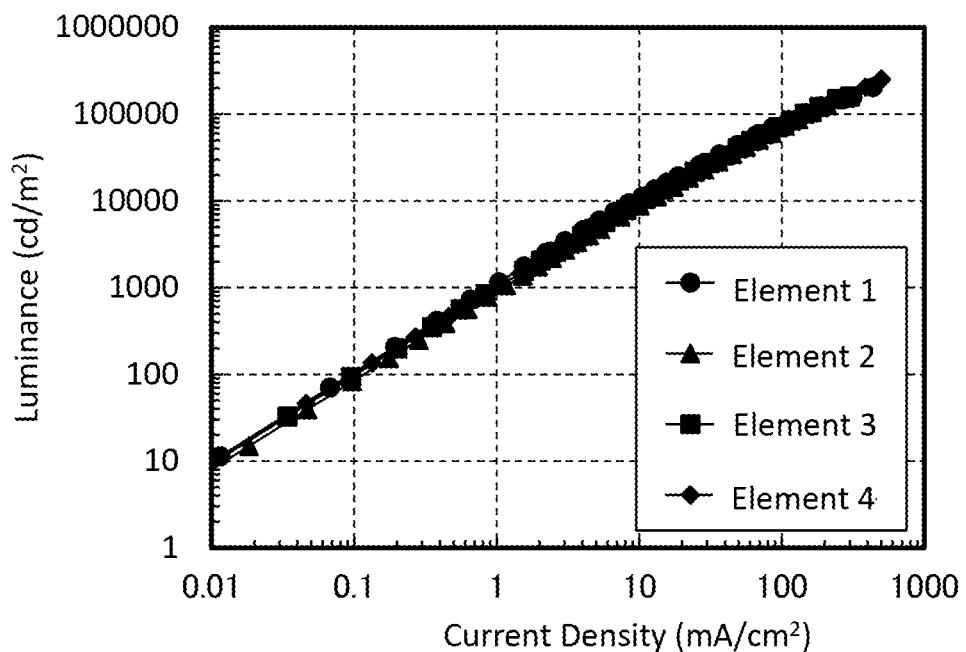
FIG. 24 shows current density—luminance characteristics of light-emitting elements 1 to 4.
Figure 25:
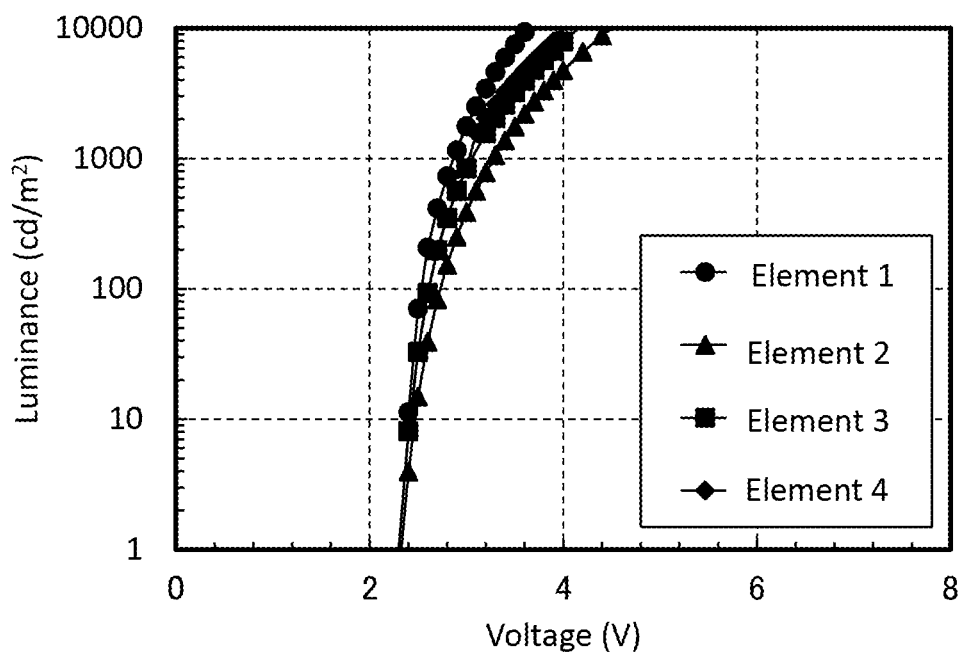
FIG. 25 shows voltage—luminance characteristics of the light-emitting elements 1 to 4.
Figure 26:
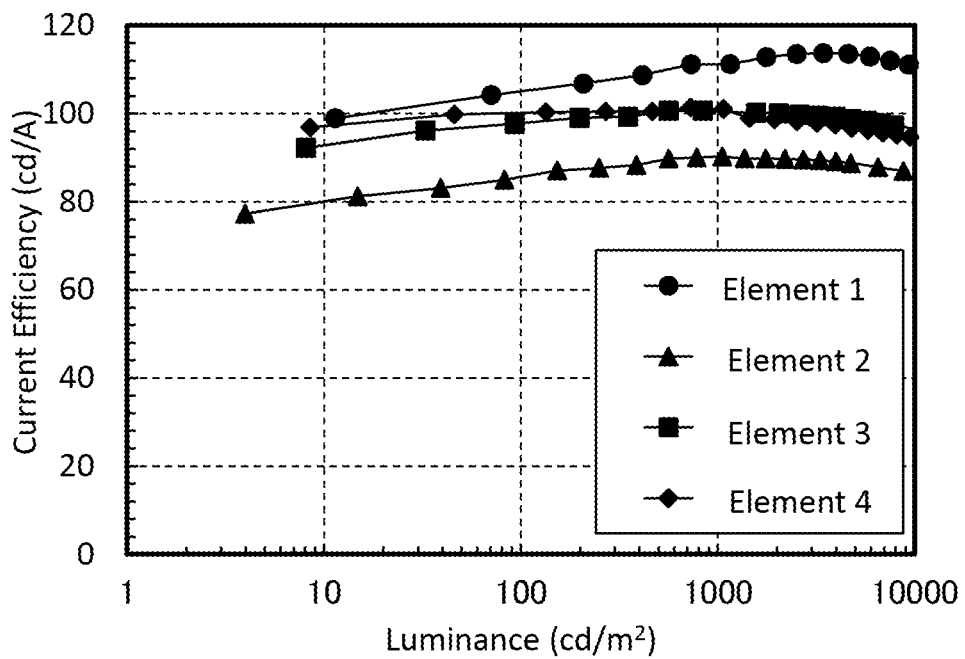
FIG. 26 shows luminance—current efficiency characteristics of the light-emitting elements 1 to 4.
Figure 27:
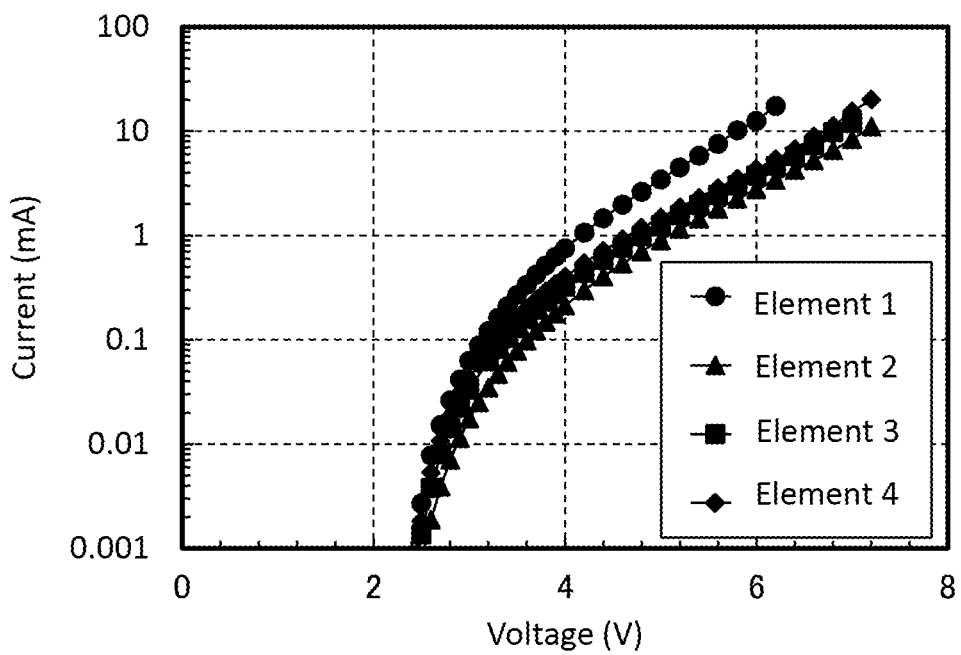
FIG. 27 shows voltage—current characteristics of the light-emitting elements 1 to 4.

In this example, a light-emitting element 1 using the 2mBbfPDBq (the structural formula (101)), a light-emitting element 2 using the 2mBbf(II)PDBq (the structural formula (107)), a light-emitting element 3 using the 2mBbf(III)PDBq (the structural formula (149)), and a light-emitting element 4 using the 2mBbf(III)BPDBq (the structural formula (150)), which are each a heterocyclic compound of one embodiment of the present invention, were fabricated. Furthermore, a comparative light-emitting element 5 using 2mDBTBPDBq-II having a dibenzothiophen structure was fabricated for comparison. Note that the fabrication of the light-emitting elements 1 to 4 and the comparative light-emitting element 5 is described with reference to FIG. 23. Chemical formulae of materials used in this example are shown below.

[Chemical Formulae 63]

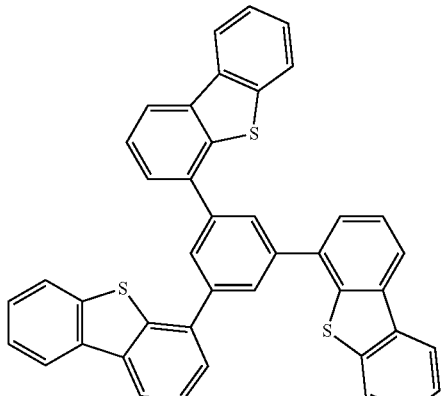

DBT3P-II

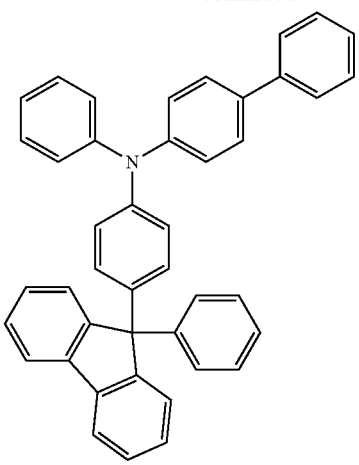

BPAFLP

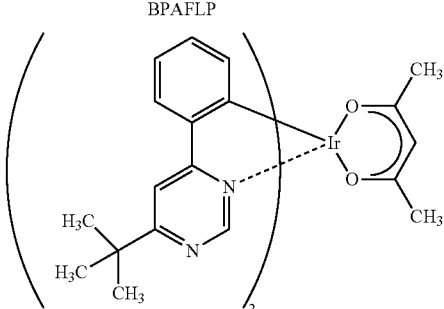

[Ir(tBuppm)$_2$(acac)]

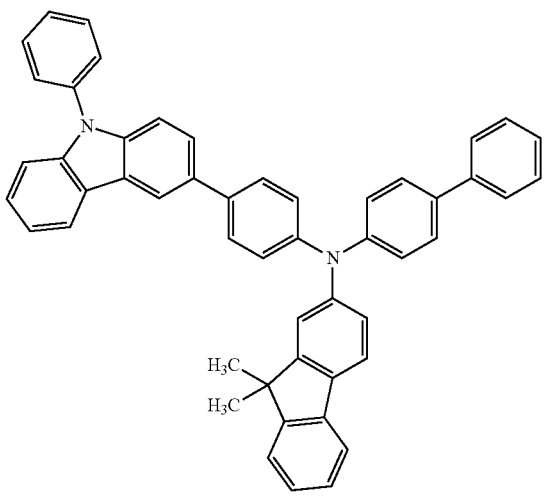

PCBBiF

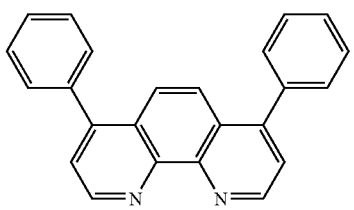

Bphen

[Chemical Formulae 64]

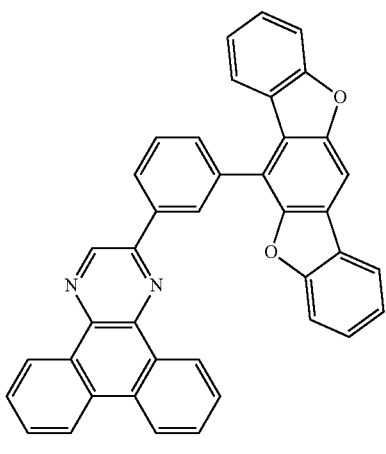

2mBbfPDBq

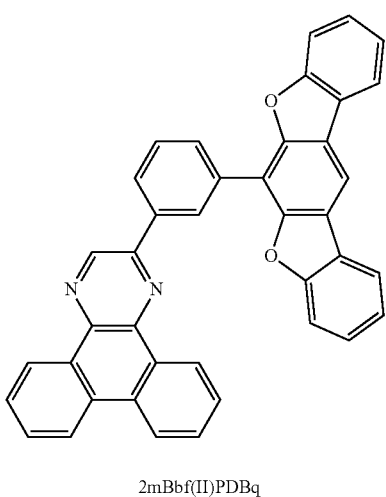

2mBbf(II)PDBq

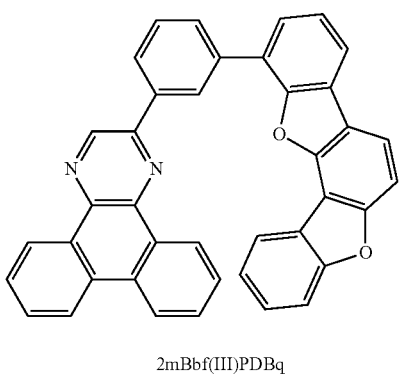

2mBbf(III)PDBq

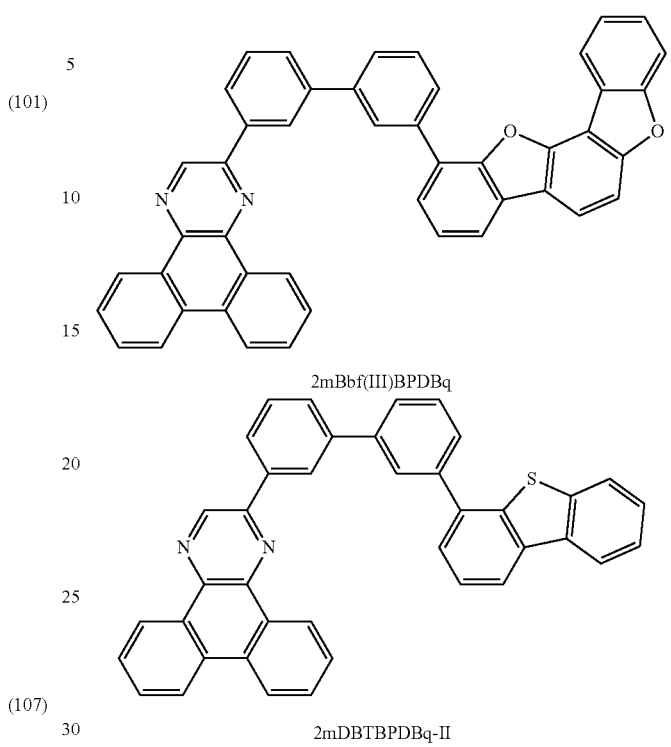

2mBbf(III)BPDBq

2mDBTBPDBq-II

<<Fabrication of Light-Emitting Elements 1 to 4 and Comparative Light-Emitting Element 5>>

First, indium tin oxide (ITO) containing silicon oxide was deposited over a glass substrate 900 by a sputtering method, whereby a first electrode 901 functioning as an anode was formed. Note that the thickness was set to 110 nm and the electrode area was set to 2 mm×2 mm.

Next, as pretreatment for fabricating the light-emitting element 1 over the substrate 900, UV ozone treatment was performed for 370 seconds after washing of a surface of the substrate with water and baking that was performed at 200° C. for 1 hour.

After that, the substrate was transferred into a vacuum evaporation apparatus where the pressure had been reduced to approximately $10^{-4}$ Pa, and subjected to vacuum baking at 170° C. in a heating chamber of the vacuum evaporation apparatus for 30 minutes, and then the substrate 900 was cooled down for approximately 30 minutes.

Next, the substrate 900 was fixed to a holder provided in the vacuum evaporation apparatus so that a surface of the substrate provided with the first electrode 901 faced downward. In this example, a case is described in which a hole-injection layer 911, a hole-transport layer 912, a light-emitting layer 913, an electron-transport layer 914, and an electron-injection layer 915, which were included in an EL layer 902, were sequentially formed by a vacuum evaporation method.

After the pressure in the vacuum apparatus was reduced to $10^{-4}$ Pa, 1,3,5-tri(dibenzothiophen-4-yl)benzene (abbreviation: DBT3P-II) and molybdenum oxide were deposited by co-evaporation so that the mass ratio of DBT3P-II to molybdenum oxide was 4:2, whereby the hole-injection layer 911 was formed over the first electrode 901. The thickness of the hole-injection layer 911 was set to 20 nm. Note that co-evaporation is an evaporation method in which a plurality of different substances are concurrently vaporized from different evaporation sources.

Then, 4-phenyl-4'-(9-phenylfluoren-9-yl)triphenylamine (abbreviation: BPAFLP) was deposited by evaporation to a thickness of 20 nm, whereby the hole-transport layer 912 was formed.

Next, the light-emitting layer 913 was formed over the hole-transport layer 912.

In the case of the light-emitting element 1, 2-[3-(benzo[1,2-b:4,5-b']bisbenzofuran-6-yl)phenyl]dibenzo[f,h]quinoxaline (abbreviation: 2mBbfPDBq), N-(1,1'-biphenyl-4-yl)-9,9-dimethyl-N-[4-(9-phenyl-9H-carbazol-3-yl)phenyl]-9H-fluoren-2-amine (abbreviation: PCBBiF), and [Ir(tBuppm)$_2$(acac)] were deposited by co-evaporation so that the mass ratio of 2mBbfPDBq to PCBBiF and [Ir(tBuppm)$_2$(acac)] was 0.7:0.3:0.05. The thickness was set to 20 nm. Furthermore, 2mBbfPDBq, PCBBiF, and [Ir(tBuppm)$_2$(acac)] were deposited by co-evaporation to a thickness of 20 nm so that the mass ratio of 2mBbfPDBq to PCBBiF and [Ir(tBuppm)$_2$(acac)] was 0.8:0.2:0.05. In this manner, the light-emitting layer 913 having a stacked-layer structure and a thickness of 40 nm was formed.

In the Case of the Light-Emitting Element 2, 2-[3-(benzo[1,2-b:5,4-b']bisbenzofuran-6-yl)phenyl]dibenzo[f,h]quinoxaline (abbreviation: 2mBbf(II)PDBq), PCBBiF, and [Ir(tBuppm)$_2$(acac)] were deposited by co-evaporation to a thickness of 20 nm so that the mass ratio of 2mBbf(II)PDBq to PCBBiF and [Ir(tBuppm)$_2$(acac)] was 0.7:0.3:0.05. Then, 2mBbf(II)PDBq, PCBBiF, and [Ir(tBuppm)$_2$(acac)] were deposited by co-evaporation to a thickness of 20 nm so that the mass ratio of 2mBbf(II)PDBq to PCBBiF and [Ir(tBuppm)$_2$(acac)] was 0.8:0.2:0.05. In this manner, the light-emitting layer 913 having a stacked-layer structure and a thickness of 40 nm was formed.

In the case of the light-emitting element 3, 2-[3-(benzo[1,2-b:5,6-b']bisbenzofuran-4-yl)phenyl]dibenzo[f,h]quinoxaline (abbreviation: 2mBbf(III)PDBq), PCBBiF, and [Ir(tBuppm)$_2$(acac)] were deposited by co-evaporation to a thickness of 20 nm so that the mass ratio of 2mBbf(III)PDBq to PCBBiF and [Ir(tBuppm)$_2$(acac)] was 0.7:0.3:0.05. Then, 2mBbf(III)PDBq, PCBBiF, and [Ir(tBuppm)$_2$(acac)] were deposited by co-evaporation to a thickness of 20 nm so that the mass ratio of 2mBbf(III)PDBq to PCBBiF and [Ir(tBuppm)$_2$(acac)] was 0.8:0.2:0.05. In this manner, the light-emitting layer 913 having a stacked-layer structure and a thickness of 40 nm was formed.

In the case of the light-emitting element 4, 2-[3'-(benzo[1,2-b:5,6-b']bisbenzofuran-4-yl)-1,1'-biphenyl-3-yl]dibenzo[f,h]quinoxaline (abbreviation: 2mBbf(III)BPDBq), PCBBiF, and [Ir(tBuppm)$_2$(acac)] were deposited by co-evaporation to a thickness of 20 nm so that the mass ratio of 2mBbf(III)BPDBq to PCBBiF and [Ir(tBuppm)$_2$(acac)] was 0.7:0.3:0.05. Then, 2mBbf(III)BPDBq, PCBBiF, and [Ir(tBuppm)$_2$(acac)] were deposited by co-evaporation to a thickness of 20 nm so that the mass ratio of 2mBbf(III)BPDBq to PCBBiF and [Ir(tBuppm)$_2$(acac)] was 0.8:0.2:0.05. In this manner, the light-emitting layer 913 having a stacked-layer structure and a thickness of 40 nm was formed.

In the case of the comparative light-emitting element 5, 2-[3'-(dibenzothiophen-4-yl)biphenyl-3-yl]dibenzo[f,h]quinoxaline (abbreviation: 2mDBTBPDBq-II), PCBBiF, and [Ir(tBuppm)$_2$(acac)] were deposited by co-evaporation to a thickness of 20 nm so that the mass ratio of 2mDBTBPDBq-II to PCBBiF and [Ir(tBuppm)$_2$(acac)] was 0.7:0.3:0.05. Then, 2mDBTBPDBq-II, PCBBiF, and [Ir(tBuppm)$_2$(acac)] were deposited by co-evaporation to a thickness of 20 nm so that the mass ratio of 2mDBTBPDBq-II to PCBBiF and [Ir(tBuppm)$_2$(acac)] was 0.8:0.2:0.05. In this manner, the light-emitting layer 913 having a stacked-layer structure and a thickness of 40 nm was formed.

Next, over the light-emitting layer 913, the electron-transport layer 914 was formed. In the light-emitting element 1, the electron-transport layer 914 was formed by depositing 2mBbfPDBq by evaporation to a thickness of 20 nm and then depositing Bphen by evaporation to a thickness of 10 nm. In the light-emitting element 2, the electron-transport layer 914 was formed by depositing 2mBbf(II)PDBq by evaporation to a thickness of 20 nm and then depositing Bphen by evaporation to a thickness of 10 nm. In the light-emitting element 3, the electron-transport layer 914 was formed by depositing 2mBbf(III)PDBq by evaporation to a thickness of 20 nm and then depositing Bphen by evaporation to a thickness of 10 nm. In the light-emitting element 4, the electron-transport layer 914 was formed by depositing 2mBbf(III)BPDBq by evaporation to a thickness of 20 nm and then depositing Bphen by evaporation to a thickness of 10 nm.

Furthermore, over the electron-transport layer 914 of the light-emitting elements 1 to 4, lithium fluoride was deposited by evaporation to a thickness of 1 nm to form the electron-injection layer 915.

Finally, aluminum was deposited to a thickness of 200 nm over the electron-injection layer 915 by evaporation, whereby a second electrode 903 functioning as a cathode was formed. Through the above-described steps, the light-emitting elements 1 to 4 were fabricated. Note that in all the above evaporation steps, evaporation was performed by a resistance-heating method.

Table 1 shows the element structures of the light-emitting elements 1 to 4 and the comparative light-emitting element 5 fabricated by the above-described method.

TABLE 1

| | First Electrode | Hole-Injection Layer | Hole-Transporting Layer | Light-Emitting Layer | Electron-Transporting Layer | Electron-Injection Layer | Second Electrode |
|---|---|---|---|---|---|---|---|
| Light-Emitting Element 1 | ITO (110 nm) | DBT3P-II:MoO$x$ (4:2 20 nm) | BPAFLP (20 nm) | * | 2mBbfPDBq (20 nm) | Bphen (10 nm) | LiF (1 nm) | Al (200 nm) |
| Light-Emitting Element 2 | ITO (110 nm) | DBT3P-II:MoO$x$ (4:2 20 nm) | BPAFLP (20 nm) | ** | 2mBbf(II)PDBq (20 nm) | Bphen (10 nm) | LiF (1 nm) | Al (200 nm) |
| Light-Emitting Element 3 | ITO (110 nm) | DBT3P-II:MoO$x$ (4:2 20 nm) | BPAFLP (20 nm) | *** | 2mBbf(III)PDBq (20 nm) | Bphen (10 nm) | LiF (1 nm) | Al (200 nm) |

TABLE 1-continued

| | First Electrode | Hole-Injenction Layer | Hole-Transporting Layer | Light-Emitting Layer | Electron-Transporting Layer | Electron-Injection Layer | Second Electrode |
|---|---|---|---|---|---|---|---|
| Light-Emitting Element 4 | ITO (110 nm) | DBT3P-II:MoOx (4:2 20 nm) | BPAFLP (20 nm) | **** | 2mBbf(III)BPDBq (20 nm) | Bphen (10 nm) | LiF (1 nm) | Al (200 nm) |
| Comparative Light-Emitting Element 5 | ITO (110 nm) | DBT3P-II:MoOx (4:2 20 nm) | BPAFLP (20 nm) | ***** | 2mDBTBPDBq-II (20 nm) | Bphen (10 nm) | LiF (1 nm) | Al (200 nm) |

\* 2mBbfPDBq:PCBBiF:[Ir(tBuppm)$_2$(acac)] (0.7:0.3:0.05 20 nm\0.8:0.2:0.05 20 nm)
\*\* 2mBbf(II)PDBq:PCBBiF:[Ir(tBuppm)$_2$(acac)] (0.7:0.3:0.05 20 nm\0.8:0.2:0.05 20 nm)
\*\*\* 2mBbf(III)PDBq:PCBBiF:[Ir(tBuppm)$_2$(acac)] (0.7:0.3:0.05 20 nm\0.8:0.2:0.05 20 nm)
\*\*\*\* 2mBbf(III)BPDBq:PCBBiF:[Ir(tBuppm)$_2$(acac)] (0.7:0.3:0.05 20 nm\0.8:0.2:0.05 20 nm)
\*\*\*\*\* 2mDBTBPDBq-II:PCBBiF:[Ir(tBuppm)$_2$(acac)] (0.7:0.3:0.05 20 nm\0.8:0.2:0.05 20 nm)

The fabricated light-emitting elements 1 to 4 and the comparative light-emitting element 5 were sealed in a glove box under a nitrogen atmosphere so as not to be exposed to the air (a sealant was applied to surround the elements, and at the time of sealing, UV treatment was performed and heat treatment was performed at 80° C. for 1 hour).

<<Operation Characteristics of Light-Emitting Elements 1 to 4 and Comparative Light-Emitting Element 5>>

Operation characteristics of the fabricated light-emitting elements 1 to 4 were measured. Note that the measurement was carried out at room temperature (in an atmosphere kept at 25° C.).

FIG. 24, FIG. 25, FIG. 26, and FIG. 27 show current density—luminance characteristics, voltage—luminance characteristics, luminance—current efficiency characteristics, and voltage—current characteristics, respectively, of the light-emitting elements 1 to 4 (the light-emitting elements 1 to 4 are designated as Elements 1 to 4 in FIG. 24, FIG. 25, FIG. 26, and FIG. 27).

Table 2 shows main values of initial characteristics of the light-emitting elements 1 to 4 and the comparative light-emitting element 5 at a luminance of approximately 1000 cd/m². Note that the comparative light-emitting element 5 has initial characteristics as good as those of the light-emitting elements 1 to 4.

at around 546 nm and it is suggested that the peak is derived from green light emission of the organometallic complex, [Ir(tBuppm)$_2$(acac)], used in the EL layer of each light-emitting element. Note that the emission spectrum of the comparative light-emitting element 5 also has the peak derived from green light emission of [Ir(tBuppm)$_2$(acac)], similar to those of the light-emitting elements 1 to 4.

Figure 29:
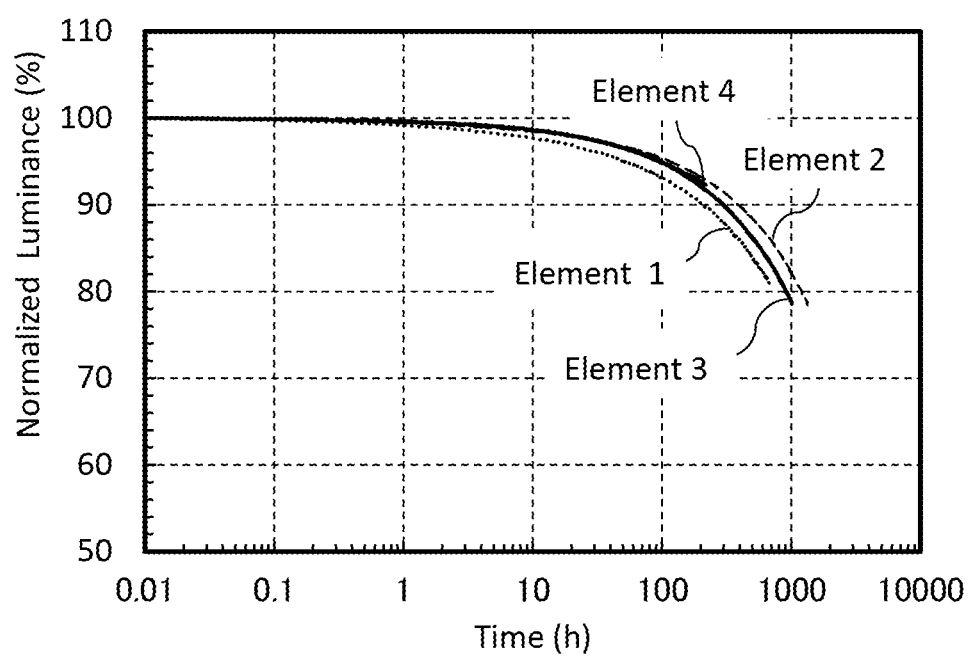
FIG. 29 shows reliability of the light-emitting elements 1 to 4.

Next, a reliability test was performed on the light-emitting elements 1 to 4. FIG. 29 shows results of the reliability test (the light-emitting elements 1 to 4 are designated as Elements 1 to 4 in FIG. 29). In FIG. 29, the vertical axis represents normalized luminance (%) with an initial luminance of 100%, and the horizontal axis represents driving time (h) of the light-emitting elements. Note that in the reliability test, the light-emitting elements 1 to 4 were driven under the conditions where the initial luminance was set to 5000 cd/m² and the current density was constant.

Note that the light-emitting elements 1 to 4 using the heterocyclic compound of one embodiment of the present invention each have high reliability as shown in FIG. 29. Thus, it is found that long lifetime of the light-emitting elements can be achieved with the heterocyclic compound of one embodiment of the present invention.

The light-emitting elements 1 to 3 and the comparative light-emitting element 5 were subjected to a preservation

TABLE 2

| | Voltage (V) | Current (mA) | Current Density (mA/cm²) | Chromaticity (x, y) | Luminance (cd/m²) | Current Density (cd/A) | Power Efficiency (lm/W) | External Quantum Efficiency (%) |
|---|---|---|---|---|---|---|---|---|
| Light-Emitting Element 1 | 2.9 | 0.041 | 1 | (0.42, 0.57) | 1200 | 110 | 120 | 29 |
| Light-Emitting Element 2 | 3.3 | 0.047 | 1.2 | (0.42, 0.57) | 1100 | 90 | 86 | 24 |
| Light-Emitting Element 3 | 3.1 | 0.047 | 1.2 | (0.42, 0.57) | 1200 | 100 | 100 | 27 |
| Light-Emitting Element 4 | 3.0 | 0.042 | 1.1 | (0.43, 0.56) | 1100 | 100 | 110 | 27 |
| Comparative Light-Emitting Element 5 | 3.0 | 0.039 | 1.0 | (0.42, 0.57) | 1000 | 100 | 110 | 27 |

Figure 28:
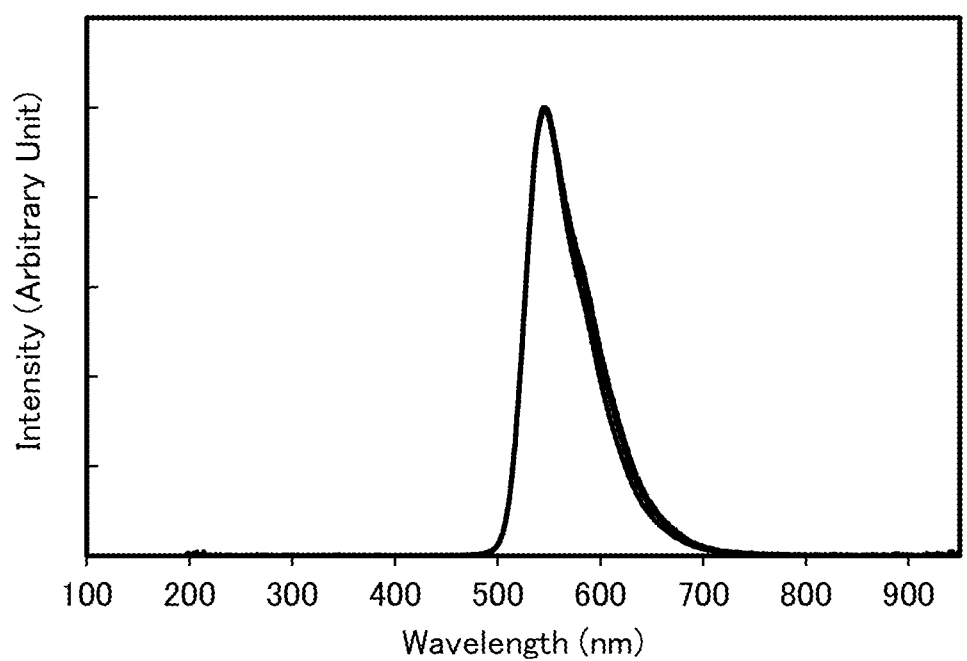
FIG. 28 shows emission spectra of the light-emitting elements 1 to 4.

FIG. 28 shows emission spectra of the light-emitting elements 1 to 4 to which current was applied at a current density of 25 mA/cm². As shown in FIG. 28, the emission spectra of the light-emitting elements 1 to 4 each have a peak test. In preservation test, the light-emitting elements each were not driven and preserved in a thermostatic oven maintained at 100° C. for a predetermined time, and the operation characteristics were measured. Note that the operation characteristics were measured at room temperature (in an atmosphere kept at 25° C.) after the light-emitting elements were taken out of the thermostatic oven.

Figure 30:
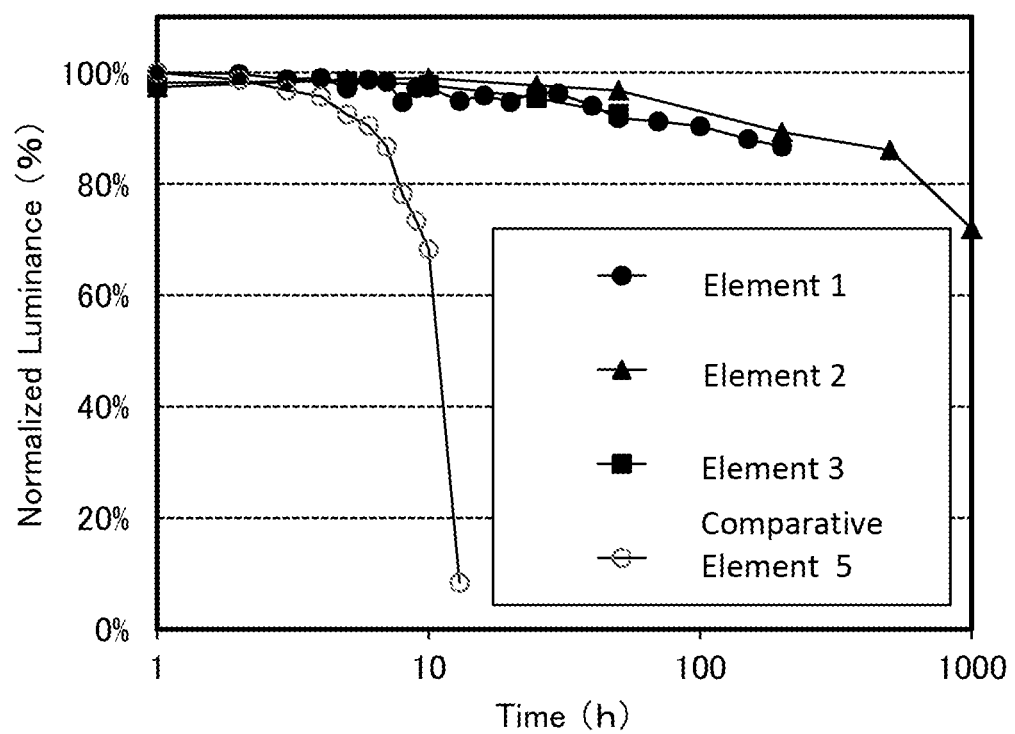
FIG. 30 shows time changes in external quantum efficiency characteristics of the light-emitting elements 1 to 3 and a comparative light-emitting element 5.

FIG. 30 shows measurement results of external quantum efficiency over time of the light-emitting elements 1 to 3 and the comparative light-emitting element 5 (the light-emitting elements 1 to 3 and the comparative light emitting element 5 are designated as Elements 1 to 3 and Comparative Element 5 in FIG. 30). The above results show that, even when the light-emitting elements 1 to 3 of one embodiment of the present invention are preserved at 100° C. for a long time, the initial external quantum efficiency can be maintained and therefore favorable heat resistance can be maintained. In contrast, in the comparative light-emitting element 5, the external quantum efficiency was markedly reduced within around 10 hours.

Note that the molecular weight of each of the 2mBbfP-DBq used for the light-emitting element 1, the 2mBbf(II)PDBq used for the light-emitting element 2, and the 2mBbf(III)PDBq used for the light-emitting element 3 is 562, and the molecular weight of the 2mDBTBPDBq-II used for the comparative light-emitting element 5 is 564. That is, although the light-emitting elements used for the preservation test have the same molecular weights, there is a great difference between the light-emitting elements 1 to 3 and the comparative light-emitting element 5 in heat resistance in the preservation test at 100° C.

The light-emitting elements 1 to 3 each have a molecular structure including benzobisbenzofuran which is a condensed aromatic ring, unlike the comparative light-emitting element 5. The difference in heat resistance observed in the preservation test is due to this molecular structure. A compound and a light-emitting element having this molecular structure can have extremely high heat resistance without increasing the molecular weight. Thus, the use of the condensed aromatic ring is highly effective.

EXAMPLE 6

In this example, the HOMO level and the LUMO level of 2-[3-(benzo[1,2-b:4,5-b']bisbenzofuran-6-yl)phenyl]dibenzo[f,h]quinoxaline (abbreviation: 2mBbfPDBq), which is a heterocyclic compound of one embodiment of the present invention represented by the following structural formula (101), were obtained through a cyclic voltammetry (CV) measurement. A calculation method is shown below.

[Chemical Formula 65] (101)

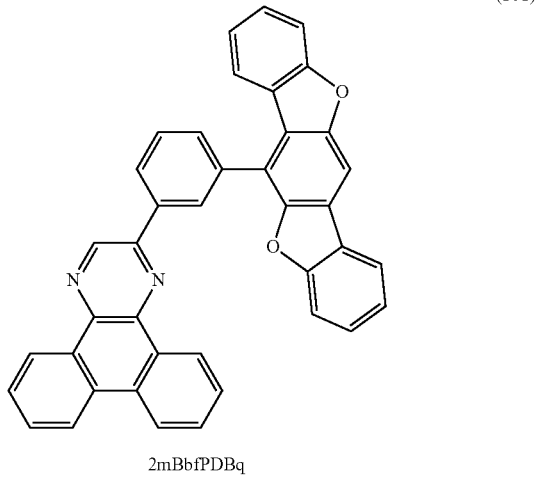

2mBbfPDBq

An electrochemical analyzer (ALS model 600A or 600C, manufactured by BAS Inc.) was used as a measurement apparatus. As for a solution used in the CV measurement, dehydrated dimethylformamide (DMF) (manufactured by Aldrich, 99.8%, catalog number: 227056) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (PTE platinum electrode, manufactured by BAS Inc.) was used as a working electrode, another platinum electrode (Pt counter electrode for VC-3 (5 cm), manufactured by BAS Inc.) was used as an auxiliary electrode, and an Ag/Ag$^+$ electrode (RE7 reference electrode for nonaqueous solvent, manufactured by BAS Inc.) was used as a reference electrode. Note that the measurement was performed at room temperature (20° C. to 25° C.). In addition, the scan speed at the CV measurement was set to 0.1 V/sec, and an oxidation potential Ea[V] and a reduction potential Ec [V] with respect to the reference electrode were measured. Note that Ea represents an intermediate potential of an oxidation-reduction wave, and Ec represents an intermediate potential of a reduction-oxidation wave. Here, the potential energy of the reference electrode used in this example with respect to the vacuum level is found to be −4.94 [eV], and thus, the HOMO level and the LUMO level can be obtained from the following formula: HOMO level [eV]=−4.94−Ea and LUMO level [eV]=−4.94−Ec. Furthermore, the CV measurement was repeated 100 times, and the oxidation-reduction wave at the hundredth cycle and the oxidation-reduction wave at the first cycle were compared with each other to examine the electric stability of the compound.

As a result, in the measurement of the oxidation potential Ea [V] of 2mBbfPDBq, an oxidation peak was not clearly observed in the measurement range of 0.2 eV to 1.5 eV. In contrast, the LUMO level was found to be −2.97 eV. When the oxidation-reduction wave was repeatedly measured, the peak intensity of the oxidation-reduction wave after the hundredth cycle maintained 73% of that of the oxidation-reduction wave at the first cycle; thus, resistance to reduction of 2mBbfPDBq was found to be extremely favorable.

Thermogravimetry-differential thermal analysis (TG-DTA) was performed on 2mBbfPDBq. The measurement was conducted by using a high vacuum differential type differential thermal balance (TG-DTA 2410SA, manufactured by Bruker AXS K.K.). The measurement was conducted under a nitrogen stream (flow rate: 200 mL/min) at normal pressure at a temperature increase rate of 10° C./min. It was found from the relationship between weight and temperature (thermogravimetry) that the 5% weight loss temperature of 2mBbfPDBq was approximately 442° C. This indicates that 2mBbfPDBq has high heat resistance.

Further, differential scanning calorimetry (DSC measurement) was performed by Pyris1DSC manufactured by PerkinElmer, Inc. In the differential scanning calorimetry, after the temperature was raised from −10° C. to 370° C. at a temperature increase rate of 50° C./min, the temperature was held for a minute and then cooled to −10° C. at a temperature reduction rate of 50° C./min. This operation is repeated twice successively and the second measurement result was employed. It was found from the DSC measurement that the glass transition temperature of 2mBbfPDBq was 147° C. and thus had high heat resistance.

Next, 2mBbfPDBq obtained in this example was analyzed by liquid chromatography mass spectrometry (LC/MS).

In the LC/MS analysis, liquid chromatography (LC) was carried out with ACQUITY UPLC (registered trademark) (manufactured by Waters Corporation), and mass spectrometry (MS) was carried out with Xevo G2 Tof MS (manufactured by Waters Corporation). ACQUITY UPLC (registered trademark) BEH $C_8$ (2.1×100 mm, 1.7 μm) (manufactured by Waters Corporation) was used as a column for the LC separation, and the column temperature was set to 40° C. Acetonitrile was used for Mobile Phase A and a 0.1% formic acid aqueous solution was used for Mobile Phase B.

Further, a sample was prepared in such a manner that 2mBbfPDBq was dissolved in N-methyl-2-pyrrolidone at a given concentration and the mixture was diluted with acetonitrile. The injection amount was set to 5.0 μL.

In the LC separation, a gradient method in which the composition of mobile phases is changed was employed. The ratio of Mobile Phase A to Mobile Phase B was 65:35 for 0 to 1 minute after the start of the measurement, and then the composition was changed so that the ratio of Mobile Phase A to Mobile Phase B 10 minutes after the start of the measurement was 95:5. The analysis time was 10 minutes in total. The composition was changed linearly.

In the MS analysis, ionization was carried out by an electrospray ionization (ESI) method. At this time, the capillary voltage and the sample cone voltage were set to 3.0 kV and 30 V, respectively, and detection was performed in a positive mode. A mass range for the measurement was m/z=100 to 1200.

Figure 31:
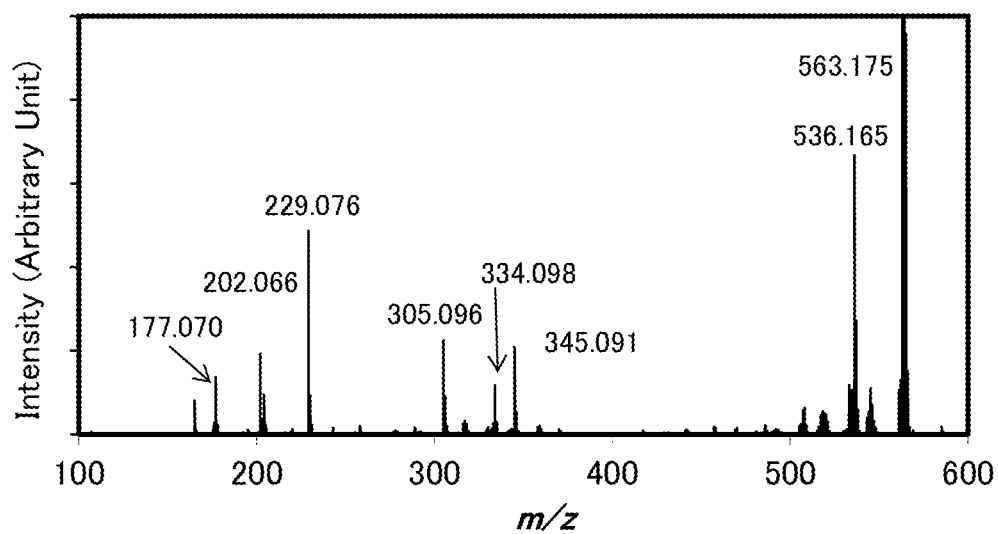
FIG. 31 shows mass spectra of 2mBbfPDBq.
Figure 32:
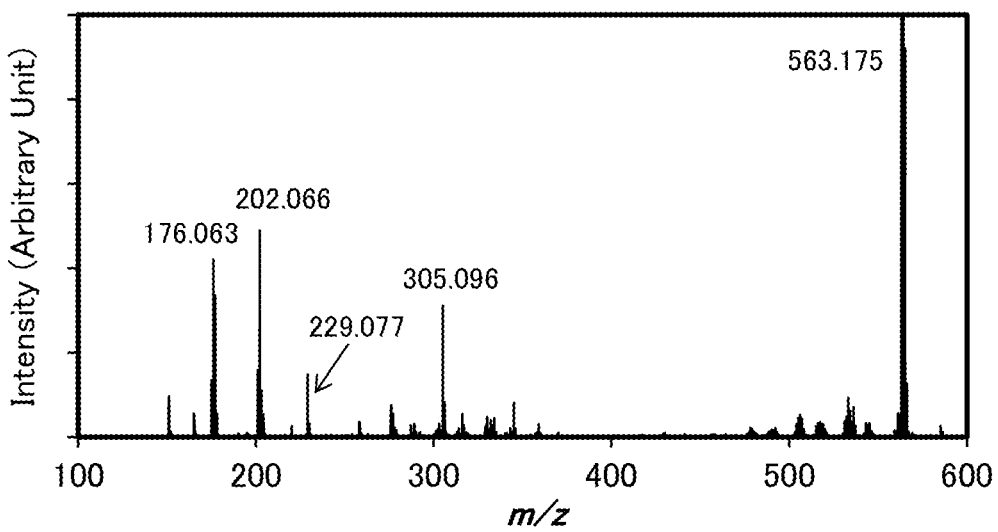
FIG. 32 shows mass spectra of 2mBbfPDBq.

LC-MS measurement was carried out under the above conditions, and an ion derived from 2mBbfPDBq was detected from a mass-to-charge ratio (m/z)=563.175 (the theoretical value of 2mBbfPDBq, i.e., [M+H$^+$]=562.175). Then, an ion (a precursor ion) with a mass-to-charge ratio (m/z) of 563.175 was collided with an argon gas in a collision cell to dissociate. Energy (collision energy) for the collision of the precursor ion with argon was set to 50 eV and 70 eV. FIG. 31 shows mass spectra of product ions generated by the collision of the precursor ion and an argon gas when a collision energy detected by time-of-flight (TOF) detector is 50 eV, and FIG. 32 shows mass spectra of the product ions when the collision energy is 70 eV.

The result in FIG. 31 shows that product ions of 2mBbfPDBq represented by the structural formula (101) are detected mainly around m/z=536.165, around m/z=345.091, around m/z=334.098, around m/z=305.096, around m/z=229.076, around m/z=202.066, and around m/z=177.070. The result in FIG. 32 shows that product ions of 2mBbfPDBq represented by the structural formula (101) at the collision energy of 70 eV are detected mainly around m/z=305.096, around m/z=229.077, around m/z=202.066, and around m/z=176.063. Note that the results in FIG. 31 and FIG. 32 show characteristics derived from 2mBbfPDBq and thus can be regarded as important data for identifying 2mBbfPDBq contained in a mixture.

Note that the product ion detected around m/z=536.165 is probably generated owing to a cleavage of a ring including nitrogen of dibenzo[f,h]quinoxaline in the compound represented by the structural formula (101) as shown in the following formula (a). The product ion around m/z=345.091 is probably derived from dibenzo[f,h]quinoxaline generated owing to a cleavage of a bond at the 2-position of dibenzo [f,h]quinoxaline in the compound represented by the structural formula (101) as shown in the following formula (b). The product ion around m/z=334.098 is probably derived from 6-phenylbenzo[1,2-b:4,5-b']bisbenzofuran generated owing to a cleavage of a bond at the 2-position of dibenzo [f,h]quinoxaline in the compound represented by the structural formula (101) as shown in the following formula (c). The product ion around m/z=305.096 is probably derived from 2-phenyldibenzo[f,h]quinoxaline generated owing to a cleavage of a bond at the 6-position of benzo[1,2-b:4,5-b'] bisbenzofuran in the compound represented by the structural formula (101) as shown in the following formula (d). The product ion around m/z=229.076 is probably derived from dibenzo[f,h]quinoxaline generated owing to a cleavage of a bond at the 2-position of dibenzo[f,h]quinoxaline in the compound represented by the structural formula (101) as shown in the following formula (e). The product ion around m/z=202.066 is probably an ion generated owing to a further cleavage of the product ion around m/z=536.165 as shown in the following formula (f). The product ion around m/z=177.070 is probably an ion generated owing to a further cleavage of the product ion around m/z=536.165 as shown in the following formula (g). In particular, an ion shown by the formula (a) of the ion generated owing to the cleavage of a ring including nitrogen of dibenzon[f,h]quinoxaline in the compound represented by the structural formula (101) and ions shown by the formulae (b) to (d) of the ions generated owing to the cleavage of a bond between rings are each one of features of 2mBbfPDBq and thus can be regarded as important data for identifying 2mBbfPDBq contained in a mixture.

[Chemical Formulae 66]

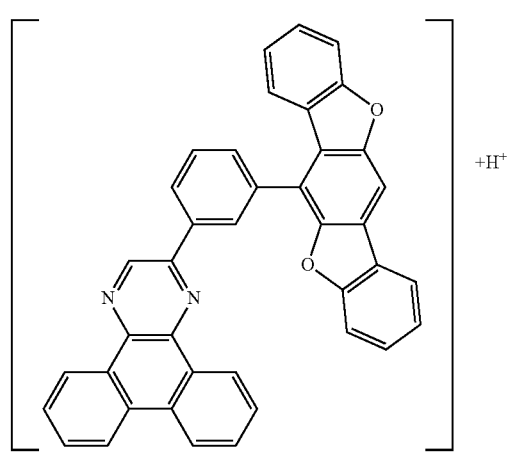

$C_{40}H_{23}N_2O_2^+$
Exact Mass: 563.1754
Precursor Ion

-continued (a)

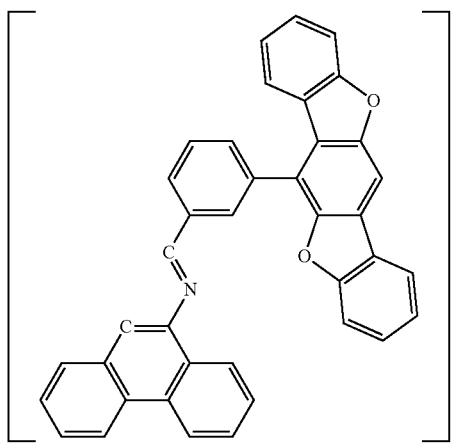

C₃₉H₂₂NO₂⁺
Exact Mass: 536.16451

+H⁺

(b)

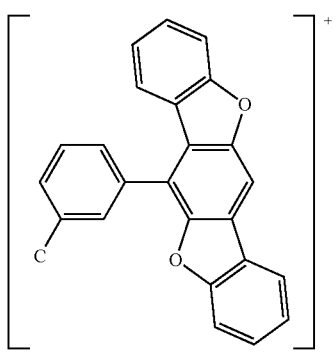

C₂₅H₁₃O₂
Exact Mass: 345.09155

(c)

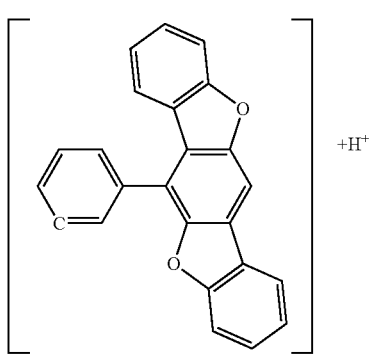

+H⁺

C₂₄H₁₄O₂⁺
Exact Mass: 334.09883

-continued (d)

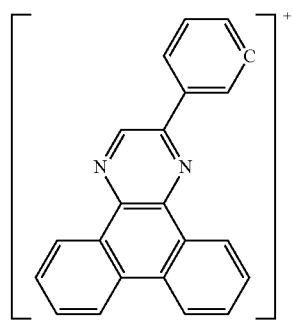

C₂₂H₁₃N₂
Exact Mass: 305.10787

(e)

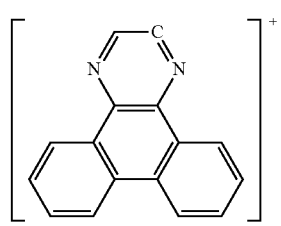

C₁₆H₉N₂
Exact Mass: 229.07657

(f)

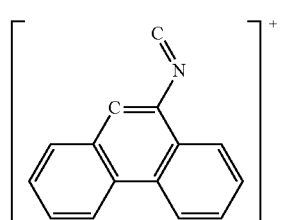

C₁₅H₈N
Exact Mass: 202.06567

(g)

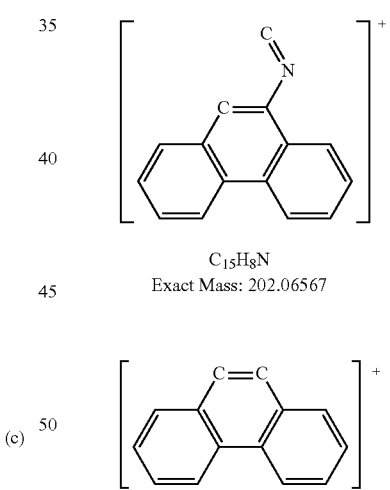

C₁₄H₈
Exact Mass: 176.0626

EXAMPLE 7

In this example, the HOMO level and the LUMO level of 2-[3-(benzo[1,2-b:5,4-b']bisbenzofuran-6-yl)phenyl]dibenzo[f,h]quinoxaline (abbreviation: 2mBbf(II)PDBq), which is a heterocyclic compound of one embodiment of the present invention represented by the following structural formula (107), were obtained through a cyclic voltammetry (CV) measurement. A calculation method is shown below.

[Chemical Formula 67]

(107)

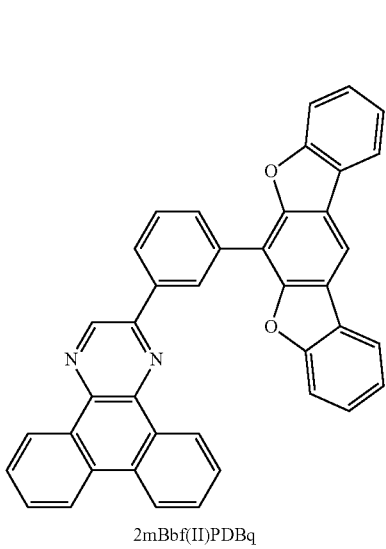

2mBbf(II)PDBq

The HOMO level and the LUMO level of 2mBbf(II)PDBq were obtained through a cyclic voltammetry (CV) measurement. The CV measurements and calculation for the HOMO level and the LUMO level were the same as those in Example 6.

As a result, in the measurement of the oxidation potential Ea [V] of 2mBbf(II)PDBq, an oxidation peak was not clearly observed in the measurement range of −0.2 eV to 1.5 eV. In contrast, the LUMO level was found to be −2.94 eV. When the oxidation-reduction wave was repeatedly measured, the peak intensity of the oxidation-reduction wave after the hundredth cycle maintained 87% of that of the oxidation-reduction wave at the first cycle; thus, resistance to reduction of 2mBbf(II)PDBq was found to be extremely favorable.

Thermogravimetry-differential thermal analysis was performed on 2mBbf(II)PDBq. The analysis method was the same as that described in Example 6. It was found from the measurement result that the 5% weight loss temperature of 2mBbf(II)PDBq was approximately 459° C. This indicates that 2mBbf(II)PDBq has high heat resistance.

EXAMPLE 8

In this example, the HOMO level and the LUMO level of 2-[3-(benzo[1,2-b:5,6-b']bisbenzofuran-4-yl)phenyl]dibenzo[f,h]quinoxaline (abbreviation: 2mBbf(III)PDBq), which is a heterocyclic compound of one embodiment of the present invention represented by the following structural formula (149), were obtained through a cyclic voltammetry (CV) measurement. A calculation method is shown below.

[Chemical Formula 68]

(149)

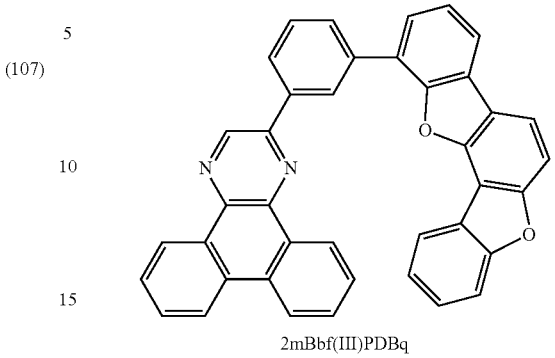

2mBbf(III)PDBq

The HOMO level and the LUMO level of 2mBbf(III)PDBq were obtained through a cyclic voltammetry (CV) measurement. The CV measurements and calculation for the HOMO level and the LUMO level were the same as those in Example 6.

As a result, in the measurement of the oxidation potential Ea [V] of 2mBbf(III)PDBq, an oxidation peak was not clearly observed in the measurement range of 0 eV to 1.5 eV. In contrast, the LUMO level was found to be −2.95 eV. When the oxidation-reduction wave was repeatedly measured, the peak intensity of the oxidation-reduction wave after the hundredth cycle maintained 79% of that of the oxidation-reduction wave at the first cycle; thus, resistance to reduction of 2mBbf(III)PDBq was found to be extremely favorable.

Thermogravimetry-differential thermal analysis was performed on 2mBbf(III)PDBq. The analysis method was the same as that described in Example 6. It was found from the measurement result that the 5% weight loss temperature of 2mBbf(III)PDBq was approximately 454° C. This indicates that 2mBbf(III)PDBq has high heat resistance.

EXAMPLE 9

In this example, the HOMO level and the LUMO level of 2-[3'-(benzo[1,2-b:5,6-b']bisbenzofuran-4-yl)-1,1'-biphenyl-3-yl]dibenzo[f,h]quinoxaline (abbreviation: 2mBbf(III)BPDBq), which is a heterocyclic compound of one embodiment of the present invention represented by the following structural formula (150), were obtained through a cyclic voltammetry (CV) measurement. A calculation method is shown below.

[Chemical Formula 69]

(150)

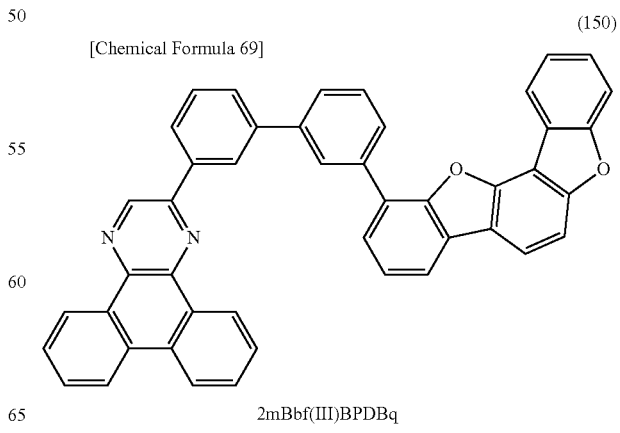

2mBbf(III)BPDBq

The HOMO level and the LUMO level of 2mBbf(III)BPDBq were obtained through a cyclic voltammetry (CV) measurement. The CV measurements and calculation for the HOMO level and the LUMO level were the same as those in Example 6.

As a result, in the measurement of the oxidation potential Ea [V] of 2mBbf(III)BPDBq, an oxidation peak was not clearly observed in the measurement range of 0.1 eV to 1.5 eV. In contrast, the LUMO level was found to be −2.98 eV. When the oxidation-reduction wave was repeatedly measured, the peak intensity of the oxidation-reduction wave after the hundredth cycle maintained 71% of that of the oxidation-reduction wave at the first cycle; thus, resistance to reduction of 2mBbf(III)BPDBq was found to be extremely favorable.

This application is based on Japanese Patent Application serial no. 2015-127571 filed with Japan Patent Office on Jun. 25, 2015, the entire contents of which are hereby incorporated by reference.

What is claimed is:

1. A heterocyclic compound represented by a general formula (G1):

DBq-(-Ar$^1$-)$_n$-Ar$^2$-A  (G1)

wherein DBq represents a substituted or unsubstituted dibenzo[f,h]quinoxalinyl group,
wherein Ar$^1$ represents a substituted or unsubstituted arylene group having 6 to 13 carbon atoms,
wherein n represents 0 or 1,
wherein Ar$^2$ represents a substituted or unsubstituted arylene group having 6 to 13 carbon atoms, and
wherein A represents a substituted or unsubstituted benzobisbenzofuranyl group.

2. The heterocyclic compound according to claim 1, wherein the arylene group of Ar$^2$ has substituents which are bonded to each other to form a ring.

3. The heterocyclic compound according to claim 1, wherein in the general formula (G1), Ar$^2$ represents a substituted or unsubstituted phenylene group or a substituted or unsubstituted biphenyldiyl group, and wherein n represents 0.

4. The heterocyclic compound according to claim 1, wherein in the general formula (G1), Ar$^2$ represents a substituted or unsubstituted m-phenylene group or a substituted or unsubstituted biphenyl-3,3'-diyl group, and wherein n represents 0.

5. The heterocyclic compound according to claim 1, wherein A in the general formula (G1) is any one of general formulae (A1) to (A3)

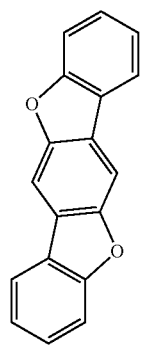

(A1)

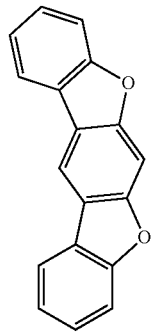

(A2)

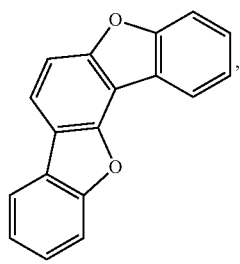

(A3)

and wherein among carbon atoms that do not form a furan ring in the general formulae (A1) to (A3), any one of carbon atoms adjacent to a carbon atom of the furan ring, which is bonded to oxygen, is bonded to Ar$^2$.

6. A light-emitting element comprising the heterocyclic compound according to claim 1.

7. A light-emitting element comprising a light-emitting layer including the heterocyclic compound according to claim 1 and a light-emitting substance.

8. A light-emitting device comprising:
the light-emitting element according to claim 7; and
a transistor.

9. A heterocyclic compound represented by a general formula (G1):

DBq-(-Ar$^1$-)$_n$-Ar$^2$-A  (G1)

wherein DBq represents a substituted or unsubstituted dibenzo[f,h]quinoxalinyl group,
wherein Ar$^1$ represents a substituted or unsubstituted arylene group having 6 to 13 carbon atoms,
wherein n represents 0 or 1,
wherein Ar$^2$ represents a substituted or unsubstituted arylene group having 6 to 13 carbon atoms,
wherein A represents a substituted or unsubstituted benzobisbenzofuranyl group, and
wherein, among carbon atoms that do not form a furan ring in the benzobisbenzofuranyl group, any one of carbon atoms adjacent to a carbon atom of the furan ring, which is bonded to oxygen, is bonded to Ar$^2$.

10. The heterocyclic compound according to claim 9, wherein the arylene group of Ar$^2$ has substituents which are bonded to each other to form a ring.

11. The heterocyclic compound according to claim 9, wherein in the general formula (G1), Ar$^2$ represents a substituted or unsubstituted phenylene group or a substituted or unsubstituted biphenyldiyl group, and wherein n represents 0.

12. The heterocyclic compound according to claim 9,
wherein in the general formula (G1), Ar² represents a substituted or unsubstituted m-phenylene group or a substituted or unsubstituted biphenyl-3,3'-diyl group, and
wherein n represents 0.

13. The heterocyclic compound according to claim 9,
wherein A in the general formula (G1) is any one of general formulae (A1) to (A3)

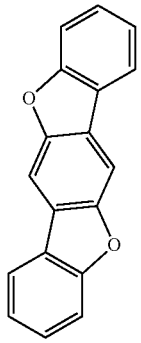

(A1)

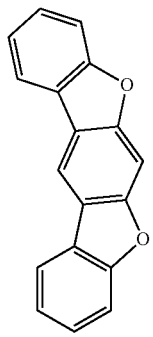

(A2)

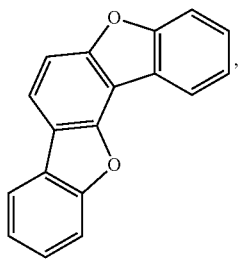

(A3)

and
wherein among carbon atoms that do not form a furan ring in the general formulae (A1) to (A3), any one of carbon atoms adjacent to a carbon atom of the furan ring, which is bonded to oxygen, is bonded to the Ar².

14. A light-emitting element comprising the heterocyclic compound according to claim 9.

15. A light-emitting element comprising a light-emitting layer including the heterocyclic compound according to claim 9 and a light-emitting substance.

16. A light-emitting device comprising:
the light-emitting element according to claim 15; and
a transistor.

17. A heterocyclic compound represented by a general formula (G2):

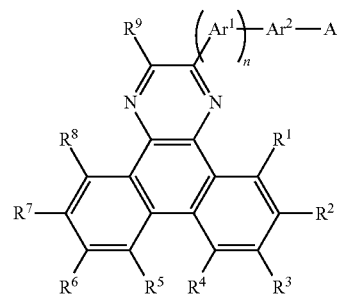

(G2)

wherein A represents a substituted or unsubstituted benzobisbenzofuranyl group, wherein R¹ to R⁹ independently represent any of hydrogen, an alkyl group having 1 to 4 carbon atoms, and a substituted or unsubstituted aryl group having 6 to 13 carbon atoms, wherein Ar¹ represents a substituted or unsubstituted arylene group having 6 to 13 carbon atoms, wherein n represents 0 or 1, and wherein Ar² represents a substituted or unsubstituted arylene group having 6 to 13 carbon atoms.

18. The heterocyclic compound according to claim 17,
wherein the arylene group of Ar² has substituents which are bonded to each other to form a ring.

19. The heterocyclic compound according to claim 17,
wherein in the general formula (G2), Ar² represents a substituted or unsubstituted phenylene group or a substituted or unsubstituted biphenyldiyl group, and
wherein n represents 0.

20. The heterocyclic compound according to claim 17,
wherein in the general formula (G2), Ar² represents a substituted or unsubstituted m-phenylene group or a substituted or unsubstituted biphenyl-3,3'-diyl group, and
wherein n represents 0.

21. The heterocyclic compound according to claim 17,
wherein A in the general formula (G2) is any one of general formulae (A1) to (A3)

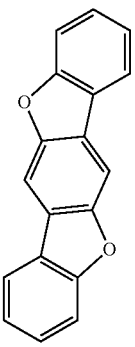

(A1)

-continued (A2)

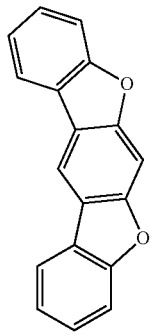

(A3)

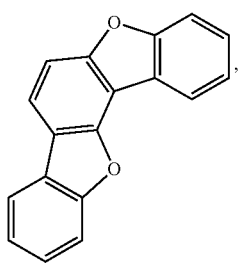

and wherein among carbon atoms that do not form a furan ring in the general formulae (A1) to (A3), any one of carbon atoms adjacent to a carbon atom of the furan ring, which is bonded to oxygen, is bonded to the $Ar^2$.

22. A light-emitting element comprising the heterocyclic compound according to claim 17.

23. A light-emitting element comprising a light-emitting layer including the heterocyclic compound according to claim 17 and a light-emitting substance.

24. A light-emitting device comprising:
    the light-emitting element according to claim 23; and
    a transistor.

25. A heterocyclic compound represented by any one of a structural formula (101), a structural formula (107), a structural formula (149), and a structural formula (150):

(101)

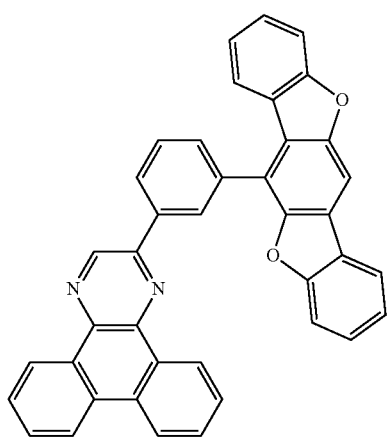

-continued (107)

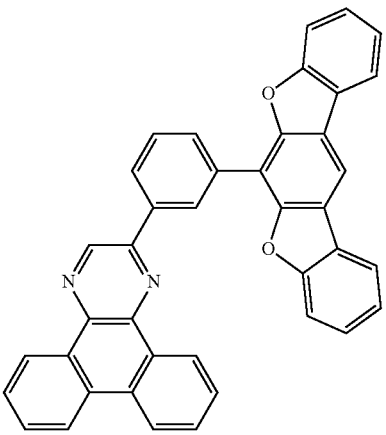

(149)

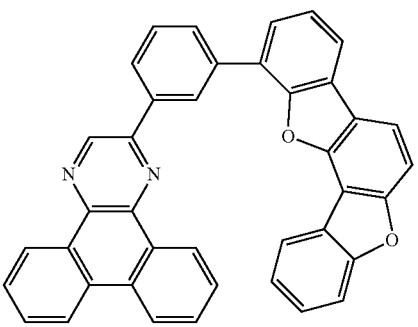

(150)

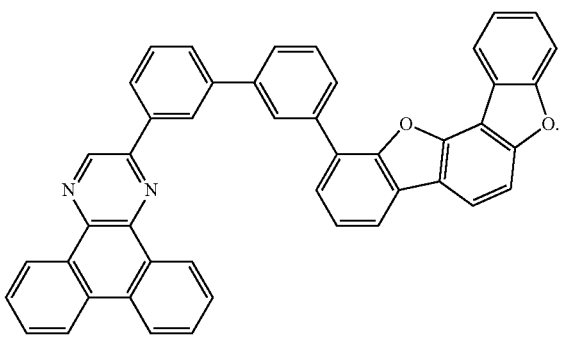

26. A light-emitting element comprising the heterocyclic compound according to claim 25.

27. A light-emitting element comprising a light-emitting layer including the heterocyclic compound according to claim 25 and a light-emitting substance.

28. A light-emitting device comprising:
    the light-emitting element according to claim 27; and
    a transistor.

29. A light-emitting element comprising a heterocyclic compound, wherein the heterocyclic compound comprises a substituted or unsubstituted dibenzo[f,h]quinoxalinyl group bonded to a substituted or unsubstituted benzobisbenzofuranyl group via a substituted or unsubstituted arylene group.

30. The light-emitting element according to claim 29,
    wherein the light-emitting element comprises a light-emitting layer, and
    wherein the light-emitting layer comprises the heterocyclic compound and a light-emitting substance.

31. A light-emitting device comprising:
the light-emitting element according to claim 30; and
a transistor.

32. A light-emitting element comprising a heterocyclic compound,
- wherein the heterocyclic compound comprises a substituted or unsubstituted dibenzo[f,h]quinoxalinyl group bonded to a substituted or unsubstituted benzobisbenzofuranyl group via a substituted or unsubstituted arylene group, and
- wherein among carbon atoms that do not form a furan ring in the benzobisbenzofuranyl group, any one of carbon atoms adjacent to a carbon atom of the furan ring, which is bonded to oxygen, is bonded to the arylene group.

33. The light-emitting element according to claim 32,
- wherein the light-emitting element comprises a light-emitting layer, and
- wherein the light-emitting layer comprises the heterocyclic compound and a light-emitting substance.

34. A light-emitting device comprising:
the light-emitting element according to claim 33; and
a transistor.

* * * * *